(12) United States Patent
Grogan et al.

(10) Patent No.: US 10,611,836 B2
(45) Date of Patent: *Apr. 7, 2020

(54) METHODS OF TREATING CANCER USING PD-1 AXIS BINDING ANTAGONISTS AND TIGIT INHIBITORS

(71) Applicant: Genentech, Inc., South San Francisco, CA (US)

(72) Inventors: Jane Grogan, San Francisco, CA (US); Robert J. Johnston, San Francisco, CA (US); Bryan Irving, San Francisco, CA (US); Jason Hackney, San Carlos, CA (US); Xin Yu, South San Francisco, CA (US); Dan Eaton, San Rafael, CA (US); Kristin Bowles, South San Francisco, CA (US); Laetitia Comps-Agrar, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 456 days.

This patent is subject to a terminal disclaimer.

(21) Appl. No.: 15/239,569

(22) Filed: Aug. 17, 2016

(65) Prior Publication Data

US 2017/0044256 A1    Feb. 16, 2017

Related U.S. Application Data

(62) Division of application No. 14/333,375, filed on Jul. 16, 2014, now Pat. No. 9,873,740.

(60) Provisional application No. 61/992,109, filed on May 12, 2014, provisional application No. 61/985,884, filed on Apr. 29, 2014, provisional application No. 61/950,754, filed on Mar. 10, 2014, provisional application No. 61/865,582, filed on Aug. 13, 2013, provisional application No. 61/846,941, filed on Jul. 16, 2013.

(51) Int. Cl.

| *C07K 16/28* | (2006.01) |
|---|---|
| *A61K 39/395* | (2006.01) |
| *A01K 67/027* | (2006.01) |
| *C07K 14/705* | (2006.01) |
| *A61K 45/06* | (2006.01) |
| *C07K 16/30* | (2006.01) |
| *A61K 39/00* | (2006.01) |

(52) U.S. Cl.
CPC ...... *C07K 16/2803* (2013.01); *A01K 67/0276* (2013.01); *A61K 39/3955* (2013.01); *A61K 39/39558* (2013.01); *A61K 45/06* (2013.01); *C07K 14/70596* (2013.01); *C07K 16/2818* (2013.01); *C07K 16/2827* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3061* (2013.01); *C07K 16/3069* (2013.01); *A01K 2217/075* (2013.01); *A01K 2227/105* (2013.01); *A01K 2267/0331* (2013.01); *A01K 2267/0387* (2013.01); *A61K 2039/507* (2013.01); *C07K 2319/30* (2013.01); *Y02A 50/466* (2018.01)

(58) Field of Classification Search
None
See application file for complete search history.

(56) References Cited

U.S. PATENT DOCUMENTS

| 5,364,934 | A | 11/1994 | Drayna et al. |
|---|---|---|---|
| 5,750,345 | A | 5/1998 | Bowie |
| 5,989,811 | A | 11/1999 | Veltri et al. |
| 6,518,033 | B1 | 2/2003 | Gromeier et al. |
| 7,193,069 | B2 | 3/2007 | Isogai et al. |
| 7,282,570 | B2 | 10/2007 | Goddard et al. |
| 8,217,149 | B2 | 7/2012 | Irving et al. |
| 8,431,350 | B2 | 4/2013 | Baldwin et al. |
| 8,728,474 | B2 | 5/2014 | Honjo et al. |
| 9,499,596 | B2 | 11/2016 | Clark et al. |
| RE46,534 | E | 9/2017 | Baldwin et al. |
| 9,873,740 | B2 | 1/2018 | Grogan et al. |
| 9,920,123 | B2 | 3/2018 | Irving et al. |
| RE46,805 | E | 4/2018 | Baldwin et al. |
| RE46,816 | E | 5/2018 | Baldwin et al. |
| 9,994,637 | B2 | 6/2018 | Gao et al. |
| 2004/0005560 | A1 | 1/2004 | Isogai et al. |
| 2004/0101876 | A1 | 5/2004 | Mintz et al. |
| 2004/0121343 | A1 | 6/2004 | Buechler et al. |
| 2004/0121370 | A1 | 6/2004 | Baldwin et al. |
| 2004/0219521 | A1 | 11/2004 | Tang et al. |
| 2004/0258678 | A1 | 12/2004 | Bodary et al. |
| 2006/0105376 | A1 | 5/2006 | Isogai et al. |
| 2006/0199181 | A1 | 9/2006 | Bodary et al. |
| 2007/0041985 | A1 | 2/2007 | Unger et al. |
| 2007/0054360 | A1 | 3/2007 | Gao et al. |
| 2007/0243584 | A1 | 10/2007 | West |
| 2007/0254339 | A1 | 11/2007 | West et al. |

(Continued)

FOREIGN PATENT DOCUMENTS

| CN | 101035807 A | 9/2007 |
|---|---|---|
| CN | 103073644 A | 5/2013 |

(Continued)

OTHER PUBLICATIONS

Powles et al. (2014) Nature; 515(7528): 558-562.*

(Continued)

*Primary Examiner* — Ilia I Ouspenski
(74) *Attorney, Agent, or Firm* — Clark & Elbing LLP; Karen L. Elbing

(57) ABSTRACT

The present invention describes combination treatment comprising a PD-1 axis binding antagonist and an agent that decreases or inhibits TIGIT expression and/or activity and methods for use thereof, including methods of treating conditions where enhanced immunogenicity is desired such as increasing tumor immunogenicity for the treatment of cancer or chronic infection.

12 Claims, 53 Drawing Sheets

Specification includes a Sequence Listing.

(56) References Cited

U.S. PATENT DOCUMENTS

| | | |
|---|---|---|
| 2008/0038264 A1 | 2/2008 | Bodary et al. |
| 2008/0050809 A1 | 2/2008 | Abuin et al. |
| 2009/0156495 A1 | 6/2009 | Gao et al. |
| 2009/0181024 A1 | 7/2009 | Baldwin et al. |
| 2009/0258013 A1 | 10/2009 | Clark et al. |
| 2010/0075377 A1 | 3/2010 | West et al. |
| 2010/0316646 A1 | 12/2010 | Gao et al. |
| 2011/0104170 A1 | 5/2011 | Baldwin et al. |
| 2012/0219540 A1 | 8/2012 | Gao et al. |
| 2013/0095102 A1 | 4/2013 | Levin et al. |
| 2013/0251720 A1 | 9/2013 | Clark et al. |
| 2014/0186380 A1* | 7/2014 | Gurney .................. A61K 38/19 424/185.1 |
| 2014/0341902 A1 | 11/2014 | Maecker et al. |
| 2015/0216970 A1 | 8/2015 | Grogan et al. |
| 2016/0152720 A1 | 6/2016 | Kim et al. |
| 2017/0008971 A1 | 1/2017 | Dennis et al. |
| 2017/0037127 A1 | 2/2017 | Grogan et al. |
| 2017/0088613 A1 | 3/2017 | Grogan et al. |
| 2017/0107287 A1 | 4/2017 | Irving et al. |
| 2017/0143825 A1 | 5/2017 | Grogan |
| 2017/0145093 A1 | 5/2017 | Clark et al. |
| 2017/0267763 A1 | 9/2017 | Gao et al. |
| 2018/0169239 A1 | 6/2018 | Grogan |
| 2019/0016807 A1 | 1/2019 | Irving et al. |
| 2019/0119376 A1 | 4/2019 | Grogan et al. |

FOREIGN PATENT DOCUMENTS

| | | |
|---|---|---|
| CN | 108290946 A | 7/2018 |
| EP | 1516629 A2 | 3/2005 |
| EP | 1516629 B1 | 4/2013 |
| GB | 2408508 A | 6/2005 |
| JP | 2006-508649 A | 3/2006 |
| JP | 2006-521082 A | 9/2006 |
| JP | 2011-523034 A | 8/2011 |
| WO | WO-99/63063 A1 | 12/1999 |
| WO | WO-00/53758 A2 | 9/2000 |
| WO | WO-00/58334 A1 | 10/2000 |
| WO | WO-01/05972 A1 | 1/2001 |
| WO | WO-01/29221 A2 | 4/2001 |
| WO | WO-01/75116 A2 | 10/2001 |
| WO | WO-01/75166 A2 | 10/2001 |
| WO | WO-01/94413 A2 | 12/2001 |
| WO | WO-03/054152 A2 | 7/2003 |
| WO | WO-03/068943 A2 | 8/2003 |
| WO | WO-03/072035 A2 | 9/2003 |
| WO | WO-2004/024068 A2 | 3/2004 |
| WO | WO-2004/024072 A2 | 3/2004 |
| WO | WO-2004/074324 A2 | 9/2004 |
| WO | WO-2005/052005 A1 | 6/2005 |
| WO | WO-2006/042240 A2 | 4/2006 |
| WO | WO-2006/121168 A1 | 11/2006 |
| WO | WO-2006/124667 A2 | 11/2006 |
| WO | WO-2007/124383 A2 | 11/2007 |
| WO | WO-2009/126688 A2 | 10/2009 |
| WO | WO-2010/077634 A1 | 7/2010 |
| WO | WO-2011/066342 A2 | 6/2011 |
| WO | WO-2013/019906 A1 | 2/2013 |
| WO | WO-2013/119202 A1 | 8/2013 |
| WO | WO-2014/089113 A1 | 6/2014 |
| WO | WO-2014/116846 A2 | 7/2014 |
| WO | WO-2014/151006 A2 | 9/2014 |
| WO | WO-2015/009856 A2 | 1/2015 |
| WO | WO-2015/037005 A1 | 3/2015 |
| WO | WO-2015/095418 A1 | 6/2015 |
| WO | WO-2015/153513 A1 | 10/2015 |
| WO | WO-2015/153514 A1 | 10/2015 |
| WO | WO-2016/011264 A1 | 1/2016 |
| WO | WO-2016/054555 A2 | 4/2016 |
| WO | WO-2016/073282 A1 | 5/2016 |
| WO | WO-2017/053748 A2 | 3/2017 |
| WO | WO-2017/220990 A1 | 12/2017 |

OTHER PUBLICATIONS

"FDA approves new, targeted treatment for bladder cancer," <http://www.fda.gov/NewsEvents/Newsroom/PressAnnouncements/ucm501762.htm>, retrieved on Sep. 19, 2016, dated May 18, 2016 (3 pages).

Butte et al., "Programmed death-1 ligand 1 interacts specifically with the B7-1 costimulatory molecule to inhibit T cell responses," Immunity. 27(1):111-22 (2007).

Danisch et al., "CD226 interaction with CD155 impacts on retention and negative selection of CD8 positive thymocytes as well as T cell differentiation to follicular helper cells in Peyer's Patches," Immunobiology. 218(2):152-8 (2013).

Edgar, "T cell immunodeficiency," J Clin Pathol. 61(9):988-93 (2008).

Hou et al., "Recombinant soluble CD226 protein directly inhibits cancer cell proliferation in vitro," Int Immunopharmacol. 19(1):119-26 (2014).

Inoue et al., "Cancer-associated fibroblast suppresses killing activity of natural killer cells through downregulation of poliovirus receptor (PVR/CD155), a ligand of activating NK receptor," Int J Oncol. 49(4):1297-304 (2016).

Inozume et al., "Melanoma Cells Control Antimelanoma CTL Responses via Interaction between TIGIT and CD155 in the Effector Phase," J Invest Dermatol. 136(1):255-63 (2016).

Johnston et al., "The immunoreceptor TIGIT regulates antitumor and antiviral CD8(+) T cell effector function," Cancer Cell. 26(6):923-37 (2014).

Lee et al., "Macrophage PD-L1 strikes back: PD-1/PD-L1 interaction drives macrophages toward regulatory subsets," Adv Biosci Biotechnol. 4:19-29 (2013).

Maier et al., "The adhesion receptor CD155 determines the magnitude of humoral immune responses against orally ingested antigens," Eur J Immunol. 37(8):2214-25 (2007).

Martinet et al., "Balancing natural killer cell activation through paired receptors," Nat Rev Immunol. 15(4):243-54 (2015).

Qiu et al., "CD155 is involved in negative selection and is required to retain terminally maturing CD8 T cells in thymus," J Immunol. 184(4):1681-9 (2010).

Qu et al., "Loss of CD155 expression predicts poor prognosis in hepatocellular carcinoma," Histopathology. 66(5):706-14 (2015) Abstract only (2 pages).

Rosenblatt et al., "Targetting the PD-L1/PD-1 axis holds promise in the treatment of malignancy," Transl Cancer Res. 1(4):283-6 (2012).

Sequence Alignment with U.S. Appl. No. 14/236,064, filed Jan. 29, 2014 (2 pages).

Stanietsky et al., "Mouse TIGIT inhibits NK-cell cytotoxicity upon interaction with PVR," Eur J Immunol. 43(8):2138-50 (2013).

Xiao et al., "RGMb is a novel binding partner for PD-L2 and its engagement with PD-L2 promotes respiratory tolerance," J Exp Med. 211(5):943-59 (2014).

Xu et al., "A novel interface consisting of homologous immunoglobulin superfamily members with multiple functions," Cell Mol Immunol. 7(1):11-9 (2010).

Yamashita-Kanemaru et al., "CD155 (PVR/Necl5) mediates a costimulatory signal in CD4+ T cells and regulates allergic inflammation," J Immunol. 194(12):5644-53 (2015).

Zhan et al., "From monoclonal antibodies to small molecules: the development of inhibitors targeting the PD-1/PD-L1 pathway," Drug Discov Today. 21(6):1027-36 (2016).

Zheng et al., "Human Cancer Immunotherapy with PD-1/PD-L1 Blockade," Biomark Cancer. 7(Suppl 2):15-8 (2015).

Office Action for U.S. Appl. No. 14/333,375, dated Sep. 23, 2016 (27 pages).

"VSTM3_HUMAN," <http://www.uniprot.org/uniprot/Q495A1.txt?version=27>, retrieved on Aug. 8, 2014 (3 pages).

Abbas et al., "Immune response in silico (IRIS): immune-specific genes identified from a compendium of microarray expression data," Genes Immun. 6(4):319-31 (2005).

Aebersold et al., "Perspective: a program to improve protein biomarker discovery for cancer," J Proteome Res. 4(4):1104-9 (2005).

(56) References Cited

OTHER PUBLICATIONS

Ahn et al., "Dendritic cells partially abrogate the regulatory activity of CD4+CD25+ T cells present in the human peripheral blood," Int Immunol. 19(3):227-37 (2007).
Baury et al., "Identification of secreted CD155 isoforms," Biochem Biophys Res Commun. 309(1):175-82 (2003).
Beers et. al., Neurologic Disorders. The Merck Manual of Diagnosis and Therapy, Beers & Berkow, 1474-6 (1999).
Blackburn et al., "Coregulation of CD8+ T cell exhaustion during chronic viral infection by multiple inhibitory receptors," available in PMC Jul. 1, 2009, published in final edited form as: Nat Immunol. 10(1):29-37 (2009) (22 pages).
Blalock et al., "Harnessing the power of gene microarrays for the study of brain aging and Alzheimer's disease: statistical reliability and functional correlation," Ageing Res Rev. 4(4):481-512 (2005).
Bolton, "Recent advances in the pharmacological control of experimental allergic encephalomyelitis (EAE) and the implications for multiple sclerosis treatment," Mult Scler. 1(3):143-9 (1995).
Bottino et al., "Identification of PVR (CD155) and Nectin-2 (CD112) as cell surface ligands for the human DNAM-1 (CD226) activating molecule," J Exp Med. 198(4):557-67 (2003).
Bruder et al., "Neuropilin-1: a surface marker of regulatory T cells," Eur J Immunol. 34(3):623-30 (2004).
Burshtyn et al., "A novel phosphotyrosine motif with a critical amino acid at position -2 for the SH2 domain-mediated activation of the tyrosine phosphatase SHP-1," J Biol Chem. 272(20):13066-72 (1997).
Chan et al., "Receptors that interact with nectin and nectin-like proteins in the immunosurveillance and immunotherapy of cancer," Curr Opin Immunol. 24(2):246-51 (2012).
Correale et al., "Patterns of cytokine secretion by autoreactive proteolipid protein-specific T cell clones during the course of multiple sclerosis," J Immunol. 154(6):2959-68 (1995).
Dardalhon et al., "CD226 is specifically expressed on the surface of Th1 cells and regulates their expansion and effector functions," J Immunol. 175(3):1558-65 (2005).
Dong et al., "Crystal structure of the V domain of human Nectin-like molecule-1/Syncam3/Tsll1/Igsf4b, a neural tissue-specific immunoglobulin-like cell-cell adhesion molecule," J Biol Chem. 281(15):10610-7 (2006).
Elder et al., "Growth factor and proto-oncogene expression in psoriasis," J Invest Dermatol. 95(5 Suppl):7S-9S (1990).
Fallarino et al., "Modulation of tryptophan catabolism by regulatory T cells," Nat Immunol. 4(12):1206-12 (2003).
Fehérvari et al., "Development and function of CD25+CD4+ regulatory T cells," Curr Opin Immunol. 16(2):203-8 (2004).
Finch et al., "Analysis of the cellular basis of keratinocyte growth factor overexpression in inflammatory bowel disease," Gut. 45(6):848-55 (1999).
Fuchs et al., "Cutting edge: CD96 (tactile) promotes NK cell-target cell adhesion by interacting with the poliovirus receptor (CD155)," J Immunol. 172(7):3994-8 (2004).
Fuchs et al., "The role of NK cell recognition of nectin and nectin-like proteins in tumor immunosurveillance," Semin Cancer Biol. 16(5):359-66 (2006).
Greenwald et al., "The B7 family revisited," Annu Rev Immunol. 23:515-48 (2005).
Guo et al., "PD-1 blockade and OX40 triggering synergistically protects against tumor growth in a murine model of ovarian cancer," PLoS One. 9(2):e89350 (2014) (10 pages).
He et al., "Complexes of poliovirus serotypes with their common cellular receptor, CD155," J Virol. 77(8):4827-35 (2003).
Hori et al., "Control of regulatory T cell development by the transcription factor Foxp3," Science. 299(5609):1057-61 (2003).
Inozume et al., "Development of a novel immunotherapy for melanoma which inhibits interaction between CD155 on melanoma cells and TIGIT on activated CTL," J Invest Dermatol. 133:S3 (2013).

Issekutz et al., "Treatment of established adjuvant arthritis in rats with monoclonal antibody to CD18 and very late activation antigen-4 integrins suppresses neutrophil and T-lymphocyte migration to the joints and improves clinical disease," Immunology. 88(4):569-76 (1996).
Janeway et al., B-cell heterogeneity. Immunobiology, 3rd edition. Garland Publications Inc., 5:23-26, 8:3, and 9:23-9:27 (1997).
Jiang et al., "Disruption of E-cadherin-mediated adhesion induces a functionally distinct pathway of dendritic cell maturation," Immunity. 27(4):610-24 (2007).
Joller et al., "Immune checkpoints in CNS autoimmunity," available in PMC Jul. 1, 2013, published in final edited form as: Immunol Rev. 248(1):122-39 (2012) (28 pages).
Ju et al., "Immunoglobulin-like transcripts ILT2, ILT3 and ILT7 are expressed by human dendritic cells and down-regulated following activation," Gene. 331:159-64 (2004).
Kashiwada et al., "Immunoreceptor tyrosine-based inhibitory motif of the IL-4 receptor associates with SH2-containing phosphatases and regulates IL-4-induced proliferation," J Immunol. 167(11):6382-7 (2001).
Kisseleva et al., "Signaling through the JAK/STAT pathway, recent advances and future challenges," Gene. 285(1-2):1-24 (2002).
Levin et al., "Identification and characterization of Vsig9 as an inhibitory member of the CD28 family," Keystone Symposia on Molecular and Cellular Biology: Tolerance in Transplantation and Autoimmunity, Jan. 29-Feb. 3, Keystone, Colorado. 74, 217 (2008).
Levin et al., "Vstm3 is a member of the CD28 family and an important modulator of T-cell function," available in PMC Aug. 5, 2013, published in final edited form as: Eur J Immunol. 41(4):902-15 (2011) (22 pages).
Liebman, "Biomedical informatics: the future for drug development," Drug Discov Today. 7(20 Suppl):S197-203 (2002).
Linsley et al., "Immunosuppression in vivo by a soluble form of the CTLA-4 T cell activation molecule," Science. 257(5071):792-5 (1992).
Luo et al., "Delayed-type hypersensitivity," Curr Protoc Immunolog. Chapter 4:Unit 4.5 (2001) (5 pages).
McHugh et al., "CD4(+)CD25(+) immunoregulatory T cells: gene expression analysis reveals a functional role for the glucocorticoid-induced TNF receptor," Immunity. 16(2):311-23 (2002).
Morales-Kastresana et al., "Combined immunostimulatory monoclonal antibodies extend survival in an aggressive transgenic hepatocellular carcinoma mouse model," Clin Cancer Res. 19(22):6151-62 (2013).
NCBI Blast for Accession No. gi256600228. Retrieved on Jun. 17, 2004 (1 page).
NCBI Blast for Accession No. gi57997171. Retrieved on Nov. 20, 2003 (1 page).
NCBI Blast for Accession No. Q8N877. Retrieved on Oct. 20, 2004 (2 pages).
NCBI Blast for Accession No. AL833175 GI:21733802. Retrieved on Oct. 19, 2004 (3 pages).
Nickoloff et al., "Severe combined immunodeficiency mouse and human psoriatic skin chimeras. Validation of a new animal model," Am J Pathol. 146(3):580-8 (1995).
Nobis et al., "Production of a monoclonal antibody against an epitope on HeLa cells that is the functional poliovirus binding site," J Gen Virol. 66(Pt 12):2563-9 (1985).
Ota et al., "Complete sequencing and characterization of 21,243 full-length human cDNAs," Nat Genet. 36(1):40-5 (2004).
Pende et al., "Expression of the DNAM-1 ligands, Nectin-2 (CD112) and poliovirus receptor (CD155), on dendritic cells: relevance for natural killer-dendritic cell interaction," Blood. 107(5):2030-6 (2006).
Read et al., "Cytotoxic T lymphocyte-associated antigen 4 plays an essential role in the function of CD25(+)CD4(+) regulatory cells that control intestinal inflammation," J Exp Med. 192(2):295-302 (2000).
Redmond et al., "Combined targeting of co-stimulatory (OX40) and co-inhibitory (CTLA-4) pathways elicits potent effector T cells capable of driving robust antitumor immunity," available in PMC Feb. 1, 2013, published in final edited form as: Cancer Immunol Res. 2(2):142-53 (2014) (20 pages).

(56) References Cited

OTHER PUBLICATIONS

Reymond et al., "DNAM-1 and PVR regulate monocyte migration through endothelial junctions," J Exp Med. 199(10):1331-41 (2004).
Sakaguchi et al., "Immunologic self-tolerance maintained by activated T cells expressing IL-2 receptor alpha-chains (CD25). Breakdown of a single mechanism of self-tolerance causes various autoimmune diseases," J Immunol. 155(3):1151-64 (1995).
Sakisaka et al., "Biology and pathology of nectins and nectin-like molecules," Curr Opin Cell Biol. 16(5):513-21 (2004).
Satoh-Horikawa et al., "Nectin-3, a new member of immunoglobulin-like cell adhesion molecules that shows homophilic and heterophilic cell-cell adhesion activities," J Biol Chem. 275(14):10291-9 (2000).
Schaerli et al., "CXC chemokine receptor 5 expression defines follicular homing T cells with B cell helper function," J Exp Med. 192(11):1553-62 (2000).
Schneider, "A rational approach to maximize success rate in target discovery," Arch Pharm (Weinheim). 337(12):625-33 (2004).
Serra et al., "CD40 ligation releases immature dendritic cells from the control of regulatory CD4+CD25+ T cells," Immunity. 19(6):877-89 (2003).
Seth et al., "The poliovirus receptor/CD155 is a potential modulator of the T cell response," Immunobiology. 210(6-8):542 (2005).
Shimizu et al., "Stimulation of CD25(+)CD4(+) regulatory T cells through GITR breaks immunological self-tolerance," Nat Immunol. 3(2):135-42 (2002).
Sicotte et al., "Onset of multiple sclerosis associated with anti-TNF therapy," Neurology. 57(10):1885-8 (2001).
Skolnick et al., "From genes to protein structure and function: novel applications of computational approaches in the genomic era," Trends Biotechnol. 18(1):34-9 (2000).
Smith, "Drug target validation: Hitting the target," Nature. 422(6929):341-7 (2003).
Tahara-Hanaoka et al., "Functional characterization of DNAM-1 (CD226) interaction with its ligands PVR (CD155) and nectin-2 (PRR-2/CD112)," Int Immunol. 16(4):533-8 (2004).
Takahashi et al., "Immunologic self-tolerance maintained by CD25(+)CD4(+) regulatory T cells constitutively expressing cytotoxic T lymphocyte-associated antigen 4," J Exp Med. 192(2):303-9 (2000).
Tarbell et al., "CD25+CD4+ T cells, expanded with dendritic cells presenting a single autoantigenic peptide, suppress autoimmune diabetes," J Exp Med. 199(11):1467-77 (2004).
Thornton et al., "CD4+CD25+ immunoregulatory T cells suppress polyclonal T cell activation in vitro by inhibiting interleukin 2 production," J Exp Med. 188(2):287-96 (1998).
Velten et al., "A gene signature of inhibitory MHC receptors identifies a BDCA3(+) subset of IL-10-induced dendritic cells with reduced allostimulatory capacity in vitro," Eur J Immunol. 34(10):2800-11 (2004).
Vinuesa et al., "Follicular B helper T cells in antibody responses and autoimmunity," Nat Rev Immunol. 5(11):853-65 (2005).
Wang et al., "Regulatory T cells and cancer," Curr Opin Immunol. 19(2):217-23 (2007).
Whisstock et al., "Prediction of protein function from protein sequence and structure," Q Rev Biophys. 36(3):307-40 (2003).
Wiesmann et al., "Nerve growth factor: structure and function," Cell Mol Life Sci. 58(5-6):748-59 (2001).
Xia et al., "Suppression of interleukin-12 production through endogenously secreted interleukin-10 in activated dendritic cells: involvement of activation of extracellular signal-regulated protein kinase," Scand J Immunol. 58(1):23-32 (2003).
Yamazaki et al., "Effective expansion of alloantigen-specific Foxp3+ CD25+ CD4+ regulatory T cells by dendritic cells during the mixed leukocyte reaction," Proc Natl Acad Sci USA. 103(8):2758-63 (2006).
Yu et al "Simultaneous inhibition of two regulatory T-cell subsets enhanced Interleukin-15 efficacy in a prostate tumor model," Proc Natl Acad Sci USA. 109(16):6187-92 (2012).
Yu et al., "The surface protein TIGIT suppresses T cell activation by promoting the generation of mature immunoregulatory dendritic cells" Nat Immunol. 10(1):48-57 (2009).
Zhou et al., "Coexpression of Tim-3 and PD-1 identifies a CD8+ T-cell exhaustion phenotype in mice with disseminated acute myelogenous leukemia," Blood. 117(17):4501-10 (2011).
Ziegler, "FOXP3: not just for regulatory T cells anymore," Eur J Immunol. 37(1):21-3 (2007).
English Translation of Office Action for Chinese Application No. 200980121734.2, dated Sep. 22, 2013 (2 pages).
Examination Report for Australian Application No. 2009233708, dated Sep. 6, 2013 (3 pages).
International Search Report and Written Opinion for International Application No. PCT/US2009/039868, dated Oct. 23, 2009 (25 pages).
International Search Report and Written Opinion for International Application No. PCT/US2014/046896, dated Mar. 2, 2015 (21 pages).
International Search Report and Written Opinion for International Patent Application No. PCT/US2015/058087, dated Apr. 8, 2016 (22 pages).
Invitation to Pay Additional Fees for International Patent Application No. PCT/US2015/058087, dated Jan. 27, 2016 (10 pages).
Notice of Preliminary Rejection for Korean Patent Application No. 10-2010-7025044, dated Nov. 13, 2015 (6 pages).
Office Action for U.S. Appl. No. 14/228,172, dated Feb. 12, 2015 (14 pages).
Office Action for U.S. Appl. No. 14/228,173, dated Mar. 11, 2015 (18 pages).
Office Action for U.S. Appl. No. 14/699,845, dated Jun. 9, 2016 (11 pages).
Bergers et al., "Extrinsic regulators of epithelial tumor progression: metalloproteinases," Curr Opin Genet Dev. 10(1):120-7 (2000).
Caldas et al., "Humanization of the anti-CD18 antibody 6.7: An unexpected effect of a framework residue in binding to antigen," Mol Immunol. 39(15):941-52 (2003).
Callahan et al., "Anti-CTLA-4 antibody therapy: immune monitoring during clinical development of a novel immunotherapy," Semin Oncol. 37(5):473-84 (2010).
Casset et al., "A peptide mimetic of an anti-CD4 monoclonal antibody by rational design," Biochem Biophys Res Commun. 307(1):198-205 (2003).
Chang et al., "Loop-sequence features and stability determinants in antibody variable domains by high-throughput experiments," Structure. 22(1):9-21 (2014).
Chien et al., "Significant structural and functional change of an antigen-binding site by a distant amino acid substitution: proposal of a structural mechanism," Proc Natl Acad Sci U S A. 86(14):5532-6 (1989).
Chin et al., "Immune intervention with monoclonal antibodies targeting CD152 (CTLA-4) for autoimmune and malignant diseases," Chang Gung Med J. 31(1):1-15 (2008).
Comps-Agrar et al., "TIGIT mediated T cell exhaustion in cancer is dependent on TIGIT/CD226 interaction (TUM2P.907)," Immunology 2014 Meeting Abstracts, J Immunol. 192(Suppl 1):71.31 (2014) (5 pages).
De Pascalis et al., "Grafting of "abbreviated" complementarity-determining regions containing specificity-determining residues essential for ligand contact to engineer a less immunogenic humanized monoclonal antibody," J Immunol. 169(6):3076-84 (2002).
Dennis, "Cancer: off by a whisker," Nature. 442(7104):739-41 (2006).
Flies et al., "Blockade of the B7-H1/PD-1 pathway for cancer immunotherapy," Yale J Biol Med. 84(4):409-21 (2011).
Foks et al., "Agonistic anti-TIGIT treatment inhibits T cell responses in LDLr deficient mice without affecting atherosclerotic lesion development," PLoS One. 8(12):e83134 (2013) (7 pages).
Giusti et al. "Somatic diversification of S107 from an antiphosphocholine to an anti-DNA autoantibody is due to a single base change in its heavy chain variable region," Proc Natl Acad Sci U S A. 84(9):2926-30 (1987).
Goding et al., "Restoring immune function of tumor-specific CD4+ T cells during recurrence of melanoma," J Immunol. 190(9):4899-909 (2013).

(56) References Cited

OTHER PUBLICATIONS

Grogan et al., "TIGIT inhibits CD8+ T cell effector function during chronic viral infection and cancer (TUM7P.933)," J Immunol. 192(Suppl 1):203.15 (2014) (1 page) (Abstract Only).
Gura, "Systems for identifying new drugs are often faulty," Science. 278(5340):1041-2 (1997).
Güssow et al., "Humanization of monoclonal antibodies," Methods Enzymol. 203:99-121 (1991).
Holm et al., "Functional mapping and single chain construction of the anti-cytokeratin 8 monoclonal antibody TS1," Mol Immunol. 44(6):1075-84 (2007).
Huang, "Structural chemistry and therapeutic intervention of protein-protein interactions in immune response, human immunodeficiency virus entry, and apoptosis," Pharmacol Ther. 86(3):201-15 (2000).
Inozume et al., "CD155 is highly expressed by melanoma tissues and it suppresses the activation of melanoma specific CTLs via interaction with TIGIT," Journal of Dermatological Science. 69(2):e67-e68, Abstract P10-01 (2013) (2 pages).
Jiang et al., "A novel peptide isolated from a phage display peptide library with trastuzumab can mimic antigen epitope of HER-2," J Biol Chem. 280(6):4656-62 (2005).
Jin et al., "Cooperation of Tim-3 and PD-1 in CD8 T-cell exhaustion during chronic viral infection," Proc Natl Acad Sci U S A. 107(33):14733-8 (2010).
Joller et al., "Cutting edge: TIGIT has T cell-intrinsic inhibitory functions," J Immunol. 186(3)1338-42 (2011).
Kelland, "Of mice and men: values and liabilities of the athymic nude mouse model in anticancer drug development," Eur J Cancer. 40(6):827-36 (2004).
Kruisbeek et al., Proliferative Assays for T Cell Function. *Current Protocols in Immunology*. John Wiley & Sons, Inc. 3.12.1-3.12.14 (1991) (26 pages).
MacCallum et al., "Antibody-antigen interactions: contact analysis and binding site topography," J Mol Biol. 262(5):732-45 (1996).
Mariuzza et al., "The structural basis of antigen-antibody recognition," Annu Rev Biophys Biophys Chem. 16:139-59 (1987).
Melero et al., "Evolving synergistic combinations of targeted immunotherapies to combat cancer," Nat Rev Cancer. 15(8):457-72 (2015).
Riemer et al., "Matching of trastuzumab (Herceptin) epitope mimics onto the surface of Her-2/neu-a new method of epitope definition," Mol Immunol. 42(9):1121-4 (2005).
Rudikoff et al., "Single amino acid substitution altering antigen-binding specificity," Proc Natl Acad Sci U S A. 79(6):1979-83 (1982).
Saijo, "What are the reasons for negative phase III trials of molecular-target-based drugs?" Cancer Sci. 95(10):772-6 (2004).
Sakuishi et al., "Targeting Tim-3 and PD-1 pathways to reverse T cell exhaustion and restore anti-tumor immunity," J Exp Med. 207(10):2187-94 (2010).
Thaventhiran et al., "T cell co-inhibitory receptors: functions and signalling mechanisms," J Clin Cell Immunol. S12:004 (2012) (12 pages).
Vajdos et al., "Comprehensive functional maps of the antigen-binding site of an anti-ErbB2 antibody obtained with shotgun scanning mutagenesis," J Mol Biol. 320(2):415-28 (2002).
Winkler et al., "Changing the antigen binding specificity by single point mutations of an anti-p24 (HIV-1) antibody," J Immunol. 165(8):4505-14 (2000).
Wolchok et al., "Nivolumab plus ipilimumab in advanced melanoma," N. Engl J Med. 369(2):122-33 (2013).
Wu et al., "Humanization of a murine monoclonal antibody by simultaneous optimization of framework and CDR residues," J Mol Biol. 294(1):151-62 (1999).
Yu et al., "Rationalization and design of the complementarity determining region sequences in an antibody-antigen recognition interface," PLoS One. 7(3):e33340 (2012) (15 pages).
Communication pursuant to Article 94(3) for European Patent Application No. 14750063.1, dated Oct. 18, 2017 (9 pages).
International Preliminary Report on Patentability for International Patent Application No. PCT/US2015/040770, dated Jan. 17, 2017 (11 pages).
International Search Report and Written Opinion for International Patent Application No. PCT/US2015/040770, dated Oct. 16, 2015 (13 pages).
International Search Report and Written Opinion for International Patent Application No. PCT/US2016/053368, dated Mar. 31, 2017 (19 pages).
Invitation to Pay Additional Fees for International Patent Application No. PCT/US2016/053368, dated Feb. 2, 2017 (8 pages).
Search Report for Singaporean Patent Application No. 11201600310Q, dated Mar. 9, 2017 (5 pages).
Written Opinion for Singaporean Patent Application No. 11201600310Q, dated Apr. 6, 2017 (10 pages).
Chauvin et al., "TIGIT and PD-1 impair tumor antigen-specific CD8+ T cells in melanoma patients," J Clin Invest. 125(5):2046-58 (2015) (13 pages).
Joller et al., "Cutting edge: TIGIT has T cell-intrinsic inhibitory functions," J Immunol. 186(3):1338-42 (2011) (6 pages).
Lozano et al., "The TIGIT/CD226 Axis Regulates Human T Cell Function," J Immunol. 188(8):3869-75 (2012).
Norde et al., "PD-1/PD-L1 interactions contribute to functional T-cell impairment in patients who relapse with cancer after allogeneic stem cell transplantation," Cancer Res. 71(15):5111-22 (2011).
English Translation of Office Action for Chinese Patent Application No. 201480047388.9, dated Nov. 9, 2018 (6 pages).
English Translation of Vyshkovsky (ed.), "Encyclopedia of medicines for radar, M. 2008 (16) Proleikin," p. 239, col. 3 (2008) (2 pages).
English Translation of Vyshkovsky (ed.), "Encyclopedia of medicines for radar therapy M. 2008 (16) Dakarbazin Medak," p. 278, col. 2 (2008) (1 page).
Examination Report for GCC Patent Application No. 2014-27568, dated Aug. 13, 2018 (5 pages).
Notice of Reasons for Rejection for Japanese Patent Application No. 2016-527082, dated May 8, 2018 (18 pages).
Notice for Reasons of Rejection for Japanese Patent Application No. 2016-527082, dated Feb. 5, 2019 (6 pages).
Office Action for Russian Patent Application No. 2016104880, dated Jul. 3, 2018 (17 pages).
Official Action for Russian Patent Application No. 2016104880/04(007849), dated Dec. 7, 2018 (13 pages).
Office Action for Israeli Patent Application No. 243324, dated Nov. 22, 2018 (6 pages).
Search Report for Russian Patent Application No. 2016104880, dated Jun. 6, 2018 (6 pages).
Kurtulus et al., "Mechanisms of TIGIT-driven immune suppression in cancer," J Immunother Cancer. 2(Suppl 3): O13 (2014) (1 page).
Stancovski et al., "Mechanistic aspects of the opposing effects of monoclonal antibodies to the ERBB2 receptor on tumor growth," Proc Natl Acad Sci U S A. 88(19):8691-5 (1991).
International Preliminary Report on Patentability for International Patent Application No. PCT/US2016/053368, dated Mar. 27, 2018 (10 pages).
Office Action for Canadian Patent Application No. 2,719,189, dated Mar. 2, 2018 (4 pages).
Office Action for Indian Patent Applcation No. 6588/DELNP/2010, dated May 12, 2017 (9 pages).
Search Report for Singaporean Patent Application No. 11201700258V, dated Jan. 18, 2018 (3 pages).
Search Report for Singaporean Patent Application No. 11201703376Q, dated Apr. 4, 2018 (5 pages).
Written Opinion for Singaporean Patent Application No. 10201402815V, dated Mar. 28, 2018 (8 pages).
Written Opinion for Singaporean Patent Application No. 11201700258V, dated Jan. 18, 2018 (6 pages).
Written Opinion for Singaporean Patent Application No. 11201703376Q, dated Apr. 4, 2018 (9 pages).
Clarivate Analytics Integrity Database Entry Number: 925174—Update History, <https://integrity.clarivate.com/integrity/xmlxsl/record_updates_ui_pkg.recordChangeLogForm?p_subsystem=PRO&p_subsystemId=925174>, retrieved Jul. 29, 2019 (1 page).

(56) References Cited

OTHER PUBLICATIONS

Clarivate Analytics Integrity Database Entry Number: 925174, <https://integrity.clarivate.com/integrity/xmlxsl/pk_qcksrch.show_records?sessionID=1&history=&query=MTIG-7192-A%20%20&abbreviation=PRO&language=en> retrieved Jul. 29, 2019 (1 page).
Mellman, "Developments in cancer immunotherapy," Nov. 2017 (20 pages).
Powels et al., "MPDL3280A (anti-PD-L1) treatment leads to clinical activity in metastatic bladder cancer," Nature. 515(7528):558-69 (2014).
Tahara-Hanaoka et al., "Tumor rejection by the poliovirus receptor family ligands of the DNAM-1 (CD226) receptor," Blood. 107(4):1491-6 (2006) (7 pages).
U.S. National Library of Medicine, "History of Changes for Study: NCT02525757-MPDL3280A with chemoradiation for lung cancer," <https://clinicaltrials.gov/ct2/history/NCT02525757?V_23=View#StudyPageTop>, dated Feb. 6, 2018, retrieved on Jul. 26, 2019 (10 pages).
U.S. National Library of Medicine, "History of Changes for Study: NCT02794571—Safety and pharmacokinetics (PK) of escalating doses of MTIG7192A as a single agent and in combination with atezolizumab in locally advanced or metastic tumors," <https://clinicaltrials.gov/ct2/history/NCT02794571?V_12=View#StudyPageTOP> dated Feb. 1, 2018, retrieved on Jul. 25, 2019 (9 pages).
U.S. National Library of Medicine, "History of Changes for Study: NCT02848651—A study of atezolizumab as first-line monotherapy for advanced or metastatic non-small cell lung cancer (B-F1RST)," <https://clinicaltrials.gov/ct2/history/NCT02848651?V_20=View#StudyPageTop>, dated Jan. 8, 2018, retrieved on Jul. 26, 2019 (9 pages).
Communication pursuant to Article 94(3) for European Patent Application No. 14750063.1, dated Jul. 19, 2019 (6 pages).
Decision to Grant for Russian Patent Application No. 2016104880, dated Jul. 26, 2019 (15 pages).
Examination Report for Gulf Cooperation Council Patent Application No. GC 2014-36982, dated Jun. 25, 2019 (5 pages).
Notification of Defects for Israeli Patent Application No. 243324, dated Aug. 29, 2019 (6 pages).
Office Action for U.S. Appl. No. 15/239,524, dated Jun. 17, 2019 (19 pages).

\* cited by examiner

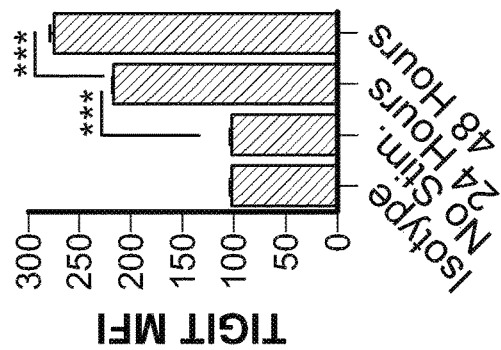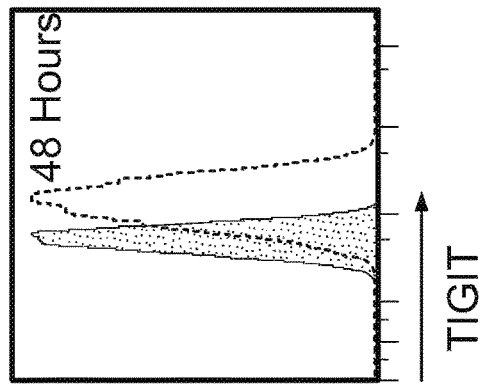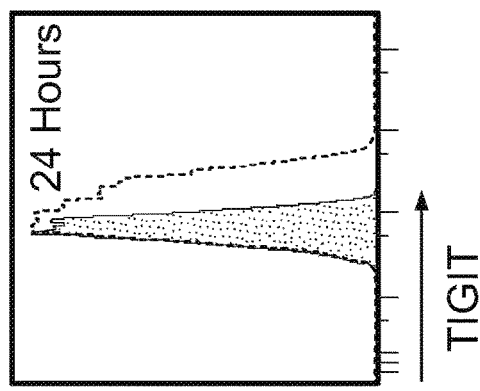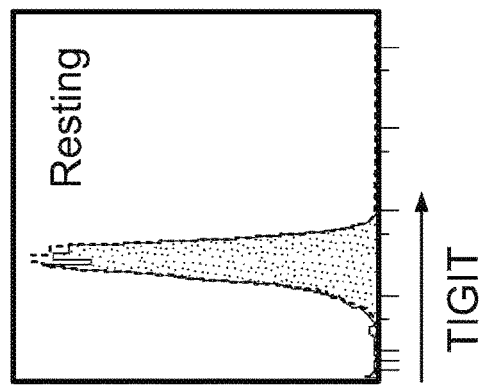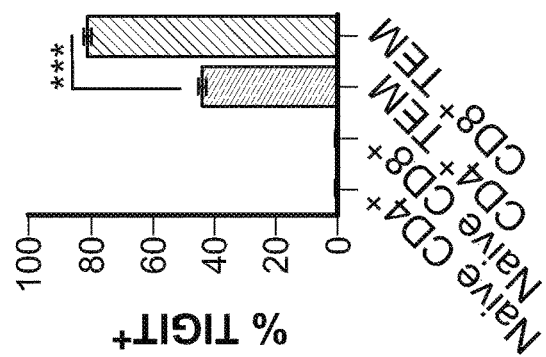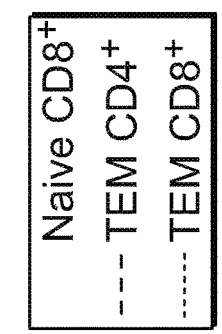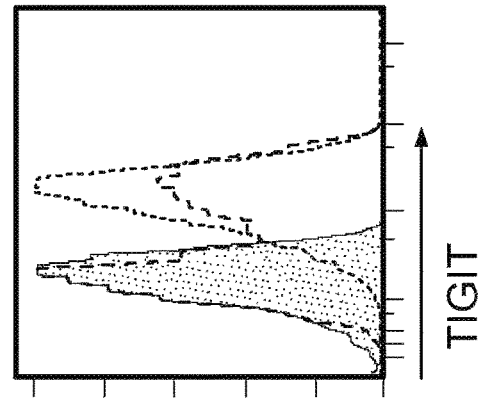
FIG. 1A
FIG. 1B

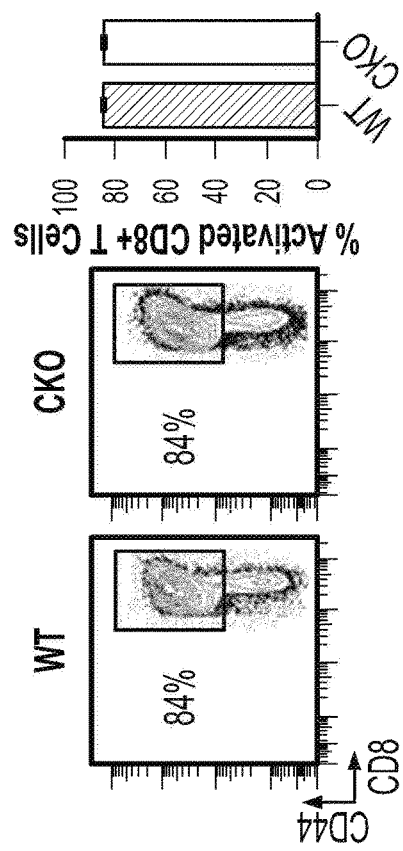
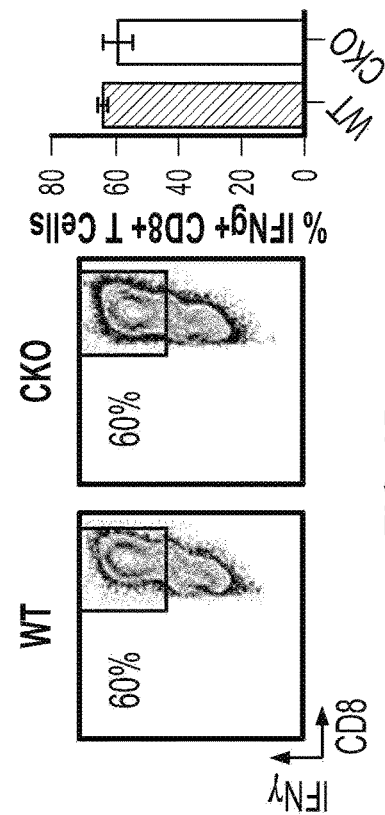
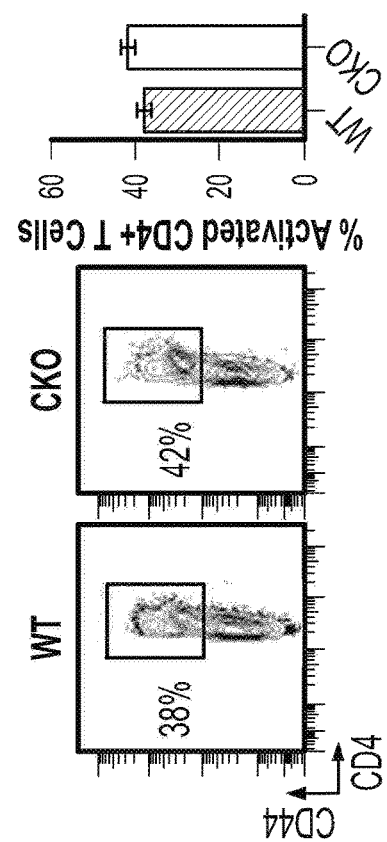
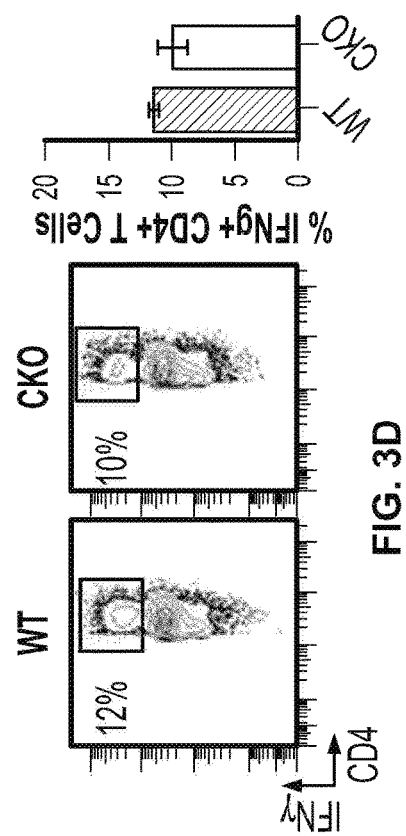
FIG. 3A
FIG. 3B
FIG. 3C
FIG. 3D

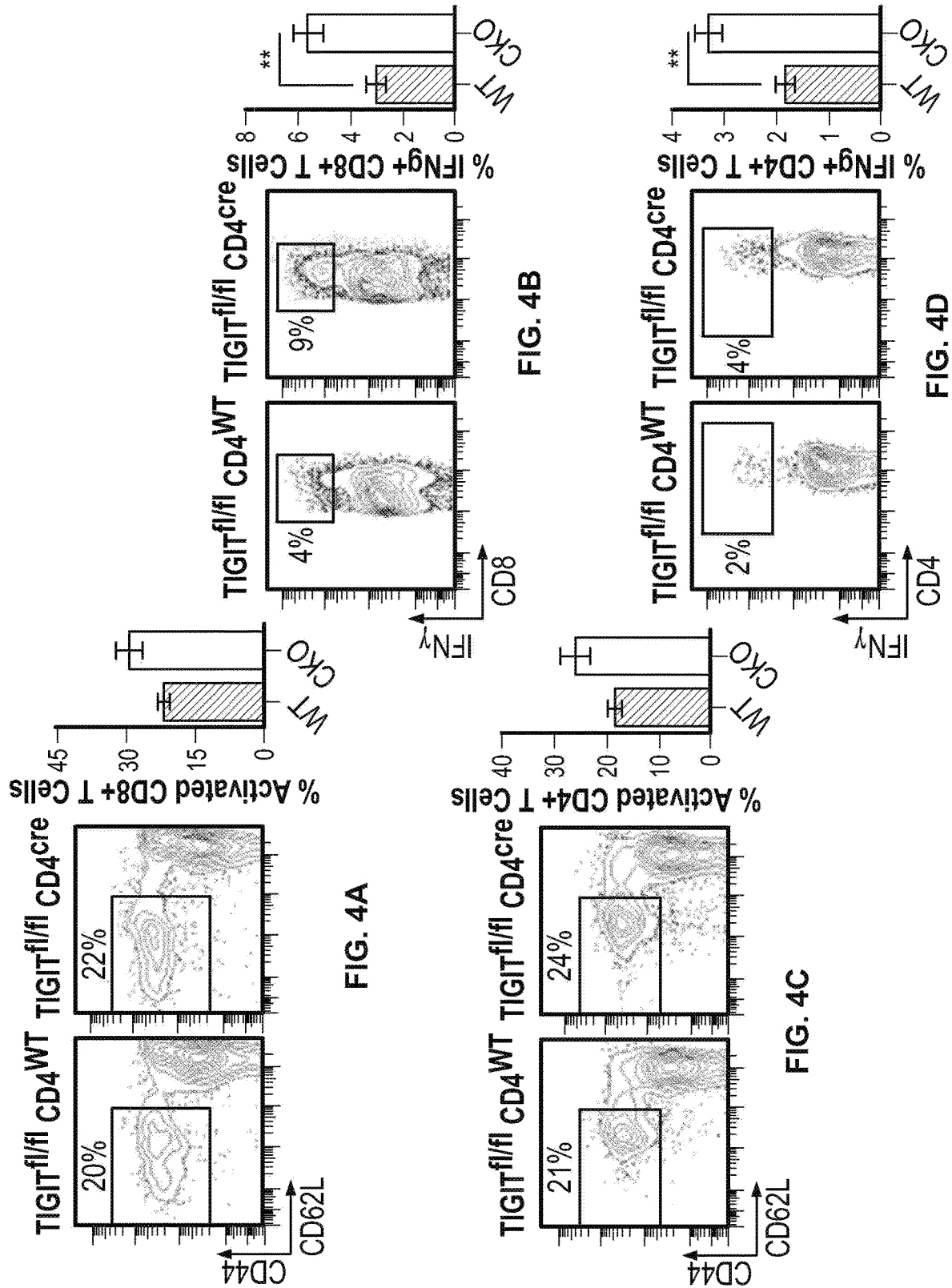

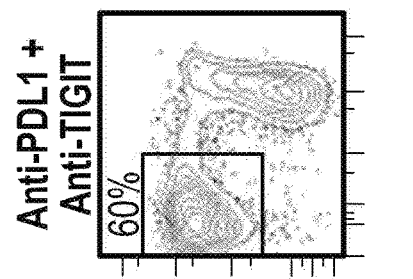
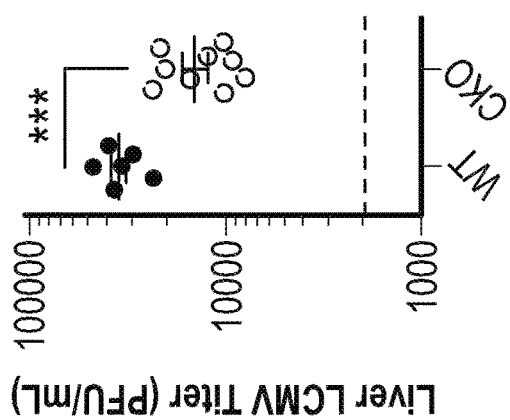
FIG. 4E
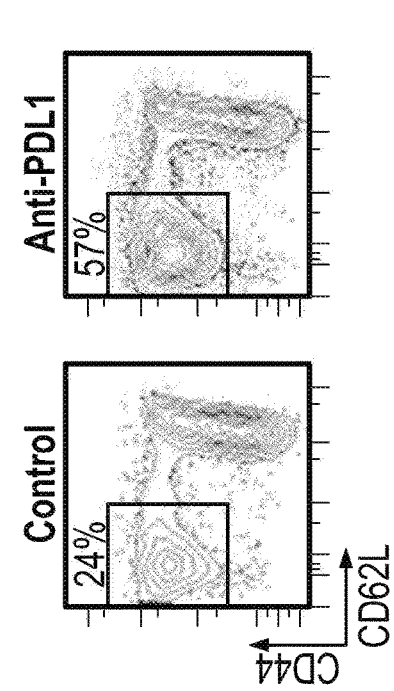
FIG. 4F

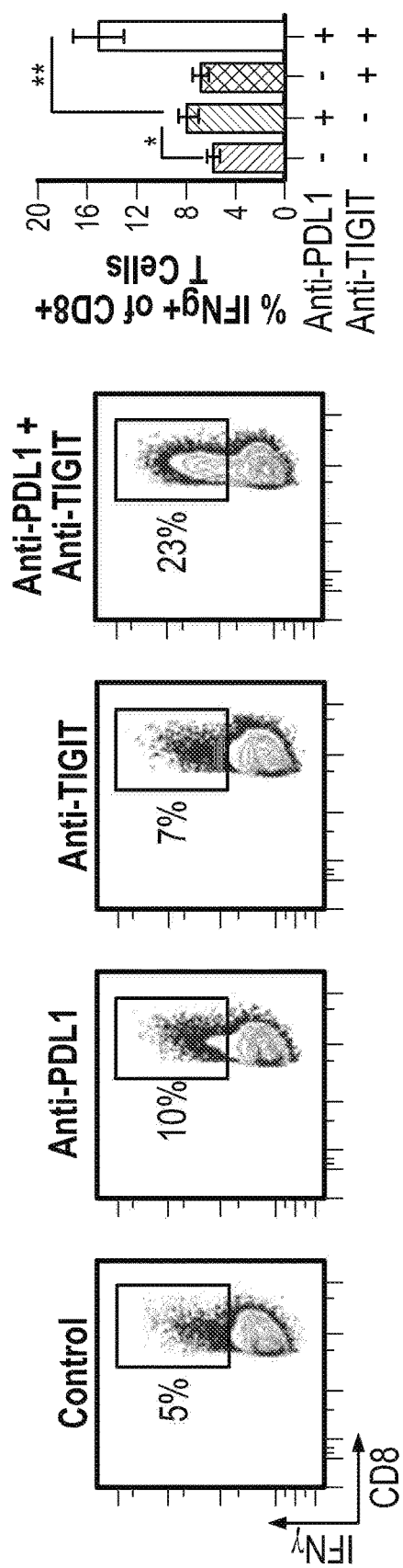
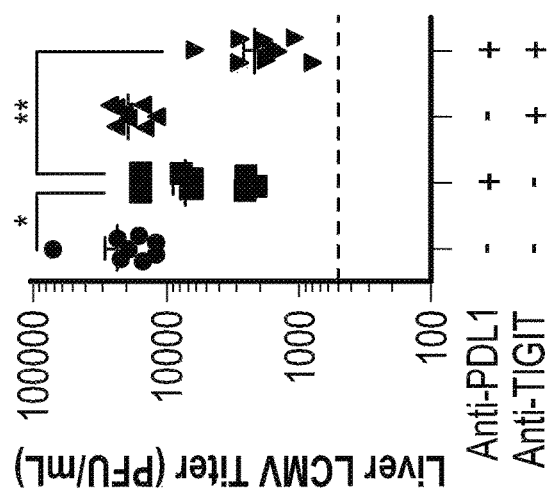
FIG. 4G
FIG. 4H

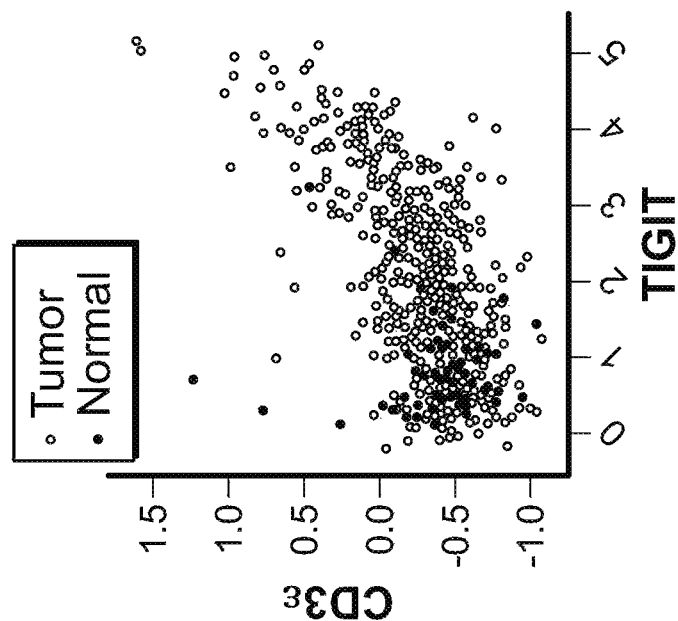
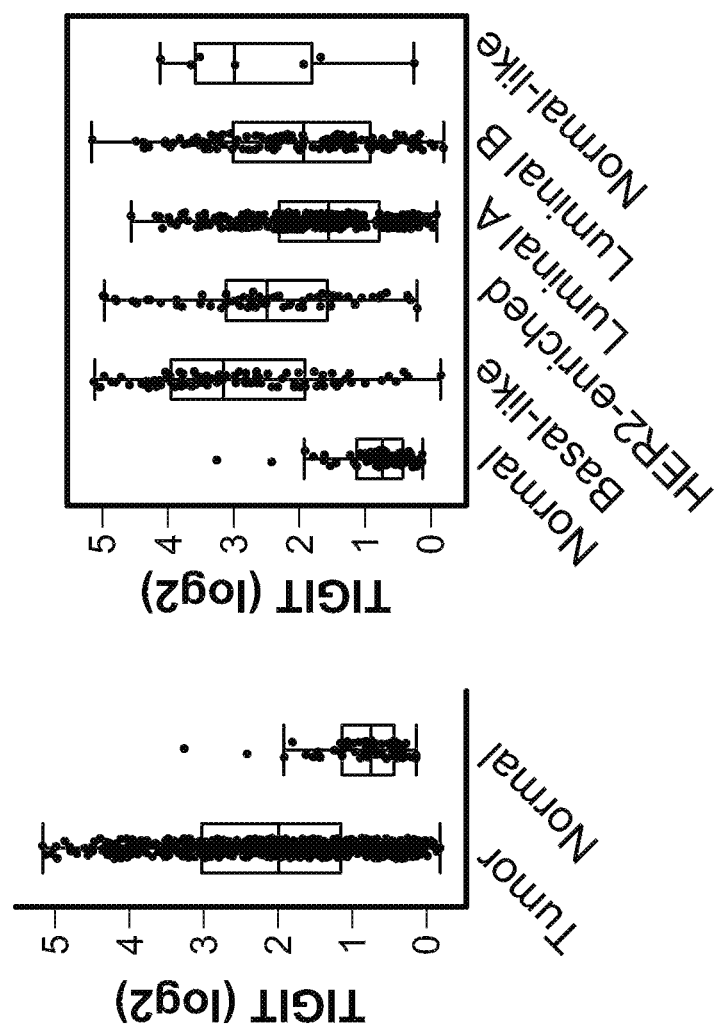
FIG. 6B
FIG. 6A

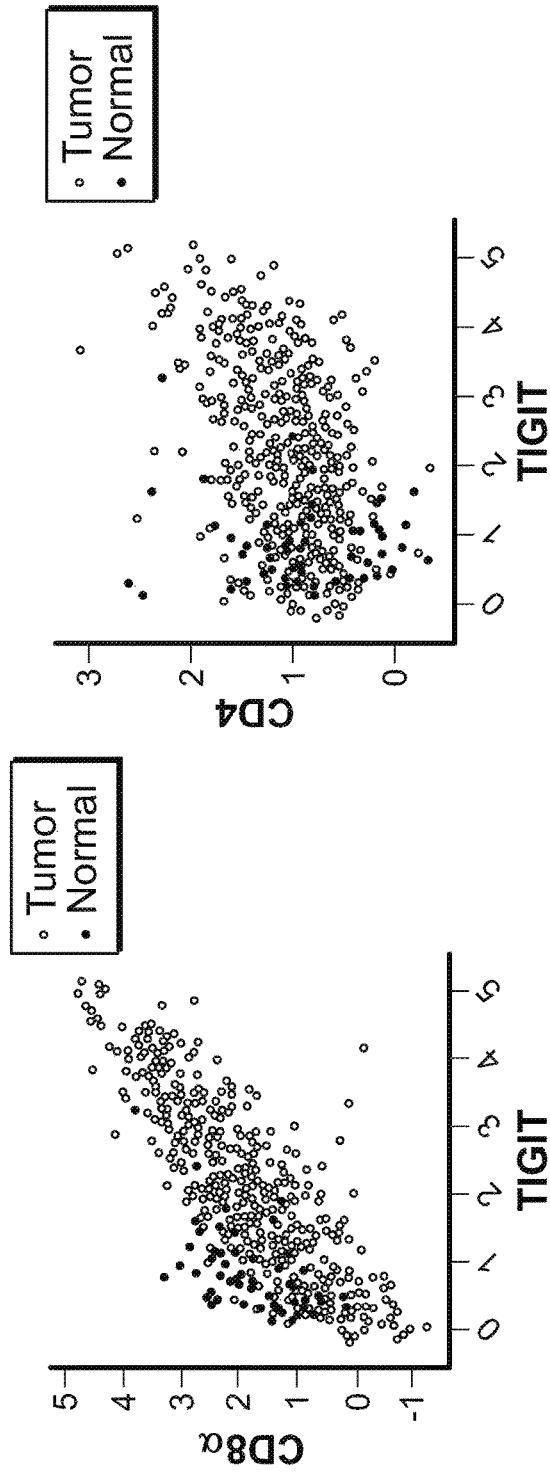
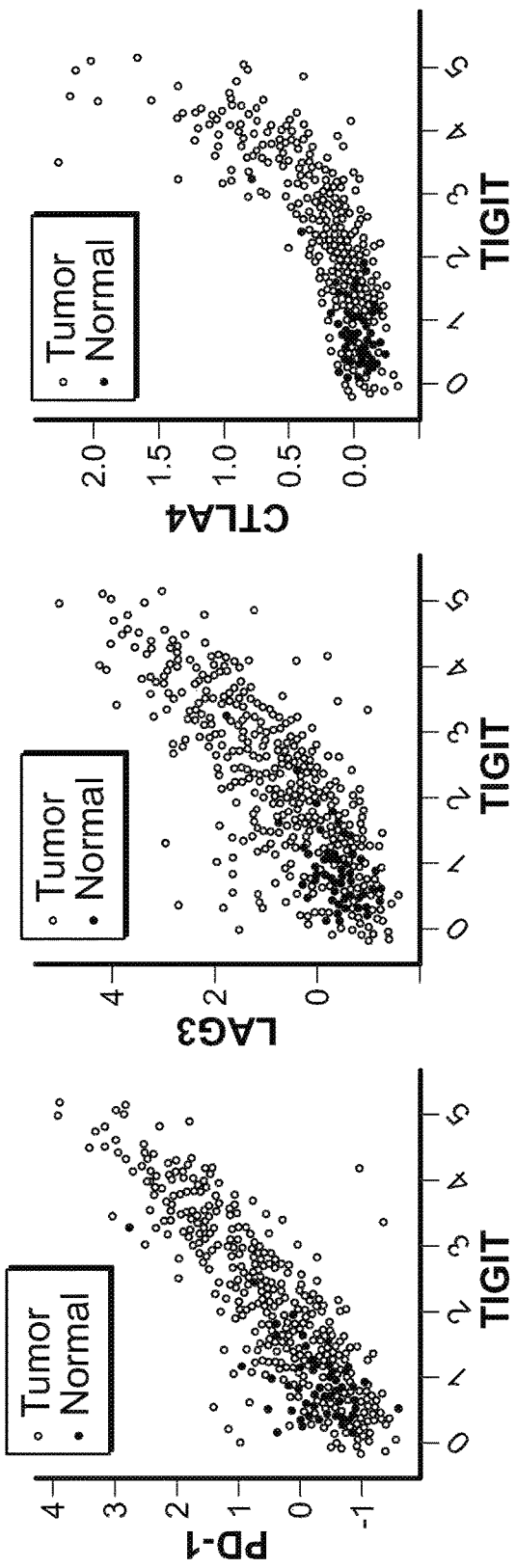
FIG. 6C
FIG. 6D

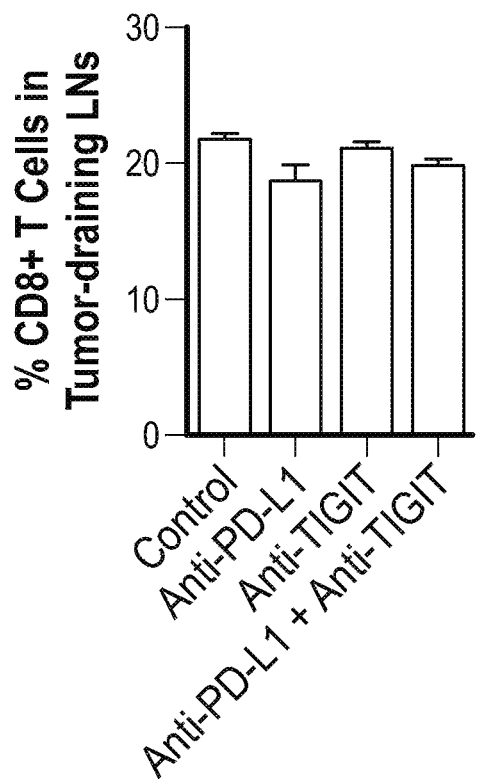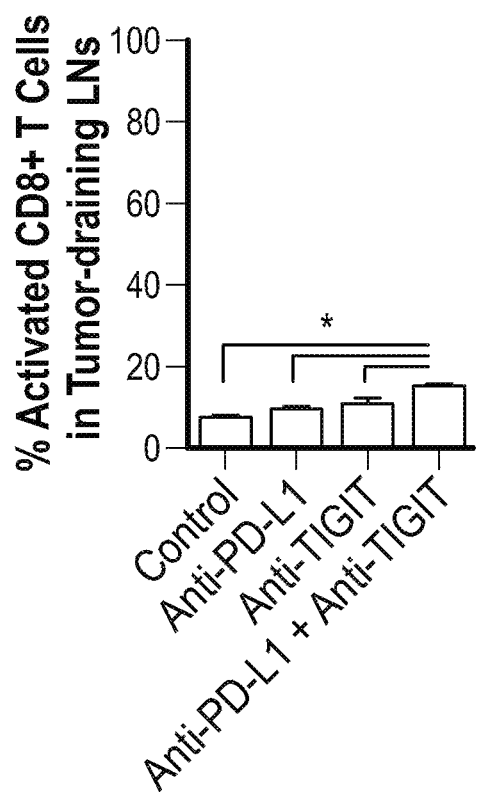
FIG. 13B
FIG. 13C
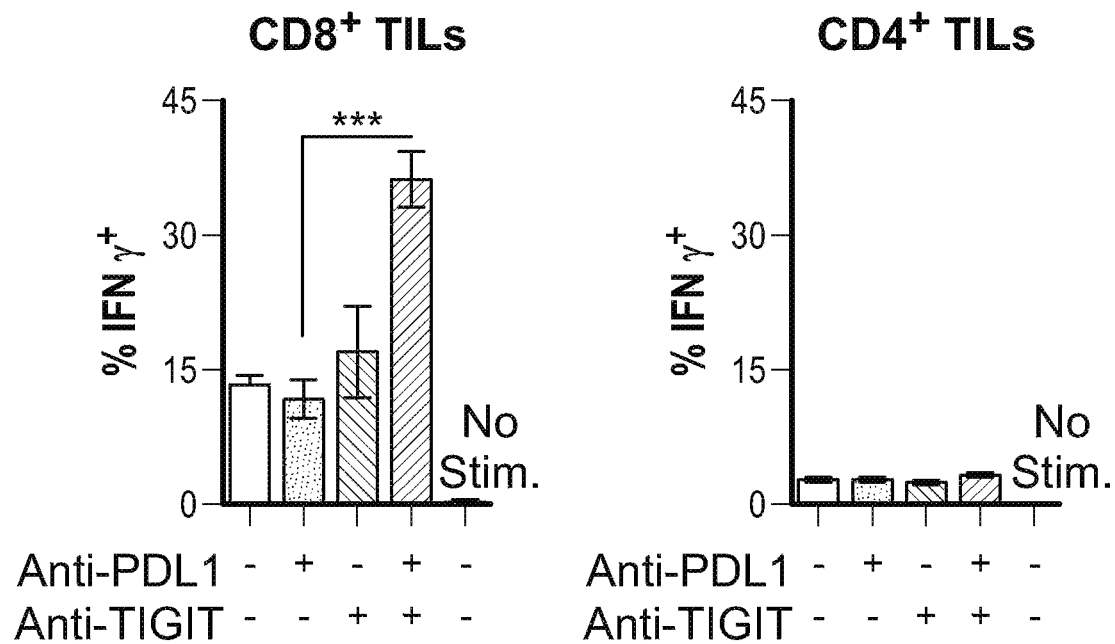
FIG. 13D

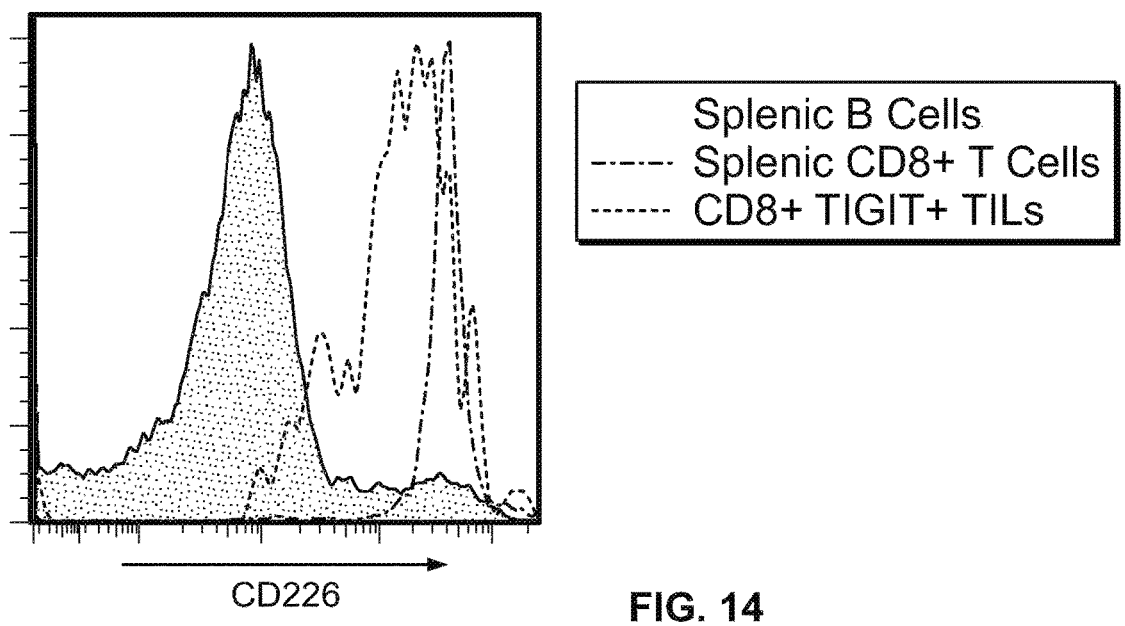
FIG. 14
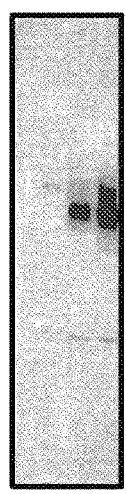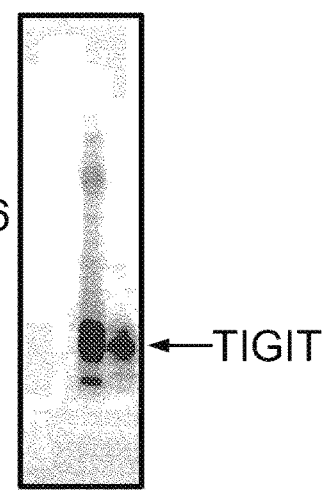
FIG. 15

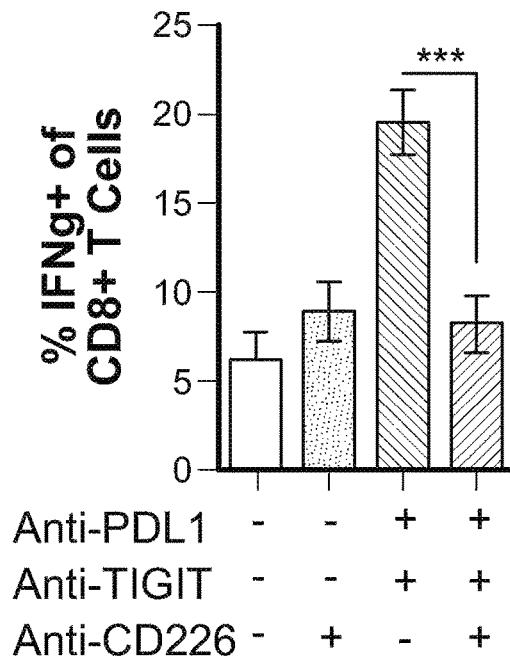
FIG. 19C
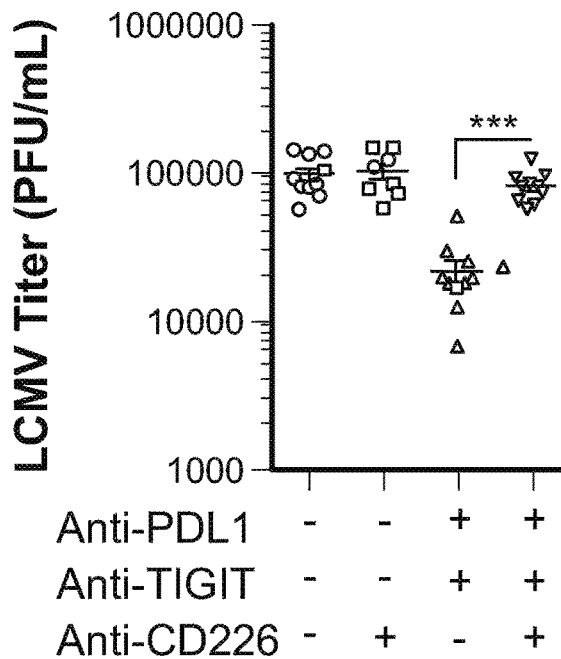
FIG. 19D
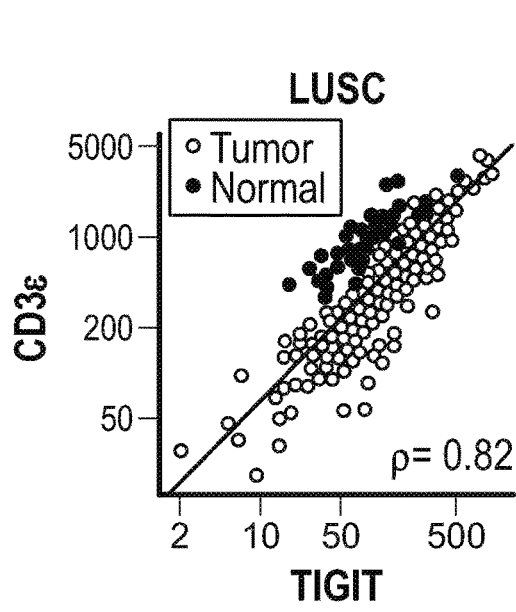
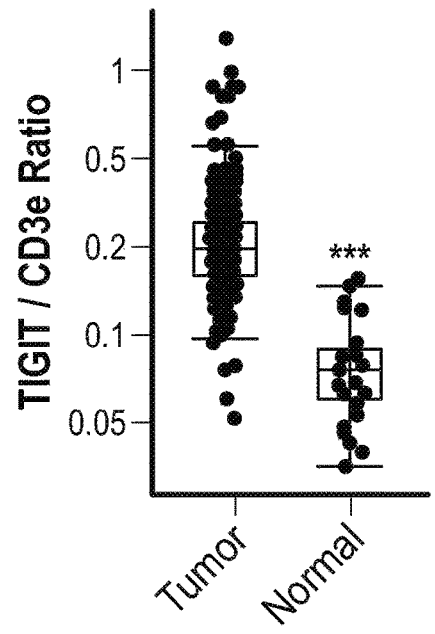
FIG. 20A

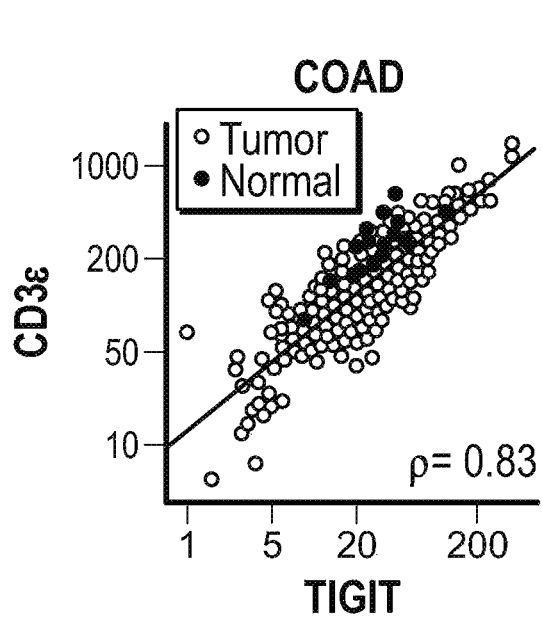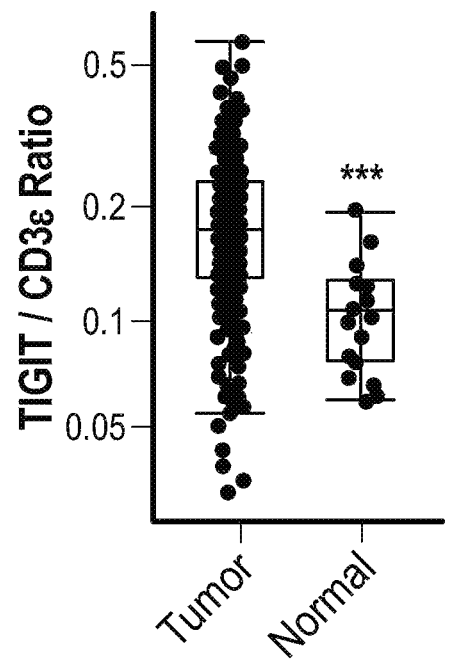
FIG. 20B
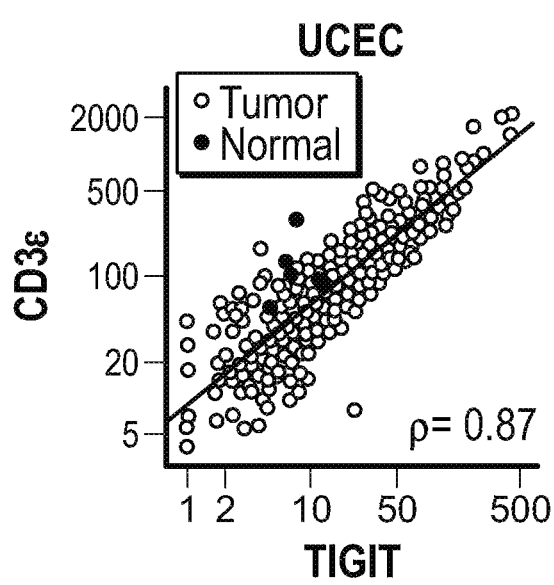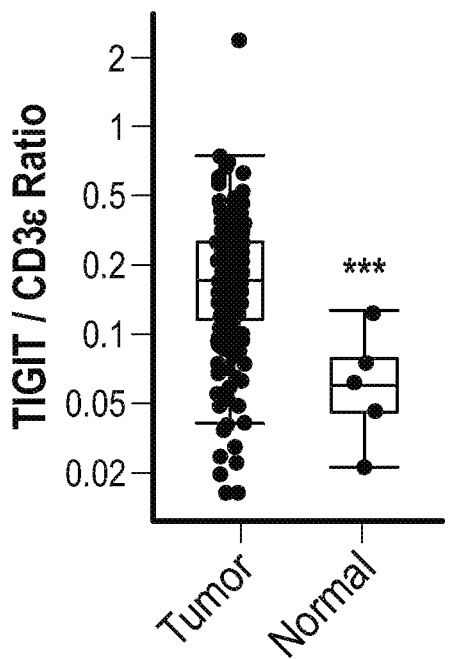
FIG. 20C

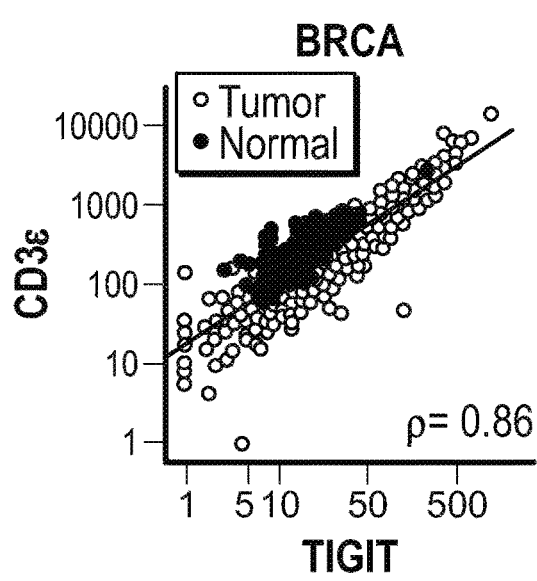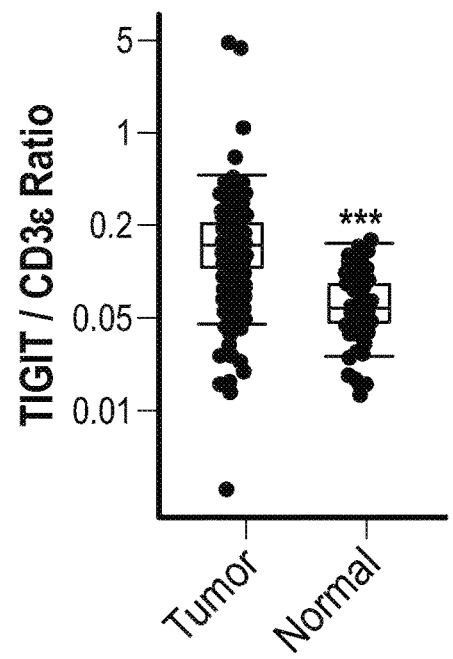
FIG. 20D
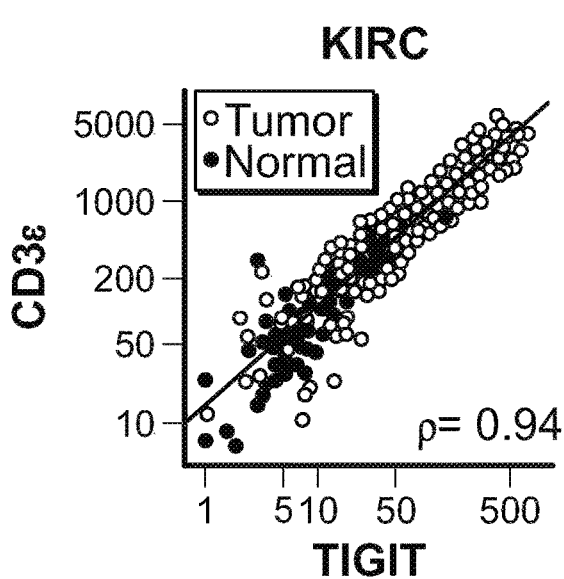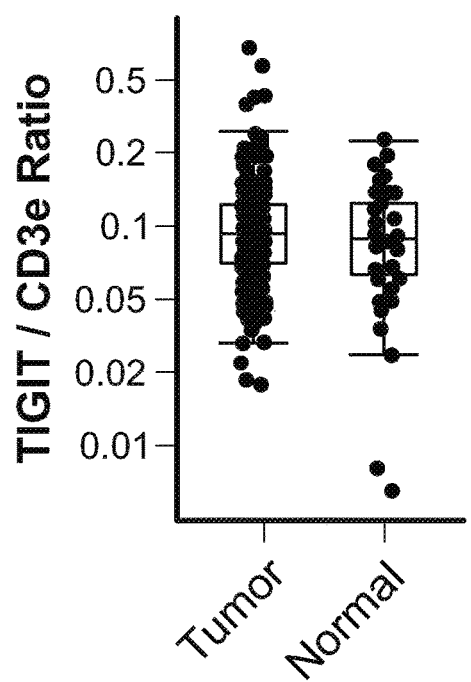
FIG. 20E

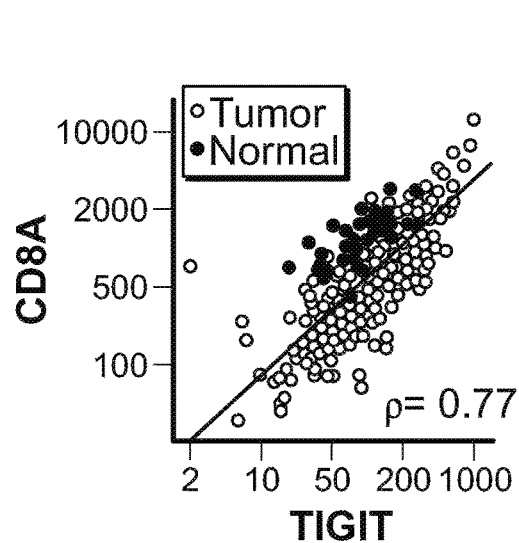
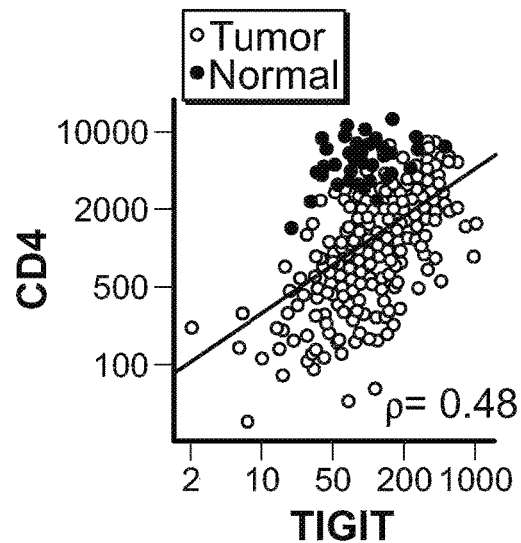
FIG. 20F
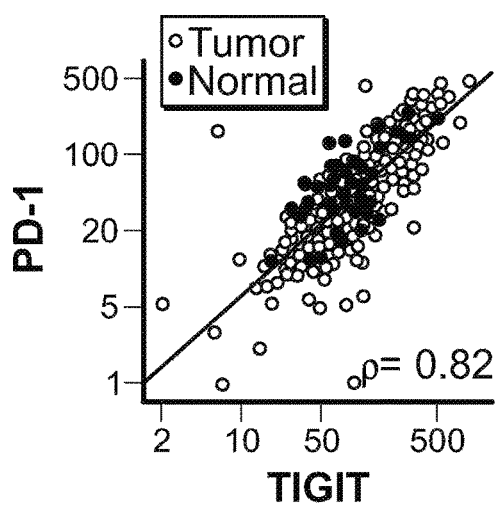
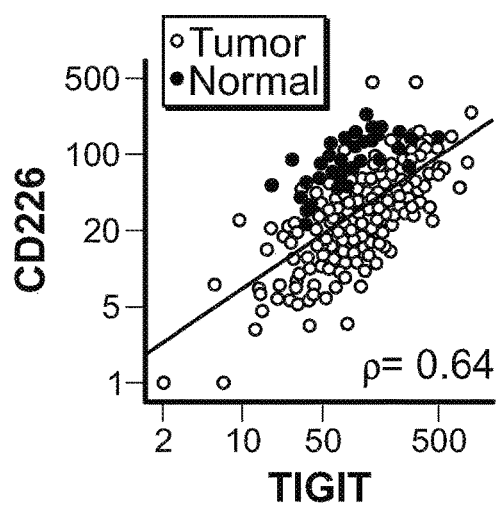
FIG. 20G
FIG. 20H

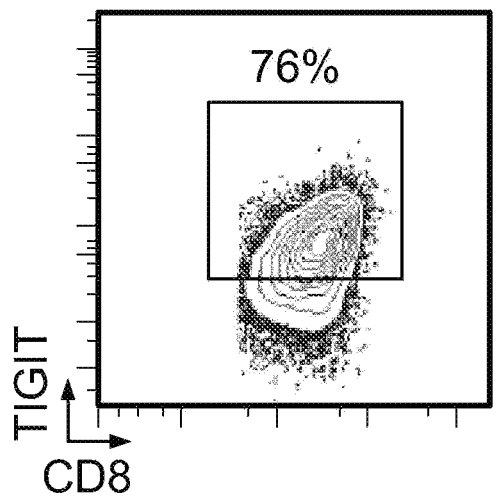
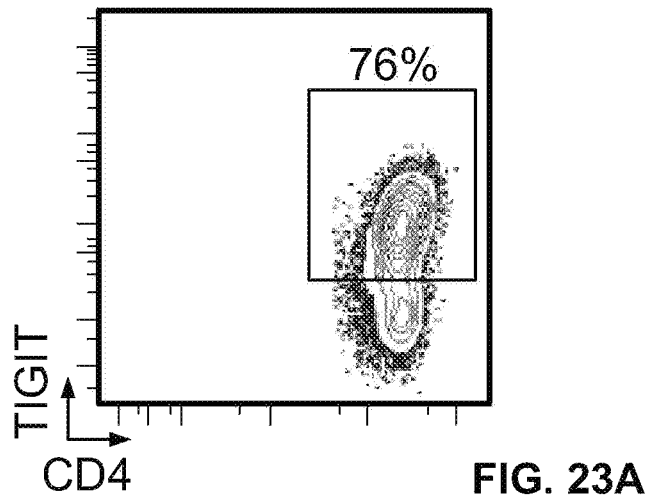
FIG. 23A
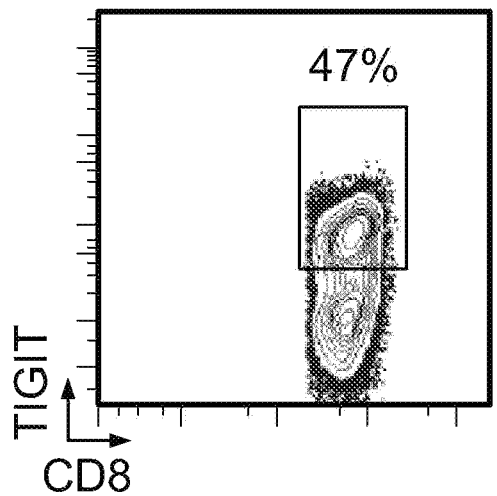
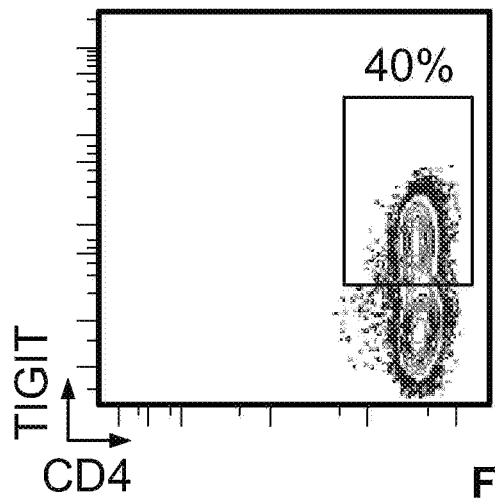
FIG. 23B
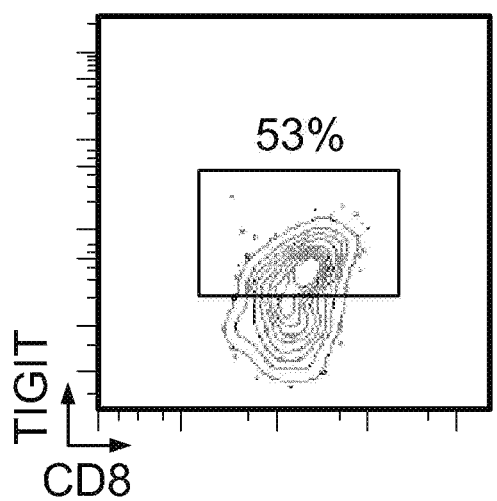
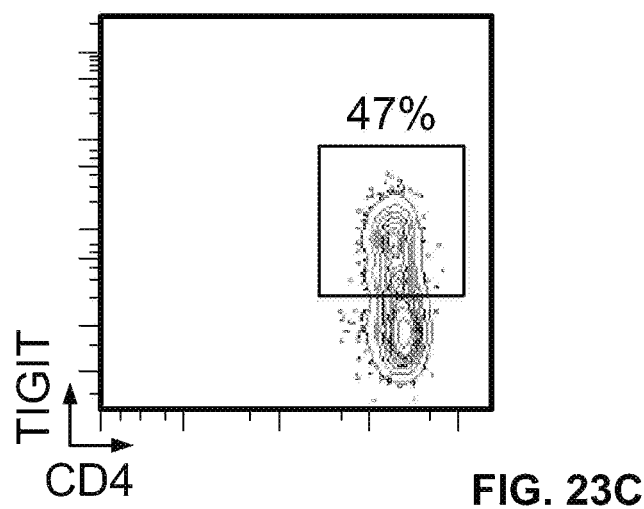
FIG. 23C

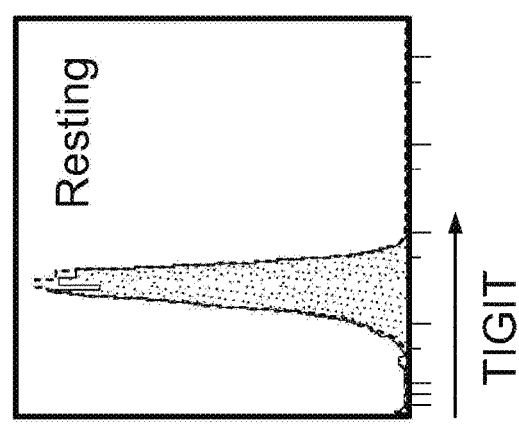
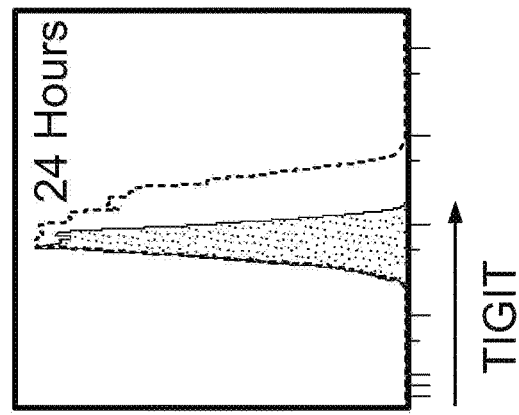
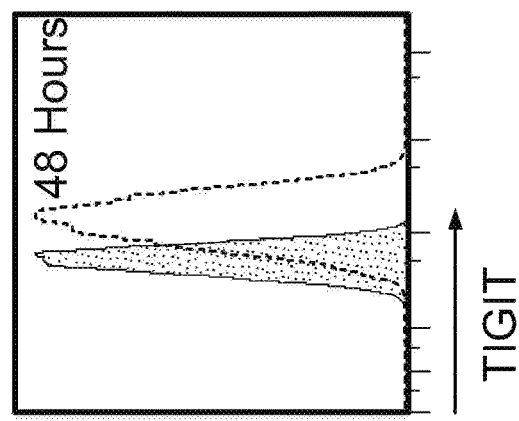
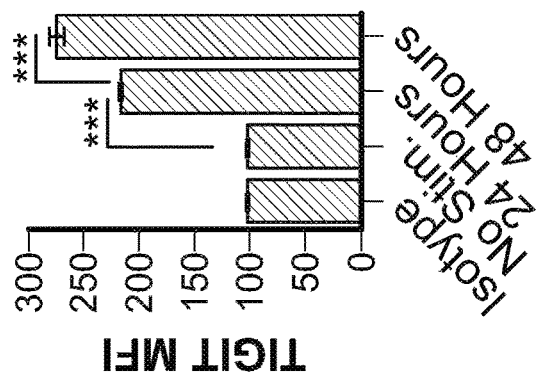
FIG. 26A
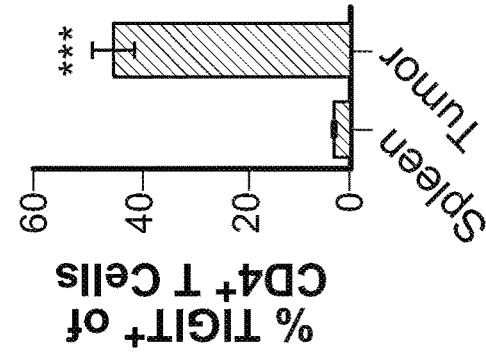
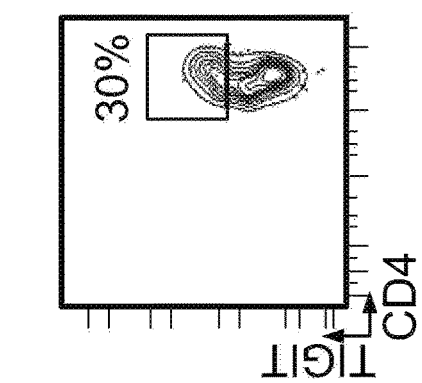
FIG. 26C
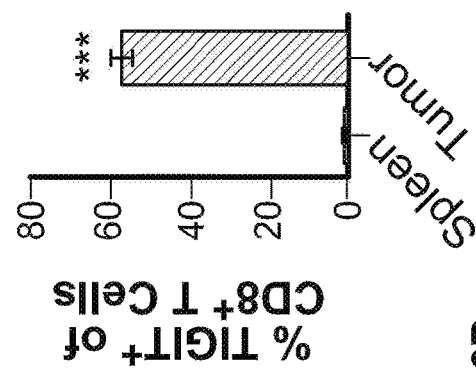
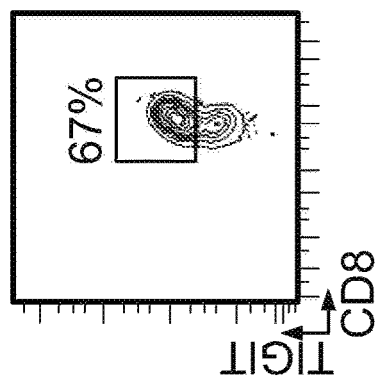
FIG. 26B

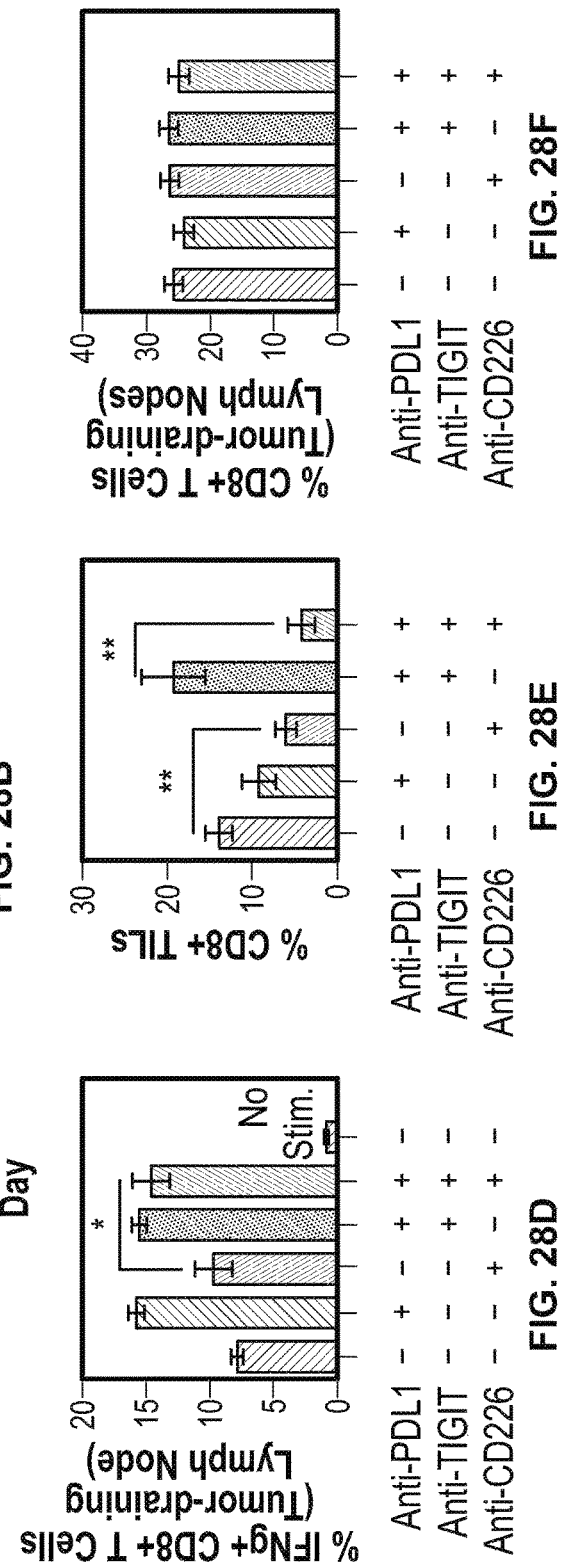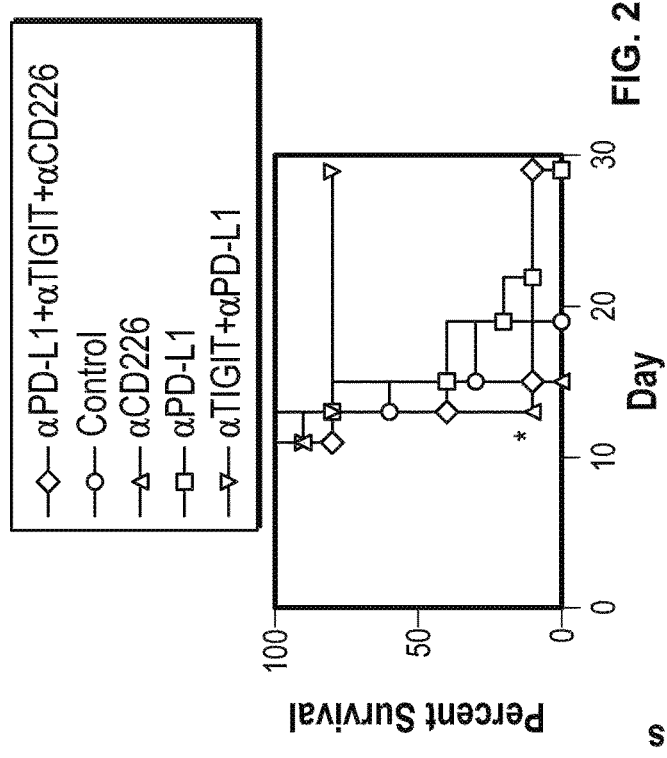

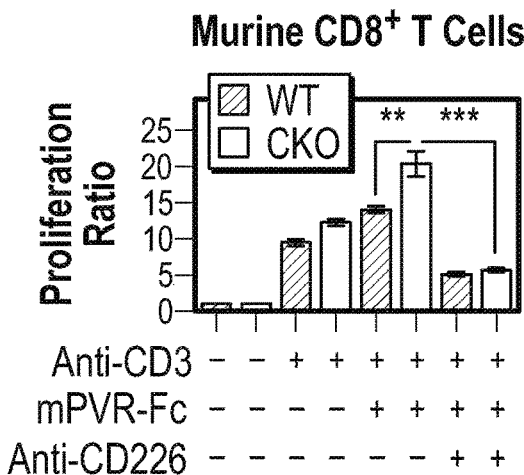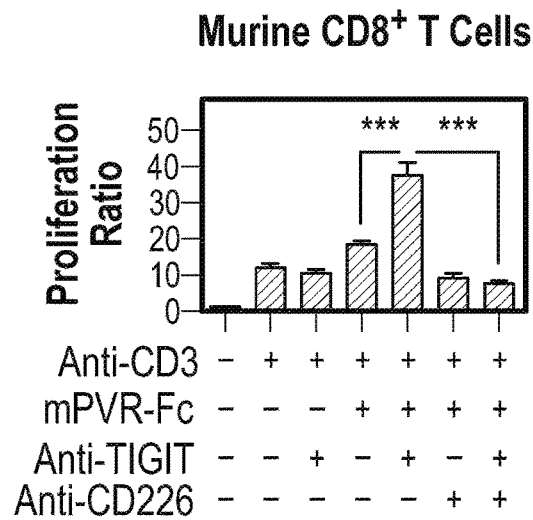
FIG. 29A
FIG. 29B
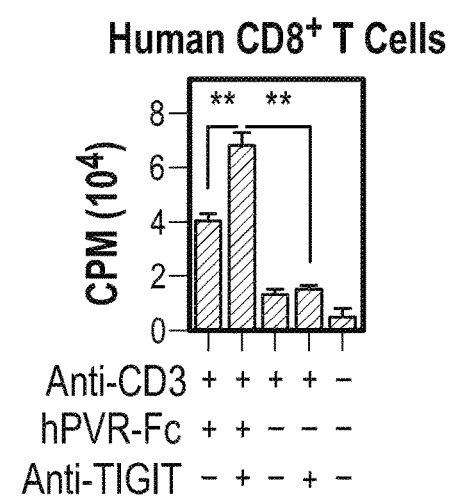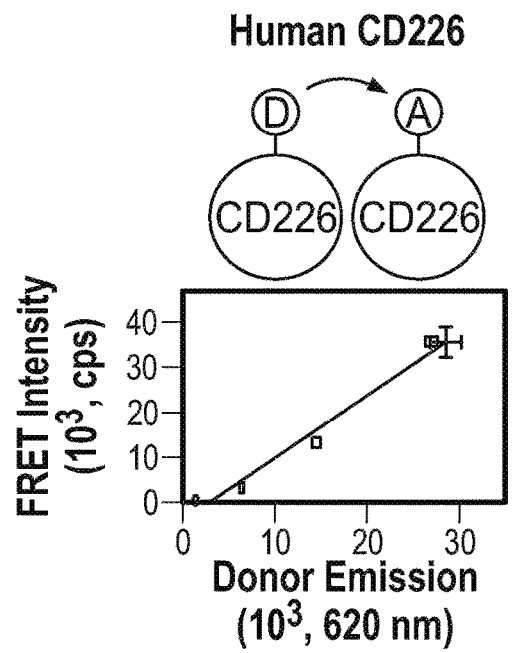
FIG. 29C
FIG. 29D

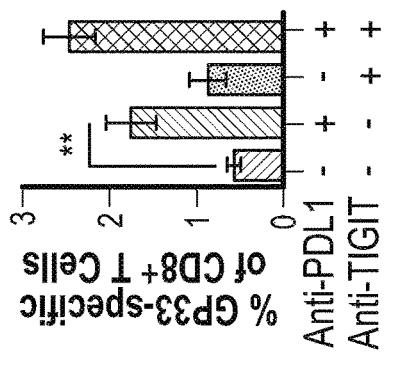
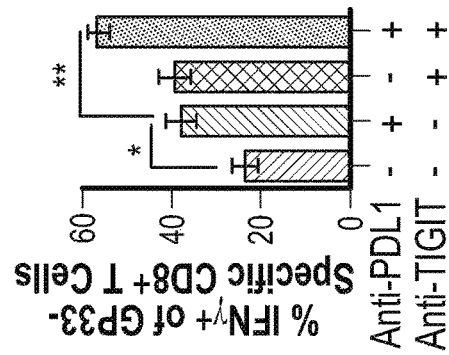
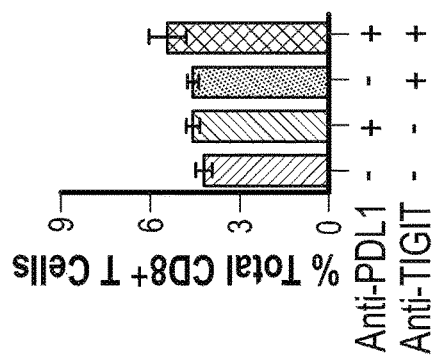
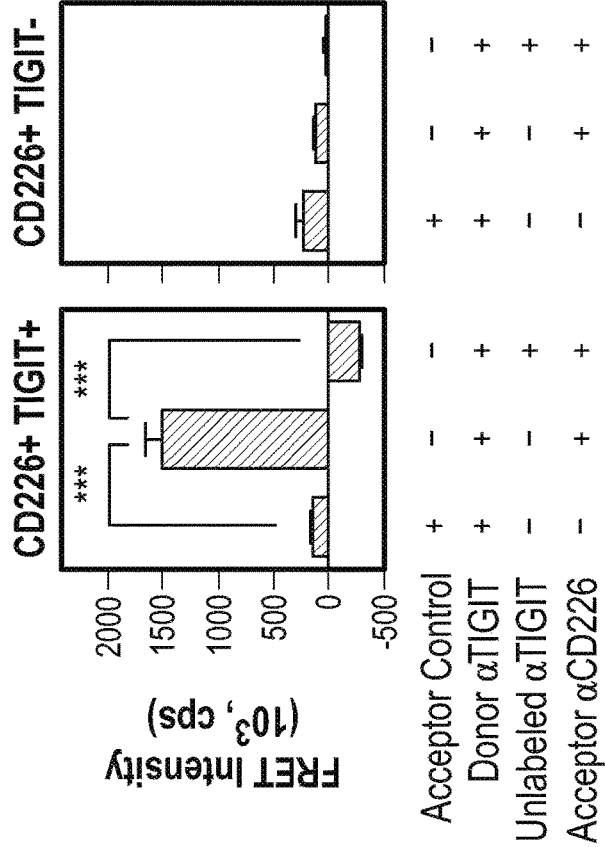
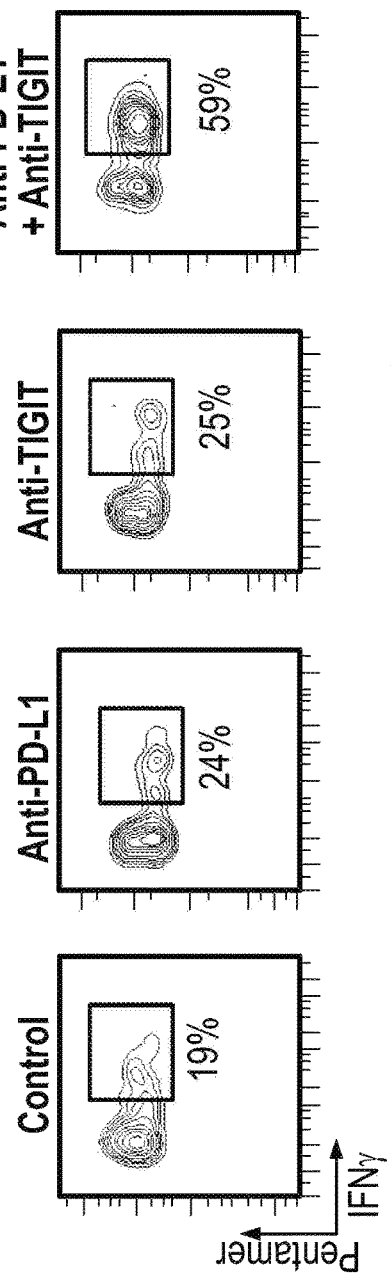

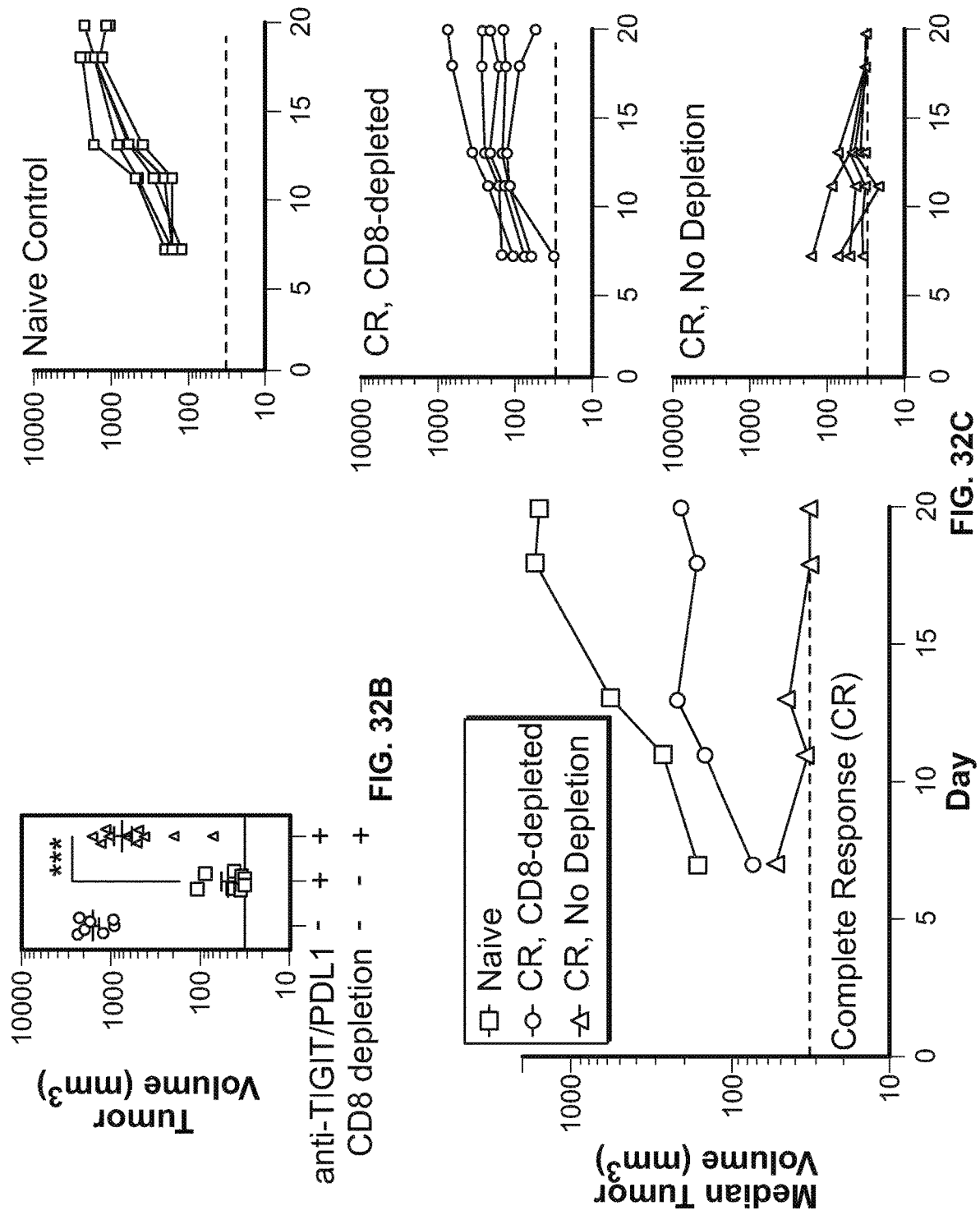

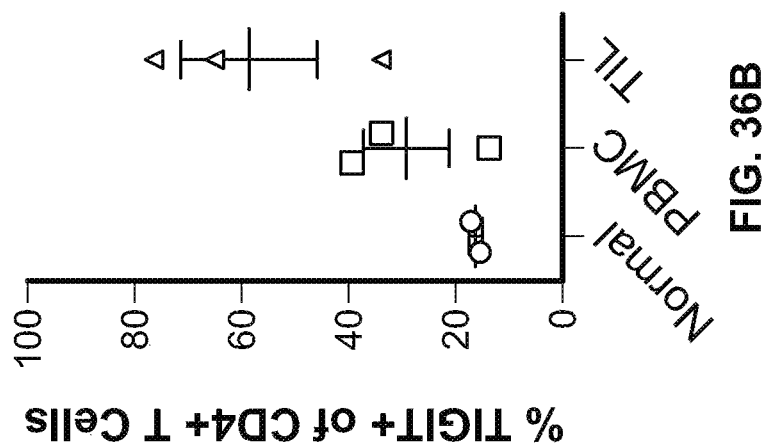
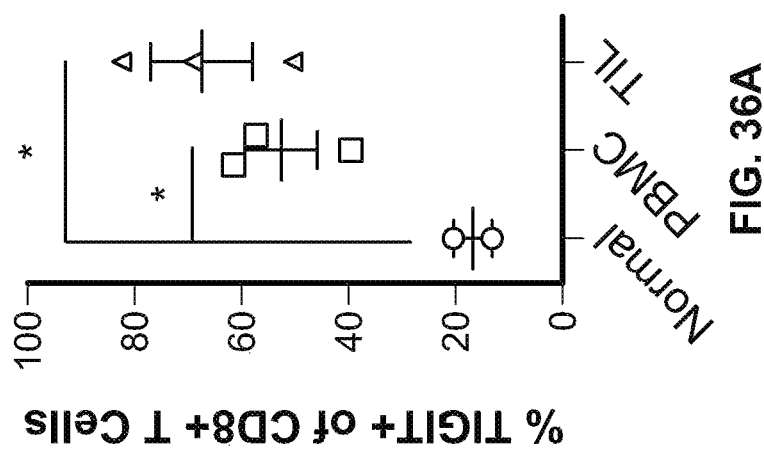
FIG. 36A
FIG. 36B

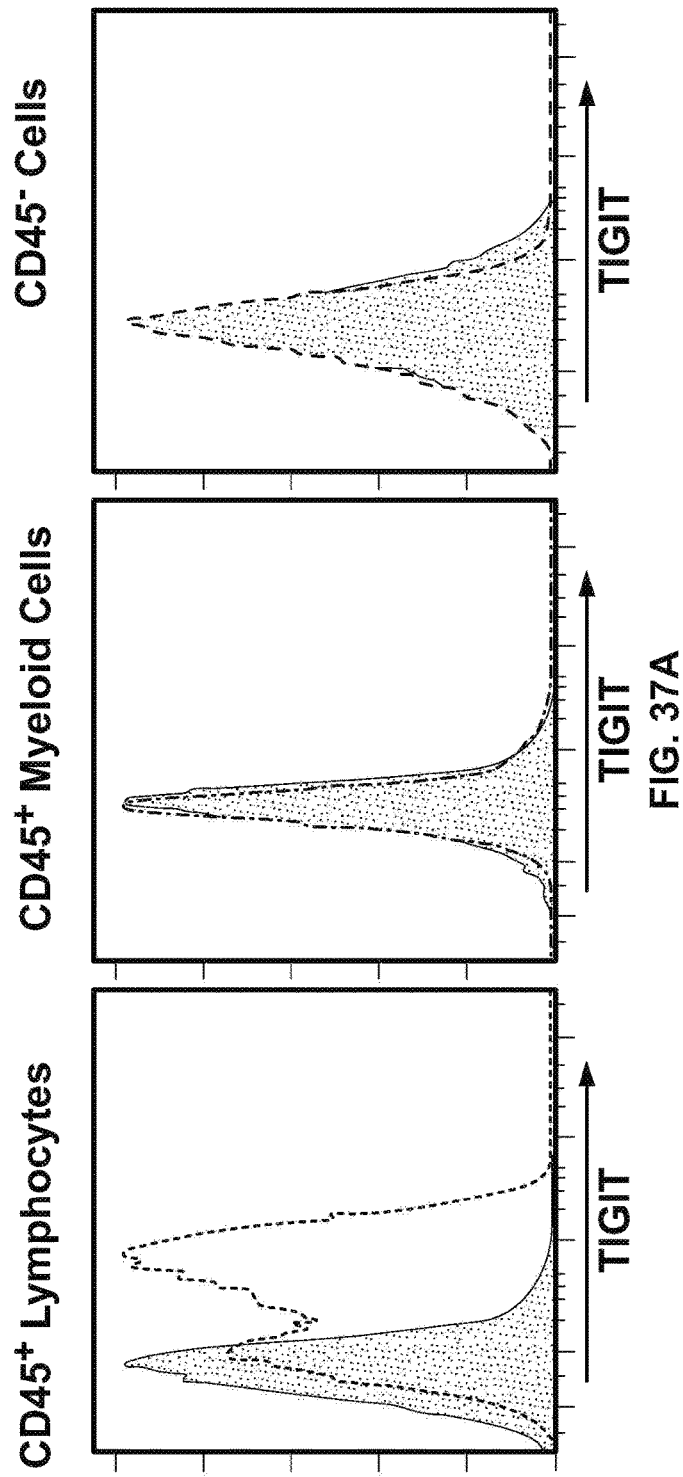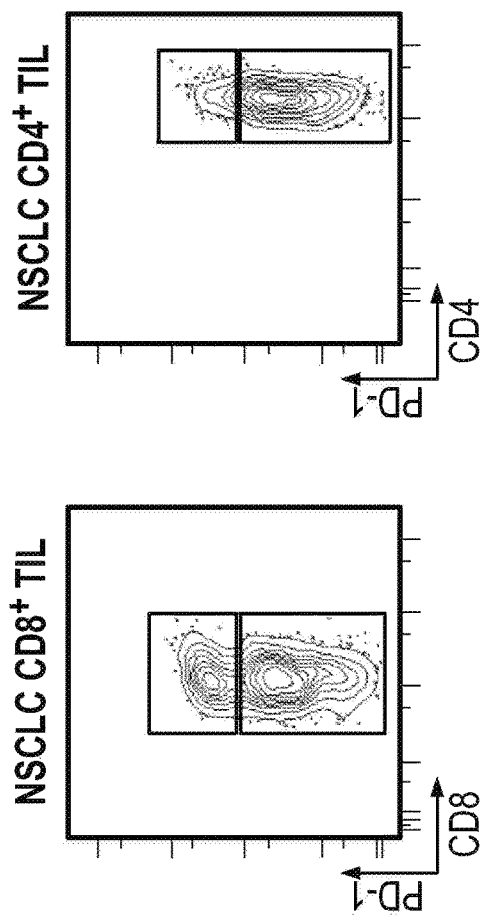
FIG. 37A
FIG. 37B

SEQUENCE LISTING

```
<160> NUMBER OF SEQ ID NOS: 49

<210> SEQ ID NO 1
<211> LENGTH: 17
<212> TYPE: PRT
<213> ORGANISM: Artificial Sequence
<220> FEATURE:
<223> OTHER INFORMATION: Synthetic Construct

<400> SEQUENCE: 1

Lys Ser Ser Gln Ser Leu Tyr Tyr Ser Gly Val Lys Glu Asn Leu Leu
1               5                   10                  15

Ala

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 2

Ala Ser Ile Arg Phe Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Gln Gln Gly Ile Asn Asn Pro Leu Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Phe Thr Phe Ser Ser Phe Thr Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

Phe Ile Arg Ser Gly Ser Gly Ile Val Phe Tyr Ala Asp Ala Val Arg
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Arg Pro Leu Gly His Asn Thr Phe Asp Ser
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Arg Ser Ser Gln Ser Leu Val Asn Ser Tyr Gly Asn Thr Phe Leu Ser
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 8

Gly Ile Ser Asn Arg Phe Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Leu Gln Gly Thr His Gln Pro Pro Thr
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Gly Tyr Ser Phe Thr Gly His Leu Met Asn
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Leu Ile Ile Pro Tyr Asn Gly Gly Thr Ser Tyr Asn Gln Lys Phe Lys
1               5                   10                  15

Gly

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Gly Leu Arg Gly Phe Tyr Ala Met Asp Tyr
1               5                   10

<210> SEQ ID NO 13
<211> LENGTH: 114
<212> TYPE: PRT
<213> ORGANISM: Artificial Sequence
<220> FEATURE:
<223> OTHER INFORMATION: Synthetic Construct

<400> SEQUENCE: 13

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45
```

```
Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65              70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg
```

<210> SEQ ID NO 14
<211> LENGTH: 112
<212> TYPE: PRT
<213> ORGANISM: Artificial Sequence
<220> FEATURE:
<223> OTHER INFORMATION: Synthetic Construct

<400> SEQUENCE: 14

```
Asp Val Val Leu Thr Gln Thr Pro Leu Ser Leu Ser Val Ser Phe Gly
1               5                   10                  15

Asp Gln Val Ser Ile Ser Cys Arg Ser Ser Gln Ser Leu Val Asn Ser
            20                  25                  30

Tyr Gly Asn Thr Phe Leu Ser Trp Tyr Leu His Lys Pro Gly Gln Ser
        35                  40                  45

Pro Gln Leu Leu Ile Phe Gly Ile Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Thr Ile Lys Pro Glu Asp Leu Gly Met Tyr Tyr Cys Leu Gln Gly
                85                  90                  95

Thr His Gln Pro Pro Thr Phe Gly Pro Gly Thr Lys Leu Glu Val Lys
            100                 105                 110
```

<210> SEQ ID NO 15
<211> LENGTH: 119
<212> TYPE: PRT
<213> ORGANISM: Artificial Sequence
<220> FEATURE:
<223> OTHER INFORMATION: Synthetic Construct

<400> SEQUENCE: 15

```
Glu Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Tyr Ala Asp Ala Val
    50                  55                  60

Arg Gly Arg Phe Thr Ile Ser Arg Asp Asn Ala Lys Asn Leu Leu Phe
65              70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser
            115
```

```
<210> SEQ ID NO 16
<211> LENGTH: 119
<212> TYPE: PRT
<213> ORGANISM: Artificial Sequence
<220> FEATURE:
<223> OTHER INFORMATION: Synthetic Construct

<400> SEQUENCE: 16
```

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly His
            20                  25                  30

Leu Met Asn Trp Val Lys Gln Ser His Gly Lys Asn Leu Glu Trp Ile
        35                  40                  45

Gly Leu Ile Ile Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Asp Asp Ser Ala Val Tyr Phe Cys
                85                  90                  95

Ser Arg Gly Leu Arg Gly Phe Tyr Ala Met Asp Tyr Trp Gly Gln Gly
            100                 105                 110

Thr Ser Val Thr Val Ser Ser
        115

```
<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17
```

Gly Phe Thr Phe Ser Asp Ser Trp Ile His
1               5                   10

```
<210> SEQ ID NO 18
<211> LENGTH: 18
<212> TYPE: PRT
<213> ORGANISM: Artificial Sequence
<220> FEATURE:
<223> OTHER INFORMATION: Synthetic Construct

<400> SEQUENCE: 18
```

Ala Trp Ile Ser Pro Tyr Gly Gly Ser Thr Tyr Tyr Ala Asp Ser Val
1               5                   10                  15

Lys Gly

```
<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19
```

Arg His Trp Pro Gly Gly Phe Asp Tyr
1               5

```
<210> SEQ ID NO 20
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 20

Arg Ala Ser Gln Asp Val Ser Thr Ala Val Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Ser Ala Ser Phe Leu Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Tyr Leu Tyr His Pro Ala Thr
1               5

<210> SEQ ID NO 23
<211> LENGTH: 118
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 24
<211> LENGTH: 108
<212> TYPE: PRT
<213> ORGANISM: Artificial Sequence
<220> FEATURE:
<223> OTHER INFORMATION: Synthetic Construct
```

-continued

```
<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 26
<211> LENGTH: 13
<212> TYPE: PRT
<213> ORGANISM: Artificial Sequence
<220> FEATURE:
<223> OTHER INFORMATION: Synthetic Construct

<400> SEQUENCE: 26

Trp Val Arg Gln Ala Pro Gly Lys Gly Leu Glu Trp Val
1               5                   10

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 28

Trp Gly Gln Gly Thr Leu Val Thr Val Ser Ala
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp Tyr Gln Gln Lys Pro Gly Lys Ala Pro Lys Leu Leu Ile Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Phe Gly Gln Gly Thr Lys Val Glu Ile Lys Arg
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (6)..(6)
<223> OTHER INFORMATION: Xaa = Asp or Gly

<400> SEQUENCE: 33

Gly Phe Thr Phe Ser Xaa Ser Trp Ile His
1               5                   10
```

```
<210> SEQ ID NO 34
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = Ser or Leu
<220> FEATURE:
<221> NAME/KEY: VARIANT
<222> LOCATION: (10)..(10)
<223> OTHER INFORMATION: Xaa = Thr or Ser

<400> SEQUENCE: 34

Ala Trp Ile Xaa Pro Tyr Gly Gly Ser Xaa Tyr Tyr Ala Asp Ser Val
1               5                   10                  15

Lys Gly

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: Xaa = Asp or Val
<220> FEATURE:
<221> NAME/KEY: VARIANT
<222> LOCATION: (6)..(6)
<223> OTHER INFORMATION: Xaa = Val or Ile
<220> FEATURE:
<221> NAME/KEY: VARIANT
<222> LOCATION: (7)..(7)
<223> OTHER INFORMATION: Xaa = Ser or Asn
<220> FEATURE:
<221> NAME/KEY: VARIANT
<222> LOCATION: (9)..(9)
<223> OTHER INFORMATION: Xaa = Ala or Phe
<220> FEATURE:
<221> NAME/KEY: VARIANT
<222> LOCATION: (10)..(10)
<223> OTHER INFORMATION: Xaa = Val or Leu

<400> SEQUENCE: 35

Arg Ala Ser Gln Xaa Xaa Xaa Thr Xaa Xaa Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = Phe or Thr
<220> FEATURE:
<221> NAME/KEY: VARIANT
<222> LOCATION: (6)..(6)
<223> OTHER INFORMATION: Xaa = Tyr or Ala

<400> SEQUENCE: 36

Ser Ala Ser Xaa Leu Xaa Ser
1               5
```

```
<210> SEQ ID NO 37
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa = Tyr, Gly, Phe, or Ser
<220> FEATURE:
<221> NAME/KEY: VARIANT
<222> LOCATION: (4)..(4)
<223> OTHER INFORMATION: Xaa = Leu, Tyr, Phe or Trp
<220> FEATURE:
<221> NAME/KEY: VARIANT
<222> LOCATION: (5)..(5)
<223> OTHER INFORMATION: Xaa = Tyr, Asn, Ala, Thr, Gly, Phe or Ile
<220> FEATURE:
<221> NAME/KEY: VARIANT
<222> LOCATION: (6)..(6)
<223> OTHER INFORMATION: Xaa = His, Val, Pro, Thr or Ile
<220> FEATURE:
<221> NAME/KEY: VARIANT
<222> LOCATION: (8)..(8)
<223> OTHER INFORMATION: Xaa = Ala, Trp, Arg, Pro or Thr

<400> SEQUENCE: 37

Gln Gln Xaa Xaa Xaa Xaa Pro Xaa Thr
1               5

<210> SEQ ID NO 38
<211> LENGTH: 336
<212> TYPE: DNA
<213> ORGANISM: Artificial Sequence
<220> FEATURE:
<223> OTHER INFORMATION: Synthetic Construct

<400> SEQUENCE: 38
gatgttgtgt tgactcaaac tccactctcc ctgtctgtca gctttggaga tcaagtttct      60
atctcttgca ggtctagtca gagtcttgta acagttatg ggaacaccttt tttgtcttgg    120 tacctgcaca agcctggcca gtctccacag ctcctcatct ttgggatttc aacagattt     180 tctggggtgc cagacaggtt cagtggcagt ggttcaggga cagatttcac actcaagatc    240
agcacaataa agcctgagga cttgggaatg tattactgct acaaggtac gcatcagcct     300 cccacgttcg gtcctgggac caagctggag gtgaaa                              336

<210> SEQ ID NO 39
<211> LENGTH: 357
<212> TYPE: DNA
<213> ORGANISM: Artificial Sequence
<220> FEATURE:
<223> OTHER INFORMATION: Synthetic Construct

<400> SEQUENCE: 39
gaggtccagc tgcaacagtc tggacctgag ctggtgaagc ctggaacttc aatgaagata     60
tcctgcaagg cttctggtta ctcattcact ggccatctta tgaactgggt gaagcagagc    120
catggaaaga accttgagtg gattggactt attattcctt acaatggtgg tacaagctat    180
aaccagaagt tcaagggcaa ggccacattg actgtagaca gtcatccag cacagcctac     240 atggagctcc tcagtctgac ttctgatgac tctgcagtct atttctgttc aagaggcctt    300
aggggcttct atgctatgga ctactgggt caaggaacct cagtcaccgt ctcctca        357
```

<210> SEQ ID NO 40
<211> LENGTH: 122
<212> TYPE: PRT
<213> ORGANISM: Artificial Sequence
<220> FEATURE:
<223> OTHER INFORMATION: Synthetic Construct

<400> SEQUENCE: 40

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ser Ala Ser Thr Lys
        115                 120
```

<210> SEQ ID NO 41
<211> LENGTH: 118
<212> TYPE: PRT
<213> ORGANISM: Artificial Sequence
<220> FEATURE:
<223> OTHER INFORMATION: Synthetic Construct

<400> SEQUENCE: 41

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Ser
            20                  25                  30
Trp Ile His Trp Val Arg Gln Ala Pro Gly Lys Gly Leu Glu Trp Val
        35                  40                  45
Ala Trp Ile Ser Pro Tyr Gly Gly Ser Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg His Trp Pro Gly Gly Phe Asp Tyr Trp Gly Gln Gly Thr
            100                 105                 110
Leu Val Thr Val Ser Ser
        115
```

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

```
Trp Gly Gln Gly Thr Leu Val Thr Val Ser Ser
1               5                   10
```

<210> SEQ ID NO 43
<211> LENGTH: 30
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 44
<211> LENGTH: 14
<212> TYPE: PRT
<213> ORGANISM: Artificial Sequence
<220> FEATURE:
<223> OTHER INFORMATION: Synthetic Construct

<400> SEQUENCE: 44

Trp Val Arg Gln Ala Pro Gly Lys Gly Leu Glu Trp Val Ala
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Construct

<400> SEQUENCE: 45

Trp Gly Gln Gly Thr Leu Val Thr Val Ser Ser
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Phe Gly Gln Gly Thr Lys Val Glu Ile Lys
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct

<400> SEQUENCE: 47

Trp Gly Gln Gly Thr Leu Val Thr Val Ser Ser Ala Ser Thr Lys
1               5                   10                  15

<210> SEQ ID NO 48
<211> LENGTH: 447
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

-continued

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 49
<211> LENGTH: 214
<212> TYPE: PRT
<213> ORGANISM: Artificial Sequence
<220> FEATURE:
<223> OTHER INFORMATION: Synthetic Construct

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

METHODS OF TREATING CANCER USING PD-1 AXIS BINDING ANTAGONISTS AND TIGIT INHIBITORS

CROSS REFERENCES TO RELATED APPLICATIONS

This application is a divisional application of U.S. application Ser. No. 14/333,375, filed Jul. 16, 2014, which claims the priority benefit of U.S. Provisional Application No. 61/846,941, filed Jul. 16, 2013, U.S. Provisional Application No. 61/865,582, filed Aug. 13, 2013, U.S. Provisional Application No. 61/950,754, filed Mar. 10, 2014, U.S. Provisional Application No. 61/985,884, filed Apr. 29, 2014, and U.S. Provisional Application No. 61/992,109, filed May 12, 2014, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392025900SEQLISTING.TXT, date recorded: Jul. 16, 2014, size: 25 KB).

BACKGROUND OF THE INVENTION

The provision of two distinct signals to T-cells is a widely accepted model for lymphocyte activation of resting T lymphocytes by antigen-presenting cells (APCs). Lafferty et al, Aust. J. Exp. Biol. Med. ScL 53: 27-42 (1975). This model further provides for the discrimination of self from non-self and immune tolerance. Bretscher et al, Science 169: 1042-1049 (1970); Bretscher, P. A., P.N.A.S. USA 96: 185-190 (1999); Jenkins et al, J. Exp. Med. 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. Lenschow et al., Ann. Rev. Immunol. 14:233 (1996). In the absence of co-stimulation, T-cells can become refractory to antigen stimulation, which results in a tolerogenic response to either foreign or endogenous antigens.

In the two-signal model, T-cells receive both positive co-stimulatory and negative co-inhibitory signals. The regulation of such positive and negative signals is critical to maximize the host's protective immune responses, while maintaining immune tolerance and preventing autoimmunity. Negative signals seem necessary for induction of T-cell tolerance, while positive signals promote T-cell activation.

Both co-stimulatory and co-inhibitory signals are provided to antigen-exposed T cells, and the interplay between co-stimulatory and co-inhibitory signals is essential to controlling the magnitude of an immune response. Further, the signals provided to the T cells change as an infection or immune provocation is cleared, worsens, or persists, and these changes powerfully affect the responding T cells and re-shape the immune response.

The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting of PD-1 and other molecules which signal through interactions with PD-1, such as programmed death ligand 1 (PD-L1) and programmed death ligand 2 (PD-L2) are an area of intense interest.

PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction may enhance CD8+ T cell-mediated killing of tumors.

The inhibition of PD-1 axis signaling through its direct ligands (e.g., PD-L1, PD-L2) has been proposed as a means to enhance T cell immunity for the treatment of cancer (e.g., tumor immunity). Moreover, similar enhancements to T cell immunity have been observed by inhibiting the binding of PD-L1 to the binding partner B7-1. Furthermore, combining inhibition of PD-1 signaling with other signaling pathways that are deregulated in tumor cells may further enhance treatment efficacy. There remains a need for such an optimal therapy for treating, stabilizing, preventing, and/or delaying development of various cancers.

All references, publications, and patent applications disclosed herein are hereby incorporated by reference in their entirety.

BRIEF SUMMARY OF THE INVENTION

The present invention describes a combination treatment comprising a PD-1 axis binding antagonist and an agent that decreases or inhibits TIGIT expression and/or activity.

Provided herein are methods for treating or delaying progression of cancer in an individual comprising administering to the individual an effective amount of a PD-1 axis binding antagonist and an agent that decreases or inhibits TIGIT expression and/or activity.

Provided herein are also methods for reducing or inhibiting cancer relapse or cancer progression in an individual comprising administering to the individual an effective amount of a PD-1 axis binding antagonist and an agent that decreases or inhibits TIGIT expression and/or activity.

Provided herein are also methods for treating or delaying progression of an immune related disease in an individual comprising administering to the individual an effective amount of a PD-1 axis binding antagonist and an agent that decreases or inhibits TIGIT expression and/or activity.

Provided herein are also methods for reducing or inhibiting progression of an immune related disease in an individual comprising administering to the individual an effective amount of a PD-1 axis binding antagonist and an agent that decreases or inhibits TIGIT expression and/or activity.

In some embodiments, the immune related disease is associated with a T cell dysfunctional disorder. In some embodiments, the T cell dysfunctional disorder is characterized by decreased responsiveness to antigenic stimulation. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the immune related disease is selected from the group consisting of unresolved acute infection, chronic infection and tumor immunity.

Provided herein are also methods of increasing, enhancing or stimulating an immune response or function in an individual by administering to the individual an effective amount of a PD-1 axis binding antagonist and an agent that decreases or inhibits TIGIT expression and/or activity.

Provided herein are also methods of treating or delaying progression of cancer in an individual comprising administering to the individual an effective amount of a PD-1 axis binding antagonist and an agent that modulates the CD226 expression and/or activity.

Provided herein are also methods for reducing or inhibiting cancer relapse or cancer progression in an individual comprising administering to the individual an effective amount of a PD-1 axis binding antagonist and an agent that modulates the CD226 expression and/or activity.

Provided herein are also methods for treating or delaying progression of an immune related disease in an individual comprising administering to the individual an effective amount of a PD-1 axis binding antagonist and an agent that modulates the CD226 expression and/or activity.

Provided herein are also methods for reducing or inhibiting progression of an immune related disease in an individual comprising administering to the individual an effective amount of a PD-1 axis binding antagonist and agent that modulates the CD226 expression and/or activity.

In some embodiments, the immune related disease is associated with a T cell dysfunctional disorder. In some embodiments, the T cell dysfunctional disorder is characterized by decreased responsiveness to antigenic stimulation. In some embodiments, the T cell dysfunctional disorder is characterized by T cell anergy, or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the immune related disease is selected from the group consisting of unresolved acute infection, chronic infection and tumor immunity.

Provided herein are also methods of increasing, enhancing or stimulating an immune response or function in an individual by administering to the individual an effective amount of a PD-1 axis binding antagonist and an agent that modulates the CD226 expression and/or activity.

In some embodiments, the agent that modulates the CD226 expression and/or activity is capable of increasing and/or stimulating CD226 expression and/or activity.

In some embodiments, the agent that modulates the CD226 expression and/or activity is selected from an agent that inhibits and/or blocks the interaction of CD226 with TIGIT, an antagonist of TIGIT expression and/or activity, an antagonist of PVR expression and/or activity, an agent that inhibits and/or blocks the interaction of TIGIT with PVR, an agent that inhibits and/or blocks the intracellular signaling mediated by TIGIT binding to PVR.

In some embodiments, the agent that inhibits and/or blocks the interaction of CD226 with TIGIT is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of CD226 with TIGIT is an anti-TIGIT antibody or antigen-binding fragment thereof.

In some embodiments, the antagonist of TIGIT expression and/or activity is a small molecule inhibitor, an inhibitory antibody or antigen-binding fragment thereof, an aptamer, an inhibitory nucleic acid, and an inhibitory polypeptide. In some embodiments, the antagonist of TIGIT expression and/or activity is an anti-TIGIT antibody or antigen-binding fragment thereof.

In some embodiments, the antagonist of PVR expression and/or activity is a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVR is a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVR is a small molecule inhibitor, an inhibitory antibody or antigen-binding fragment thereof, an aptamer, an inhibitory nucleic acid, and an inhibitory polypeptide.

The present invention also describes a combination treatment comprising an agent that decreases or inhibits TIGIT expression and/or activity and an agent that decreases or inhibits one or more additional immune co-inhibitory receptors.

Provided herein are methods of increasing, enhancing or stimulating an immune response or function in an individual by administering to the individual an effective amount of an agent that decreases or inhibits TIGIT expression and/or activity and an agent that decreases or inhibits one or more additional immune co-inhibitory receptors.

In some embodiments, the one or more additional immune co-inhibitory receptor is selected from the group consisting of PD-1, CTLA-4, LAG3, TIM3, BTLA and VISTA. In some embodiments, the one or more additional immune co-inhibitory receptor is selected from the group of PD-1, CTLA-4, LAG3 and TIM3.

The present invention also describes a combination treatment comprising an agent that decreases or inhibits TIGIT expression and/or activity and an agent that increases or activates one or more additional immune co-stimulatory receptor.

Provided herein are methods of increasing, enhancing or stimulating an immune response or function in an individual by administering to the individual an effective amount of an agent that decreases or inhibits TIGIT expression and/or activity and an agent that increases or activates one or more additional immune co-stimulatory receptor.

In some embodiments, the one or more additional immune co-stimulatory receptor is selected from the group consisting of CD226, OX-40, CD28, CD27, CD137, HVEM, and GITR. In some embodiments, the one or more additional immune co-stimulatory receptor is selected from the group of CD226, OX-40, CD27, CD137, HVEM and GITR. In some embodiments, the one or more additional immune co-stimulatory receptor is selected from the group consisting of OX-40 and CD27.

In some embodiments, any of the above methods further comprise administering at least one chemotherapeutic agent.

In some embodiments, the individual in any of the above methods has cancer. In some embodiments, the individual in any of the above methods is a human.

In some embodiments, the CD4 and/or CD8 T cells in the individual have increased or enhanced priming, activation, proliferation, cytokine release and/or cytolytic activity relative to prior to the administration of the combination.

In some embodiments, the number of CD4 and/or CD8 T cells is elevated relative to prior to administration of the combination. In some embodiments, the number of activated CD4 and/or CD8 T cells is elevated relative to prior to administration of the combination. In some embodiments, the activated CD4 and/or CD8 T cells is characterized by γ-IFN$^+$ producing CD4 and/or CD8 T cells and/or enhanced cytolytic activity relative to prior to the administration of the combination. In some embodiments, the CD4 and/or CD8 T cells exhibit increased release of cytokines selected from the group consisting of IFN-γ, TNF-α, and interleukins.

In some embodiments, the CD4 and/or CD8 T cell is an effector memory T cell. In some embodiments, the CD4 and/or CD8 effector memory T cell is characterized by γ-IFN$^+$ producing CD4 and/or CD8 T cells and/or enhanced cytolytic activity. In some embodiments, the CD4 and/or CD8 effector memory T cell is characterized by having the expression of CD44$^{high}$ CD62L$^{low}$.

In some embodiments, the cancer in any of the above methods has elevated levels of T cell infiltration.

In some embodiments, the agent that decreases or inhibits TIGIT expression and/or activity is selected from the group consisting of an antagonist of TIGIT expression and/or activity, an antagonist of PVR expression and/or activity, and an agent that inhibits the interaction and/or the intracellular signaling mediated by TIGIT binding to PVR.

In some embodiments, the antagonist of TIGIT expression and/or activity is selected from the group consisting of a small molecule inhibitor, an inhibitory antibody or antigen-binding fragment thereof, an aptamer, an inhibitory nucleic acid, and an inhibitory polypeptide.

In some embodiments, the antagonist of PVR expression and/or activity is selected from the group consisting of a small molecule inhibitor, an inhibitory antibody or antigen-binding fragment thereof, an aptamer, an inhibitory nucleic acid, and an inhibitory polypeptide.

In some embodiments, the agent that inhibits the intracellular signaling mediated by TIGIT binding to PVR is selected from the group consisting of a small molecule inhibitor, an inhibitory antibody or antigen-binding fragment thereof, an aptamer, an inhibitory nucleic acid, and an inhibitory polypeptide.

In some embodiments, the antagonist of TIGIT expression and/or activity is an anti-TIGIT antibody or antigen-binding fragment thereof.

In some embodiments, the anti-TIGIT antibody or antigen-binding fragment thereof comprises at least one HVR comprising an amino acid sequence selected from the amino acid sequences KSSQSLYYSGVKENLLA (SEQ ID NO:1), ASIRFT (SEQ ID NO:2), QQGINNPLT (SEQ ID NO:3), GFTFSSFTMH (SEQ ID NO:4), FIRSGSGIVFYADAVRG (SEQ ID NO:5), and RPLGHNTFDS (SEQ ID NO:6) or RSSQSLVNSYGNTFLS (SEQ ID NO:7), GISNRFS (SEQ ID NO:8), LQGTHQPPT (SEQ ID NO:9), GYSFTGHLMN (SEQ ID NO:10), LIIPYNGGTSYNQKFKG (SEQ ID NO:11), and GLRGFYAMDY (SEQ ID NO:12).

In some embodiments, the anti-TIGIT antibody or antigen-binding fragment thereof comprises a light chain comprising the amino acid sequence set forth in DIVMTQSPSSLAVSPGEKVTMTCKSSQSLYYSGVKENLLAWYQQKPGQS PKLLIYYASIRFTGVPDRFTGSGSGTDYTLTITSVQAEDMGQYFCQQGINNPLTFGDGTK LEIKR (SEQ ID NO:13) or DVVLTQTPLSLSVSFGDQVSISCRSSQSLVNSYGNTFLSWYLHKPGQSPQLLIFGISNRFS GVPDRFSGSGSGTDFTLKISTIKPEDLGMYYCLQGTHQPPTFGPGTKLEVK (SEQ ID NO:14).

In some embodiments, the anti-TIGIT antibody or antigen-binding fragment thereof comprises a heavy chain comprising the amino acid sequence set forth in EVQLVESGGGLTQPGKSLKLSCEASGFTFSSFTMHWVRQSPGKGLEWVAFIRSGSGIVF YADAVRGRFTISRDNAKNLLFLQMNDLKSEDTAMYYCARRPLGHNTFDSWGQGTLVT VSS (SEQ ID NO:15) or EVQLQQSGPELVKPGTSMKISCKASGYSFTGHLMNWVKQSHGKNLEWIGLIIPYNGGTS YNQKFKGKATLTVDKSSSTAYMELLSLTSDDSAVYFCSRGLRGFYAMDYWGQGTSVT VSS (SEQ ID NO:16).

In some embodiments, the anti-TIGIT antibody or antigen-binding fragment thereof comprises a light chain comprising the amino acid sequence set forth in DIVMTQSPSSLAVSPGEKVTMTCKSSQSLYYSGVKENLLAWYQQKPGQS PKLLIYYASIRFTGVPDRFTGSGSGTDYTLTITSVQAEDMGQYFCQQGINNPLTFGDGTK LEIKR (SEQ ID NO:13) or DVVLTQTPLSLSVSFGDQVSISCRSSQSLVNSYGNTFLSWYLHKPGQSPQLLIFGISNRFS GVPDRFSGSGSGTDFTLKISTIKPEDLGMYYCLQGTHQPPTFGPGTKLEVK (SEQ ID NO:14) and the antibody heavy chain comprises the amino acid sequence set forth in EVQLVESGGGLTQPGKSLKLSCEASGFTFSSFTMHWVRQSPGKGLEWVAFIRSGSGIVF YADAVRGRFTISRDNAKNLLFLQMNDLKSEDTAMYYCARRPLGHNTFDSWGQGTLVT VSS (SEQ ID NO:15) or EVQLQQSGPELVKPGTSMKISCKASGYSFTGHLMNWVKQSHGKNLEWIGLIIPYNGGTS YNQKFKGKATLTVDKSSSTAYMELLSLTSDDSAVYFCSRGLRGFYAMDYWGQGTSVT VSS (SEQ ID NO:16).

In some embodiments, the anti-TIGIT antibody or antigen-binding fragment thereof, wherein the antibody is selected from a humanized antibody, a chimeric antibody, a bispecific antibody, a heteroconjugate antibody, and an immunotoxin.

In some embodiments, the anti-TIGIT antibody or antigen-binding fragment thereof comprises at least one HVR is at least 90% identical to an HVR set forth in any of KSSQSLYYSGVKENLLA (SEQ ID NO:1), ASIRFT (SEQ ID NO:2), QQGINNPLT (SEQ ID NO:3), GFTFSSFTMH (SEQ ID NO:4), FIRSGSGIVFYADAVRG (SEQ ID NO:5), and RPLGHNTFDS (SEQ ID NO:6) or RSSQSLVNSYGNTFLS (SEQ ID NO:7), GISNRFS (SEQ ID NO:8), LQGTHQPPT (SEQ ID NO:9), GYSFTGHLMN (SEQ ID NO:10), LIIPYNGGTSYNQKFKG (SEQ ID NO:11), and GLRGFYAMDY (SEQ ID NO:12).

In some embodiments, the anti-TIGIT antibody or fragment thereof comprises the light chain and/or heavy chain comprising amino acid sequences at least 90% identical to the amino acid sequences set forth in DIVMTQSPSSLAVSPGEKVTMTCKSSQSLYYSGVKENLLAWYQQKPGQS PKLLIYYASIRFTGVPDRFTGSGSGTDYTLTITSVQAEDMGQYFCQQGINNPLTFGDGTK LEIKR (SEQ ID NO:13) or DVVLTQTPLSLSVSFGDQVSISCRSSQSLVNSYGNTFLSWYLHKPGQSPQLLIFGISNRFS GVPDRFSGSGSGTDFTLKISTIKPEDLGMYYCLQGTHQPPTFGPGTKLEVK (SEQ ID NO:14), or EVQLVESGGGLTQPGKSLKLSCEASGFTFSSFTMHWVRQSPGKGLEWVAFIRSGSGIVF YADAVRGRFTISRDNAKNLLFLQMNDLKSEDTAMYYCARRPLGHNTFDSWGQGTLVT VSS (SEQ ID NO:15) or EVQLQQSGPELVKPGTSMKISCKASGYSFTGHLMN-WVKQSHGKNLEWIGLIIPYNGGTS YNQKFKG-KATLTVDKSSSTAYMELLSLTSDDSAVYFCSRGLRG-FYAMDYWGQGTSVT VSS (SEQ ID NO:16), respectively.

In some embodiments, the PD-1 axis binding antagonist is selected from the group consisting of a PD-1 binding antagonist, a PD-L1 binding antagonist and a PD-L2 binding antagonist.

In some embodiments, the PD-1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an antibody. In some embodiments, the PD-1 binding antagonist is MDX-1106 (nivolumab). In some embodiments, the PD-1 binding antagonist is Merck 3475 (lambrolizumab). In some embodiments, the PD-1 binding antagonist is CT-011 (pidilizumab). In some embodiments, the PD-1 binding antagonist is AMP-224.

In some embodiments, the PD-1 axis binding antagonist is a PD-L1 binding antagonist. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an antibody.

In some embodiments, the PD-L1 binding antagonist is selected from the group consisting of: YW243.55.S70, MPDL3280A, MDX-1105 and MEDI 4736.

In some embodiments, the anti-PD-L1 antibody comprises a heavy chain comprising HVR-H1 sequence of GFTFSDSWIH (SEQ ID NO:17), HVR-H2 sequence of AWISPYGGSTYYADSVKG (SEQ ID NO:18), and HVR-H3 sequence of RHWPGGFDY (SEQ ID NO:19); and a light chain comprising HVR-L1 sequence of RASQDVSTAVA (SEQ ID NO:20), HVR-L2 sequence of SASFLYS (SEQ ID NO:21), and HVR-L3 sequence of QQYLYHPAT (SEQ ID NO:22).

In some embodiments, the anti-PD-L1 antibody comprises a heavy chain variable region comprising the amino acid sequence of EVQLVESGGGLVQPGGSLRLSCAAS-GFTFSDSWIHWVRQAPGKGLEWVAWISPYGGST YYADSVKGRFTISADTSKNTAYLQMNSLRAED-TAVYYCARRHWPGGFDYWGQGTLVT VSA (SEQ ID NO:23) and a light chain variable region comprising the amino acid sequence of DIQMTQSPSSLSASVGDRVTIT-CRASQDVSTAVAWYQQKPGKAPKLLIYSASFLYS-GVPS RFSGSGSGTDFTLTISSLQPEDFATYYCQQY-LYHPATFGQGTKVEIKR (SEQ ID NO:24).

In some embodiments, the PD-1 axis binding antagonist is a PD-L2 binding antagonist. In some embodiments, the PD-L2 binding antagonist is an antibody. In some embodiments, the PD-L2 binding antagonist is an immunoadhesin.

In some embodiments, the cancer being treated is selected from the group consisting of non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies.

In some embodiments, the agent that decreases or inhibits TIGIT expression and/or activity is administered continuously. In some embodiments, the agent that decreases or inhibits TIGIT expression and/or activity is administered intermittently. In some embodiments, the agent that decreases or inhibits TIGIT expression and/or activity is administered before the PD-1 axis binding antagonist. In some embodiments, the agent that decreases or inhibits TIGIT expression and/or activity is administered simultaneous with the PD-1 axis binding antagonist. In some embodiments, the agent that decreases or inhibits TIGIT expression and/or activity is administered after the PD-1 axis binding antagonist.

Also provided herein are kits comprising a PD-1 axis binding antagonist and a package insert comprising instructions for using the PD-1 axis binding antagonist in combination with an agent that decreases or inhibits TIGIT expression and/or activity to treat or delay progression of cancer in an individual.

Also provided herein are kits comprising a PD-1 axis binding antagonist and an agent that decreases or inhibits TIGIT expression and/or activity, and a package insert comprising instructions for using the PD-1 axis binding antagonist and the agent that decreases or inhibits TIGIT expression and/or activity to treat or delay progression of cancer in an individual.

Also provided herein are kits comprising an agent that decreases or inhibits TIGIT expression and/or activity and a package insert comprising instructions for using the agent that decreases or inhibits TIGIT expression and/or activity in combination with a PD-1 axis binding antagonist to treat or delay progression of cancer in an individual.

Also provided herein are kits comprising a PD-1 axis binding antagonist and a package insert comprising instructions for using the PD-1 axis binding antagonist in combination with an agent that decreases or inhibits TIGIT expression and/or activity to enhance immune function of an individual having cancer.

Also provided herein are kits comprising a PD-1 axis binding antagonist and an agent that decreases or inhibits TIGIT expression and/or activity, and a package insert comprising instructions for using the PD-1 axis binding antagonist and the agent that decreases or inhibits TIGIT expression and/or activity to enhance immune function of an individual having cancer.

Also provided herein are kits comprising an agent that decreases or inhibits TIGIT expression and/or activity and a package insert comprising instructions for using the agent that decreases or inhibits TIGIT expression and/or activity in combination with a PD-1 axis binding antagonist to enhance immune function of an individual having cancer.

Also provided herein are kits comprising a PD-1 axis binding antagonist and a package insert comprising instructions for using the PD-1 axis binding antagonist in combination with an agent that modulates the CD226 expression and/or activity to treat or delay progression of cancer in an individual.

Also provided herein are kits comprising a PD-1 axis binding antagonist and an agent that modulates the CD226 expression and/or activity, and a package insert comprising instructions for using the PD-1 axis binding antagonist and the agent that modulates the CD226 expression and/or activity to treat or delay progression of cancer in an individual.

Also provided herein are kits comprising an agent that modulates the CD226 expression and/or activity and a package insert comprising instructions for using the agent modulates the CD226 expression and/or activity in combination with a PD-1 axis binding antagonist to treat or delay progression of cancer in an individual.

Also provided herein are kits comprising a PD-1 axis binding antagonist and a package insert comprising instructions for using the PD-1 axis binding antagonist in combination with an agent that modulates the CD226 expression and/or activity to enhance immune function of an individual having cancer.

Also provided herein are kits comprising a PD-1 axis binding antagonist and an agent that modulates the CD226 expression and/or activity, and a package insert comprising instructions for using the PD-1 axis binding antagonist and the agent that modulates the CD226 expression and/or activity to enhance immune function of an individual having cancer.

Also provided herein are kits comprising an agent modulates the CD226 expression and/or activity and a package insert comprising instructions for using the agent that modulates the CD226 expression and/or activity in combination with a PD-1 axis binding antagonist to enhance immune function of an individual having cancer.

In some embodiments, the kits comprising the PD-1 axis binding antagonist is an anti-PD-L1 antibody. In some embodiments, the kits comprising the PD-1 axis binding antagonist is an anti-PD-1 antibody. In some embodiments, the kits comprising the agent that decreases or inhibits TIGIT expression and/or activity is selected from the group consisting of an antagonist of TIGIT expression and/or activity, an antagonist of PVR expression and/or activity, and an agent that inhibits the interaction and/or the intracellular signaling mediated by TIGIT binding to PVR. In some embodiments, the kits comprising the antagonist of TIGIT expression and/or activity is an anti-TIGIT antibody or antigen-binding fragment thereof.

In some embodiments, the kits comprises an agent that modulates the CD226 expression and/or activity which is capable of increasing and/or stimulating CD226 expression and/or activity. In some embodiments, the kits comprising the agent that modulates the CD226 expression and/or activity is selected from an agent that inhibits and/or blocks the interaction of CD226 with TIGIT, an antagonist of TIGIT expression and/or activity, an antagonist of PVR expression and/or activity, an agent that inhibits and/or blocks the interaction of TIGIT with PVR, an agent that inhibits and/or blocks the intracellular signaling mediated by TIGIT binding to PVR. In some embodiments, the kits comprising the agent that inhibits and/or blocks the interaction of CD226 with TIGIT and/or the antagonist of TIGIT expression and/or activity is an anti-TIGIT antibody or antigen-binding fragment thereof.

In certain aspects, the present disclosure provides a method for treating or delaying progression of cancer in an individual comprising administering to the individual an effective amount of a PD-1 axis binding antagonist and an agent that decreases or inhibits TIGIT expression and/or activity. In other aspects, the present disclosure provides use of an effective amount of a PD-1 axis binding antagonist in the manufacture of a medicament for treating or delaying progression of cancer in an individual, wherein the PD-1 axis binding agent is used in combination with an agent that decreases or inhibits TIGIT expression and/or activity. In other aspects, the present disclosure provides use of an effective amount of an agent that decreases or inhibits TIGIT expression and/or activity in the manufacture of a medicament for treating or delaying progression of cancer in an individual, wherein the an agent that decreases or inhibits TIGIT expression and/or activity is used in combination with a PD-1 axis binding antagonist. In other aspects, the present disclosure provides a pharmaceutical composition comprising a PD-1 axis binding antagonist for use in treating or delaying progression of cancer in combination with an agent that decreases or inhibits TIGIT expression and/or activity. In other aspects, the present disclosure provides a pharmaceutical composition comprising an agent that decreases or inhibits TIGIT expression and/or activity for use in treating or delaying progression of cancer in combination with a PD-1 axis binding antagonist.

In other aspects, the present disclosure provides a method for reducing or inhibiting cancer relapse or cancer progression in an individual comprising administering to the individual an effective amount of a PD-1 axis binding antagonist and an agent that decreases or inhibits TIGIT expression and/or activity. In other aspects, the present disclosure provides use of an effective amount of a PD-1 axis binding antagonist in the manufacture of a medicament for reducing or inhibiting cancer relapse or cancer progression in an individual, wherein the PD-1 axis binding agent is used in combination with an agent that decreases or inhibits TIGIT expression and/or activity. In other aspects, the present disclosure provides use of an effective amount of an agent that decreases or inhibits TIGIT expression and/or activity in the manufacture of a medicament for reducing or inhibiting cancer relapse or cancer progression in an individual, wherein the agent that decreases or inhibits TIGIT expression and/or activity is used in combination with a PD-1 axis binding antagonist. In other aspects, the present disclosure provides a pharmaceutical composition comprising a PD-1 axis binding antagonist for use in reducing or inhibiting cancer relapse or cancer progression in combination with an agent that decreases or inhibits TIGIT expression and/or activity. In other aspects, the present disclosure provides a pharmaceutical composition comprising an agent that decreases or inhibits TIGIT expression and/or activity for use in reducing or inhibiting cancer relapse or cancer progression in combination with a PD-1 axis binding antagonist.

In other aspects, the present disclosure provides a method for treating or delaying progression of an immune related disease in an individual comprising administering to the individual an effective amount of a PD-1 axis binding antagonist and an agent that decreases or inhibits TIGIT expression and/or activity. In other aspects, the present disclosure provides use of an effective amount of a PD-1 axis binding antagonist in the manufacture of a medicament for treating or delaying progression of an immune related disease in an individual, wherein the PD-1 axis binding agent is used in combination with an agent that decreases or inhibits TIGIT expression and/or activity. In other aspects, the present disclosure provides use of an effective amount of an agent that decreases or inhibits TIGIT expression and/or activity in the manufacture of a medicament for treating or delaying progression of an immune related disease in an individual, wherein the agent that decreases or inhibits TIGIT expression and/or activity is used in combination with a PD-1 axis binding antagonist. In other aspects, the present disclosure provides a pharmaceutical composition comprising a PD-1 axis binding antagonist for use in treating or delaying progression of an immune related disease in combination with an agent that decreases or inhibits TIGIT expression and/or activity. In other aspects, the present disclosure provides a pharmaceutical composition comprising an agent that decreases or inhibits TIGIT expression and/or activity for use in treating or delaying progression of an immune related disease in combination with a PD-1 axis binding antagonist.

In other aspects, the present disclosure provides a combination comprising an effective amount of a PD-1 axis binding antagonist and an agent that decreases or inhibits TIGIT expression and/or activity.

In other aspects, the present disclosure provides a method for reducing or inhibiting progression of an immune related disease in an individual comprising administering to the individual an effective amount of a PD-1 axis binding antagonist and an agent that decreases or inhibits TIGIT expression and/or activity. In other aspects, the present disclosure provides use of an effective amount of a PD-1 axis binding antagonist in the manufacture of a medicament for reducing or inhibiting progression of an immune related disease in an individual, wherein the PD-1 axis binding agent is used in combination with an agent that decreases or inhibits TIGIT expression and/or activity. In other aspects, the present disclosure provides use of an effective amount of an agent that decreases or inhibits TIGIT expression and/or activity in the manufacture of a medicament for reducing or inhibiting progression of an immune related disease in an individual, wherein the agent that decreases or inhibits TIGIT expression and/or activity is used in combination with a PD-1 axis binding antagonist. In other aspects, the present disclosure provides a pharmaceutical composition comprising a PD-1 axis binding antagonist for use in reducing or inhibiting progression of an immune related disease in combination with an agent that decreases or inhibits TIGIT expression and/or activity. In other aspects, the present disclosure provides a pharmaceutical composition comprising an agent that decreases or inhibits TIGIT expression and/or activity for use in reducing or inhibiting progression of an immune related disease in combination with a PD-1 axis binding antagonist.

In certain embodiments that may be combined with any of the preceding embodiments, the immune related disease is associated with a T cell dysfunctional disorder. In certain embodiments that may be combined with any of the preceding embodiments, the immune related disease is a viral infection. In certain embodiments that may be combined with any of the preceding embodiments, the viral infection is a chronic viral infection. In certain embodiments that may be combined with any of the preceding embodiments, the T cell dysfunctional disorder is characterized by decreased responsiveness to antigenic stimulation. In certain embodiments that may be combined with any of the preceding embodiments, the T cell dysfunctional disorder is characterized by T cell anergy or decreased ability to secrete cytokines, proliferate or execute cytolytic activity. In certain embodiments that may be combined with any of the preceding embodiments, the T cell dysfunctional disorder is characterized by T cell exhaustion. In certain embodiments that may be combined with any of the preceding embodiments, the T cells are CD4+ and CD8+ T cells. In certain embodiments that may be combined with any of the preceding embodiments, the immune related disease is selected from the group consisting of unresolved acute infection, chronic infection, and tumor immunity.

In other aspects, the present disclosure provides a method of increasing, enhancing or stimulating an immune response or function in an individual comprising administering to the individual an effective amount of a PD-1 axis binding antagonist and an agent that decreases or inhibits TIGIT expression and/or activity. In other aspects, the present disclosure provides use of an effective amount of a PD-1 axis binding antagonist in the manufacture of a medicament for enhancing or stimulating an immune response or function in an individual, wherein the PD-1 axis binding agent is used in combination with an agent that decreases or inhibits TIGIT expression and/or activity. In other aspects, the present disclosure provides use of an effective amount of an agent that decreases or inhibits TIGIT expression and/or activity in the manufacture of a medicament for enhancing or stimulating an immune response or function in an individual, wherein the agent that decreases or inhibits TIGIT expression and/or activity is used in combination with a PD-1 axis binding antagonist. In other aspects, the present disclosure provides a pharmaceutical composition comprising a PD-1 axis binding antagonist for use in enhancing or stimulating an immune response or function in combination with an agent that decreases or inhibits TIGIT expression and/or activity. In other aspects, the present disclosure provides a pharmaceutical composition comprising an agent that decreases or inhibits TIGIT expression and/or activity for use in enhancing or stimulating an immune response or function in combination with a PD-1 axis binding antagonist. In other aspects, the present disclosure provides a combination comprising an effective amount of a PD-1 axis binding antagonist and an agent that decreases or inhibits TIGIT expression and/or activity.

In other aspects, the present disclosure provides a method of treating or delaying progression of cancer in an individual comprising administering to the individual an effective amount of a PD-1 axis binding antagonist and an agent that modulates CD226 expression and/or activity. In other aspects, the present disclosure provides use of an effective amount of a PD-1 axis binding antagonist in the manufacture of a medicament for treating or delaying progression of cancer in an individual, wherein the PD-1 axis binding agent is used in combination with an agent that modulates CD226 expression and/or activity. In other aspects, the present disclosure provides use of an effective amount of an agent that modulates CD226 expression and/or activity in the manufacture of a medicament for treating or delaying progression of cancer in an individual, wherein the agent that modulates CD226 expression and/or activity is used in combination with a PD-1 axis binding antagonist. In other aspects, the present disclosure provides a pharmaceutical composition comprising a PD-1 axis binding antagonist for use in treating or delaying progression of cancer in combination with an agent that modulates CD226 expression and/or activity. In other aspects, the present disclosure provides a pharmaceutical composition comprising an agent that modulates CD226 expression and/or activity for use in treating or delaying progression of cancer in combination with a PD-1 axis binding antagonist.

In other aspects, the present disclosure provides a method for reducing or inhibiting cancer relapse or cancer progression in an individual comprising administering to the individual an effective amount of a PD-1 axis binding antagonist and an agent that modulates CD226 expression and/or activity. In other aspects, the present disclosure provides use of an effective amount of a PD-1 axis binding antagonist in the manufacture of a medicament for reducing or inhibiting cancer relapse or cancer progression in an individual, wherein the PD-1 axis binding agent is used in combination with an agent that modulates CD226 expression and/or activity. In other aspects, the present disclosure provides use of an effective amount of an agent that modulates CD226 expression and/or activity in the manufacture of a medicament for reducing or inhibiting cancer relapse or cancer progression in an individual, wherein the agent that modulates CD226 expression and/or activity is used in combination with a PD-1 axis binding antagonist. In other aspects, the present disclosure provides a pharmaceutical composition comprising a PD-1 axis binding antagonist for use in reducing or inhibiting cancer relapse or cancer progression in combination with an agent that modulates CD226 expression and/or activity. In other aspects, the present disclosure provides a pharmaceutical composition comprising an agent that modulates CD226 expression and/or activity for use in reducing or inhibiting cancer relapse or cancer progression in combination with a PD-1 axis binding antagonist.

In other aspects, the present disclosure provides a method for treating or delaying progression of an immune related disease in an individual comprising administering to the individual an effective amount of a PD-1 axis binding antagonist and an agent that modulates CD226 expression and/or activity. In other aspects, the present disclosure provides use of an effective amount of a PD-1 axis binding antagonist in the manufacture of a medicament for treating or delaying progression of an immune related disease in an individual, wherein the PD-1 axis binding agent is used in combination with an agent that modulates CD226 expression and/or activity. In other aspects, the present disclosure provides use of an effective amount of an agent that modulates CD226 expression and/or activity in the manufacture of a medicament for treating or delaying progression of an immune related disease in an individual, wherein the agent that modulates CD226 expression and/or activity is used in combination with a PD-1 axis binding antagonist. In other aspects, the present disclosure provides a pharmaceutical composition comprising a PD-1 axis binding antagonist for use in treating or delaying progression of an immune related disease in combination with an agent that modulates CD226 expression and/or activity. In other aspects, the present disclosure provides a pharmaceutical composition comprising an agent that modulates CD226 expression and/or activity for use in treating or delaying progression of an immune related disease in combination with a PD-1 axis binding antagonist.

In other aspects, the present disclosure provides a combination comprising an effective amount of a PD-1 axis binding antagonist and an agent that modulates CD226 expression and/or activity.

In other aspects, the present disclosure provides a method for reducing or inhibiting progression of an immune related disease in an individual comprising administering to the individual an effective amount of a PD-1 axis binding antagonist and an agent that modulates CD226 expression and/or activity. In other aspects, the present disclosure provides use of an effective amount of a PD-1 axis binding antagonist in the manufacture of a medicament for reducing or inhibiting progression of an immune related disease in an individual, wherein the PD-1 axis binding agent is used in combination with an agent that modulates CD226 expression and/or activity. In other aspects, the present disclosure provides use of an effective amount of an agent that modulates CD226 expression and/or activity in the manufacture of a medicament for reducing or inhibiting progression of an immune related disease in an individual, wherein the agent that modulates CD226 expression and/or activity is used in combination with a PD-1 axis binding antagonist. In other aspects, the present disclosure provides a pharmaceutical composition comprising a PD-1 axis binding antagonist for use in reducing or inhibiting progression of an immune related disease in combination with an agent that modulates CD226 expression and/or activity. In other aspects, the present disclosure provides a pharmaceutical composition comprising an agent that modulates CD226 expression and/or activity for use in reducing or inhibiting progression of an immune related disease in combination with a PD-1 axis binding antagonist.

In certain embodiments that may be combined with any of the preceding embodiments, the immune related disease is associated with a T cell dysfunctional disorder. In certain embodiments that may be combined with any of the preceding embodiments, the immune related disease is a viral infection. In certain embodiments that may be combined with any of the preceding embodiments, the viral infection is a chronic viral infection. In certain embodiments that may be combined with any of the preceding embodiments, the T cell dysfunctional disorder is characterized by decreased responsiveness to antigenic stimulation. In certain embodiments that may be combined with any of the preceding embodiments, the T cell dysfunctional disorder is characterized by T cell anergy, or decreased ability to secrete cytokines, proliferate or execute cytolytic activity. In certain embodiments that may be combined with any of the preceding embodiments, the T cell dysfunctional disorder is characterized by T cell exhaustion. In certain embodiments that may be combined with any of the preceding embodiments, the T cells are CD4+ and CD8+ T cells. In certain embodiments that may be combined with any of the preceding embodiments, the immune related disease is selected from the group consisting of unresolved acute infection, chronic infection and tumor immunity.

In other aspects, the present disclosure provides a method of increasing, enhancing, or stimulating an immune response or function in an individual comprising administering to the individual an effective amount of a PD-1 axis binding antagonist and an agent that modulates CD226 expression and/or activity. In other aspects, the present disclosure provides use of an effective amount of a PD-1 axis binding antagonist in the manufacture of a medicament for enhancing or stimulating an immune response or function in an individual, wherein the PD-1 axis binding agent is used in combination with an agent that modulates CD226 expression and/or activity. In other aspects, the present disclosure provides use of an effective amount of an agent that modulates CD226 expression and/or activity in the manufacture of a medicament for enhancing or stimulating an immune response or function in an individual, wherein the an agent that modulates CD226 expression and/or activity is used in combination with a PD-1 axis binding antagonist. In other aspects, the present disclosure provides a pharmaceutical composition comprising a PD-1 axis binding antagonist for use in enhancing or stimulating an immune response or function in combination with an agent that modulates CD226 expression and/or activity. In other aspects, the present disclosure provides a pharmaceutical composition comprising an agent that modulates CD226 expression and/or activity for use in enhancing or stimulating an immune response or function in combination with a PD-1 axis binding antagonist. In other aspects, the present disclosure provides a combination comprising an effective amount of a PD-1 axis binding antagonist and an agent that modulates CD226 expression and/or activity.

In certain embodiments that may be combined with any of the preceding embodiments, the agent that modulates CD226 expression and/or activity is an agent that increases and/or stimulates CD226 expression and/or activity. In certain embodiments that may be combined with any of the preceding embodiments, the agent that modulates CD226 expression and/or activity is an agent that increases and/or stimulates the interaction of CD226 with PVR. In certain embodiments that may be combined with any of the preceding embodiments, the agent that modulates CD226 expression and/or activity is an agent that increases and/or stimulates the intracellular signaling mediated by CD226 binding to PVR. In certain embodiments that may be combined with any of the preceding embodiments, the agent that modulates CD226 expression and/or activity is selected from the group consisting of an agent that inhibits and/or blocks the interaction of CD226 with TIGIT, an antagonist of TIGIT expression and/or activity, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, an agent that inhibits and/or blocks the intracellular signaling mediated by TIGIT binding to PVRL3, and combinations thereof. In certain embodiments that may be combined with any of the preceding embodiments, the agent that modulates CD226 expression and/or activity is an agent that inhibits and/or blocks the interaction of CD226 with TIGIT. In certain embodiments that may be combined with any of the preceding embodiments, the agent that inhibits and/or blocks the interaction of CD226 with TIGIT is a small molecule inhibitor, an inhibitory antibody or antigen-binding fragment thereof, an aptamer, an inhibitory nucleic acid, or an inhibitory polypeptide. In certain embodiments that may be combined with any of the preceding embodiments, the agent that inhibits and/or blocks the interaction of CD226 with TIGIT is an anti-TIGIT antibody or antigen-binding fragment thereof. In certain embodiments that may be combined with any of the preceding embodiments, the agent that inhibits and/or blocks the interaction of CD226 with TIGIT is an inhibitory nucleic acid selected from the group consisting of an antisense polynucleotide, an interfering RNA, a catalytic RNA, and an RNA-DNA chimera. In certain embodiments that may be combined with any of the preceding embodiments, the antisense polynucleotide targets TIGIT. In certain embodiments that may be combined with any of the preceding embodiments, the interfering RNA targets TIGIT. In certain embodiments that may be combined with any of the preceding embodiments, the catalytic RNA targets TIGIT. In certain embodiments that may be combined with any of the preceding embodiments, the RNA-DNA chimera targets TIGIT. In certain embodiments that may be combined with any of the preceding embodiments, the agent that modulates CD226 expression and/or activity is an antagonist of TIGIT expression and/or activity. In certain embodiments that may be combined with any of the preceding embodiments, the antagonist of TIGIT expression and/or activity is a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the antagonist of TIGIT expression and/or activity is an anti-TIGIT antibody or antigen-binding fragment thereof. In certain embodiments that may be combined with any of the preceding embodiments, the antagonist of TIGIT expression and/or activity is an inhibitory nucleic acid selected from the group consisting of an antisense polynucleotide, an interfering RNA, a catalytic RNA, and an RNA-DNA chimera. In certain embodiments that may be combined with any of the preceding embodiments, the antagonist of PVR expression and/or activity is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVR is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVRL2 is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVRL3 is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the intracellular signaling mediated by TIGIT binding to PVR is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVRL2 is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVRL3 is selected from the group consisting of a small molecule inhibitor, an inhibitory antibody or antigen-binding fragment thereof, an aptamer, an inhibitory nucleic acid, and an inhibitory polypeptide.

In other aspects, the present disclosure provides a method of increasing, enhancing, or stimulating an immune response or function in an individual comprising administering to the individual an effective amount of an agent that decreases or inhibits TIGIT expression and/or activity and an agent that decreases or inhibits one or more additional immune co-inhibitory receptors. In other aspects, the present disclosure provides use of an effective amount of an agent that decreases or inhibits TIGIT expression and/or activity in the manufacture of a medicament for enhancing or stimulating an immune response or function in an individual, wherein the agent that decreases or inhibits TIGIT expression and/or activity is used in combination with an agent that decreases or inhibits one or more additional immune co-inhibitory receptors. In other aspects, the present disclosure provides use of an effective amount of an agent that decreases or inhibits one or more additional immune co-inhibitory receptors in the manufacture of a medicament for enhancing or stimulating an immune response or function in an individual, wherein the agent that decreases or inhibits one or more additional immune co-inhibitory receptors is used in combination with an agent that decreases or inhibits TIGIT expression and/or activity. In other aspects, the present disclosure provides a pharmaceutical composition comprising an agent that decreases or inhibits TIGIT expression and/or activity for use in enhancing or stimulating an immune response or function in combination with an agent that decreases or inhibits one or more additional immune co-inhibitory receptors. In other aspects, the present disclosure provides a pharmaceutical composition comprising an agent that decreases or inhibits one or more additional immune co-inhibitory receptors for use in enhancing or stimulating an immune response or function in combination with an agent that decreases or inhibits TIGIT expression and/or activity. In other aspects, the present disclosure provides a combination comprising an effective amount of an agent that decreases or inhibits TIGIT expression and/or activity and an agent that decreases or inhibits one or more additional immune co-inhibitory receptors. In certain embodiments that may be combined with any of the preceding embodiments, the one or more additional immune co-inhibitory receptor is selected from the group consisting of PD-1, CTLA-4, LAG3, TIM3, BTLA, VISTA, B7H4, and CD96. In certain embodiments that may be combined with any of the preceding embodiments, the one or more additional immune co-inhibitory receptor is selected from the group consisting of PD-1, CTLA-4, LAG3 and TIM3.

In other aspects, the present disclosure provides a method of increasing, enhancing, or stimulating an immune response or function in an individual comprising administering to the individual an effective amount of an agent that decreases or inhibits TIGIT expression and/or activity and an agent that increases or activates one or more additional immune co-stimulatory receptors. In other aspects, the present disclosure provides use of an effective amount of an agent that decreases or inhibits TIGIT expression and/or activity in the manufacture of a medicament for enhancing or stimulating an immune response or function in an individual, wherein the agent that decreases or inhibits TIGIT expression and/or activity is used in combination with an agent that increases or activates one or more additional immune co-stimulatory receptors. In other aspects, the present disclosure provides use of an effective amount of an a agent that increases or activates one or more additional immune co-stimulatory receptors in the manufacture of a medicament for enhancing or stimulating an immune response or function in an individual, wherein the a agent that increases or activates one or more additional immune co-stimulatory receptors is used in combination with an agent that decreases or inhibits TIGIT expression and/or activity. In other aspects, the present disclosure provides a pharmaceutical composition comprising an agent that decreases or inhibits TIGIT expression and/or activity for use in enhancing or stimulating an immune response or function in combination with an agent that increases or activates one or more additional immune co-stimulatory receptors. In other aspects, the present disclosure provides a pharmaceutical composition comprising an agent that increases or activates one or more additional immune co-stimulatory receptors for use in enhancing or stimulating an immune response or function in combination with an agent that decreases or inhibits TIGIT expression and/or activity. In other aspects, the present disclosure provides a combination comprising an effective amount of an agent that decreases or inhibits TIGIT expression and/or activity and an agent that increases or activates one or more additional immune co-stimulatory receptors. In certain embodiments that may be combined with any of the preceding embodiments, the one or more additional immune co-stimulatory receptors is selected from the group consisting of CD226, OX-40, CD28, CD27, CD137, HVEM, GITR, MICA, ICOS, NKG2D, and 2B4. In certain embodiments that may be combined with any of the preceding embodiments, the one or more additional immune co-stimulatory receptors is selected from the group consisting of CD226, OX-40, CD27, CD137, HVEM and GITR. In certain embodiments that may be combined with any of the preceding embodiments, the one or more additional immune co-stimulatory receptors is selected from the group consisting of OX-40 and CD27.

In certain embodiments that may be combined with any of the preceding embodiments, the method further comprises administering at least one chemotherapeutic agent. In certain embodiments that may be combined with any of the preceding embodiments, the individual has cancer. In certain embodiments that may be combined with any of the preceding embodiments, the individual is a human. In certain embodiments that may be combined with any of the preceding embodiments, CD4 and/or CD8 T cells in the individual have increased or enhanced priming, activation, proliferation, cytokine release and/or cytolytic activity relative to prior to the administration of the combination. In certain embodiments that may be combined with any of the preceding embodiments, the number of CD4 and/or CD8 T cells is elevated relative to prior to administration of the combination. In certain embodiments that may be combined with any of the preceding embodiments, the number of activated CD4 and/or CD8 T cells is elevated relative to prior to administration of the combination. In certain embodiments that may be combined with any of the preceding embodiments, activated CD4 and/or CD8 T cells are characterized by γ-IFN$^+$ producing CD4 and/or CD8 T cells and/or enhanced cytolytic activity relative to prior to the administration of the combination. In certain embodiments that may be combined with any of the preceding embodiments, the CD4 and/or CD8 T cells exhibit increased release of cytokines selected from the group consisting of IFN-γ, TNF-α and interleukins. In certain embodiments that may be combined with any of the preceding embodiments, the CD4 and/or CD8 T cells are effector memory T cells. In certain embodiments that may be combined with any of the preceding embodiments, the CD4 and/or CD8 effector memory T cells are characterized by γ-IFN$^+$ producing CD4 and/or CD8 T cells and/or enhanced cytolytic activity. In certain embodiments that may be combined with any of the preceding embodiments, the CD4 and/or CD8 effector memory T cells are characterized by having the expression of CD44$^{high}$ CD62L$^{low}$. In certain embodiments that may be combined with any of the preceding embodiments, the cancer has elevated levels of T cell infiltration. In certain embodiments that may be combined with any of the preceding embodiments, the agent that decreases or inhibits TIGIT expression and/or activity is selected from the group consisting of an antagonist of TIGIT expression and/or activity, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, an agent that inhibits and/or blocks the intracellular signaling mediated by TIGIT binding to PVRL3, and combinations thereof. In certain embodiments that may be combined with any of the preceding embodiments, the antagonist of TIGIT expression and/or activity is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the antagonist of PVR expression and/or activity is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVR is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVRL2 is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the interaction of TIGIT with PVRL3 is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the intracellular signaling mediated by TIGIT binding to PVR is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the intracellular signaling mediated by TIGIT binding to PVRL2 is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the agent that inhibits and/or blocks the intracellular signaling mediated by TIGIT binding to PVRL3 is selected from the group consisting of a small molecule inhibitor, an inhibitory antibody or antigen-binding fragment thereof, an aptamer, an inhibitory nucleic acid, and an inhibitory polypeptide. In certain embodiments that may be combined with any of the preceding embodiments, the antagonist of TIGIT expression and/or activity is an inhibitory nucleic acid selected from the group consisting of an antisense polynucleotide, an interfering RNA, a catalytic RNA, and an RNA-DNA chimera. In certain embodiments that may be combined with any of the preceding embodiments, the antisense polynucleotide targets TIGIT.

In certain embodiments that may be combined with any of the preceding embodiments, the interfering RNA targets TIGIT. In certain embodiments that may be combined with any of the preceding embodiments, the catalytic RNA targets TIGIT. In certain embodiments that may be combined with any of the preceding embodiments, the RNA-DNA chimera targets TIGIT. In certain embodiments that may be combined with any of the preceding embodiments, the antagonist of TIGIT expression and/or activity is an anti-TIGIT antibody or antigen-binding fragment thereof. In certain embodiments that may be combined with any of the preceding embodiments, the anti-TIGIT antibody or antigen-binding fragment thereof comprises at least one HVR comprising an amino acid sequence selected from the amino acid sequences (1) KSSQSLYYSGVKENLLA (SEQ ID NO:1), ASIRFT (SEQ ID NO:2), QQGINNPLT (SEQ ID NO:3), GFTFSSFTMH (SEQ ID NO:4), FIRSGSGIVFYADAVRG (SEQ ID NO:5), and RPLGHNTFDS (SEQ ID NO:6); or (2) RSSQSLVNSYGNTFLS (SEQ ID NO:7), GISNRFS (SEQ ID NO:8), LQGTHQPPT (SEQ ID NO:9), GYSFTGHLMN (SEQ ID NO:10), LIIPYNGGTSYNQKFKG (SEQ ID NO:11), and GLRGFYAMDY (SEQ ID NO:12). In certain embodiments that may be combined with any of the preceding embodiments, the anti-TIGIT antibody or antigen-binding fragment thereof, wherein the antibody light chain comprises the amino acid sequence set forth in DIVMTQSPSSLAVSPGEKVTMTCKSSQSLYYS-GVKENLLAWYQQKPGQS PKLLIYYASIRFTGVP-DRFTGSGSGTDYTLTITSVQAEDMGQYFCQQGIN-NPLTFGDGT KLEIKR (SEQ ID NO:13) or DVVLTQTPLSLSVSFGDQVSISCRSSQSLVNSYGNT-FLSWYLHKPGQSPQLLIFGISNRF SGVPDRFSGSGS-GTDFTLKISTIKPEDLGMYYCLQGTHQPPTFGPGT-KLEVK (SEQ ID NO:14). In certain embodiments that may be combined with any of the preceding embodiments, the anti-TIGIT antibody or antigen-binding fragment thereof, wherein the antibody heavy chain comprises the amino acid sequence set forth in EVQLVESGGGLTQPGKSLKLS-CEASGFTFSSFTMHWVRQSPGKGLEWVAFIRSGSGIV FYADAVRGRFTISRDNAKNLLFLQMNDLKSED-TAMYYCARRPLGHNTFDSWGQGTLV TVSS (SEQ ID NO:15) or EVQLQQSGPELVKPGTSMKISCKASGYSFT-GHLMNWVKQSHGKNLEWIGLIIPYNGGT SYNQKFK-GKATLTVDKSSSTAYMELLSLTSDDSAVYFCSRGL-RGFYAMDYWGQGTSV TVSS (SEQ ID NO:16). In certain embodiments that may be combined with any of the preceding embodiments, the anti-TIGIT antibody or antigen-binding fragment thereof, wherein the antibody light chain comprises the amino acid sequence set forth in DIVMTQSPSSLAVSPGEKVTMTCKSSQSLYYS-GVKENLLAWYQQKPGQS PKLLIYYASIRFTGVP-DRFTGSGSGTDYTLTITSVQAEDMGQYFCQQGIN-NPLTFGDGT KLEIKR (SEQ ID NO:13) or DVVLTQTPLSLSVSFGDQVSISCRSSQSLVNSYGNT-FLSWYLHKPGQSPQLLIFGISNRF SGVPDRFSGSGS-GTDFTLKISTIKPEDLGMYYCLQGTHQPPTFGPGT-KLEVK (SEQ ID NO:14), and the antibody heavy chain comprises the amino acid sequence set forth in EVQLVES-GGGLTQPGKSLKLSCEASGFTFSSFTMHWVRQSPGK-GLEWVAFIRSGSGIV FYADAVRGRFTISRDNAKNLL-FLQMNDLKSEDTAMYYCARRPLGHNTFDSWGQGT-LV TVSS (SEQ ID NO:15) or EVQLQQSGPELVK-PGTSMKISCKASGYSFTGHLMNWVKQSHGKN-LEWIGLIIPYNGGT SYNQKFKGKATLT-VDKSSSTAYMELLSLTSDDSAVYFCSRGLRGFYAMD-YWGQGTSV TVSS (SEQ ID NO: 16). In certain embodiments that may be combined with any of the preceding embodiments, the anti-TIGIT antibody or antigen-binding fragment thereof, wherein the antibody is selected from the group consisting of a humanized antibody, a chimeric antibody, a bispecific antibody, a heteroconjugate antibody, and an immunotoxin. In certain embodiments that may be combined with any of the preceding embodiments, the anti-TIGIT antibody or antigen-binding fragment thereof comprises at least one HVR that is at least 90% identical to an HVR set forth in any one of (1) KSSQSLYYSGVKENLLA (SEQ ID NO:1), ASIRFT (SEQ ID NO:2), QQGINNPLT (SEQ ID NO:3), GFTFSSFTMH (SEQ ID NO:4), FIRSGS-GIVFYADAVRG (SEQ ID NO:5), and RPLGHNTFDS (SEQ ID NO:6); or (2) RSSQSLVNSYGNTFLS (SEQ ID NO:7), GISNRFS (SEQ ID NO:8), LQGTHQPPT (SEQ ID NO:9), GYSFTGHLMN (SEQ ID NO:10), LIIPYNGGT-SYNQKFKG (SEQ ID NO:11), and GLRGFYAMDY (SEQ ID NO:12). In certain embodiments that may be combined with any of the preceding embodiments, the anti-TIGIT antibody or fragment thereof comprises the light chain comprising amino acid sequences at least 90% identical to the amino acid sequences set forth in DIVMTQSPSSLAVSPGEKVTMTCKSSQSLYYSGVKENLLAWYQQKPGQS PKLLIYYASIRFTGVPDRFTGSGSGTDYTLTITSVQAEDMGQYFCQQGINNPLTFGDGT KLEIKR (SEQ ID NO:13) or DVVLTQTPLSLSVSFGDQVSISCRSSQSLVNSYGNTFLSWYLHKPGQSPQLLIFGISNRF SGVPDRFSGSGSGTDFTLKISTIKPEDLGMYYCLQGTHQPPTFGPGTKLEVK (SEQ ID NO:14); and/or the heavy chain comprising amino acid sequences at least 90% identical to the amino acid sequences set forth in EVQLVESGGGLTQPGKSLKLSCEASGFTFSSFTMHWVRQSPGKGLEWVAFIRSGSGIV FYADAVRGRFTISRDNAKNLLFLQMNDLKSEDTAMYYCARRPLGHNTFDSWGQGTLV TVSS (SEQ ID NO:15) or EVQLQQSGPELVKPGTSMKISCKASGYSFTGHLMNWVKQSHGKNLEWIGLIIPYNGGT SYNQKFKGKATLTVDKSSSTAYMELLSLTSDDSAVYFCSRGLRGFYAMDYWGQGTSV TVSS (SEQ ID NO:16). In certain embodiments that may be combined with any of the preceding embodiments, the PD-1 axis binding antagonist is selected from the group consisting of a PD-1 binding antagonist, a PD-L1 binding antagonist and a PD-L2 binding antagonist. In certain embodiments that may be combined with any of the preceding embodiments, the PD-1 axis binding antagonist is a PD-1 binding antagonist. In certain embodiments that may be combined with any of the preceding embodiments, the PD-1 binding antagonist inhibits the binding of PD-1 to its ligand binding partners. In certain embodiments that may be combined with any of the preceding embodiments, the PD-1 binding antagonist inhibits the binding of PD-1 to PD-L1. In certain embodiments that may be combined with any of the preceding embodiments, the PD-1 binding antagonist inhibits the binding of PD-1 to PD-L2. In certain embodiments that may be combined with any of the preceding embodiments, the PD-1 binding antagonist inhibits the binding of PD-1 to both PD-L1 and PD-L2. In certain embodiments that may be combined with any of the preceding embodiments, the PD-1 binding antagonist is an antibody. In certain embodiments that may be combined with any of the preceding embodiments, the PD-1 binding antagonist is MDX-1106. In certain embodiments that may be combined with any of the preceding embodiments, the PD-1 binding antagonist is MK-3475. In certain embodiments that may be combined with any of the preceding embodiments, the PD-1 binding antagonist is CT-011. In certain embodiments that may be combined with any of the preceding embodiments, the PD-1 binding antagonist is AMP-224. In certain embodiments that may be combined with any of the preceding embodiments, the PD-1 axis binding antagonist is a PD-L1 binding antagonist. In certain embodiments that may be combined with any of the preceding embodiments, the PD-L1 binding antagonist inhibits the binding of PD-L1 to PD-1. In certain embodiments that may be combined with any of the preceding embodiments, the PD-L1 binding antagonist inhibits the binding of PD-L1 to B7-1. In certain embodiments that may be combined with any of the preceding embodiments, the PD-L1 binding antagonist inhibits the binding of PD-L1 to both PD-1 and B7-1. In certain embodiments that may be combined with any of the preceding embodiments, the PD-L1 binding antagonist is an anti-PD-L1 antibody. In certain embodiments that may be combined with any of the preceding embodiments, the PD-L1 binding antagonist is selected from the group consisting of YW243.55.S70, MPDL3280A, MDX-1105, and MEDI4736. In certain embodiments that may be combined with any of the preceding embodiments, the anti-PD-L1 antibody comprises a heavy chain comprising HVR-H1 sequence of GFTFSDSWIH (SEQ ID NO:17), HVR-H2 sequence of AWISPYGGSTYYADSVKG (SEQ ID NO:18), and HVR-H3 sequence of RHWPGGFDY (SEQ ID NO:19); and a light chain comprising HVR-L1 sequence of RASQDVSTAVA (SEQ ID NO:20), HVR-L2 sequence of SASFLYS (SEQ ID NO:21), and HVR-L3 sequence of QQYLYHPAT (SEQ ID NO:22). In certain embodiments that may be combined with any of the preceding embodiments, the anti-PD-L1 antibody comprises a heavy chain variable region comprising the amino acid sequence of EVQLVESGGGLVQPGGSLRLSCAASGFTFSDSWIHWVRQAPGKGLEWVAWISPYGGST YYADSVKGRFTISADTSKNTAYLQMNSLRAEDTAVYYCARRHWPGGFDYWGQGTLVT VSA (SEQ ID NO:23), EVQLVESGGGLVQPGGSLRLSCAASGFTFSDSWIHWVRQAPGKGLEWVAWISPYGGST YYADSVKGRFTISADTSKNTAYLQMNSLRAEDTAVYYCARRHWPGGFDYWGQGTLVT VSSASTK (SEQ ID NO:40), or EVQLVESGGGLVQPGGSLRLSCAASGFTFSDSWIHWVRQAPGKGLEWVAWISPYGGST YYADSVKGRFTISADTSKNTAYLQMNSLRAEDTAVYYCARRHWPGGFDYWGQGTLVT VSS (SEQ ID NO:41), and a light chain variable region comprising the amino acid sequence of DIQMTQSPSSLSASVGDRVTITCRASQDVSTAVAWYQQKPGKAPKLLIYSASFLYSGVPS RFSGSGSGTDFTLTISSLQPEDFATYYCQQYLYHPATFGQGTKVEIKR (SEQ ID NO:24). In certain embodiments that may be combined with any of the preceding embodiments, the PD-1 axis binding antagonist is a PD-L2 binding antagonist. In certain embodiments that may be combined with any of the preceding embodiments, the PD-L2 binding antagonist is an antibody. In certain embodiments that may be combined with any of the preceding embodiments, the PD-L2 binding antagonist is an immunoadhesin. In certain embodiments that may be combined with any of the preceding embodiments, the cancer is selected from the group consisting of non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies. In certain embodiments that may be combined with any of the preceding embodiments, the agent that decreases or inhibits TIGIT expression and/or activity is administered continuously. In certain embodiments that may be combined with any of the preceding embodiments, the agent that decreases or inhibits TIGIT expression and/or activity is administered intermittently. In certain embodiments that may be combined with any of the preceding embodiments, the agent that decreases or inhibits TIGIT expression and/or activity is administered before the PD-1 axis binding antagonist. In certain embodiments that may be combined with any of the preceding embodiments, the agent that decreases or inhibits TIGIT expression and/or activity is administered simultaneous with the PD-1 axis binding antagonist. In certain embodiments that may be combined with any of the preceding embodiments, the agent that decreases or inhibits TIGIT expression and/or activity is administered after the PD-1 axis binding antagonist. In certain embodiments that may be combined with any of the preceding embodiments, the PD-1 axis binding antagonist is administered before the agent that modulates CD226 expression and/or activity. In certain embodiments that may be combined with any of the preceding embodiments, the PD-1 axis binding antagonist is administered simultaneous with the agent that modulates CD226 expression and/or activity. In certain embodiments that may be combined with any of the preceding embodiments, the PD-1 axis binding antagonist is administered after the agent that modulates CD226 expression and/or activity. In certain embodiments that may be combined with any of the preceding embodiments, the agent that decreases or inhibits TIGIT expression and/or activity is administered before the agent that decreases or inhibits one or more additional immune co-inhibitory receptors. In certain embodiments that may be combined with any of the preceding embodiments, the agent that decreases or inhibits TIGIT expression and/or activity is administered simultaneous with the agent that decreases or inhibits one or more additional immune co-inhibitory receptors. In certain embodiments that may be combined with any of the preceding embodiments, the agent that decreases or inhibits TIGIT expression and/or activity is administered after the agent that decreases or inhibits one or more additional immune co-inhibitory receptors. In certain embodiments that may be combined with any of the preceding embodiments, the agent that decreases or inhibits TIGIT expression and/or activity is administered before the agent that increases or activates one or more additional immune co-stimulatory receptors. In certain embodiments that may be combined with any of the preceding embodiments, the agent that decreases or inhibits TIGIT expression and/or activity is administered simultaneous with the agent that increases or activates one or more additional immune co-stimulatory receptors. In certain embodiments that may be combined with any of the preceding embodiments, the agent that decreases or inhibits TIGIT expression and/or activity is administered after the agent that increases or activates one or more additional immune co-stimulatory receptors.

In other aspects, the present disclosure provides a kit comprising a PD-1 axis binding antagonist and a package insert comprising instructions for using the PD-1 axis binding antagonist in combination with an agent that decreases or inhibits TIGIT expression and/or activity to treat or delay progression of cancer in an individual.

In other aspects, the present disclosure provides a kit comprising a PD-1 axis binding antagonist and an agent that decreases or inhibits TIGIT expression and/or activity, and a package insert comprising instructions for using the PD-1 axis binding antagonist and the agent that decreases or inhibits TIGIT expression and/or activity to treat or delay progression of cancer in an individual.

In other aspects, the present disclosure provides a kit comprising an agent that decreases or inhibits TIGIT expression and/or activity and a package insert comprising instructions for using the agent that decreases or inhibits TIGIT expression and/or activity in combination with a PD-1 axis binding antagonist to treat or delay progression of cancer in an individual.

In other aspects, the present disclosure provides a kit comprising a PD-1 axis binding antagonist and a package insert comprising instructions for using the PD-1 axis binding antagonist in combination with an agent that decreases or inhibits TIGIT expression and/or activity to enhance immune function of an individual having cancer.

In other aspects, the present disclosure provides a kit comprising a PD-1 axis binding antagonist and an agent that decreases or inhibits TIGIT expression and/or activity, and a package insert comprising instructions for using the PD-1 axis binding antagonist and the agent that decreases or inhibits TIGIT expression and/or activity to enhance immune function of an individual having cancer.

In other aspects, the present disclosure provides a kit comprising an agent that decreases or inhibits TIGIT expression and/or activity and a package insert comprising instructions for using the agent that decreases or inhibits TIGIT expression and/or activity in combination with a PD-1 axis binding antagonist to enhance immune function of an individual having cancer.

In other aspects, the present disclosure provides a kit comprising a PD-1 axis binding antagonist and a package insert comprising instructions for using the PD-1 axis binding antagonist in combination with an agent that modulates CD226 expression and/or activity to treat or delay progression of cancer in an individual.

In other aspects, the present disclosure provides a kit comprising a PD-1 axis binding antagonist and an agent that modulates CD226 expression and/or activity, and a package insert comprising instructions for using the PD-1 axis binding antagonist and the agent that modulates CD226 expression and/or activity to treat or delay progression of cancer in an individual.

In other aspects, the present disclosure provides a kit comprising an agent that modulates CD226 expression and/or activity and a package insert comprising instructions for using the agent modulates CD226 expression and/or activity in combination with a PD-1 axis binding antagonist to treat or delay progression of cancer in an individual.

In other aspects, the present disclosure provides a kit comprising a PD-1 axis binding antagonist and a package insert comprising instructions for using the PD-1 axis binding antagonist in combination with an agent that modulates CD226 expression and/or activity to enhance immune function of an individual having cancer.

In other aspects, the present disclosure provides a kit comprising a PD-1 axis binding antagonist and an agent that modulates CD226 expression and/or activity, and a package insert comprising instructions for using the PD-1 axis binding antagonist and the agent that modulates CD226 expression and/or activity to enhance immune function of an individual having cancer.

In other aspects, the present disclosure provides a kit comprising an agent modulates CD226 expression and/or activity and a package insert comprising instructions for using the agent that modulates CD226 expression and/or activity in combination with a PD-1 axis binding antagonist to enhance immune function of an individual having cancer.

In certain embodiments that may be combined with any of the preceding embodiments, the PD-1 axis binding antagonist is an anti-PD-L1 antibody. In certain embodiments that may be combined with any of the preceding embodiments, the anti-PD-L1 antibody is selected from the group consisting of YW243.55.S70, MPDL3280A, MDX-1105 and MEDI4736. In certain embodiments that may be combined with any of the preceding embodiments, the anti-PD-L1 antibody comprises a heavy chain comprising HVR-H1 sequence of GFTFSDSWIH (SEQ ID NO:17), HVR-H2 sequence of AWISPYGGSTYYADSVKG (SEQ ID NO:18), and HVR-H3 sequence of RHWPGGFDY (SEQ ID NO:19); and a light chain comprising HVR-L1 sequence of RASQD-VSTAVA (SEQ ID NO:20), HVR-L2 sequence of SASFLYS (SEQ ID NO:21), and HVR-L3 sequence of QQYLYHPAT (SEQ ID NO:22). In certain embodiments that may be combined with any of the preceding embodiments, the anti-PD-L1 antibody comprises a heavy chain variable region comprising the amino acid sequence of EVQLVES-GGGLVQPGGSLRLSCAASGFTFSDSWIHWVRQAPG-KGLEWVAWISPYGGST YYADSVKGRFTISADTSKN-TAYLQMNSLRAEDTAVYYCARRHWPGGFDYWGQG-TLVT VSA (SEQ ID NO:23), EVQLVESGGGLVQPGG-SLRLSCAASGFTFSDSWIHWVRQAPGK-GLEWVAWISPYGGST YYADSVKGRFTISADTSKN-TAYLQMNSLRAEDTAVYYCARRHWPGGFDYWGQG-TLVT VSSASTK (SEQ ID NO:40), or EVQLVES-GGGLVQPGGSLRLSCAASGFTFSDSWIHWVRQAPG-KGLEWVAWISPYGGST YYADSVKGRFTISADTSKN-TAYLQMNSLRAEDTAVYYCARRHWPGGFDYWGQG-TLVT VSS (SEQ ID NO:41), and a light chain variable region comprising the amino acid sequence of DIQMTQSPSSLSASVGDRVTITCRASQDVSTAVAWY-QQKPGKAPKLLIYSASFLYSGVPS RFSGSGSGTD-FTLTISSLQPEDFATYYCQQYLYHPATFGQGTKVEIKR (SEQ ID NO:24). In certain embodiments that may be combined with any of the preceding embodiments, the PD-1 axis binding antagonist is an anti-PD-1 antibody. In certain embodiments that may be combined with any of the preceding embodiments, the anti-PD-1 antibody is MDX-1106, MK-3475, or CT-011. In certain embodiments that may be combined with any of the preceding embodiments, the PD-1 axis binding antagonist is AMP-224. In certain embodiments that may be combined with any of the preceding embodiments, the PD-1 axis binding antagonist is a PD-L2 binding antagonist. In certain embodiments that may be combined with any of the preceding embodiments, the PD-L2 binding antagonist is an antibody. In certain embodiments that may be combined with any of the preceding embodiments, the PD-L2 binding antagonist is an immunoadhesin.

In other aspects, the present disclosure provides a kit comprising an agent that decreases or inhibits TIGIT expression and/or activity and a package insert comprising instructions for using the agent that decreases or inhibits TIGIT expression and/or activity in combination with an agent that decreases or inhibits one or more additional immune co-inhibitory receptors to treat or delay progression of cancer in an individual. In other aspects, the present disclosure provides a kit comprising an agent that decreases or inhibits TIGIT expression and/or activity and an agent that decreases or inhibits one or more additional immune co-inhibitory receptors, and a package insert comprising instructions for using the agent that decreases or inhibits TIGIT expression and/or activity and the agent that decreases or inhibits one or more additional immune co-inhibitory receptors to treat or delay progression of cancer in an individual. In other aspects, the present disclosure provides a kit comprising an agent that decreases or inhibits one or more additional immune co-inhibitory receptors and a package insert comprising instructions for using the agent that decreases or inhibits one or more additional immune co-inhibitory receptors in combination with an agent that decreases or inhibits TIGIT expression and/or activity to treat or delay progression of cancer in an individual. In other aspects, the present disclosure provides a kit comprising an agent that decreases or inhibits TIGIT expression and/or activity and a package insert comprising instructions for using the agent that decreases or inhibits TIGIT expression and/or activity in combination with an agent that decreases or inhibits one or more additional immune co-inhibitory receptors to enhance immune function of an individual having cancer. In other aspects, the present disclosure provides a kit comprising an agent that decreases or inhibits TIGIT expression and/or activity and an agent that decreases or inhibits one or more additional immune co-inhibitory receptors, and a package insert comprising instructions for using the agent that decreases or inhibits TIGIT expression and/or activity and the agent that decreases or inhibits one or more additional immune co-inhibitory receptors to enhance immune function of an individual having cancer. In other aspects, the present disclosure provides a kit comprising an agent that decreases or inhibits one or more additional immune co-inhibitory receptors and a package insert comprising instructions for using the agent that decreases or inhibits one or more additional immune co-inhibitory receptors in combination with an agent that decreases or inhibits TIGIT expression and/or activity to enhance immune function of an individual having cancer. In certain embodiments that may be combined with any of the preceding embodiments, the one or more additional immune co-inhibitory receptor is selected from the group consisting of PD-1, CTLA-4, LAG3, TIM3, BTLA, VISTA, B7H4, and CD96. In certain embodiments that may be combined with any of the preceding embodiments, the one or more additional immune co-inhibitory receptor is selected from the group consisting of PD-1, CTLA-4, LAG3 and TIM3.

In other aspects, the present disclosure provides a kit comprising an agent that decreases or inhibits TIGIT expression and/or activity and a package insert comprising instructions for using the agent that decreases or inhibits TIGIT expression and/or activity in combination with an agent that increases or activates one or more additional immune co-stimulatory receptors to treat or delay progression of cancer in an individual. In other aspects, the present disclosure provides a kit comprising an agent that decreases or inhibits TIGIT expression and/or activity and an agent that increases or activates one or more additional immune co-stimulatory receptors, and a package insert comprising instructions for using the agent that decreases or inhibits TIGIT expression and/or activity and the agent that increases or activates one or more additional immune co-stimulatory receptors to treat or delay progression of cancer in an individual. In other aspects, the present disclosure provides a kit comprising an agent that increases or activates one or more additional immune co-stimulatory receptors and a package insert comprising instructions for using the agent that increases or activates one or more additional immune co-stimulatory receptors in combination with an agent that decreases or inhibits TIGIT expression and/or activity to treat or delay progression of cancer in an individual. In other aspects, the present disclosure provides a kit comprising an agent that decreases or inhibits TIGIT expression and/or activity and a package insert comprising instructions for using the agent that decreases or inhibits TIGIT expression and/or activity in combination with an agent that increases or activates one or more additional immune co-stimulatory receptors to enhance immune function of an individual having cancer. In other aspects, the present disclosure provides a kit comprising an agent that decreases or inhibits TIGIT expression and/or activity and an agent that increases or activates one or more additional immune co-stimulatory receptors, and a package insert comprising instructions for using the agent that decreases or inhibits TIGIT expression and/or activity and the agent that increases or activates one or more additional immune co-stimulatory receptors to enhance immune function of an individual having cancer. In other aspects, the present disclosure provides a kit comprising an agent that increases or activates one or more additional immune co-stimulatory receptors and a package insert comprising instructions for using the agent that increases or activates one or more additional immune co-stimulatory receptors in combination with an agent that decreases or inhibits TIGIT expression and/or activity to enhance immune function of an individual having cancer. In certain embodiments that may be combined with any of the preceding embodiments, the or more additional immune co-stimulatory receptor is selected from the group consisting of CD226, OX-40, CD28, CD27, CD137, HVEM, GITR, MICA, ICOS, NKG2D, and 2B4. In certain embodiments that may be combined with any of the preceding embodiments, the one or more additional immune co-stimulatory receptor is selected from the group consisting of CD226, OX-40, CD27, CD137, HVEM and GITR. In certain embodiments that may be combined with any of the preceding embodiments, the one or more additional immune co-stimulatory receptor is selected from the group consisting of OX-40 and CD27.

In certain embodiments that may be combined with any of the preceding embodiments, the individual is a human. In certain embodiments that may be combined with any of the preceding embodiments, the agent that decreases or inhibits TIGIT expression and/or activity is selected from the group consisting of an antagonist of TIGIT expression and/or activity, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, and an agent that inhibits and/or blocks the intracellular signaling mediated by TIGIT binding to PVRL3. In certain embodiments that may be combined with any of the preceding embodiments, the antagonist of TIGIT expression and/or activity is an anti-TIGIT antibody or antigen-binding fragment thereof. In certain embodiments that may be combined with any of the preceding embodiments, the agent that modulates CD226 expression and/or activity is an agent that increases and/or stimulates CD226 expression and/or activity. In certain embodiments that may be combined with any of the preceding embodiments, the agent that modulates CD226 expression and/or activity is an agent that increases and/or stimulates the interaction of CD226 with PVR. In certain embodiments that may be combined with any of the preceding embodiments, the agent that modulates CD226 expression and/or activity is an agent that increases and/or stimulates the intracellular signaling mediated by CD226 binding to PVR. In certain embodiments that may be combined with any of the preceding embodiments, the agent that modulates CD226 expression and/or activity is selected from the group consisting of an agent that inhibits and/or blocks the interaction of CD226 with TIGIT, an antagonist of TIGIT expression and/or activity, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, and an agent that inhibits and/or blocks the intracellular signaling mediated by TIGIT binding to PVRL3. In certain embodiments that may be combined with any of the preceding embodiments, the agent that modulates CD226 expression and/or activity is an agent that inhibits and/or blocks the interaction of CD226 with TIGIT. In certain embodiments that may be combined with any of the preceding embodiments, the agent that inhibits and/or blocks the interaction of CD226 with TIGIT is a small molecule inhibitor, an inhibitory antibody or antigen-binding fragment thereof, an aptamer, an inhibitory nucleic acid, or an inhibitory polypeptide. In certain embodiments that may be combined with any of the preceding embodiments, the agent that inhibits and/or blocks the interaction of CD226 with TIGIT is an anti-TIGIT antibody or antigen-binding fragment thereof. In certain embodiments that may be combined with any of the preceding embodiments, the anti-TIGIT antibody or antigen-binding fragment thereof comprises at least one HVR comprising an amino acid sequence selected from the amino acid sequences (1) KSSQSLYYSGVKENLLA (SEQ ID NO:1), ASIRFT (SEQ ID NO:2), QQGINNPLT (SEQ ID NO:3), GFTFSSFTMH (SEQ ID NO:4), FIRSGSGIVFYADAVRG (SEQ ID NO:5), and RPLGHNTFDS (SEQ ID NO:6); or (2) RSSQSLVNSYGNTFLS (SEQ ID NO:7), GISNRFS (SEQ ID NO:8), LQGTHQPPT (SEQ ID NO:9), GYSFTGHLMN (SEQ ID NO:10), LIIPYNGGTSYNQKFKG (SEQ ID NO:11), and GLRGFYAMDY (SEQ ID NO:12). In certain embodiments that may be combined with any of the preceding embodiments, the anti-TIGIT antibody or antigen-binding fragment thereof, wherein the antibody light chain comprises the amino acid sequence set forth in DIVMTQSPSSLAVSPGEKVTMTCKSSQSLYYSGVKENLLAWYQQKPGQS PKLLIYYASIRFTGVPDRFTGSGSGTDYTLTITSVQAEDMGQYFCQQGINNPLTFGDGT KLEIKR (SEQ ID NO:13) or DVVLTQTPLSLSVSFGDQVSISCRSSQSLVNSYGNTFLSWYLHKPGQSPQLLIFGISNRF SGVPDRFSGSGSGTDFTLKISTIKPEDLGMYYCLQGTHQPPTFGPGTKLEVK (SEQ ID NO:14). In certain embodiments that may be combined with any of the preceding embodiments, the anti-TIGIT antibody or antigen-binding fragment thereof, wherein the antibody heavy chain comprises the amino acid sequence set forth in EVQLVESGGGLTQPGKSLKLSCEASGFTFSSFTMHWVRQSPGKGLEWVAFIRSGSGIV FYADAVRGRFTISRDNAKNLLFLQMNDLKSEDTAMYYCARRPLGHNTFDSWGQGTLV TVSS (SEQ ID NO:15) or EVQLQQSGPELVKPGTSMKISCKASGYSFTGHLMNWVKQSHGKNLEWIGLIIPYNGGT SYNQKFKGKATLTVDKSSSTAYMELLSLTSDDSAVYFCSRGLRGFYAMDYWGQGTSV TVSS (SEQ ID NO:16). In certain embodiments that may be combined with any of the preceding embodiments, the anti-TIGIT antibody or antigen-binding fragment thereof, wherein the antibody light chain comprises the amino acid sequence set forth in DIVMTQSPSSLAVSPGEKVTMTCKSSQSLYYSGVKENLLAWYQQKPGQS PKLLIYYASIRFTGVPDRFTGSGSGTDYTLTITSVQAEDMGQYFCQQGINNPLTFGDGT KLEIKR (SEQ ID NO:13) or DVVLTQTPLSLSVSFGDQVSISCRSSQSLVNSYGNTFLSWYLHKPGQSPQLLIFGISNRF SGVPDRFSGSGSGTDFTLKISTIKPEDLGMYYCLQGTHQPPTFGPGTKLEVK (SEQ ID NO:14), and the antibody heavy chain comprises the amino acid sequence set forth in EVQLVESGGGLTQPGKSLKLSCEASGFTFSSFTMHWVRQSPGKGLEWVAFIRSGSGIV FYADAVRGRFTISRDNAKNLLFLQMNDLKSEDTAMYYCARRPLGHNTFDSWGQGTLV TVSS (SEQ ID NO:15) or EVQLQQSGPELVKPGTSMKISCKASGYSFTGHLMNWVKQSHGKNLEWIGLIIPYNGGT SYNQKFKGKATLTVDKSSSTAYMELLSLTSDDSAVYFCSRGLRGFYAMDYWGQGTSV TVSS (SEQ ID NO: 16).

BRIEF DESCRIPTION OF THE DRAWINGS

FIGS. 1A-1D show that TIGIT is highly expressed on exhausted CD8+ and CD4+ T cells. FIG. 1A depicts MACS-enriched C57BL6/J splenic CD8+ T cells that were stimulated with plate-bound anti-CD3 and anti-CD28 for 24-48 hours in vitro. Flow cytometry histograms representative of TIGIT expression (red) relative to isotype staining (gray). Quantitation of TIGIT MFI is also shown. *, P<0.001. Data are representative of 2 independent experiments; n=3. In FIGS. 1B-1C, C57BL6/J mice were infected with Armstrong strain LCMV, and splenocytes were analyzed 7 days after infection. Data are representative of 2 independent experiments; n=5. FIG. 1B shows flow cytometry histogram representative of TIGIT expression by nave (CD44$^{low}$/CD62L$^{high}$) and effector memory (CD44$^{high}$ CD62L$^{low}$) CD4+ and CD8+ T cells. Quantitation of TIGIT MFI is also shown. *, P<0.001. FIG. 1C shows flow cytometry histogram representative of TIGIT expression by PD-1$^{high}$ and PD-1$^{low}$ effector memory CD8+ T cells. Quantitation of TIGIT MFI is also shown. *, P<0.001. FIG. 1D shows that C57BL6/J mice were briefly depleted of CD4+ T cells and infected with Clone 13 strain LCMV. Splenocytes were analyzed 42 days after infection. Flow cytometry histogram representative of TIGIT expression by naïve (CD44$^{low}$/CD62L$^{high}$), central memory (CD44$^{high}$ CD62L$^{high}$), and effector memory (CD44$^{high}$ CD62L$^{low}$) CD8+ T cells. Quantitation of TIGIT MFI is also shown. *, P<0.001. Data are representative of 2 independent experiments; n=5. Error bars depict the standard error of the mean.

FIGS. 3A-3D show that TIGIT-deficient CD8+ and CD4+ T cells respond normally to acute viral infection. TIGIT$^{fl/fl}$ CD4$^{cre}$ (CKO) and TIGIT$^{fl/fl}$ littermates (WT) were infected with Armstrong strain LCMV. Splenocytes were analyzed 7 days after infection. Data are representative of two independent experiments; n=5. FIG. 3A shows representative FACS plots gated on CD8+ T cells, with activated (CD44$^{high}$) cells boxed. Quantitation of activated CD8+ T cells as a percentage of total CD8+ T cells. FIG. 3B shows representative FACS plots gated on CD8+ T cells after stimulation in vitro, with IFNg-producing cells boxed. Quantitation of IFNg-producing cells as a percentage of total CD8+ T cells. FIG. 3C shows representative FACS plots gated on CD4+ T cells, with activated (CD44$^{high}$) cells boxed. Quantitation of activated CD4+ T cells as a percentage of total CD4+ T cells. FIG. 3D shows representative FACS plots gated on CD4+ T cells after stimulation in vitro, with IFNg-producing cells boxed. Quantitation of IFNg-producing cells as a percentage of total CD4+ T cells. Error bars depict the standard error of the mean.

FIGS. 4A-4H show that TIGIT and PD-1 synergistically regulate the effector function of exhausted T cells in vivo. In FIGS. 4A-4E, TIGIT$^{fl/fl}$ CD4-cre− (WT) and TIGIT$^{fl/fl}$ CD4-cre+ (CKO) mice were briefly depleted of CD4+ T cells and infected with Clone 13 strain LCMV. Splenocytes and liver viral titers were analyzed 42 days after infection. Data are representative of 2 independent experiments, and n=6-9 per group. FIG. 4A depicts representative FACS plots gated on CD8+ T cells, with activated cells (CD44$^{high}$ CD62L$^{low}$) boxed. Quantitation of activated cells as a percentage of total CD8+ T cells. FIG. 4B depicts representative FACS plots gated on CD8+ T cells after stimulation in vitro, with IFNγ+ cells boxed. Quantitation of IFNγ-producing cells as a percentage of CD8+ T cells. FIG. 4C depicts representative FACS plots gated on CD4+ T cells, with activated cells (CD44$^{high}$ CD62L$^{low}$) boxed. Quantitation of activated cells as a percentage of total CD4+ T cells. FIG. 4D depicts representative FACS plots gated on CD4+ T cells after stimulation in vitro, with IFNγ+ cells boxed. Quantitation of IFNγ-producing cells as a percentage of CD4+ T cells. FIG. 4E depicts quantitation of liver LCMV titers. *, P<0.0001. In FIGS. 4F-4H, C57BL6/J mice were briefly depleted of CD4+ T cells and infected with Clone 13 strain LCMV. Mice were treated with isotype-matched control, anti-PD-L1, anti-TIGIT, or anti-PD-L1+anti-TIGIT antibodies starting 28 days after infection. Splenocytes and liver viral titers were analyzed 42 days after infection. Data are representative of 2 independent experiments; n=10. FIG. 4F depicts representative FACS plots gated on CD8+ T cells, with activated cells (CD44$^{high}$ CD62L$^{low}$) boxed. Quantitation of activated cells as a percentage of total CD8+ T cells. *, P<0.0001. FIG. 4G depicts representative FACS plots gated on activated CD8+ T cells after stimulation in vitro, with IFNγ+ cells boxed. Quantitation of IFNγ-producing cells as a percentage of activated CD8+ T cells. *. P=0.0352. **, P=0.0047. FIG. 4H depicts quantitation of liver LCMV titers. *, P=0.0106. **, P=0.0047. Error bars depict the standard error of the mean.

FIG. 5A depicts representative FACS plots gated on CD4+ T cells, with activated cells (CD44$^{high}$ CD62L$^{low}$) boxed. Quantitation of activated CD4+ T cells as a percentage of total CD4+ T cells. FIG. 5B depicts representative FACS plots gated on CD4+ T cells after stimulation in vitro, with IFNγ-producing cells boxed. Quantitation of IFNγ-producing cells as a percentage of total CD4+ T cells. *, P=0.019. Error bars depict the standard error of the mean.

FIGS. 6A-6D show that TIGIT expression is elevated in human breast cancer and correlated with expression of CD8 and inhibitory co-receptors. Breast cancer gene expression microarray data generated by the Cancer Gene Atlas Network was analyzed. Gene expression data is normalized and expressed as relative ratios (log 2). FIG. 6A depicts TIGIT expression in normal and all breast tumor samples (left) and in breast tumor subtypes (right). ***, P=6×10-12. Box and whisker plots are shown. FIG. 6B depicts correlation of TIGIT and CD3ε expression. R2=0.61. FIG. 6C depicts the correlation of TIGIT and CD8α (left, R2=0.80) or CD4 (right, R2=0.42). FIG. 6D depicts the correlation of TIGIT and PD-1 (left, $R^2$=0.87), LAG3 (center, $R^2$=0.80), and CTLA4 (right, $R^2$=0.76).

In FIGS. 7A-7B, BALB/C mice were inoculated with CT26 colorectal carcinoma cells. Splenocytes and tumor-infiltrating lymphocytes (TILs) were analyzed 14 days after inoculation, when tumors had reached approximately 200 mm$^3$ in size. Data are representative of one experiment; n=6. FIG. 7A depicts flow cytometry histogram representative of TIGIT expression by splenic and tumor-infiltrating CD8+ T cells. Quantitation of TIGIT MFI is also shown. , P=0.0023. FIG. 7B depicts flow cytometry histogram representative of TIGIT expression by splenic and tumor-infiltrating CD4+ T cells. Quantitation of TIGIT MFI is also shown. *, P=0.0002. In FIGS. 7C-7E, BALB/C mice were inoculated with CT26 colorectal carcinoma cells. When tumors reached approximately 200 mm3 in size, mice were treated with isotype control, anti-PD-L1, anti-TIGIT, or anti-PD-L1+anti-TIGIT antibodies for three weeks. Data are representative of two independent experiments; n=10-20 (FIGS. 7C-7D) or 7-10 (FIG. 7E). FIG. 7C depicts median CT26 tumor volumes over time. FIG. 7D depicts mouse survival. FIG. 7E shows that approximately 60 days after initial inoculation, mice in complete remission (CR) that had received anti-TIGIT+anti-PD-L1, as well as nave BALB/c mice, were inoculated with CT26 cells in their left thoracic flanks and inoculated with EMT6 breast carcinoma cells in their mammary fat pads. Median (left) and individual (right) tumor volumes for CT26 (squares) and EMT6 (triangles) in CR mice (purple and green) and nave mice (black and orange) tumors are shown. FIG. 7F shows that mice were inoculated with CT26 tumors and treated as in FIG. 7C. Tumor-infiltrating and tumor-draining lymph node resident T cells were analyzed by flow cytometry. Representative FACS plots of CD8+ TILs after stimulation in vitro, with IFNγ-producing cells boxed. Quantitation of IFNγ-producing CD8+ TILs as a percentage of total CD8+ TILs. ***, P=0.0003. Data are representative of two independent experiments; n=5. Error bars depict the standard error of the mean.

FIG. 8A depicts representative histogram of TIGIT expression by splenic and tumor-infiltrating CD8+ T cells. Quantitation of TIGIT MFI. , P=0.0026. FIG. 8B depicts representative histogram of TIGIT expression by splenic and tumor-infiltrating CD4+ T cells. Quantitation of TIGIT MFI. *, P<0.0001. Error bars depict the standard error of the mean.

FIG. 9A depicts representative histogram of TIGIT expression by splenic and tumor-infiltrating CD8+ T cells. Quantitation of TIGIT MFI. ***, P<0.0001. FIG. 9B depicts representative histogram of TIGIT expression by splenic and tumor-infiltrating CD4+ T cells. Quantitation of TIGIT MFI. *, P=0.0136. **, P=0.0029. Error bars depict the standard error of the mean.

FIG. 11C depicts quantitation of CD4+ T cells as a percentage of total TILs. *, P=0.016. FIG. 11D depicts quantitation of activated CD4+ T cells as a percentage of total CD4+ TILs. FIG. 11E depicts quantitation of CD4+ T cells as a percentage of total tumor-draining lymph node cells. FIG. 11F depicts quantitation of activated CD4+ T cells as a percentage of total CD4+ T cells in the tumor-draining lymph node. FIG. 11A depicts quantitation of IFNγ+ cells as a percentage of CD4+ TILs after stimulation in vitro. FIG. 11B depicts quantitation of IFNγ+ cells as a percentage of CD4+ T cells in the tumor-draining lymph node after stimulation in vitro. Error bars depict the standard error of the mean.

FIG. 12A depicts quantitation of TNFα+ cells as a percentage of total CD8+ TILs. , P<0.01. FIG. 12B depicts quantitation of CD8+ TILs as a percentage of total TILs. , P<0.01. FIG. 12C depicts quantitation of activated (CD44$^{high}$ CD62L$^{low}$) CD8+ TILs as a percentage of total CD8+ TILs. *, P<0.05. Error bars depict the standard error of the mean.

FIGS. 13A-13D show the flow cytometric analysis of tumor-draining lymph node resident CD8+ T cells. BALB/C mice were inoculated with CT26 colorectal carcinoma cells and treated with isotype control, anti-PD-L1, anti-TIGIT, or anti-PD-L1+anti-TIGIT antibodies as described in FIGS. 4A-4H. Tumor-draining lymph nodes were harvested after 7 days of treatment and analyzed by flow cytometry. Data are representative of two independent experiments; n=5. FIG. 13A depicts representative FACS plots gated on tumor-draining lymph node resident CD8+ T cells after stimulation in vitro, with IFNγ-producing cells boxed. Quantitation of IFNγ+ cells as a percentage of total CD8+ T cells. ***, P<0.001. FIG. 13B depicts quantitation of CD8+ T cells as a percentage of total cells in the tumor-draining lymph node. FIG. 13C depicts quantitation of activated (CD44$^{high}$ CD62L$^{low}$) CD8+ T cells as a percentage of total CD8+ T cells. *, P<0.05. Error bars depict the standard error of the mean. FIG. 13D depicts quantitation of TNFα-producing cells as a percentage of total tumor-draining lymph node CD8+ T cells.

FIG. 14 shows co-expression of CD226 and TIGIT by tumor-infiltrating CD8+ T cells. C57BL6/J mice were inoculated with MC38 colorectal carcinoma cells. Splenocytes and tumor-infiltrating lymphocytes (TILs) were analyzed approximately 14 days after inoculation, when tumors had reached approximately 200 mm$^3$ in size. Representative histogram of CD226 expression by splenic B cells (gray), splenic CD8+ T cells (blue), and TIGIT+ tumor-infiltrating CD8+ T cells (red). Data are representative of two independent experiments; n=5.

FIG. 15 shows CD226 and TIGIT Co-Immunoprecipate (co-IP) on transfected cells. COS7 cells were co-transfected with expression plasmids containing the cDNA for either TIGIT-HA (5 ng) or CD226-Flag (10 ng) tagged proteins, or a control plasmid (pRK). Following transfection, the cells were washed and centrifuged and cell pellets lysed. The resultant supernatant was pre-cleared and centrifuged and then equally split into two tubes and immuno-precipitated with either an anti-HA or an anti-flag using standard procedures. The immune-precipitated proteins were subjected to SDS-PAGE and western blotted. Western blots were probed with either anti-Flag-HRP or anti-HA-HRP.

FIG. 17A depicts the dissociation of Flag-ST-CD226 homodimers by HA-TIGIT. FRET ratio between Flag-ST-CD226 measured on COS-7 cells expressing a constant amount of Flag-S T-CD226 and increasing concentrations of HA-TIGIT. FIG. 17B depicts FRET ratio between Flag-ST-CD226 recorded after a 15-min incubation of either PBS (white bar) or anti-TIGIT antibody (black bar). FIG. 17C depicts the association of Flag-ST-CD226 with HA-TIGIT. FRET intensity between Flag-ST-CD226 and HA-TIGIT over the Flag-ST-CD226 expression as measured by an anti-Flag ELISA on the same batch of transfected COS-7 cells. FIG. 17D depicts FRET variation between Flag-ST-CD226 and HA-TIGIT after a 15-min incubation of PBS (white bar) or anti-TIGIT antibody (black bar). Data in A and C are representative of 4 independent experiments, each performed in triplicate. Data in B and D are representative of 2 independent experiments, each performed in triplicate.

FIGS. 19A-19D show that CD226 blockade reverses the enhanced anti-viral T cell response induced by TIGIT/PD-L1 co-blockade. In FIGS. 19A-19D, C57BL6/J mice were briefly depleted of CD4+ T cells and infected with Clone 13 strain LCMV. Mice were treated with isotype-matched control, anti-CD226, anti-PD-L1+anti-TIGIT, or anti-PD-L1+anti-TIGIT+anti-CD226 antibodies starting 28 days after infection. Splenocytes and liver viral titers were analyzed 42 days after infection. FIG. 19A depicts quantitation of CD8+ T cells as a percentage of splenocytes. FIG. 19B depicts quantitation of activated CD8+ T cells as a percentage of total CD8+ T cells. *, P<0.001. FIG. 19C depicts quantitation of IFNg-producing cells as a percentage of activated CD8+ T cells. *, P<0.001. FIG. 19D depicts quantitation of liver LCMV titers. ***, P<0.001. Error bars depict the standard error of the mean.

FIGS. 20A-20H show that TIGIT expression is elevated in human cancer and strongly correlated with CD8 and PD-1. Gene expression analyses of human cancers were performed as described in Example 11. Scatter plots show per-gene count data, normalized by library size. Box and whisker plots show the variance stabilized expression ratio of TIGIT and CD3e. FIG. 20A depicts the correlation of TIGIT and CD3e RNA expression in LUSC (grey) and normal lung (black). ρ=0.86. Quantification of TIGIT/CD3e expression ratios is also shown. LUSC ratio increase=372%. *, P=1.46×10$^{-46}$. FIG. 20B depicts the correlation of TIGIT and CD3e RNA expression in COAD (grey) and normal colon (black). ρ=0.83. Quantification of TIGIT/CD3e expression ratios is also shown. COAD ratio increase=116%. *, P=3.66×10$^{-6}$. FIG. 20C depicts the correlation of TIGIT and CD3e RNA expression in UCEC (grey) and normal uterine endrometrium (black). ρ=0.87. Quantification of TIGIT/CD3e expression ratios is also shown. UCEC ratio increase=419%. *, P=7.41×10$^{-5}$. FIG. 20D depicts the correlation of TIGIT and CD3e RNA expression in BRCA (grey) and normal breast (black). ρ=0.82. Quantification of TIGIT/CD3e expression ratios is also shown. BRCA ratio increase=313%. *, P=4.6×10$^{44}$. FIG. 20E depicts the correlation of TIGIT and CD3e RNA expression in kidney renal clear cell carcinoma (grey) and normal kidney (black). ρ=0.94. Quantification of TIGIT/CD3e expression ratios is also shown. FIG. 20F depicts the correlation of TIGIT and CD8A (left) or TIGIT and CD4 (right) in lung squamous cell carcinoma (grey) and normal lung (black). ρ=0.77 and 0.48 respectively. FIG. 20G depicts the correlation of TIGIT and PD-1 (Pdcd1) in lung squamous cell carcinoma (grey) and normal lung (black). ρ=0.82. FIG. 20H depicts the correlation of TIGIT and CD226 in lung squamous cell carcinoma (red) and normal lung (black). ρ=0.64.

FIGS. 22A-22C show analysis of lymphocytes from a freshly resected human NSCLC tumor, tumor-matched peripheral blood, and normal donor peripheral blood. Data are representative of two independently analyzed tumors. FIG. 22A depicts representative FACS plots representative of TIGIT expression by peripheral and tumor-infiltrating CD8+ T cells, with TIGIT+ cells boxed. FIG. 22B depicts representative FACS plots representative of TIGIT expression by peripheral and tumor-infiltrating CD4+ T cells, with TIGIT+ cells boxed. FIG. 22C depicts flow cytometry histogram representative of TIGIT expression by PD-1$^{high}$ (red) and PD-1$^{low}$ (blue) NSCLC-infiltrating CD8+ (left) and CD4+ (right) T cells. In FIGS. 22D-22G, BALB/C mice were inoculated with syngeneic CT26 colorectal carcinoma cells. Splenocytes and tumor-infiltrating lymphocytes (TILs) were analyzed 14 days after inoculation, when tumors had reached approximately 200 mm$^3$ in size. Data are representative of two independent experiments; n=5-6. FIG. 22D depicts representative FACS plot of TIGIT expression by tumor-infiltrating CD8+ T cells, with TIGIT+ cells boxed. FIG. 22E depicts representative FACS plot of TIGIT expression by tumor-infiltrating CD4+ T cells, with TIGIT+ cells boxed. Quantitation of the frequency of TIGIT+ T cells as a percentage of all T cells. *, P=0.0134. *, P<0.0001. FIG. 22F depicts flow cytometry histogram representative of TIGIT expression by PD-1$^{high}$ and PD-1$^{low}$ tumor-infiltrating CD8+ T cells and by splenic CD8+ T cells. Quantitation of TIGIT MFI is also shown. , P=0.0023. FIG. 22G depicts flow cytometry histogram representative of TIGIT expression by PD-1$^{high}$ and PD-1$^{low}$ tumor-infiltrating CD4$^+$ T cells and by splenic CD4$^+$ T cells. Quantitation of TIGIT MFI is also shown. ***, P=0.0002. Error bars depict the standard error of the mean.

FIGS. 23A-23D show the characterization of TIGIT expression by human tumor-infiltrating T cells. FIGS. 23A-23B depict FACS plots showing TIGIT expression by NSCLC tumor-infiltrating CD8+ and CD4+ T cells (FIG. 23A) and by donor-matched PBMC CD8+ and CD4+ T cells (FIG. 23B), with TIGIT+ cells boxed. FIGS. 23C-23D depict FACS plots showing TIGIT expression by CRC tumor-infiltrating CD8+ and CD4+ T cells (FIG. 23C) and by donor-matched PBMC CD8+ and CD4+ T cells (FIG. 23D), with TIGIT+ cells boxed.

In FIGS. 25A-25C, MC38 tumor-bearing mice were generated as above and treated with blocking antibodies against PD-L1 (red), TIGIT (blue), TIGIT and PD-L1 (purple) or isotype-matched control antibodies (black) for three weeks. N=10 (control, anti-PD-L1 alone, anti-TIGIT alone) or 20 (anti-TIGIT+anti-PD-L1). FIG. 25A depicts median (left) and individual (right) MC38 tumor volumes over time. FIG. 25B depicts MC38 tumor volumes after 14 days of antibody treatment. *, P=0.0005. , P=0.0093. *, P=0.0433. FIG. 25C depicts mouse survival over time. Error bars depict the standard error of the mean.

FIGS. 26A-26E show the further characterization of TIGIT expression by murine tumor-infiltrating T cells. FIG. 26A depicts that splenic C57BL6/J CD8+ T cells were enriched by MACS and cultured with plate-coated anti-CD3 and anti-CD28 agonist antibodies. Representative histograms of TIGIT (red) and isotype-matched control (solid gray) staining over time. Quantitation of TIGIT MFI. *, P<0.001. Stimulated cells inducibly expressed PD-1 and constitutively expressed CD226 (data not shown). Data are representative of two independent experiments; n=5. In FIGS. 26B-26E, wildtype C57BL6/J mice were subcutaneously inoculated with syngeneic MC38 colorectal carcinoma cells. Tumors were allowed to grow without intervention until they reached 150-200 mm$^3$ in size. Data are representative of two independent experiments; n=5. FIG. 26B depicts representative FACS plot of tumor-infiltrating CD8$^+$ T cells, with TIGIT$^+$ cells boxed. Quantitation of the frequency of TIGIT$^+$ cells as a percentage of all tumor-infiltrating or splenic CD8$^+$ T cells. *, P<0.0001. FIG. 26C depicts representative FACS plot of tumor-infiltrating CD4$^+$ T cells, with TIGIT$^+$ cells boxed. Quantitation of the frequency of TIGIT$^+$ cells as a percentage of all tumor-infiltrating or splenic CD4+ T cells. *, P<0.0001. FIG. 26D depicts representative histogram of TIGIT expression by PD-1$^{high}$ and PD-1$^{low}$ tumor-infiltrating CD8+ T cells (red and blue, respectively) and by splenic CD8$^+$ T cells (gray). Quantitation of TIGIT MFI. *, P<0.0001. FIG. 26E depicts representative histogram of TIGIT expression by PD-1$^{high}$ and PD-1$^{low}$ tumor-infiltrating CD4$^+$ T cells and by splenic CD4$^+$ T cells. Quantitation of TIGIT MFI. *, P=0.0136. **, P=0.0029. Error bars depict the standard error of the mean.

FIG. 27A depicts quantitation of CD226$^+$ CD8$^+$ T cells, CD4$^+$ T cells, and non-T cells, as a percentage of all CD8$^+$ T cells, CD4$^+$ T cells, and non-T cells respectively. FIG. 27B depicts representative histograms of CD226 expression in tumor and spleen. Data are representative of two independent experiments; n=5. Error bars depict the standard error of the mean.

FIGS. 28A-28F show that TIGIT suppression of CD8$^+$ T cell responses is dependent on CD226. BALB/C mice were subcutaneously inoculated with CT26 colorectal carcinoma cells in their right thoracic flanks. When tumors reached approximately 200 mm$^3$ in size, mice were treated with isotype control (black), anti-CD226 (orange), anti-PD-L1 (red), anti-TIGIT+anti-PD-L1 (purple), or anti-TIGIT+anti-PD-L1+anti-CD226 (green) antibodies for three weeks. Data are representative of one experiment; n=10 (A-B) or 5 (C-F). FIG. 28A depicts median (left) and individual (right) CT26 tumor volumes over time. FIG. 28B depicts mouse survival over time. In FIGS. 28C-28F, after 7 days of treatment, tumor-infiltrating lymphocytes and tumor-draining lymph node-resident lymphocytes were assessed by flow cytometry. FIG. 28C depicts quantitation of IFNγ-producing CD8$^+$ TILs as a percentage of total CD8$^+$ TILs after stimulation in vitro. **, P<0.01. FIG. 28D depicts quantitation of IFNγ-producing cells as a percentage of total CD8$^+$ T cells after stimulation in vitro. *, P<0.05. FIG. 28E depicts quantitation of CD8$^+$ TILs as a percentage of total TILs. **, P<0.01. FIG. 28F depicts quantitation of CD8$^+$ T cells as a percentage of all tumor-draining lymph node-resident lymphocytes. Error bars depict the standard error of the mean.

FIGS. 29A-29H show that TIGIT impairs CD226 function by directly disrupting CD226 homodimerization. FIG. 29A depicts that CD8$^+$ T cells were MACS-enriched from TIGIT$^{fl/fl}$ CD4$^{cre}$ (CKO) and TIGIT$^{fl/fl}$ CD4$^{wt}$ (WT) littermates and stimulated in the presence of anti-CD226 or isotype-matched control antibodies as indicated. H$^3$-thymidine uptake is shown as a ratio of cells cultured with anti-CD3+PVR-Fc to cells cultured with anti-CD3 alone. , P=0.0061. *, P<0.0001. Data are representative of two independent experiments; n=5. FIG. 29B depicts that wildtype C57BL6/J CD8$^+$ T cells were MACS-enriched and stimulated in the presence of anti-TIGIT, anti-CD226, and/or isotype-matched control antibodies as indicated. H$^3$-thymidine uptake is shown as a ratio of cells cultured with anti-CD3+PVR-Fc to cells cultured with anti-CD3 alone. *, P<0.001 in paired t tests. FIG. 29C depicts that primary human CD8$^+$ T cells were MACS-enriched from blood and stimulated with sub-optimal levels of plate-bound anti-CD3 in the presence or absence of human recombinant PVR-Fc. Anti-TIGIT antibodies or isotype-matched control antibodies were added as indicated. Quantitation of $^3$H-thymidine uptake. , P=0.0071 and 0.0014 respectively. FIG. 29D depicts that CHO cells were transiently transfected with increasing concentrations of acceptor and donor FLAG-ST-CD226, as indicated. Quantification of FRET intensity relative to donor emission. Data are representative of three independent experiments; n=3. In FIGS. 29E-29F, CHO cells were transiently transfected with FLAG-ST-CD226 and with increasing concentrations of HA-TIGIT, as indicated. Data are representative of two or more independent experiments; n=4. Data are normalized to the maximal signal. FIG. 29E depicts quantification of the CD226:CD226 FRET ratio (FRET ratio 1). FIG. 29F depicts quantification of the TIGIT:CD226 FRET ratio (FRET ratio 2). FIG. 29G depicts anti-FLAG (left) and anti-HA (right) immunoblots performed on either anti-FLAG or anti-HA immunoprecipitates prepared from COS-7 cells transfected with either an empty pRK vector or a combination of Flag-CD226 and HA-TIGIT. Data are representative of two independent experiments. FIG. 29H depicts quantification of the TIGIT:CD226 FRET ratio after incubation with PBS (white) or anti-TIGIT antibodies (red). ***, P<0.001. Data are representative of 4 independent experiments; n=3. Error bars depict the standard error of the mean.

FIG. 30 shows that primary human T cells were MACS-enriched from blood and stimulated with anti-CD3 and anti-CD28. TIGIT$^+$ and TIGIT$^-$ cells were sorted, rested, re-stimulated, and labeled for FRET with the antibodies indicated. Data are representative of two independent experiments. ***, P<0.001. Error bars depict the standard error of the mean.

FIGS. 31A-31C show that TIGIT and PD-1 co-blockade does not restore the effector function of exhausted CD4$^+$ T cells during chronic viral infection. FIG. 31A depicts quantitation of CD8$^+$ T cells as a percentage of all splenocytes. FIG. 31B depicts quantitation of GP33 Pentamer$^+$ cells as a percentage of all splenic CD8$^+$ T cells. **, P=0.0040. FIG. 31C depicts representative FACS plots gated on gp33 pentamer$^+$ CD8$^+$ T cells after stimulation in vitro, with IFNγ$^+$ cells boxed. Quantitation of IFNγ-producing cells as a percentage of all gp33 pentamer$^+$ CD8$^+$ T cells. *, P=0.0319. **, P=0.0030. Error bars depict the standard error of the mean.

FIGS. 32A-32C show that TIGIT/PD-L1 co-blockade efficacy is dependent on CD8$^+$ T cells. In FIGS. 32A-32B, wildtype BALB/c mice were inoculated with CT26 tumors as described in FIGS. 7A-7F. When tumors reached 100-150 mm$^3$ in size, mice were temporarily depleted of CD8$^+$ T cells and treated with anti-TIGIT+anti-PD-L1. Data are representative of one experiment; n=10/group. FIG. 32A depicts median (left) and individual (right) CT26 tumor volumes over time. FIG. 32B depicts quantitation of CT26 tumor volumes 17 days after the start of treatment. ***, P=0.0004. In FIG. 32C, wildtype BALB/c mice were inoculated with CT26 tumors and treated with anti-TIGIT+anti-PD-L1 and subsequently re-challenged with CT26 tumors with temporary depletion of CD8$^+$ T cells at the time of re-challenge. Data are representative of two independent experiments; n=5. FIG. 32C depicts median (left) and individual (right) CT26 tumor volumes over time. Error bars depict the standard error of the mean.

FIG. 33 depicts median (left) and individual (right) CT26 tumor volumes over time.

FIG. 34 depicts median (left) and individual (right) EMT6 tumor volumes over time.

FIG. 35A depicts quantitation of IFNγ/TNFα dual-producing dLN resident CD8$^+$ and CD4$^+$ T cells as percentages of total dLN resident CD8$^+$ and CD4$^+$ T cells respectively. Dual cytokine production by unstimulated T cells is also shown. , P=0.002, 0.003, and 0.001 respectively. FIG. 35B depicts quantitation of IFNγ/TNFα dual-producing tumor-infiltrating CD8$^+$ and CD4$^+$ T cells as percentages of total tumor-infiltrating CD8$^+$ and CD4$^+$ T cells respectively. Dual cytokine production by unstimulated T cells is also shown. *, P<0.0001. Error bars depict the standard error of the mean.

FIGS. 36A-36B show the analysis of lymphocytes from resected human NSCLC tumors, tumor-matched peripheral blood, and normal donor peripheral blood. Data are pooled from three independently acquired sets of samples. FIG. 36A depicts quantitation of TIGIT$^+$ cells as a percentage of all CD8$^+$ T cells. *, P<0.05. FIG. 36B depicts quantitation of TIGIT$^+$ cells as a percentage of all CD4$^+$ T cells.

FIGS. 37A-37B show the characterization of TIGIT expression in human tumors. FIG. 37A depicts representative flow cytometry histograms of TIGIT expression by NSCLC tumor-resident lymphocytes (red, CD45$^+$ FSC$^{low}$), myeloid cells (blue, CD45$^+$ FSC$^{high}$), and non-hematopoietic cells (green, CD45$^-$) relative to subset-matched isotype staining (gray). FIG. 37B depicts gating strategy for PD-1$^{high}$ and PD-1$^{low}$ NSCLC tumor-infiltrating CD8$^+$ and CD4$^+$ T cells.

DETAILED DESCRIPTION OF THE INVENTION

I. General Techniques

Figure 1C:
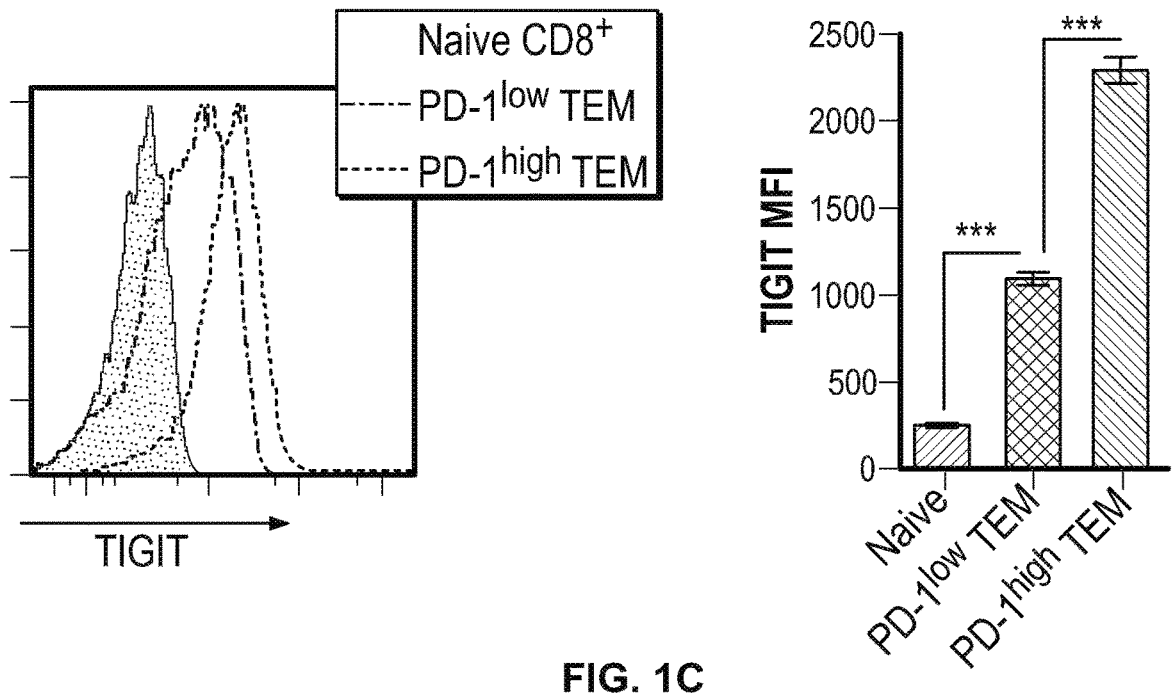

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); Oligonucleotide Synthesis (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Cabs, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein. In another specific aspect, a PD-1 binding antagonist is CT-011 described herein. In another specific aspect, a PD-1 binding antagonist is AMP-224 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein. In another specific aspect, an anti-PD-L1 antibody is MEDI 4736 described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "aptamer" refers to a nucleic acid molecule that is capable of binding to a target molecule, such as a polypeptide. For example, an aptamer of the invention can specifically bind to a TIGIT polypeptide, or to a molecule in a signaling pathway that modulates the expression of TIGIT. The generation and therapeutic use of aptamers are well established in the art. See, e.g., U.S. Pat. No. 5,475,096, and the therapeutic efficacy of Macugen® (Eyetech, New York) for treating age-related macular degeneration.

The term "antagonist" is used in the broadest sense, and includes any molecule that partially or fully blocks, inhibits, or neutralizes a biological activity of a native polypeptide disclosed herein. In a similar manner, the term "agonist" is used in the broadest sense and includes any molecule that mimics a biological activity of a native polypeptide disclosed herein. Suitable agonist or antagonist molecules specifically include agonist or antagonist antibodies or antibody fragments, fragments or amino acid sequence variants of native polypeptides, peptides, antisense oligonucleotides, small organic molecules, etc. Methods for identifying agonists or antagonists of a polypeptide may comprise contacting a polypeptide with a candidate agonist or antagonist molecule and measuring a detectable change in one or more biological activities normally associated with the polypeptide.

The terms "TIGIT antagonist" and "antagonist of TIGIT activity or TIGIT expression" are used interchangeably and refer to a compound that interferes with the normal functioning of TIGIT, either by decreasing transcription or translation of TIGIT-encoding nucleic acid, or by inhibiting or blocking TIGIT polypeptide activity, or both. Examples of TIGIT antagonists include, but are not limited to, antisense polynucleotides, interfering RNAs, catalytic RNAs, RNA-DNA chimeras, TIGIT-specific aptamers, anti-TIGIT antibodies, TIGIT-binding fragments of anti-TIGIT antibodies, TIGIT-binding small molecules, TIGIT-binding peptides, and other polypeptides that specifically bind TIGIT (including, but not limited to, TIGIT-binding fragments of one or more TIGIT ligands, optionally fused to one or more additional domains), such that the interaction between the TIGIT antagonist and TIGIT results in a reduction or cessation of TIGIT activity or expression. It will be understood by one of ordinary skill in the art that in some instances, a TIGIT antagonist may antagonize one TIGIT activity without affecting another TIGIT activity. For example, a desirable TIGIT antagonist for use in certain of the methods herein is a TIGIT antagonist that antagonizes TIGIT activity in response to one of PVR interaction, PVRL3 interaction, or PVRL2 interaction, e.g., without affecting or minimally affecting any of the other TIGIT interactions.

The terms "PVR antagonist" and "antagonist of PVR activity or PVR expression" are used interchangeably and refer to a compound that interferes with the normal functioning of PVR, either by decreasing transcription or translation of PVR-encoding nucleic acid, or by inhibiting or blocking PVR polypeptide activity, or both. Examples of PVR antagonists include, but are not limited to, antisense polynucleotides, interfering RNAs, catalytic RNAs, RNA-DNA chimeras, PVR-specific aptamers, anti-PVR antibodies, PVR-binding fragments of anti-PVR antibodies, PVR-binding small molecules, PVR-binding peptides, and other polypeptides that specifically bind PVR (including, but not limited to, PVR-binding fragments of one or more PVR ligands, optionally fused to one or more additional domains), such that the interaction between the PVR antagonist and PVR results in a reduction or cessation of PVR activity or expression. It will be understood by one of ordinary skill in the art that in some instances, a PVR antagonist may antagonize one PVR activity without affecting another PVR activity. For example, a desirable PVR antagonist for use in certain of the methods herein is a PVR antagonist that antagonizes PVR activity in response to TIGIT interaction without impacting the PVR-CD96 and/or PVR-CD226 interactions.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream T-cell effector functions, such as proliferation, cytokine production (e.g., IL-2) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of 7-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenecity" refers to the ability of a particular substance to provoke an immune response. Tumors are immunogenic and enhancing tumor immunogenicity aids in the clearance of the tumor cells by the immune response. Examples of enhancing tumor immunogenicity include but not limited to treatment with a PD-1 axis binding antagonist (e.g., anti-PD-L1 antibodies and a TIGIT inhibitor (e.g., anti-TIGIT antibodies).

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:

381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVQLVESGGGLVQPGGSLRLSCAAS (HC-FR1)(SEQ ID NO:25), WVRQAPGKGLEWV (HC-FR2), (SEQ ID NO:26), RFTISADTSKNTAYLQMNSLRAEDTAVYYCAR (HC-FR3, SEQ ID NO:27), WGQGTLVTVSA (HC-FR4), (SEQ ID NO:28).

A "VL kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSLSASVGDRVTITC (LC-FR1) (SEQ ID NO:29), WYQQKPGKAPKLLIY (LC-FR2) (SEQ ID NO:30), GVPSRFSGSGSGTDFTLTISSLQPEDFATYYC (LC-FR3)(SEQ ID NO:31), FGQGTKVEIKR (LC-FR4)(SEQ ID NO:32).

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2 (including IgG2A and IgG2B), IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. For example, useful immunoadhesins as second medicaments useful for combination therapy herein include polypeptides that comprise the extracellular or PD-1 binding portions of PD-L1 or PD-L2 or the extracellular or PD-L1 or PD-L2 binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, etc. The two portions may be linked directly by a single peptide bond or through a peptide linker but are in reading frame with each other.

A "PD-1 oligopeptide," "PD-L1 oligopeptide," or "PD-L2 oligopeptide" is an oligopeptide that binds, preferably specifically, to a PD-1, PD-L1 or PD-L2 negative costimulatory polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. *Proc. Natl. Acad. Sci. USA*, 87:6378 (1990); Lowman, H. B. et al. *Biochemistry*, 30:10832 (1991); Clackson, T. et al. *Nature*, 352: 624 (1991); Marks, J. D. et al., *J. Mol. Biol.*, 222:581(1991); Kang, A. S. et al. *Proc. Natl. Acad. Sci. USA*, 88:8363 (1991), and Smith, G. P., *Current Opin. Biotechnol.*, 2:668 (1991).

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-PD-L1 antibodies of the invention block the signaling through PD-1 so as to restore a functional response by T-cells (e.g., proliferation, cytokine production, target cell killing) from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, "reducing or inhibiting cancer relapse" means to reduce or inhibit tumor or cancer relapse or tumor or cancer progression.

As used herein, "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

As used herein, "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

As used herein, "subject" is meant a mammal, including, but not limited to, a human or non-human mammal, such as a bovine, equine, canine, ovine, or feline. Preferably, the subject is a human. Patients are also subjects herein.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; antiadrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chlorambucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

It is understood that aspects and variations of the invention described herein include "consisting" and/or "consisting essentially of" aspects and variations.

III. Methods

In one aspect, provided herein is a method for treating or delaying progression of cancer in an individual comprising administering to the individual an effective amount of a PD-1 axis binding antagonist in combination with an agent that decreases or inhibits TIGIT expression and/or activity.

In another aspect, provided herein is a method for reducing or inhibiting cancer relapse or cancer progression in an individual comprising administering to the individual an effect amount of a PD-1 axis binding antagonist in combination with an agent that that decreases or inhibits TIGIT expression and/or activity. As disclosed herein, cancer relapse and/or cancer progression include, without limitation, cancer metastasis.

In another aspect, provided herein is a method for treating or delaying progression of an immune related disease in an individual comprising administering to the individual an effect amount of a PD-1 axis binding antagonist in combination with an agent that that decreases or inhibits TIGIT expression and/or activity.

In another aspect, provided herein is a method for reducing or inhibiting progression of an immune related disease in an individual comprising administering to the individual an effect amount of a PD-1 axis binding antagonist in combination with an agent that that decreases or inhibits TIGIT expression and/or activity.

In some embodiments, the immune related disease is associated with T cell dysfunctional disorder. In some embodiments, the immune related disease is a viral infection. In certain embodiments, the viral infection is a chronic viral infection. In some embodiments, T cell dysfunctional disorder is characterized by decreased responsiveness to antigenic stimulation. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the T cell dysfunctional disorder includes unresolved acute infection, chronic infection and tumor immunity.

In another aspect, provided herein is a method for increasing, enhancing or stimulating an immune response or function in an individual comprising administering to the individual an effect amount of a PD-1 axis binding antagonist in combination with an agent that decreases or inhibits TIGIT expression and/or activity.

In another aspect, provided herein is a method of treating or delaying progression of cancer in an individual comprising administering to the individual an effective amount of a PD-1 axis binding antagonist and an agent that modulates the CD226 expression and/or activity.

In another aspect, provided herein is a method for reducing or inhibiting cancer relapse or cancer progression in an individual comprising administering to the individual an effective amount of a PD-1 axis binding antagonist and an agent that modulates the CD226 expression and/or activity.

In another aspect, provided herein is a method for treating or delaying progression of an immune related disease in an individual comprising administering to the individual an effective amount of a PD-1 axis binding antagonist and an agent that modulates the CD226 expression and/or activity.

In another aspect, provided herein is a method for reducing or inhibiting progression of an immune related disease in an individual comprising administering to the individual an effective amount of a PD-1 axis binding antagonist and agent that modulates the CD226 expression and/or activity.

In some embodiments, the immune related disease is associated with T cell dysfunctional disorder. In some embodiments, the immune related disease is a viral infection. In certain embodiments, the viral infection is a chronic viral infection. In some embodiments, the T cell dysfunctional disorder is characterized by decreased responsiveness to antigenic stimulation. In some embodiments, the T cell dysfunctional disorder is characterized by T cell anergy, or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the immune related disease is selected from the group consisting of unresolved acute infection, chronic infection and tumor immunity.

In another aspect, provided herein is a method of increasing, enhancing or stimulating an immune response or function in an individual by administering to the individual an effective amount of a PD-1 axis binding antagonist and an agent that modulates the CD226 expression and/or activity.

In some embodiments, the agent that modulates the CD226 expression and/or activity is capable of increasing and/or stimulating CD226 expression and/or activity; increasing and/or stimulating the interaction of CD226 with PVR, PVRL2, and/or PVRL3; and increasing and/or stimulating the intracellular signaling mediated by CD226 binding to PVR, PVRL2, and/or PVRL3. As used herein, an agent that is capable of increasing and/or stimulating CD226 expression and/or activity includes, without limitation, agents that increase and/or stimulate CD226 expression and/or activity. As used herein, an agent that is capable of increasing and/or stimulating the interaction of CD226 with PVR, PVRL2, and/or PVRL3 includes, without limitation, agents that increase and/or stimulate the interaction of CD226 with PVR, PVRL2, and/or PVRL3. As used herein, an agent that is capable of increasing and/or stimulating the intracellular signaling mediated by CD226 binding to PVR, PVRL2, and/or PVRL3 includes, without limitation, agents that increase and/or stimulate the intracellular signaling mediated by CD226 binding to PVR, PVRL2, and/or PVRL3.

In some embodiments, the agent that modulates the CD226 expression and/or activity is selected from an agent that inhibits and/or blocks the interaction of CD226 with TIGIT, an antagonist of TIGIT expression and/or activity, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, an agent that inhibits and/or blocks the intracellular signaling mediated by TIGIT binding to PVRL3, and combinations thereof.

In some embodiments, the agent that inhibits and/or blocks the interaction of CD226 with TIGIT is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of CD226 with TIGIT is an anti-TIGIT antibody or antigen-binding fragment thereof. In some embodiments, the agent that inhibits and/or blocks the interaction of CD226 with TIGIT is an inhibitory nucleic acid selected from an antisense polynucleotide, an interfering RNA, a catalytic RNA, and an RNA-DNA chimera.

In some embodiments, the antagonist of TIGIT expression and/or activity is a small molecule inhibitor, an inhibitory antibody or antigen-binding fragment thereof, an aptamer, an inhibitory nucleic acid, and an inhibitory polypeptide. In some embodiments, the antagonist of TIGIT expression and/or activity is an anti-TIGIT antibody or antigen-binding fragment thereof. In some embodiments, the antagonist of TIGIT expression and/or activity is an inhibitory nucleic acid selected from an antisense polynucleotide, an interfering RNA, a catalytic RNA, and an RNA-DNA chimera.

In some embodiments, the antagonist of PVR expression and/or activity is a small molecule inhibitor, an inhibitory antibody or antigen-binding fragment thereof, an aptamer, an inhibitory nucleic acid, and an inhibitory polypeptide. In some embodiments, the antagonist of PVR expression and/or activity is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVR is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of TIGIT with PVR is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVRL2 is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVRL3 is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVR is a small molecule inhibitor, an inhibitory antibody or antigen-binding fragment thereof, an aptamer, an inhibitory nucleic acid, and an inhibitory polypeptide. In some embodiments, the agent that inhibits and/or blocks the intracellular signaling mediated by TIGIT binding to PVR is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVRL2 is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVRL3 is selected from a small molecule inhibitor, an inhibitory antibody or antigen-binding fragment thereof, an aptamer, an inhibitory nucleic acid, and an inhibitory polypeptide.

In another aspect, provided herein is a method of increasing, enhancing or stimulating an immune response or function in an individual by administering to the individual an effective amount of an agent that decreases or inhibits TIGIT expression and/or activity and an agent that decreases or inhibits the expression and/or activity of one or more additional immune co-inhibitory receptors. In some embodiments, the one of more additional immune co-inhibitory receptor is selected from PD-1, CTLA-4, LAG3, TIM3, BTLA VISTA, B7H4, and CD96. In some embodiments, one of more additional immune co-inhibitory receptor is selected from PD-1, CTLA-4, LAG3 and TIM3.

In another aspect, provided herein is a method of increasing, enhancing or stimulating an immune response or function in an individual by administering to the individual an effective amount of an agent that decreases or inhibits TIGIT expression and/or activity and an agent that increases or activates the expression and/or activity of one or more additional immune co-stimulatory receptors. In some embodiments, the one of more additional immune co-stimulatory receptor is selected from CD226, OX-40, CD28, CD27, CD137, HVEM, GITR, MICA, ICOS, NKG2D, and 2B4. In some embodiments, the one or more additional immune co-stimulatory receptor is selected from CD226, OX-40, CD28, CD27, CD137, HVEM, and GITR. In some embodiments, the one of more additional immune co-stimulatory receptor is selected from OX-40 and CD27.

The methods of this invention may find use in treating conditions where enhanced immunogenicity is desired such as increasing tumor immunogenicity for the treatment of cancer or T cell dysfunctional disorders.

A variety of cancers may be treated, or their progression may be delayed.

In some embodiments, the individual has non-small cell lung cancer. The non-small cell lung cancer may be at early stage or at late stage. In some embodiments, the individual has small cell lung cancer. The small cell lung cancer may be at early stage or at late stage. In some embodiments, the individual has renal cell cancer. The renal cell cancer may be at early stage or at late stage. In some embodiments, the individual has colorectal cancer. The colorectal cancer may be at early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has pancreatic cancer. The pancreatic cancer may be at early stage or at late stage. In some embodiments, the individual has gastric carcinoma. The gastric carcinoma may be at early stage or at late stage. In some embodiments, the individual has bladder cancer. The bladder cancer may be at early stage or at late stage. In some embodiments, the individual has esophageal cancer. The esophageal cancer may be at early stage or at late stage. In some embodiments, the individual has mesothelioma. The mesothelioma may be at early stage or at late stage. In some embodiments, the individual has melanoma. The melanoma may be at early stage or at late stage. In some embodiments, the individual has head and neck cancer. The head and neck cancer may be at early stage or at late stage. In some embodiments, the individual has thyroid cancer. The thyroid cancer may be at early stage or at late stage. In some embodiments, the individual has sarcoma. The sarcoma may be at early stage or late stage. In some embodiments, the individual has prostate cancer. The prostate cancer may be at early stage or at late stage. In some embodiments, the individual has glioblastoma. The glioblastoma may be at early stage or at late stage. In some embodiments, the individual has cervical cancer. The cervical cancer may be at early stage or at late stage. In some embodiments, the individual has thymic carcinoma. The thymic carcinoma may be at early stage or at late stage. In some embodiments, the individual has leukemia. The leukemia may be at early stage or at late stage. In some embodiments, the individual has lymphomas. The lymphoma may be at early stage or at late stage. In some embodiments, the individual has myelomas. The myelomas may be at early stage or at late stage. In some embodiments, the individual has mycoses fungoids. The mycoses fungoids may be at early stage or at late stage. In some embodiments, the individual has merkel cell cancer. The merkel cell cancer may be at early stage or at late stage. In some embodiments, the individual has hematologic malignancies. The hematological malignancies may be early stage or late stage. In some embodiments, the individual is a human.

In some embodiments of the methods of this invention, the CD4 and/or CD8 T cells in the individual have increased or enhanced priming, activation, proliferation, cytokine release and/or cytolytic activity relative to prior to the administration of the combination.

In some embodiments of the methods of this invention, the number of CD4 and/or CD8 T cells is elevated relative to prior to administration of the combination. In some embodiments of the methods of this invention, the number of activated CD4 and/or CD8 T cells is elevated relative to prior to administration of the combination.

In some embodiments of the methods of this invention, the activated CD4 and/or CD8 T cells is characterized by γ-IFN$^+$ producing CD4 and/or CD8 T cells and/or enhanced cytolytic activity relative to prior to the administration of the combination.

In some embodiments of the methods of this invention, the CD4 and/or CD8 T cells exhibit increased release of cytokines selected from the group consisting of IFN-γ, TNF-α and interleukins.

In some embodiments of the methods of this invention, the CD4 and/or CD8 T cell is an effector memory T cell. In some embodiments of the methods of this invention, the CD4 and/or CD8 effector memory T cell is characterized by γ-IFN$^+$ producing CD4 and/or CD8 T cells and/or enhanced cytolytic activity. In some embodiments of the methods of this invention, the CD4 and/or CD8 effector memory T cell is characterized by having the expression of $CD44^{high}$ $CD62L^{low}$.

In some embodiments of the methods of this invention, the cancer has elevated levels of T cell infiltration.

In some embodiments, the methods of the invention may further comprise administering an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of an adjuvant or neoadjuvant therapy. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy may be one or more of the chemotherapeutic agents described hereinabove.

Any of the PD-1 axis binding antagonists and agents that decreases or inhibits TIGIT expression and/or activity described below may be used in the methods of the invention.

In some embodiments, any of the targets described herein (e.g., PD-1, PD-L1, PD-L2, CTLA-4, LAG3, TIM3, BTLA, VISTA, B7H4, CD96, B7-1, TIGIT, CD226, OX-40, CD28, CD27, CD137, HVEM, GITR, MICA, ICOS, NKG2D, 2B4, etc.) is a human protein.

PD-1 Axis Binding Antagonists

Provided herein is a method for treatment or delaying progression of cancer in an individual comprising administering to the individual an effective amount of a PD-1 axis binding antagonist in combination with an agent that decreases or inhibits TIGIT expression and/or activity. Provided herein is also a method for reducing or inhibiting cancer relapse or cancer progression in an individual comprising administering to the individual an effect amount of a PD-1 axis binding antagonist in combination with an agent that that decreases or inhibits TIGIT expression and/or activity. Provided herein is also a method for treating or delaying progression of an immune related disease in an individual comprising administering to the individual an effect amount of a PD-1 axis binding antagonist in combination with an agent that that decreases or inhibits TIGIT expression and/or activity. Provided herein is also a method for reducing or inhibiting progression of an immune related disease in an individual comprising administering to the individual an effect amount of a PD-1 axis binding antagonist in combination with an agent that that decreases or inhibits TIGIT expression and/or activity. Provided herein is also a method for increasing, enhancing or stimulating an immune response or function in an individual comprising administering to the individual an effect amount of a PD-1 axis binding antagonist in combination with an agent that decreases or inhibits TIGIT expression and/or activity.

For example, a PD-1 axis binding antagonist includes a PD-1 binding antagonist, a PD-L1 binding antagonist and a PD-L2 binding antagonist.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide.

In some embodiments, the PD-1 binding antagonist is selected from MDX-1106 (nivolumab), Merck 3745 (lambrolizumab), CT-011 (pidilizumab), and AMP-224. In some embodiments, the PD-L1 binding antagonist is selected from YW243.55.S70, MPDL3280A, MDX-1105, and MEDI 4736. In some embodiments, the PD-L2 binding antagonist is AMP-224. In some embodiments, the PD-1 binding antagonist is AMP-224. MDX-1105, also known as BMS-936559, is an anti-PD-L1 antibody described in WO2007/005874. Antibody YW243.55.S70 (SEQ ID No. 20) is an anti-PD-L1 described in WO 2010/077634 A1 and U.S. Pat. No. 8,217,149, which are incorporated herein by reference. MDX-1106, also known as MDX-1106-04, ONO-4538, BMS-936558, or nivolumab, is an anti-PD-1 antibody described in WO2006/121168. Merck 3745, also known as MK 3475, MK-3475, SCH-900475, or lambrolizumab, is an anti-PD-1 antibody described in WO2009/114335. CT-011, also known as hBAT, hBAT-1, or pidilizumab, is an anti-PD-1 antibody described in WO2009/101611. AMP-224, also known as B7-DCIg, is a PD-L2-Fc fusion soluble receptor described in WO2010/027827 and WO2011/066342.

Examples of anti-PD-L1 antibodies useful for the methods of this invention, and methods for making thereof are described in PCT patent application WO 2010/077634 A1 and U.S. Pat. No. 8,217,149, which are incorporated herein by reference.

In some embodiments, the PD-1 axis binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody.

The anti-PD-L1 antibodies useful in this invention, including compositions containing such antibodies, such as those described in WO 2010/077634 A1 and U.S. Pat. No. 8,217,149, may be used in combination with an agent that decreases or inhibits TIGIT expression and/or activity with or without any additional therapy (e.g., chemotherapy) to treat cancer or an immune related disease (e.g., T cell dysfunctional disorder, viral infection, chronic viral infection, etc.).

In one embodiment, the anti-PD-L1 antibody contains a heavy chain variable region polypeptide comprising an HVR-H1, HVR-H2 and HVR-H3 sequence, wherein:

(a)
```
                                          (SEQ ID NO: 33)
the HVR-H1 sequence is GFTFSX₁SWIH;
```

(b)
```
                                          (SEQ ID NO: 34)
the HVR-H2 sequence is AWIX₂PYGGSX₃YYADSVKG;
```

(c)
```
                                          (SEQ ID NO: 19)
the HVR-H3 sequence is RHWPGGFDY;
``` further wherein: $X_1$ is D or G; $X_2$ is S or L; $X_3$ is T or S.

In one specific aspect, $X_1$ is D; $X_2$ is S and $X_3$ is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

```
HC-FR1 is EVQLVESGGGLVQPGGSLRLSCAAS       (SEQ ID NO: 25)

HC-FR2 is WVRQAPGKGLEWV                   (SEQ ID NO: 26)

HC-FR3 is RFTISADTSKNTAYLQMNSLRAEDTAVYYCAR (SEQ ID NO: 27)

HC-FR4 is WGQGTLVTVSA.                    (SEQ ID NO: 28)
```

In a still further aspect, the heavy chain polypeptide is further combined with a variable region light chain comprising an HVR-L1, HVR-L2 and HVR-L3, wherein:

```
(a) the HVR-L1 sequence is RASQX4X5X6TX7X8A;   (SEQ ID NO: 35)

(b) the HVR-L2 sequence is SASX9LX10S,;        (SEQ ID NO: 36)

(c) the HVR-L3 sequence is QQX11X12X13X14PX15T; (SEQ ID NO: 37)
``` further wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a still further aspect, X4 is D; X5 is V; X6 is S; X7 is A; X8 is V; X9 is F; X10 is Y; X11 is Y; X12 is L; X13 is Y; X14 is H; X15 is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
LC-FR1 is DIQMTQSPSSLSASVGDRVTITC         (SEQ ID NO: 29)

LC-FR2 is WYQQKPGKAPKLLIY                 (SEQ ID NO: 30)

LC-FR3 is GVPSRFSGSGSGTDFTLTISSLQPEDFATYYC (SEQ ID NO: 31)

LC-FR4 is FGQGTKVEIKR.                    (SEQ ID NO: 32)
```

In another embodiment, provided is an isolated anti-PD-L1 antibody or antigen binding fragment comprising a heavy chain and a light chain variable region sequence, wherein:

(a) the heavy chain comprises and HVR-H1, HVR-H2 and HVR-H3, wherein further:

```
(i) the HVR-H1 sequence is GFTFSX1SWIH;          (SEQ ID NO: 33)

(ii) the HVR-H2 sequence is AWIX2PYGGSX3YYADSVKG  (SEQ ID NO: 34)

(iii) the HVR-H3 sequence is RHWPGGFDY, and     (SEQ ID NO: 19)
```

(b) the light chain comprises and HVR-L1, HVR-L2 and HVR-L3, wherein further:

```
(i) the HVR-L1 sequence is RASQX4X5X6TX7X8A       (SEQ ID NO: 35)

(ii) the HVR-L2 sequence is SASX9LX10S; and       (SEQ ID NO: 36)

(iii) the HVR-L3 sequence is QQX11X12X13X14PX15T; (SEQ ID NO: 37)
``` further wherein: $X_1$ is D or G; $X_2$ is S or L; $X_3$ is T or S; $X_4$ is D or V; $X_5$ is V on; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                          (SEQ ID NO: 25)
EVQLVESGGGLVQPGGSLRLSCAAS

HC-FR2
                                          (SEQ ID NO: 26)
WVRQAPGKGLEWV

HC-FR3
                                          (SEQ ID NO: 27)
RFTISADTSKNTAYLQMNSLRAEDTAVYYCAR

HC-FR4
                                          (SEQ ID NO: 28)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                          (SEQ ID NO: 29)
DIQMTQSPSSLSASVGDRVTITC

LC-FR2
                                          (SEQ ID NO: 30)
WYQQKPGKAPKLLIY

LC-FR3
                                          (SEQ ID NO: 31)
GVPSRFSGSGSGTDFTLTISSLQPEDFATYYC

LC-FR4
                                          (SEQ ID NO: 32)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:
(a) the heavy chain further comprises and HVR-H1, HVR-H2 and an HVR-H3 sequence having at least 85% sequence identity to GFTFSDSWIH (SEQ ID NO:17), AWISPYGGSTYYADSVKG (SEQ ID NO:18) and RHWPGGFDY (SEQ ID NO:19), respectively, or
(b) the light chain further comprises an HVR-L1, HVR-L2 and an HVR-L3 sequence having at least 85% sequence identity to RASQDVSTAVA (SEQ ID NO:20), SASFLYS (SEQ ID NO:21) and QQYLYH-PAT (SEQ ID NO:22), respectively.
(c) In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                          (SEQ ID NO: 25)
EVQLVESGGGLVQPGGSLRLSCAAS

HC-FR2
                                          (SEQ ID NO: 26)
WVRQAPGKGLEWV

HC-FR3
                                          (SEQ ID NO: 27)
RFTISADTSKNTAYLQMNSLRAEDTAVYYCAR

HC-FR4
                                          (SEQ ID NO: 28)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                          (SEQ ID NO: 29)
DIQMTQSPSSLSASVGDRVTITC

LC-FR2
                                          (SEQ ID NO: 30)
WYQQKPGKAPKLLIY

LC-FR3
                                          (SEQ ID NO: 31)
GVPSRFSGSGSGTDFTLTISSLQPEDFATYYC

LC-FR4
                                          (SEQ ID NO: 32)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:
(a) the heavy chain sequence has at least 85% sequence identity to the heavy chain sequence:

```
                                          (SEQ ID NO: 23)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSA, (SEQ ID NO: 40)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSASTK,
or (SEQ ID NO: 41)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS,
``` or
(b) the light chain sequences has at least 85% sequence identity to the light chain sequence:

```
                                          (SEQ ID NO: 24)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                      (SEQ ID NO: 25)
EVQLVESGGGLVQPGGSLRLSCAAS

HC-FR2
                                      (SEQ ID NO: 26)
WVRQAPGKGLEWV

HC-FR3
                                      (SEQ ID NO: 27)
RFTISADTSKNTAYLQMNSLRAEDTAVYYCAR

HC-FR4
                                      (SEQ ID NO: 28)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                      (SEQ ID NO: 29)
DIQMTQSPSSLSASVGDRVTITC

LC-FR2
                                      (SEQ ID NO: 30)
WYQQKPGKAPKLLIY

LC-FR3
                                      (SEQ ID NO: 31)
GVPSRFSGSGSGTDFTLTISSLQPEDFATYYC

LC-FR4
                                      (SEQ ID NO: 32)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, the invention provides for compositions comprising any of the above described anti-PD-L1 antibodies in combination with at least one pharmaceutically-acceptable carrier.

In a still further embodiment, provided is an isolated nucleic acid encoding a light chain or a heavy chain variable region sequence of an anti-PD-L1 antibody, wherein:

(a) the heavy chain further comprises and HVR-H1, HVR-H2 and an HVR-H3 sequence having at least 85% sequence identity to GFTFSDSWIH (SEQ ID NO:17), AWISPYGGSTYYADSVKG (SEQ ID NO:18) and RHWPGGFDY (SEQ ID NO:19), respectively, and (b) the light chain further comprises an HVR-L1, HVR-L2 and an HVR-L3 sequence having at least 85% sequence identity to RASQDVSTAVA (SEQ ID NO:20), SASFLYS (SEQ ID NO:21) and QQYLYHPAT (SEQ ID NO:22), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                      (SEQ ID NO: 25)
EVQLVESGGGLVQPGGSLRLSCAAS

HC-FR2
                                      (SEQ ID NO: 26)
WVRQAPGKGLEWV

HC-FR3
                                      (SEQ ID NO: 27)
RFTISADTSKNTAYLQMNSLRAEDTAVYYCAR

HC-FR4
                                      (SEQ ID NO: 28)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                      (SEQ ID NO: 29)
DIQMTQSPSSLSASVGDRVTITC

LC-FR2
                                      (SEQ ID NO: 30)
WYQQKPGKAPKLLIY

LC-FR3
                                      (SEQ ID NO: 31)
GVPSRFSGSGSGTDFTLTISSLQPEDFATYYC

LC-FR4
                                      (SEQ ID NO: 32)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In another further embodiment, provided is an isolated anti-PDL1 antibody comprising a heavy chain and a light chain variable region sequence, wherein:

(a) the heavy chain sequence has at least 85% sequence identity to the heavy chain sequence: EVQLVES-GGGLVQPGGSLRLSCAASGFTFSDSWIHWVRQAPG-KGLEWVAWIS PYGGSTYYADSVKGRFTISADTSKN-TAYLQMNSLRAEDTAVYYCARRHWPGGFDYWG QGTLVTVSS (SEQ ID NO:41), or (b) the light chain sequences has at least 85% sequence identity to the light chain sequence: DIQMTQSPSSLSAS-VGDRVTITCRASQDVSTAVAWYQQKPGKAPKLLI-YSASF LYSGVPSRFSGSGSGTDFTLTISSLQPEDFA-TYYCQQYLYHPATFGQGTKVEIKR (SEQ ID NO:24).

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                        (SEQ ID NO: 25)
EVQLVESGGGLVQPGGSLRLSCAAS

HC-FR2
                                        (SEQ ID NO: 26)
WVRQAPGKGLEWV

HC-FR3
                                        (SEQ ID NO: 27)
RFTISADTSKNTAYLQMNSLRAEDTAVYYCAR

HC-FR4
                                        (SEQ ID NO: 42)
WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                        (SEQ ID NO: 29)
DIQMTQSPSSLSASVGDRVTITC

LC-FR2
                                        (SEQ ID NO: 30)
WYQQKPGKAPKLLIY

LC-FR3
                                        (SEQ ID NO: 31)
GVPSRFSGSGSGTDFTLTISSLQPEDFATYYC

LC-FR4
                                        (SEQ ID NO: 32)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                        (SEQ ID NO: 43)
EVQLVESGGGLVQPGGSLRLSCAASGFTFS

HC-FR2
                                        (SEQ ID NO: 44)
WVRQAPGKGLEWVA

HC-FR3
                                        (SEQ ID NO: 27)
RFTISADTSKNTAYLQMNSLRAEDTAVYYCAR

HC-FR4
                                        (SEQ ID NO: 45)
WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

LC-FR1

DIQMTQSPSSLSASVGDRVTITC
(SEQ ID NO: 29)

LC-FR2

WYQQKPGKAPKLLIY
(SEQ ID NO: 30)

LC-FR3

GVPSRFSGSGSGTDFTLTISSLQPEDFATYYC
(SEQ ID NO: 31)

LC-FR4

FGQGTKVEIK.
(SEQ ID NO: 46)

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PDL1 antibody comprising a heavy chain and a light chain variable region sequence, wherein:
(d) the heavy chain further comprises and HVR-H1, HVR-H2 and an HVR-H3 sequence having at least 85% sequence identity to GFTFSDSWIH (SEQ ID NO:17), AWISPYGGSTYYADSVKG (SEQ ID NO:18) and RHWPGGFDY (SEQ ID NO:19), respectively, or
(e) the light chain further comprises an HVR-L1, HVR-L2 and an HVR-L3 sequence having at least 85% sequence identity to RASQDVSTAVA (SEQ ID NO:20), SASFLYS (SEQ ID NO:21) and QQYLYH-PAT (SEQ ID NO:22), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

HC-FR1

EVQLVESGGGLVQPGGSLRLSCAAS
(SEQ ID NO: 25)

HC-FR2

WVRQAPGKGLEWV
(SEQ ID NO: 26)

HC-FR3

RFTISADTSKNTAYLQMNSLRAEDTAVYYCAR
(SEQ ID NO: 27)

HC-FR4

WGQGTLVTVSSASTK.
(SEQ ID NO: 47)

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

LC-FR1

DIQMTQSPSSLSASVGDRVTITC
(SEQ ID NO: 29)

LC-FR2

WYQQKPGKAPKLLIY
(SEQ ID NO: 30)

LC-FR3

GVPSRFSGSGSGTDFTLTISSLQPEDFATYYC
(SEQ ID NO: 31)

LC-FR4

FGQGTKVEIKR.
(SEQ ID NO: 32)

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PDL1 antibody comprising a heavy chain and a light chain variable region sequence, wherein:
(a) the heavy chain sequence has at least 85% sequence identity to the heavy chain sequence:

(SEQ ID NO: 40)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTK, or (b) the light chain sequences has at least 85% sequence identity to the light chain sequence:

(SEQ ID NO: 24)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In some embodiments, provided is an isolated anti-PDL1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:24. In some embodiments, provided is an isolated anti-PDL1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:40. In some embodiments, provided is an isolated anti-PDL1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:24 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:40.

In a still further embodiment, provided is an isolated anti-PDL1 antibody comprising a heavy chain and a light chain sequence, wherein:

(a) the heavy chain sequence has at least 85% sequence identity to the heavy chain sequence:

(SEQ ID NO: 48)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG, or (b) the light chain sequences has at least 85% sequence identity to the light chain sequence:

(SEQ ID NO: 49)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some embodiments, provided is an isolated anti-PDL1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:49. In some embodiments, provided is an isolated anti-PDL1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:48. In some embodiments, provided is an isolated anti-PDL1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:49 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:48.

In a still further aspect, the nucleic acid further comprises a vector suitable for expression of the nucleic acid encoding any of the previously described anti-PD-L1 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The anti-PD-L1 antibody or antigen binding fragment thereof, may be made using methods known in the art, for example, by a process comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment.

In a still further embodiment, the invention provides for a composition comprising an anti-PD-L1 antibody or antigen binding fragment thereof as provided herein and at least one pharmaceutically acceptable carrier.

Agents that Decreases or Inhibits TIGIT Expression and/or Activity

Provided herein is a method for treatment or delaying progression of cancer in an individual comprising administering to the individual an effective amount of a PD-1 axis binding antagonist in combination with an agent that decreases or inhibits TIGIT expression and/or activity. Provided herein is also a method for reducing or inhibiting cancer relapse or cancer progression in an individual comprising administering to the individual an effective amount of a PD-1 axis binding antagonist in combination with an agent that decreases or inhibits TIGIT expression and/or activity. Provided herein is also a method for treating or delaying progression of an immune related disease in an individual comprising administering to the individual an effective amount of a PD-1 axis binding antagonist in combination with an agent that decreases or inhibits TIGIT expression and/or activity. Provided herein is also a method for reducing or inhibiting progression of an immune related disease in an individual comprising administering to the individual an effective amount of a PD-1 axis binding antagonist in combination with an agent that decreases or inhibits TIGIT expression and/or activity. Provided herein is also a method for increasing, enhancing or stimulating an immune response or function in an individual comprising administering to the individual an effective amount of a PD-1 axis binding antagonist in combination with an agent that decreases or inhibits TIGIT expression and/or activity. Provided herein is also a method for increasing, enhancing or stimulating an immune response or function in an individual comprising administering to the individual an effective amount of an agent that decreases or inhibits TIGIT expression and/or activity and an agent that decreases or inhibits one or more additional immune co-inhibitory receptors. Provided herein is also a method for increasing, enhancing or stimulating an immune response or function in an individual comprising administering to the individual an effective amount of an agent that decreases or inhibits TIGIT expression and/or activity and an agent that increases or activates one or more additional immune co-stimulatory receptors. For example, agent that decreases or inhibits TIGIT expression and/or activity includes an antagonist of TIGIT expression and/or activity, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, an agent that inhibits and/or blocks the intracellular signaling mediated by TIGIT binding to PVRL3, and combinations thereof.

In some embodiments, the antagonist of TIGIT expression and/or activity includes a small molecule inhibitor, an inhibitory antibody or antigen-binding fragment thereof, an aptamer, an inhibitory nucleic acid, and an inhibitory polypeptide.

In some embodiments, the antagonist of PVR expression and/or activity includes a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVR includes a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVRL2 includes a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVRL3 includes a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVR includes a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVRL2 includes a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVRL3 includes a small molecule inhibitor, an inhibitory antibody or antigen-binding fragment thereof, an aptamer, an inhibitory nucleic acid, and an inhibitory polypeptide.

In some embodiments, the antagonist of TIGIT expression and/or activity is an inhibitory nucleic acid selected from an antisense polynucleotide, an interfering RNA, a catalytic RNA, and an RNA-DNA chimera.

In some embodiments, the antagonist of TIGIT expression and/or activity is an anti-TIGIT antibody or antigen-binding fragment thereof.

The anti-TIGIT antibodies useful in this invention, including compositions containing such antibodies, such as those described in WO 2009/126688, may be used in combination with PD-1 axis binding antagonists.

Anti-TIGIT Antibodies

The present invention provides anti-TIGIT antibodies. Exemplary antibodies include polyclonal, monoclonal, humanized, bispecific, and heteroconjugate antibodies. It will be understood by one of ordinary skill in the art that the invention also provides antibodies against other polypeptides (i.e., anti-PVR antibodies) and that any of the description herein drawn specifically to the method of creation, production, varieties, use or other aspects of anti-TIGIT antibodies will also be applicable to antibodies specific for other non-TIGIT polypeptides.

Polyclonal Antibodies

The anti-TIGIT antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the TIGIT polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal Antibodies

The anti-TIGIT antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the TIGIT polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against the polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Human and Humanized Antibodies

The anti-TIGIT antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat.

No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

Bispecific Antibodies

Bispecific antibodies are monoclonal, preferably human or humanized, antibodies that have binding specificities for at least two different antigens. In the present case, one of the binding specificities is for TIGIT, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')2 bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain (V$_H$) connected to a light-chain variable domain (V$_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. As one nonlimiting example, trispecific antibodies can be prepared. See, e.g., Tutt et al., *J. Immunol.* 147:60 (1991).

Exemplary bispecific antibodies may bind to two different epitopes on a given TIGIT polypeptide herein. Alternatively, an anti-TIGIT polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular TIGIT polypeptide. Bispecific antibodies may also be used to localize cytotoxic agents to cells which express a particular TIGIT polypeptide. These antibodies possess a TIGIT-binding arm and an arm which binds a cytotoxic agent or a radionuclide chelator, such as EOTUBE, DPTA, DOTA, or TETA. Another bispecific antibody of interest binds the TIGIT polypeptide and further binds tissue factor (TF).

Heteroconjugate Antibodies

Heteroconjugate antibodies are also within the scope of the present invention.

Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.*, 176: 1191-1195 (1992) and Shopes, *J. Immunol.*, 148: 2918-2922 (1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

In some embodiment, anti-TIGIT antibodies were generated which were hamster-anti-mouse antibodies. Two antibodies, 10A7 and 1F4, also specifically bound to human TIGIT. The amino acid sequences of the light and heavy chains of the 10A7 antibody were determined using standard techniques. The light chain sequence of this antibody is: DIVMTQSPSSLAVSPGEKVTMTCKSSQSLYYS-GVKENLLAWYQQKPGQS PKLLIYYASIRFTGVP-DRFTGSGSGTDYTLTITSVQAEDMGQYFCQQGIN-NPLTFGDGTK LEIKR (SEQ ID NO:13) and the heavy chain sequence of this antibody is: EVQLVES-GGGLTQPGKSLKLSCEASGFTFSSFTMHWVRQSPGK-GLEWVAFIRSGSGIVF YADAVRGRFTISRDNAKNLL-FLQMNDLKSEDTAMYYCARRPLGHNTFDSWGQGT-LVT VSS (SEQ ID NO:15), where the complementarity determining regions (CDRs) of each chain are represented by bold text. Thus, CDR1 of the 10A7 light chain has the sequence KSSQSLYYSGVKENLLA (SEQ ID NO:1), CDR2 of the 10A7 light chain has the sequence ASIRFT (SEQ ID NO:2), and CDR3 of the 10A7 light chain has the sequence QQGINNPLT (SEQ ID NO:3). CDR1 of the 10A7 heavy chain has the sequence GFTFSSFTMH (SEQ ID NO:4), CDR2 of the 10A7 heavy chain has the sequence FIRSGSGIVFYADAVRG (SEQ ID NO:5), and CDR3 of the 10A7 heavy chain has the sequence RPLGHNTFDS (SEQ ID NO:6).

The amino acid sequences of the light and heavy chains of the 1F4 antibody were also determined. The light chain sequence of this antibody is: DVVLTQTPLSLSVSFGDQV-SISCRSSQSLVNSYGNTFLSWYLHKPGQSPQLLIFGIS-NRFS GVPDRFSGSGSGTDFTLKISTIKPEDLGMYY-CLQGTHQPPTFGPGTKLEVK (SEQ ID NO:14) and the heavy chain sequence of this antibody is: EVQLQQSGPEL-VKPGTSMKISCKASGYSFTGHLMNWVKQSHGKN-LEWIGLIIPYNGGTS YNQKFKGKATLT-VDKSSSTAYMELLSLTSDDSAVYFCSRGLRGFYAMD-YWGQGTSVT VSS (SEQ ID NO:16), where the complementarity determining regions (CDRs) of each chain are represented by bold text. Thus, CDR1 of the 1F4 light chain has the sequence RSSQSLVNSYGNTFLS (SEQ ID NO:7), CDR2 of the 1F4 light chain has the sequence GISNRFS (SEQ ID NO:8), and CDR3 of the 1F4 light chain has the sequence LQGTHQPPT (SEQ ID NO:9). CDR1 of the 1F4 heavy chain has the sequence GYSFTGHLMN (SEQ ID NO:10), CDR2 of the 1F4 heavy chain has the sequence LIIPYNGGTSYNQKFKG (SEQ ID NO:11), and CDR3 of the 1F4 heavy chain has the sequence GLRGFYAMDY (SEQ ID NO:12).

The nucleotide sequence encoding the 1F4 light chain was determined to be GATGTTGTGTTGACTCAAACTC-CACTCTCCCTGTCTGTCAGCTTTGGAGATCAAGTTT CTATCTCTTGCAGGTCTAGTCAGAGTCTTG-TAAACAGTTATGGGAACACCTTTTTGTC TTGGTAC-CTGCACAAGCCTGGCCAGTCTCCACAGCTCCT-CATCTTTGGGATTTCCAA CAGATTTTCTGGGGTGCCAGACAGGTTCAGTG-GCAGTGGTTCAGGGACAGATTTCAC ACT-CAAGATCAGCACAATAAAGCCTGAGGACT-TGGGAATGTATTACTGCTTACAAG GTACGCATCAGCCTCCCACGTTCGGTCCTGGGAC-CAAGCTGGAGGTGAAA (SEQ ID NO:38) and the nucleotide sequence encoding the 1F4 heavy chain was determined to be GAGGTCCAGCTGCAACAGTCTG-GACCTGAGCTGGTGAAGCCTGGAACTTCAATGAA GATATCCTGCAAGGCTTCTGGTTACTCATTCACTG-GCCATCTTATGAACTGGGTGAA GCAGAGCCATG-GAAAGAACCTTGAGTGGATTGGACTTATTATTCCT-TACAATGGTGG TACAAGCTATAACCAGAAGTTCAAGGGCAAGGC-CACATTGACTGTAGACAAGTCAT CCAGCACAGC-CTACATGGAGCTCCTCAGTCTGACTTCTGAT-GACTCTGCAGTCTATTT CTGTTCAAGAGGCCTTAGGGGCTTCTATGCTATG-GACTACTGGGGTCAAGGAACCTC AGTCAC-CGTCTCCTCA (SEQ ID NO:39).

In some embodiments, the anti-TIGIT antibody or antigen-binding fragment thereof comprises at least one HVR comprising an amino acid sequence selected from the amino acid sequences set forth in (1) KSSQSLYYSGVKENLLA (SEQ ID NO:1), ASIRFT (SEQ ID NO:2), QQGINNPLT (SEQ ID NO:3), GFTFSSFTMH (SEQ ID NO:4), FIRSGS-GIVFYADAVRG (SEQ ID NO:5), and RPLGHNTFDS (SEQ ID NO:6), or (2) RSSQSLVNSYGNTFLS (SEQ ID NO:7), GISNRFS (SEQ ID NO:8), LQGTHQPPT (SEQ ID NO:9), GYSFTGHLMN (SEQ ID NO:10), LIIPYNGGTSYNQKFKG (SEQ ID NO:11), and GLRGFYAMDY (SEQ ID NO:12).

In some embodiments, the anti-TIGIT antibody or antigen-binding fragment thereof, wherein the antibody light chain comprises the amino acid sequence set forth in DIVMTQSPSSLAVSPGEKVTMTCKSSQSLYYS-GVKENLLAWYQQKPGQS PKLLIYYASIRFTGVP-DRFTGSGSGTDYTLTITSVQAEDMGQYFCQQGIN-NPLTFGDGTK LEIKR (SEQ ID NO:13) or DVVLTQTPLSLSVSFGDQVSISCRSSQSLVNSYGNT-FLSWYLHKPGQSPQLLIFGISNRFS GVPDRFSGSGS-GTDFTLKISTIKPEDLGMYYCLQGTHQPPTFGPGT-KLEVK (SEQ ID NO:14).

In some embodiments, the anti-TIGIT antibody or antigen-binding fragment thereof, wherein the antibody heavy chain comprises the amino acid sequence set forth in EVQLVESGGGLTQPGKSLKLSCEASGFTFSSFTMH-WVRQSPGKGLEWVAFIRSGSGIVF YADAVRGR-FTISRDNAKNLLFLQMNDLKSEDTAMYYCARRPL-GHNTFDSWGQGTLVT VSS (SEQ ID NO:15) or EVQLQQSGPELVKPGTSMKISCKASGYSFTGHLMN-WVKQSHGKNLEWIGLIIPYNGGTS YNQKFKG-KATLTVDKSSSTAYMELLSLTSDDSAVYFCSRGLRG-FYAMDYWGQGTSVT VSS (SEQ ID NO:16).

In some embodiments, the anti-TIGIT antibody or antigen-binding fragment thereof, wherein the antibody light chain comprises the amino acid sequence set forth in DIVMTQSPSSLAVSPGEKVTMTCKSSQSLYYS-GVKENLLAWYQQKPGQS PKLLIYYASIRFTGVP-DRFTGSGSGTDYTLTITSVQAEDMGQYFCQQGIN-NPLTFGDGTK LEIKR (SEQ ID NO:13) or DVVLTQTPLSLSVSFGDQVSISCRSSQSLVNSYGNT-FLSWYLHKPGQSPQLLIFGISNRFS GVPDRFSGSGS-GTDFTLKISTIKPEDLGMYYCLQGTHQPPTFGPGT-KLEVK (SEQ ID NO:14) and the antibody heavy chain comprises the amino acid sequence set forth in EVQLVES-GGGLTQPGKSLKLSCEASGFTFSSFTMHWVRQSPGK-GLEWVAFIRSGSGIVF YADAVRGRFTISRDNAKNLL-FLQMNDLKSEDTAMYYCARRPLGHNTFDSWGQGT-LVT VSS (SEQ ID NO:15) or EVQLQQSGPELVK-PGTSMKISCKASGYSFTGHLMNWVKQSHGKN-LEWIGLIIPYNGGTS YNQKFKGKATLT-VDKSSSTAYMELLSLTSDDSAVYFCSRGLRGFYAMD-YWGQGTSVT VSS (SEQ ID NO:16).

In some embodiments, the anti-TIGIT antibody or antigen-binding fragment thereof, wherein the antibody is selected from a humanized antibody, a chimeric antibody, a bispecific antibody, a heteroconjugate antibody, and an immunotoxin.

In some embodiments, the anti-TIGIT antibody or antigen-binding fragment thereof comprises at least one HVR is at least 90% identical to an HVR set forth in any of (1) KSSQSLYYSGVKENLLA (SEQ ID NO:1), ASIRFT (SEQ ID NO:2), QQGINNPLT (SEQ ID NO:3), GFTFSSFTMH (SEQ ID NO:4), FIRSGSGIVFYADAVRG (SEQ ID NO:5), and RPLGHNTFDS (SEQ ID NO:6), or (2) RSSQSLVN-SYGNTFLS (SEQ ID NO:7), GISNRFS (SEQ ID NO:8), LQGTHQPPT (SEQ ID NO:9), GYSFTGHLMN (SEQ ID NO:10), LIIPYNGGTSYNQKFKG (SEQ ID NO:11), and GLRGFYAMDY (SEQ ID NO:12).

In some embodiments, the anti-TIGIT antibody or fragment thereof comprises the light chain and/or heavy chain comprising amino acid sequences at least 90% identical to the amino acid sequences set forth in DIVMTQSPSS-LAVSPGEKVTMTCKSSQSLYYSGVKENLLAWYQQK-PGQS PKLLIYYASIRFTGVPDRFTGSGSGTDYTLTITS-VQAEDMGQYFCQQGINNPLTFGDGTK LEIKR (SEQ ID NO:13) or DVVLTQTPLSLSVSFGDQVSISCRSSQS-LVNSYGNTFLSWYLHKPGQSPQLLIFGISNRFS GVP-DRFSGSGSGTDFTLKISTIKPEDLGMYYCLQGTH-QPPTFGPGTKLEVK (SEQ ID NO:14), or EVQLVESGGGLTQPGKSLKLSCEASGFTFSSFTMH-WVRQSPGKGLEWVAFIRSGSGIVF YADAVRGR-FTISRDNAKNLLFLQMNDLKSEDTAMYYCARRPL-GHNTFDSWGQGTLVT VSS (SEQ ID NO:15) or EVQLQQSGPELVKPGTSMKISCKASGYSFTGHLMN-WVKQSHGKNLEWIGLIIPYNGGTS YNQKFKG-KATLTVDKSSSTAYMELLSLTSDDSAVYFCSRGLRG-FYAMDYWGQGTSVT VSS (SEQ ID NO:16), respectively.

Agents that Modulate CD226 Expression and/or Activity

Provided herein is a method of treating or delaying progression of cancer in an individual comprising administering to the individual an effective amount of a PD-1 axis binding antagonist and an agent that modulates the CD226 expression and/or activity. Provided herein is also a method for reducing or inhibiting cancer relapse or cancer progression in an individual comprising administering to the individual an effective amount of a PD-1 axis binding antagonist and an agent that modulates the CD226 expression and/or activity. Provided herein is also a method for treating or delaying progression of an immune related disease in an individual comprising administering to the individual an effective amount of a PD-1 axis binding antagonist and an agent that modulates the CD226 expression and/or activity. Provided herein is also a method for reducing or inhibiting progression of an immune related disease in an individual comprising administering to the individual an effective amount of a PD-1 axis binding antagonist and agent that modulates the CD226 expression and/or activity. Provided herein is also a method of increasing, enhancing or stimulating an immune response or function in an individual by administering to the individual an effective amount of a PD-1 axis binding antagonist and an agent that modulates the CD226 expression and/or activity.

For example, agents that modulate the CD226 expression and/or activity are agents capable of increasing and/or stimulating CD226 expression and/or activity, increasing and/or stimulating the interaction of CD226 with PVR, PVRL2, and/or PVRL3, and increasing and/or stimulating the intracellular signaling mediated by CD226 binding to PVR, PVRL2, and/or PVRL3. In some embodiments, agents capable of increasing and/or stimulating CD226 expression and/or activity are agents that increase and/or stimulate CD226 expression and/or activity. In some embodiments, agents capable of increasing and/or stimulating the interaction of CD226 with PVR, PVRL2, and/or PVRL3 are agents that increase and/or stimulate the interaction of CD226 with PVR, PVRL2, and/or PVRL3. In some embodiments, agents capable of increasing and/or stimulating the intracellular signaling mediated by CD226 binding to PVR, PVRL2, and/or PVRL3 are agents that increase and/or stimulate the intracellular signaling mediated by CD226 binding to PVR, PVRL2, and/or PVRL3.

In some embodiments, the agent that modulates the CD226 expression and/or activity is selected from an agent that inhibits and/or blocks the interaction of CD226 with TIGIT, an antagonist of TIGIT expression and/or activity, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, an agent that inhibits and/or blocks the intracellular signaling mediated by TIGIT binding to PVRL3, and combinations thereof. In some embodiments, the agent that inhibits and/or blocks the interaction of CD226 with TIGIT is selected from a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of CD226 with TIGIT is an anti-TIGIT antibody or antigen-binding fragment thereof. In some embodiments, the agent that inhibits and/or blocks the interaction of CD226 with TIGIT is an inhibitory nucleic acid selected from an antisense polynucleotide, an interfering RNA, a catalytic RNA, and an RNA-DNA chimera.

In some embodiments, the antagonist of TIGIT expression and/or activity is a small molecule inhibitor, an inhibitory antibody or antigen-binding fragment thereof, an aptamer, an inhibitory nucleic acid, and an inhibitory polypeptide. In some embodiments, the antagonist of TIGIT expression and/or activity is an anti-TIGIT antibody or antigen-binding fragment thereof. In some embodiments, the antagonist of TIGIT expression and/or activity is an inhibitory nucleic acid selected from an antisense polynucleotide, an interfering RNA, a catalytic RNA, and an RNA-DNA chimera. In some embodiments, the antagonist of PVR expression and/or activity is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of TIGIT with PVR is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of TIGIT with PVRL2 is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of TIGIT with PVRL3 is a small molecule inhibitor, an inhibitory antibody or antigen-binding fragment thereof, an aptamer, an inhibitory nucleic acid, and an inhibitory polypeptide. In some embodiments, the agent that inhibits and/or blocks the intracellular signaling mediated by TIGIT binding to PVR is a small molecule inhibitor, an inhibitory antibody or antigen-binding fragment thereof, an aptamer, an inhibitory nucleic acid, and an inhibitory polypeptide. In some embodiments, the agent that inhibits and/or blocks the intracellular signaling mediated by TIGIT binding to PVRL2 is a small molecule inhibitor, an inhibitory antibody or antigen-binding fragment thereof, an aptamer, an inhibitory nucleic acid, and an inhibitory polypeptide. In some embodiments, the agent that inhibits and/or blocks the intracellular signaling mediated by TIGIT binding to PVRL3 is a small molecule inhibitor, an inhibitory antibody or antigen-binding fragment thereof, an aptamer, an inhibitory nucleic acid, and an inhibitory polypeptide.

In some embodiments, the antagonist of TIGIT expression and/or activity includes a small molecule inhibitor, an inhibitory antibody or antigen-binding fragment thereof, an aptamer, an inhibitory nucleic acid, and an inhibitory polypeptide. In some embodiments, the antagonist of PVR expression and/or activity includes a small molecule inhibitor, an inhibitory antibody or antigen-binding fragment thereof, an aptamer, an inhibitory nucleic acid, and an inhibitory polypeptide. In some embodiments, the agent that inhibits the intracellular signaling mediated by TIGIT binding to PVR is selected from the group consisting of a small molecule inhibitor, an inhibitory antibody or antigen-binding fragment thereof, an aptamer, an inhibitory nucleic acid, and an inhibitory polypeptide. In some embodiments, the antagonist of TIGIT expression and/or activity is an anti-TIGIT antibody or antigen-binding fragment thereof. In some embodiments, the antagonist of TIGIT expression and/or activity is an inhibitory nucleic acid selected from an antisense polynucleotide, an interfering RNA, a catalytic RNA, and an RNA-DNA chimera.

Combinations of T Cell Targets for Immunregulatory Antibody Therapy

In addition to specific antigen recognition through the TCR, T-cell activation is regulated through a balance of positive and negative signals provided by co-stimulatory receptors. These surface proteins are typically members of either the TNF receptor or B7 superfamilies. Activating co-stimulatory receptors include CD226, CD28, OX40, GITR, CD137, CD27, HVEM, MICA, ICOS, NKG2D, and 2B4. Inhibitory co-stimulatory receptors include CTLA-4, PD-1, TIM-3, BTLA, VISTA, LAG-3, B7H4, and CD96. Agonistic antibodies directed against activating co-stimulatory molecules and blocking antibodies against negative co-stimulatory molecules may enhance T-cell stimulation to promote tumor destruction.

Provided herein is a method of increasing, enhancing or stimulating an immune response or function in an individual by administering to the individual an effective amount of an agent that decreases or inhibits TIGIT expression and/or activity and an agent that decreases or inhibits one or more additional immune co-inhibitory receptors. In some embodiments, the one or more additional immune co-inhibitory receptor is selected from PD-1, CTLA-4, LAG3, TIM3, BTLA, VISTA, B7H4, and CD96. In some embodiments, the one or more additional immune co-inhibitory receptor is selected from PD-1, CTLA-4, LAG3 and TIM3.

Provided herein is also a method of increasing, enhancing or stimulating an immune response or function in an individual by administering to the individual an effective amount of an agent that decreases or inhibits TIGIT expression and/or activity and an agent that increases or activates one or more additional immune co-stimulatory receptor. In some embodiments, the one or more additional immune co-stimulatory receptor is selected from CD226, OX-40, CD28, CD27, CD137, HVEM, GITR, MICA, ICOS, NKG2D, and 2B4. In some embodiments, the one or more additional immune co-stimulatory receptor is selected from CD226, OX-40, CD27, CD137, HVEM and GITR. In some embodiments, the one or more additional immune co-stimulatory receptor is selected from OX-40 and CD27.

IV Kits

In another aspect, provided is a kit comprising a PD-1 axis binding antagonist and a package insert comprising instructions for using the PD-1 axis binding antagonist in combination with an agent that decreases or inhibits TIGIT expression and/or activity to treat or delay progression of cancer in an individual or for enhancing immune function of an individual having cancer. Any of the PD-1 axis binding antagonists and/or agents that decreases or inhibits TIGIT expression and/or activity described herein may be included in the kit.

In another aspect, provided is a kit comprising a PD-1 axis binding antagonist and an agent that decreases or inhibits TIGIT expression and/or activity, and a package insert comprising instructions for using the PD-1 axis binding antagonist and the agent that decreases or inhibits TIGIT expression and/or activity to treat or delay progression of cancer in an individual or for enhancing immune function of an individual having cancer. Any of the PD-1 axis binding antagonists and/or agents that decreases or inhibits TIGIT expression and/or activity described herein may be included in the kit.

In another aspect, provided is a kit comprising an agent that decreases or inhibits TIGIT expression and/or activity and a package insert comprising instructions for using the agent that decreases or inhibits TIGIT expression and/or activity in combination with a PD-1 axis binding antagonist to treat or delay progression of cancer in an individual or for enhancing immune function of an individual having cancer. Any of the PD-1 axis binding antagonists and/or agents that decreases or inhibits TIGIT expression and/or activity described herein may be included in the kit.

In another aspect, provided is a kit comprising a PD-1 axis binding antagonist and a package insert comprising instructions for using the PD-1 axis binding antagonist in combination with an agent that modulates the CD226 expression and/or activity to treat or delay progression of cancer in an individual. Any of the PD-1 axis binding antagonists and/or agents that modulate the CD226 expression and/or activity described herein may be included in the kit.

In another aspect, provided is a kit comprising a PD-1 axis binding antagonist and an agent that modulates the CD226 expression and/or activity, and a package insert comprising instructions for using the PD-1 axis binding antagonist and the agent that modulates the CD226 expression and/or activity to treat or delay progression of cancer in an individual. Any of the PD-1 axis binding antagonists and/or agents that modulate the CD226 expression and/or activity described herein may be included in the kit.

In another aspect, provided is a kit comprising an agent that modulates the CD226 expression and/or activity and a package insert comprising instructions for using the agent modulates the CD226 expression and/or activity in combination with a PD-1 axis binding antagonist to treat or delay progression of cancer in an individual. Any of the PD-1 axis binding antagonists and/or agents that modulate the CD226 expression and/or activity described herein may be included in the kit.

In another aspect, provided is a kit comprising a PD-1 axis binding antagonist and a package insert comprising instructions for using the PD-1 axis binding antagonist in combination with an agent that modulates the CD226 expression and/or activity to enhance immune function of an individual having cancer. Any of the PD-1 axis binding antagonists and/or agents that modulate the CD226 expression and/or activity described herein may be included in the kit.

In another aspect, provided is a kit comprising a PD-1 axis binding antagonist and an agent that modulates the CD226 expression and/or activity, and a package insert comprising instructions for using the PD-1 axis binding antagonist and the agent that modulates the CD226 expression and/or activity to enhance immune function of an individual having cancer. Any of the PD-1 axis binding antagonists and/or agents that modulate the CD226 expression and/or activity described herein may be included in the kit.

In another aspect, provided is a kit comprising an agent modulates the CD226 expression and/or activity and a package insert comprising instructions for using the agent that modulates the CD226 expression and/or activity in combination with a PD-1 axis binding antagonist to enhance immune function of an individual having cancer. Any of the PD-1 axis binding antagonists and/or agents that modulate the CD226 expression and/or activity described herein may be included in the kit.

In another aspect, provided is a kit comprising an agent that decreases or inhibits TIGIT expression and/or activity and a package insert comprising instructions for using the agent that decreases or inhibits TIGIT expression and/or activity in combination with an agent that decreases or inhibits one or more additional immune co-inhibitory receptors to treat or delay progression of cancer in an individual or to enhance immune function of an individual having cancer. Any of the agents that decrease or inhibit TIGIT expression and/or activity and/or agents that decrease or inhibit one or more additional immune co-inhibitory receptors described herein may be included in the kit.

In another aspect, provided is a kit comprising an agent that decreases or inhibits TIGIT expression and/or activity and an agent that decreases or inhibits one or more additional immune co-inhibitory receptors, and a package insert comprising instructions for using the agent that decreases or inhibits TIGIT expression and/or activity and the agent that decreases or inhibits one or more additional immune co-inhibitory receptors to treat or delay progression of cancer in an individual or to enhance immune function of an individual having cancer. Any of the agents that decrease or inhibit TIGIT expression and/or activity and/or agents that decrease or inhibit one or more additional immune co-inhibitory receptors described herein may be included in the kit.

In another aspect, provided is a kit comprising an agent that decreases or inhibits one or more additional immune co-inhibitory receptors and a package insert comprising instructions for using the agent that decreases or inhibits one or more additional immune co-inhibitory receptors in combination with an agent that decreases or inhibits TIGIT expression and/or activity to treat or delay progression of cancer in an individual or to enhance immune function of an individual having cancer. Any of the agents that decrease or inhibit TIGIT expression and/or activity and/or agents that decrease or inhibit one or more additional immune co-inhibitory receptors described herein may be included in the kit.

In another aspect, provided is a kit comprising an agent that decreases or inhibits TIGIT expression and/or activity and a package insert comprising instructions for using the agent that decreases or inhibits TIGIT expression and/or activity in combination with an agent that increases or activates one or more additional immune co-stimulatory receptors to treat or delay progression of cancer in an individual or to enhance immune function of an individual having cancer. Any of the agents that decrease or inhibit TIGIT expression and/or activity and/or agents that increase or activate one or more additional immune co-stimulatory receptors described herein may be included in the kit.

In another aspect, provided is a kit comprising an agent that decreases or inhibits TIGIT expression and/or activity and an agent that increases or activates one or more additional immune co-stimulatory receptors, and a package insert comprising instructions for using the agent that decreases or inhibits TIGIT expression and/or activity and the agent that increases or activates one or more additional immune co-stimulatory receptors to treat or delay progression of cancer in an individual or to enhance immune function of an individual having cancer. Any of the agents that decrease or inhibit TIGIT expression and/or activity and/or agents that increase or activate one or more additional immune co-stimulatory receptors described herein may be included in the kit.

In another aspect, provided is a kit comprising an agent that increases or activates one or more additional immune co-stimulatory receptors and a package insert comprising instructions for using the agent that increases or activates one or more additional immune co-stimulatory receptors in combination with an agent that decreases or inhibits TIGIT expression and/or activity to treat or delay progression of cancer in an individual or to enhance immune function of an individual having cancer. Any of the agents that decrease or inhibit TIGIT expression and/or activity and/or agents that increase or activate one or more additional immune co-stimulatory receptors described herein may be included in the kit.

In some embodiments, the kit comprises a container containing one or more of the PD-1 axis binding antagonists and agents that decreases or inhibits TIGIT expression and/or activity described herein. In some embodiments, the kit comprises a container containing one or more of the PD-1 axis binding antagonists and agents that modulates CD226 expression and/or activity described herein. In some embodiments, the kit comprises a container containing one or more of the agents that decrease or inhibit TIGIT expression and/or activity and agents that decrease or inhibit one or more additional immune co-inhibitory receptors described herein. In some embodiments, the kit comprises a container containing one or more of the agents that decrease or inhibit TIGIT expression and/or activity and agents that increase or activate one or more additional immune co-stimulatory receptors described herein. Suitable containers include, for example, bottles, vials (e.g., dual chamber vials), syringes (such as single or dual chamber syringes) and test tubes. The container may be formed from a variety of materials such as glass or plastic. In some embodiments, the kit may comprise a label (e.g., on or associated with the container) or a package insert. The label or the package insert may indicate that the compound contained therein may be useful or intended for treating or delaying progression of cancer in an individual or for enhancing immune function of an individual having cancer. The kit may further comprise other materials desirable from a commercial and user standpoint, including other buffers, diluents, filters, needles, and syringes.

EXAMPLES

The invention can be further understood by reference to the following examples, which are provided by way of illustration and are not meant to be limiting.

Example 1

TIGIT is Highly Expressed on Exhausted CD8$^+$ and CD4$^+$ T Cells and Correlated with PD-1 Expression To confirm that CD8$^+$ T cells are competent to express TIGIT after stimulation in vitro, MACS-enriched C57BL6/J splenic CD8$^+$ T cells were stimulated with plate-bound anti-CD3 and anti-CD28 for 24-48 hours in vitro. Flow cytometry was used to measure TIGIT expression. In line with TIGIT's expression by CD4$^+$ T cells (Yu, X., et al. The surface protein TIGIT suppresses T cell activation by promoting the generation of mature immunoregulatory dendritic cells. *Nature immunology* 10, 48-57 (2009)), murine CD8$^+$ T cells expressed TIGIT within 48 hours of stimulation in vitro (FIG. 1A).

To assess TIGIT expression by activated CD8$^+$ T cells in vivo, C57BL6/J mice were infected with Armstrong strain Lymphocytic Choriomeningitis Virus (LCMV), and splenocytes were analyzed 7 days after infection. Briefly, for acute infections, mice were intravenously infected with 2×10$^6$ plaque-forming units (PFU) Armstrong strain LCMV. Flow cytometry was used to measure TIGIT expression by naïve (CD44$^{low}$ CD62L$^{high}$) and effector memory (CD44$^{high}$ CD62L$^{low}$) CD8$^+$ and CD4+ T cells. At the peak of the LCMV T cell response, a subset of CD4$^+$ effector memory T cells (T$_{EM}$) and nearly all CD8$^+$ T$_{EM}$ cells strongly expressed TIGIT (FIG. 1B). Flow cytometry was used to measure TIGIT expression by PD-1$^{high}$ and PD-1$^{low}$ effector memory CD8$^+$ T cells. Interestingly, TIGIT expression was near perfectly correlated with PD-1 expression (FIG. 1C).

Figure 1D:
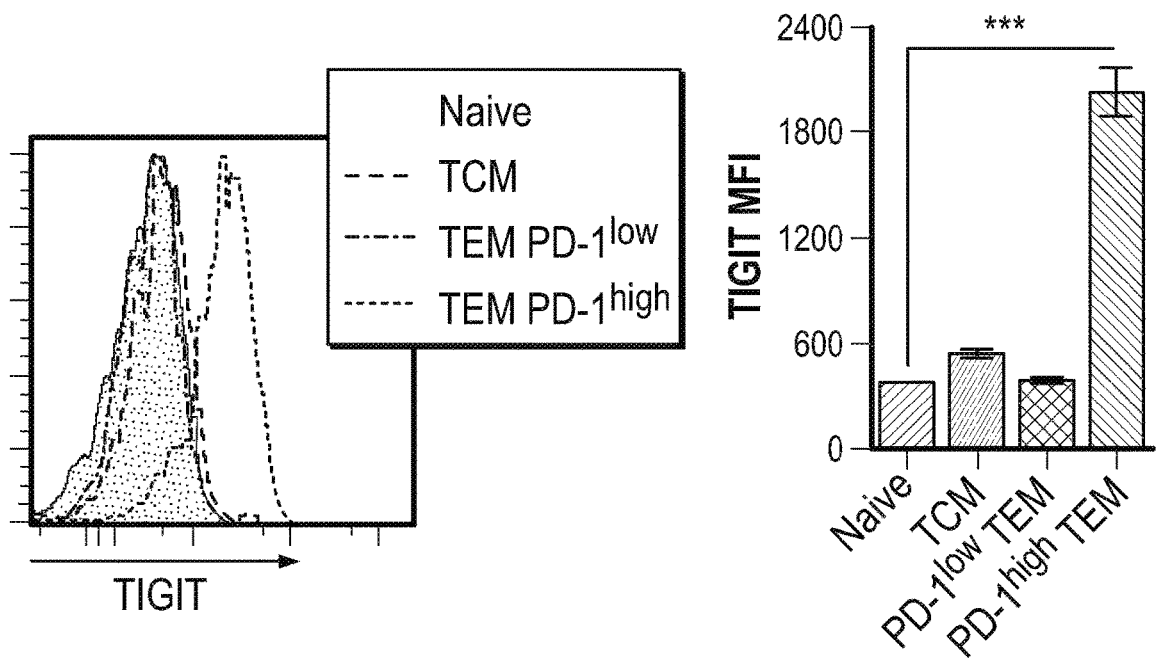

Because PD-1 is associated with T cell exhaustion, TIGIT expression was examined on chronically stimulated T cells. Briefly, for chronic infections, C57BL6/J mice were intravenously infected with 2×10$^6$ PFU Clone 13 strain LCMV and treated with 500 ug and 250 ug of depleting anti-CD4 antibodies (clone GK1.5) 3 days before and 4 days after infection, respectively. Where indicated, mice infected with Clone 13 strain LCMV received intraperitoneal injections of 200 ug of isotype control antibodies, 200 ug of anti-PD-L1 antibodies, and/or 500 ug of anti-TIGIT antibodies 3 times per week from days 28 to 42 post-infection. Splenocytes were analyzed 42 days after infection. Flow cytometry was used to measure TIGIT expression by naïve (CD44$^{low}$ CD62L$^{high}$), central memory (CD44$^{high}$ CD62L$^{high}$), and effector memory (CD44$^{high}$ CD62L$^{low}$) CD8$^+$ T cells. Indeed, in mice chronically infected with Clone 13 strain LCMV, TIGIT was highly expressed predominantly on PD-1$^{high}$ T cells but not on nave cells, PD-1$^{low}$ T$_{EM}$ cells, or central memory T cells (FIG. 1D).

Example 2

A Role of TIGIT in T Cell Exhaustion in TIGIT Deficient Mice

Figure 2:
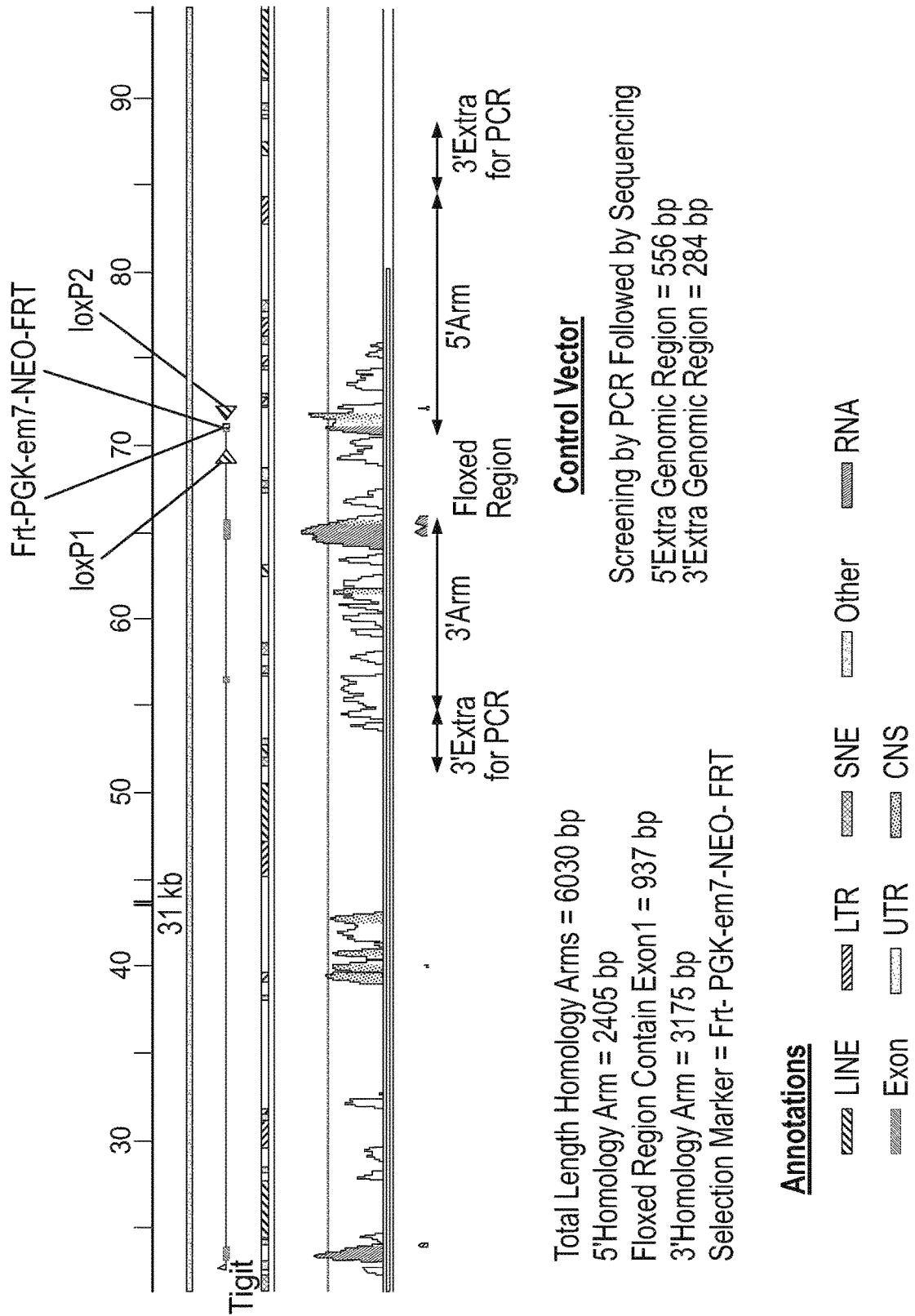
FIG. 2 shows the design of TIGIT$^{loxP/loxP}$ mice. Exon 1 of TIGIT was flanked by loxP sites using standard techniques.

To characterize the role of TIGIT in T cell exhaustion, mice in which TIGIT was conditionally deleted in T cells were generated (TIGIT$^{fl/fl}$ CD4-cre$^+$ (CKO), FIG. 2). Briefly, CD4$^{cre}$ mice and TIGIT$^{loxP/loxP}$ mice were generated on a C57BL/6J background with standard techniques and crossed. The quality-tested ES cell line (Art B6/3.6 (genetic background: C57BL/6 NTac) was grown on a mitotically inactivated feeder layer comprised of mouse embryonic fibroblasts in ES cell culture medium containing Leukemia inhibitory factor and Fetal Bovine Serum. The cells were electroporated with the linearized DNA targeting vector according to Taconic Artemis' Standard Operation Procedures. G418 and Gancyclovir selection were used as mechanisms for enrichment of homologously recombined clones. Resistant ES cell colonies (ES clones) with a distinct morphology were isolated on day 8 after transfection and analysed by Southern Blotting and/or PCR in a primary screen. Homologous recombinant ES cell clones were expanded and frozen in liquid nitrogen after extensive molecular validation. The neo cassette was removed by flpE recombinase before microinjection into Bl/6 female albino donors. Chimeric offspring were produced and tails were screened by PCR for germline transmission. TIGIT expression was ablated with 96% efficiency from T cells in TIGIT$^{loxP/loxP}$ CD4$^{cre}$ mice.

Mice whose T cells lacked TIGIT mounted a CD4$^+$ and CD8$^+$ T cell response to acute Armstrong strain LCMV infection that was similar to wild-type mice (FIGS. 3A-3D).

To assess the effect in a chronic infection setting, TIGIT$^{fl/fl}$ CD4-cre$^-$ (WT) and TIGIT$^{fl/fl}$ CD4-cre$^+$ (CKO) mice were briefly depleted of CD4$^+$ T cells and infected with Clone 13 strain LCMV. Splenocytes and liver viral titers were analyzed 42 days after infection. After chronic infection with Clone 13 strain LCMV, significantly more CD8$^+$ and CD4$^+$ T cells from TIGIT$^{fl/fl}$ CD4-cre$^+$ (CKO) mice were competent to produce interferon gamma (IFN γ) than were T cells from wildtype littermate mice (TIGIT$^{fl/fl}$ CD4-cre$^-$ (WT)) (82-86% increase, P<0.01, FIGS. 4A-4D). Furthermore, viral loads were significantly reduced in chronically infected TIGIT$^{fl/fl}$ CD4-cre$^+$ (CKO) mice (68% decrease, P<0.0001, FIG. 4E).

These results suggest that TIGIT plays an important role in regulating T cell activity and response during chronic immune responses such as during a chronic viral infection, and that TIGIT can regulate the effector function, in particular the competency to produce effector cytokines, such as IFNγ and TNFα, of chronically stimulated or exhausted CD8$^+$ and CD4$^+$ T cells.

Example 3

TIGIT and PD-1 Synergistically Regulate the Effector Function of Exhausted T Cells In Vivo Since TIGIT expression was closely correlated with PD-1 expression, especially in CD8$^+$ T cells during acute and chronic viral infection (FIGS. 1A-1D), blocking TIGIT and PD-1 in combination may restore T cell effector function to greater levels than would be obtained by blocking either co-receptor singly.

Figure 5A:
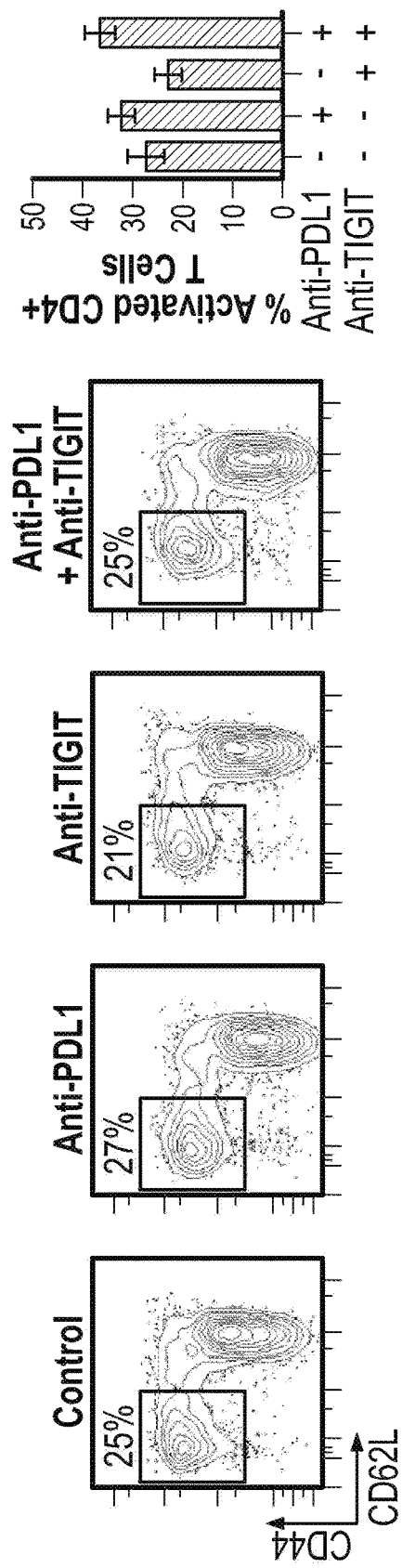
FIGS. 5A-5B show that TIGIT/PD-L1 co-blockade enhances CD4+ T cell effector function during chronic viral infection. C57BL6/J mice were depleted of CD4+ T cells and infected with Clone 13 strain LCMV. Mice were treated with isotype control, anti-PD-L1, anti-TIGIT, or anti-PD-L1+anti-TIGIT antibodies from 28 days after infection. Splenocytes and liver viral titers were analyzed 42 days after infection. Data are representative of 2 independent experiments; n=10.
Figure 5B:
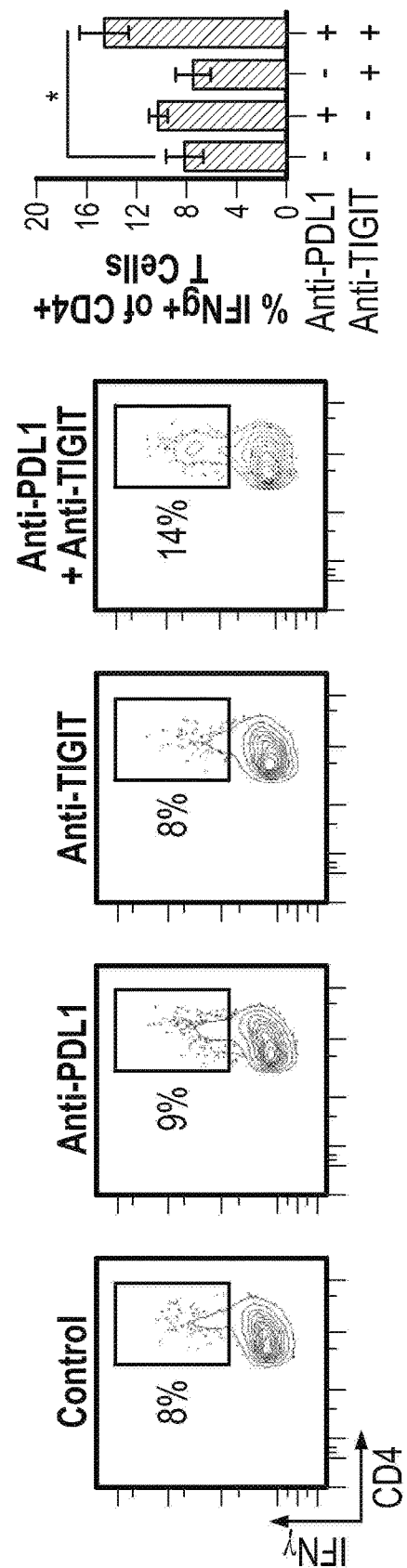

To test this hypothesis, C57BL6/J mice were briefly depleted of CD4$^+$ T cells and infected with Clone 13 strain LCMV. For chronic infections, mice were intravenously infected with 2×10$^6$ PFU Clone 13 strain LCMV and treated with 500 ug and 250 ug of depleting anti-CD4 antibodies (clone GK1.5) 3 days before and 4 days after infection, respectively. Where indicated, mice infected with Clone 13 strain LCMV received intraperitoneal injections of 200 ug of isotype control antibodies, 200 ug of anti-PD-L1 antibodies, and/or 500 ug of anti-TIGIT antibodies 3 times per week from days 28 to 42 post-infection. Treatment was started at 28 days post-infection because the T cell response is largely exhausted at this time-point in this model of chronic viral infection (Wherry et al, Molecular Signature of CD8+ T cell Exhaustion During Chronic Viral Infection, Immunity. 2007 October; 27(4):670-84). Splenocytes and liver viral titers were analyzed 42 days after infection.

n these mice, anti-PD-L1 treatment induced more robust CD8$^+$ T cell activation than did treatment with matched isotype control antibodies (88% increase, P<0.0001, FIG. 4F), as previously reported (Barber, D. L., et al. Restoring function in exhausted CD8 T cells during chronic viral infection. *Nature* 439, 682-687 (2006)). Anti-TIGIT treatment had no apparent effect on CD8$^+$ T cell activation on its own or in combination with anti-PD-L1 (FIG. 4F). Similarly, blockade of PD-1 alone moderately increased CD8$^+$ T cell cytokine competency, whereas blockade of TIGIT alone had no effect (FIG. 4G). However, the frequency of IFNγ-producing CD8$^+$ T cells was increased dramatically in mice treated with both anti-TIGIT and anti-PD-L1, and to a significantly greater extent than seen in mice treated with anti-PD-L1 alone (FIG. 4G 93% increase, P=0.0050). A similar effect was observed with CD4$^+$ T cells (FIGS. 5A-5B). As also shown in FIGS. 31A-31C, TIGIT/PD-L1 co-blockade significantly enhanced CD8$^+$ T cell effector function, but not CD4$^+$ T cell effector function, in mice compared to mice treated with anti-PD-L1 alone. Similar effects were also observed on T cell expansion and effector function in LCMV gp33 antigen-specific T cells (FIGS. 31A-31C). These results demonstrate a strong synergy between PD-1 and TIGIT on exhausted CD8$^+$ T cells, and indicate that TIGIT specifically regulates CD8$^+$ T cell cytokine competency and effector function.

Consistent with these results, LCMV viral loads were moderately reduced in mice treated with anti-PD-L1 alone, not reduced in mice treated with anti-TIGIT alone, and substantially reduced in mice treated with both anti-TIGIT and anti-PD-L1 (68% viral titer reduction with anti-PD-L1 treatment, P=0.0004. 92% viral titer reduction with anti-TIGIT+anti-PD-L1 treatment, P<0.0001, FIG. 4H). These data demonstrate a strong synergy between the inhibitory effects of PD-1 and TIGIT, and suggest that unlike PD-1, TIGIT is not a broad inhibitor of effector T cell activation, but rather has a restricted role in limiting T cell cytokine ompetency and effector function.

Example 4

TIGIT Expression is Elevated in Human Breast Cancer and Correlated with Expression of CD8 and Inhibitory Co-Receptors T cell exhaustion is also a major immunological feature of cancer, with many tumor-infiltrating lymphocytes (TILs) expressing high levels of inhibitory co-receptors and lacking the capacity to produce effector cytokines (Wherry, E. J. T cell exhaustion. *Nature immunology* 12, 492-499 (2011); Rabinovich, G. A., Gabrilovich, D. & Sotomayor, E. M. Immunosuppressive strategies that are mediated by tumor cells. *Annual review of immunology* 25, 267-296 (2007)).

To determine if TIGIT inhibits TIL effector function, breast cancer gene expression microarray data generated by the Cancer Genome Atlas Network (CGAN) was analyzed (Network, C.G.A. Comprehensive molecular portraits of human breast tumours. *Nature* 490, 61-70 (2012)).

TIGIT expression was significantly elevated in breast tumors overall (135% increase relative to normal samples, P=6×10$^{-12}$, FIG. 6A) and across the four major molecular subtypes of breast cancer (FIG. 6A) (Perou, C. M., et al. Molecular portraits of human breast tumours. *Nature* 406, 747-752 (2000); Sorlie, T., et al. Gene expression patterns of breast carcinomas distinguish tumor subclasses with clinical implications. *Proceedings of the National Academy of Sciences of the United States of America* 98, 10869-10874 (2001)). Expression of TIGIT was highly correlated with expression of CD3ε, consistent with its expression by TILs (R$^2$=0.61, FIG. 6B). Interestingly, TIGIT expression was highly correlated with CD8α but not with CD4, or only moderately correlated with CD4, suggesting that TIGIT might primarily regulate CD8$^+$ TIL function (CD8α, R$^2$=0.80. CD4, R$^2$=0.42. FIG. 6C).

Given the co-expression of TIGIT and PD-1 during chronic viral infection, we also assessed the correlation of PD-1 and other inhibitory co-receptors with TIGIT in breast cancer. Correlation between TIGIT and PD-1, CTLA4, and LAG3 was very strong (PD-1, $R^2=0.87$. CTLA4, $R^2=0.76$. LAG3, $R^2=0.80$. FIG. 6D). Collectively, these data suggested that TIGIT was expressed by TILs, especially $CD8^+$ T cells, and that it might suppress their function.

Example 5

TIGIT and PD-1 Inhibit Anti-Tumor T Cell Responses

To better characterize TIGIT by TILs in mice, BALB/C mice were inoculated with CT26 colorectal carcinoma cells. Briefly, BALB/c mice were subcutaneously inoculated with $1\times10^5$ CT26 colon carcinoma cells suspended in matrigel (BD Biosciences) into the right unilateral thoracic flank. After two weeks, mice bearing tumors of approximately 200 $mm^3$ were randomly recruited into treatment groups receiving 35 mg/kg of isotype control antibodies, anti-PD-L1 antibodies, and/or anti-TIGIT antibodies by intraperitoneal injection 3 times per week for 3 weeks. Tumors were measured 2 times per week by caliper. Animals whose tumors became ulcerated/necrotic or grew larger than 2000 $mm^3$ were euthanized. Splenocytes and tumor-infiltrating lymphocytes (TILs) were analyzed 14 days after inoculation, when tumors had reached approximately 200 $mm^3$ in size.

Figures 7A, 7B, 7C:
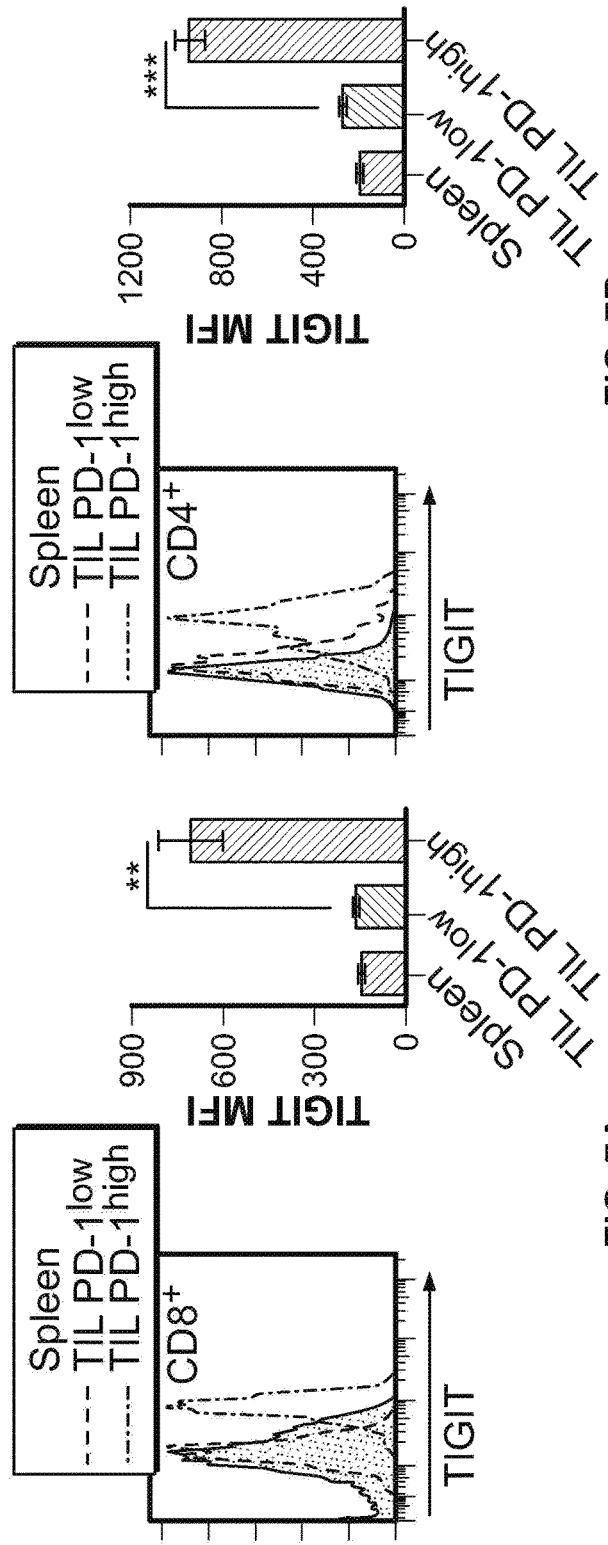
FIGS. 7A-7F show that TIGIT and PD-1 inhibit antitumor T cell responses.
Figure 8B:
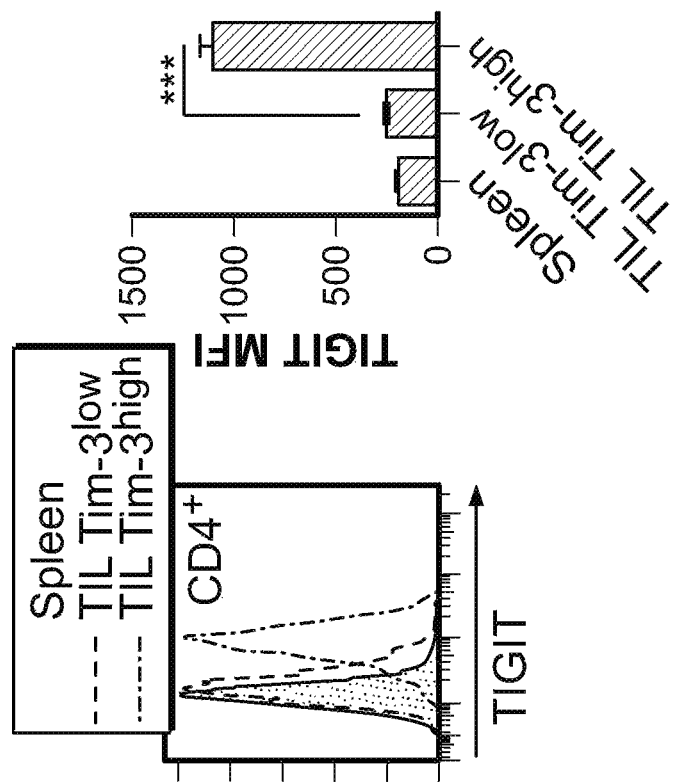
FIGS. 8A-8B show that CT26 tumor-infiltrating lymphocyte TIGIT expression is correlated with Tim-3 expression. BALB/C mice were inoculated with CT26 colorectal carcinoma cells. Splenocytes and tumor-infiltrating lymphocytes (TILs) were analyzed approximately 14 days after inoculation, when tumors had reached approximately 200 mm$^3$ in size. Data are representative of one experiment; n=6.
Figure 8A:
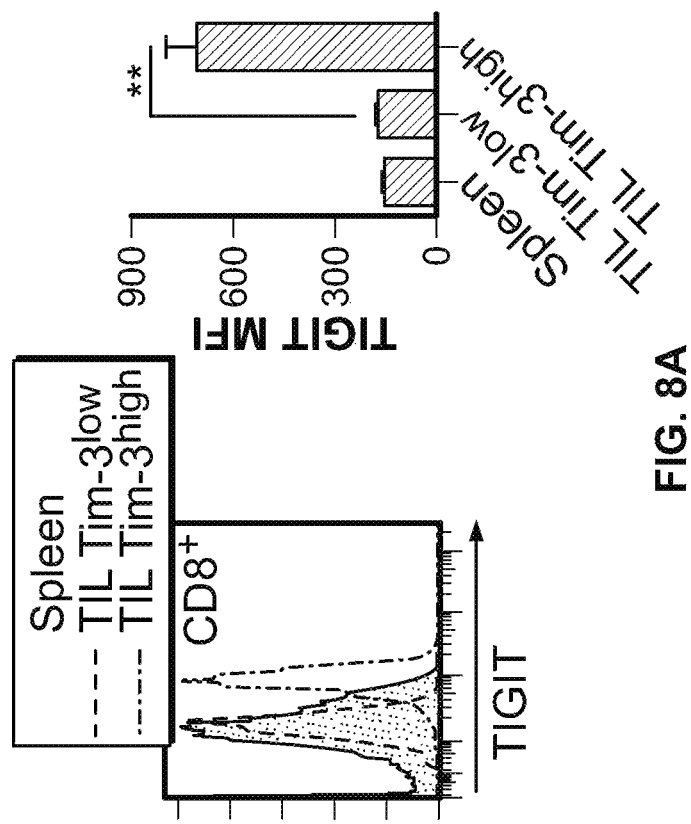
Figure 9A:
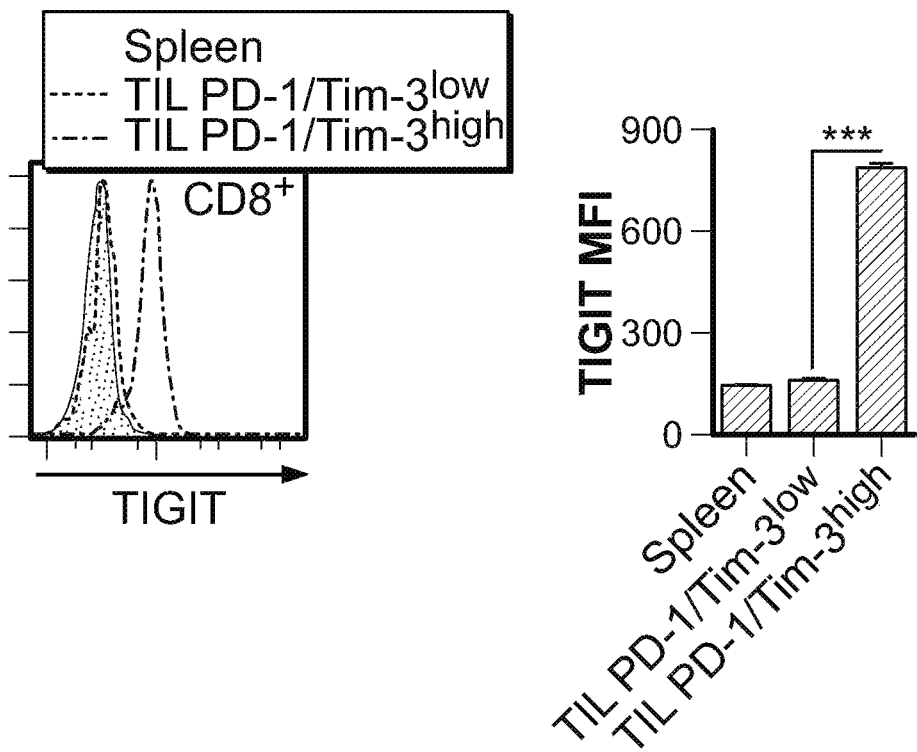
FIGS. 9A-9B show that MC38 tumor-infiltrating lymphocyte TIGIT expression is correlated with PD-1 and Tim-3 expression. C57BL6/J mice were inoculated with MC38 colorectal carcinoma cells. Splenocytes and tumor-infiltrating lymphocytes (TILs) were analyzed approximately 14 days after inoculation, when tumors had reached approximately 200 mm$^3$ in size. Data are representative of one experiment; n=5.
Figure 9B:
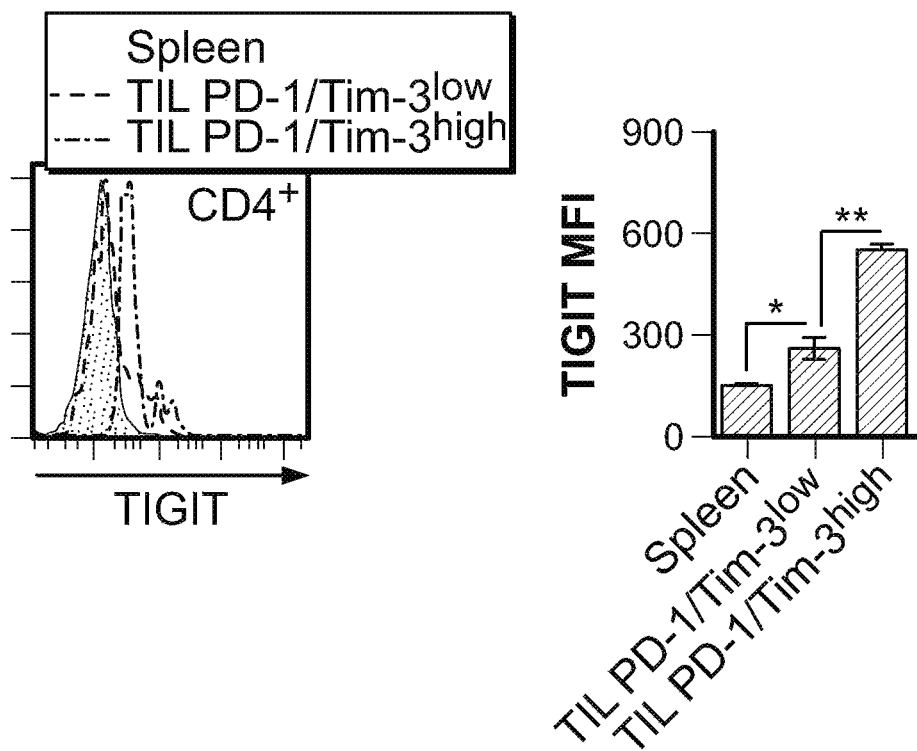

Consistent with TIGIT expression in human tumors (FIGS. 6A-6D), both $CD8^+$ and $CD4^+$ CT26 TILs expressed high levels of TIGIT (FIGS. 7A-7B). Furthermore, in line with the chronic viral infection studies, TIL TIGIT expression was tightly correlated with expression of other inhibitory co-receptors including PD-1 (FIGS. 7A-7B) and Tim-3 (FIGS. 8A-8B). A similar pattern of TIGIT expression was found in MC38 colon carcinoma tumors (FIGS. 9A-9B).

To test the physiological relevance of TIGIT expression in the context of an anti-tumor immune response, BALB/C mice with established CT26 tumors (approximately 200 $mm^3$ in size) were treated with 200 ug isotype control, 200 ug anti-PD-L1, 500 ug anti-TIGIT, or 200 ug anti-PD-L1+ 500 ug anti-TIGIT antibodies for three weeks.

Figure 7D:
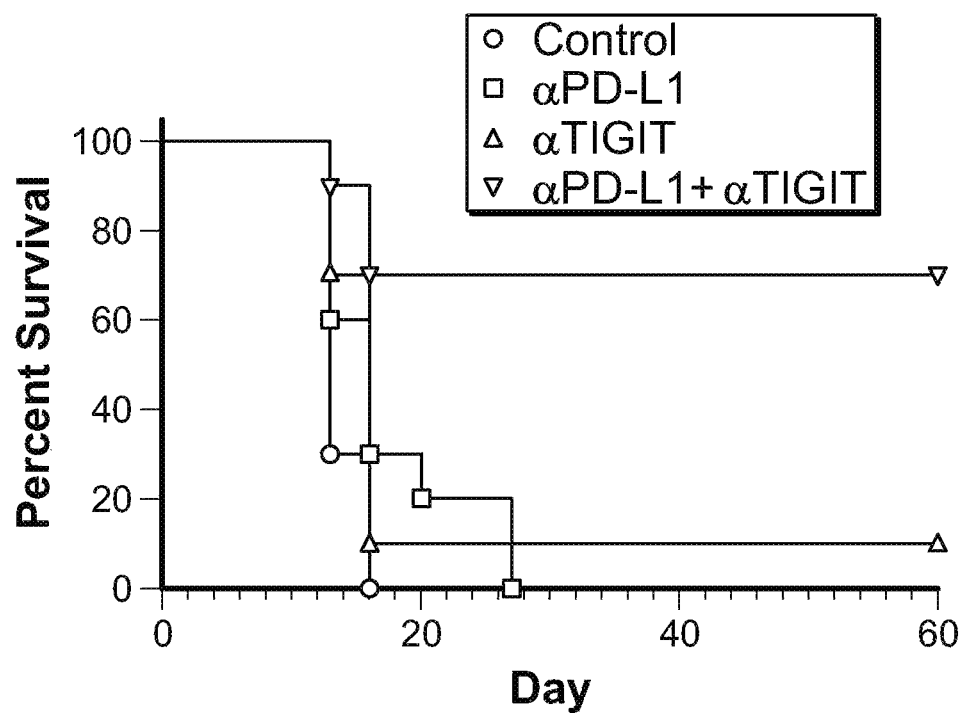
Figure 10:
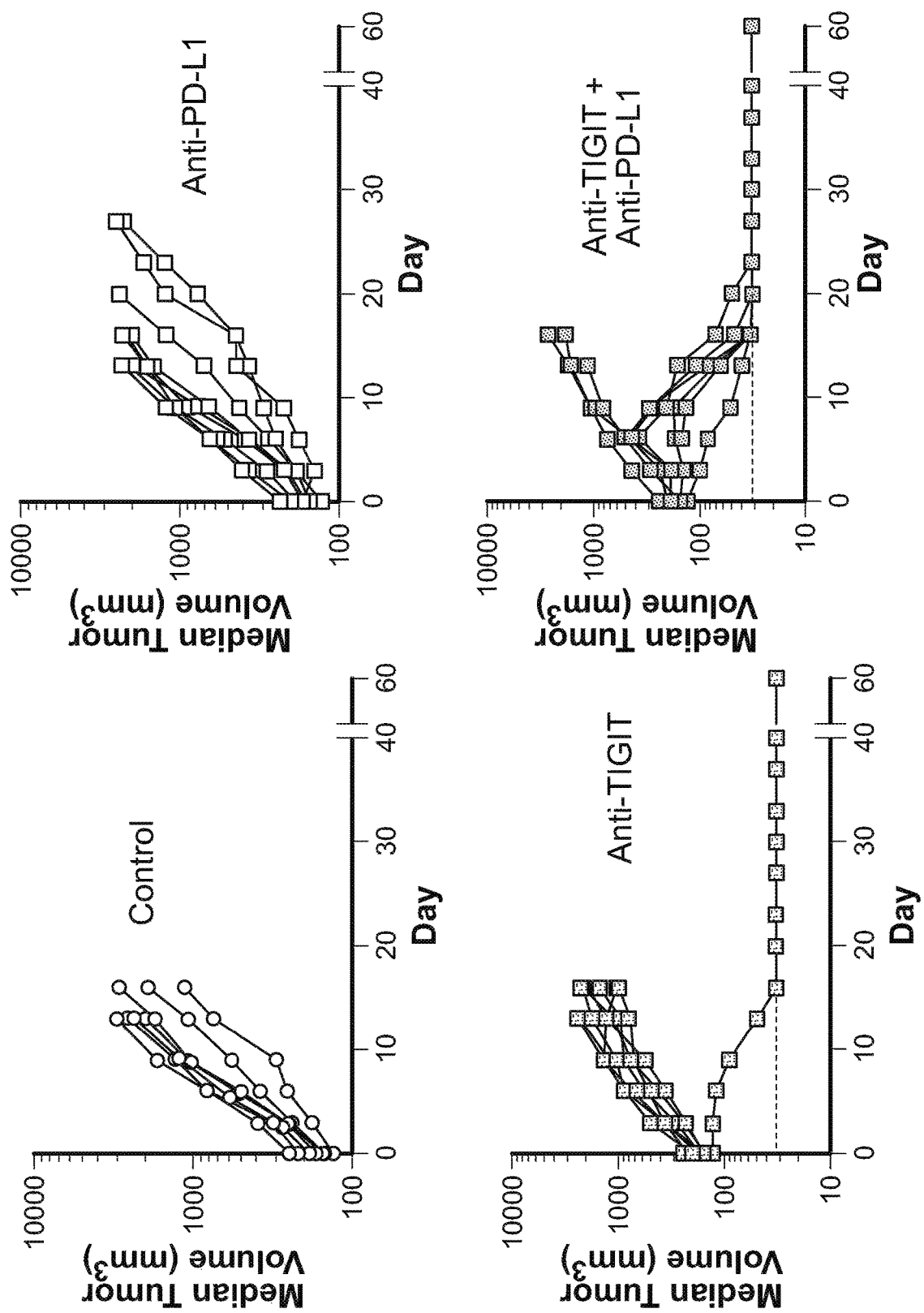
FIG. 10 shows CT26 tumor growth in mice treated with anti-PD-L1 and/or anti-TIGIT. Nave BALB/c mice were inoculated with CT26 tumor cells and treated with anti-PD-L1 and/or anti-TIGIT or isotype-matched control antibodies, as described in FIGS. 4D-4F. Tumor volumes over time for individual mice in each treatment group are shown. Data are representative of two independent experiments.
Figure 11C:
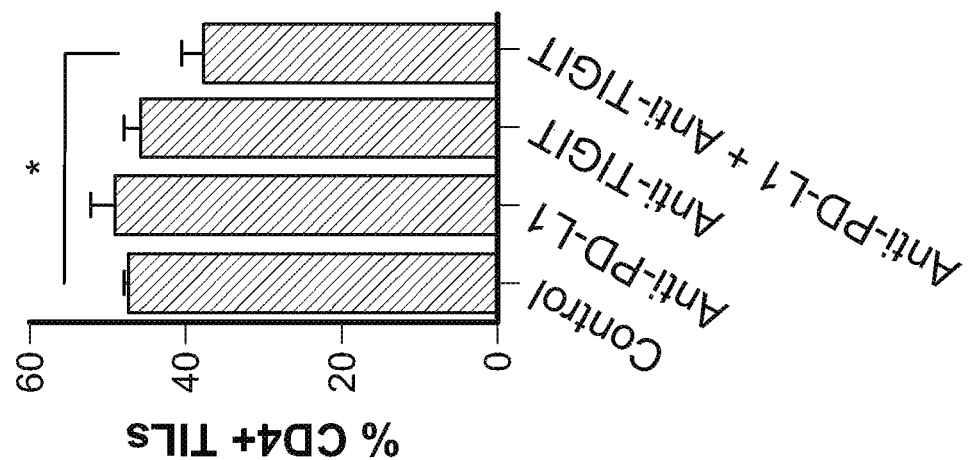
FIGS. 11A-11F show the flow cytometric analysis of CD4+ TILs and tumor-draining lymph node T cells. BALB/C mice were inoculated with CT26 colorectal carcinoma cells. When tumors reached approximately 200 mm$^3$ in size, mice were treated with isotype control, anti-PD-L1, anti-TIGIT, or anti-PD-L1+anti-TIGIT antibodies for 7 days. Tumors and tumor-draining lymph nodes were harvested. Data are representative of two independent experiments; n=5. Representative FACS plots gated on tumor-draining lymph node CD8+ T cells after stimulation in vitro, with IFNγ-producing cells boxed. Quantitation of IFNγ+ cells as a percentage of total CD8+ T cells. *, P<0.001. Quantitation of CD8+ T cells as a percentage of total TILs. , P=0.0065. Quantitation of activated (CD44$^{high}$ CD62L$^{low}$) CD8+ T cells as a percentage of total CD8+ TILs. *, P=0.012. Quantitation of CD8+ T cells as a percentage of total tumor-draining lymph node cells. Quantitation of activated CD8+ T cells as a percentage of total CD8+ T cells in the tumor-draining lymph node. *, P<0.05.
Figure 11B:
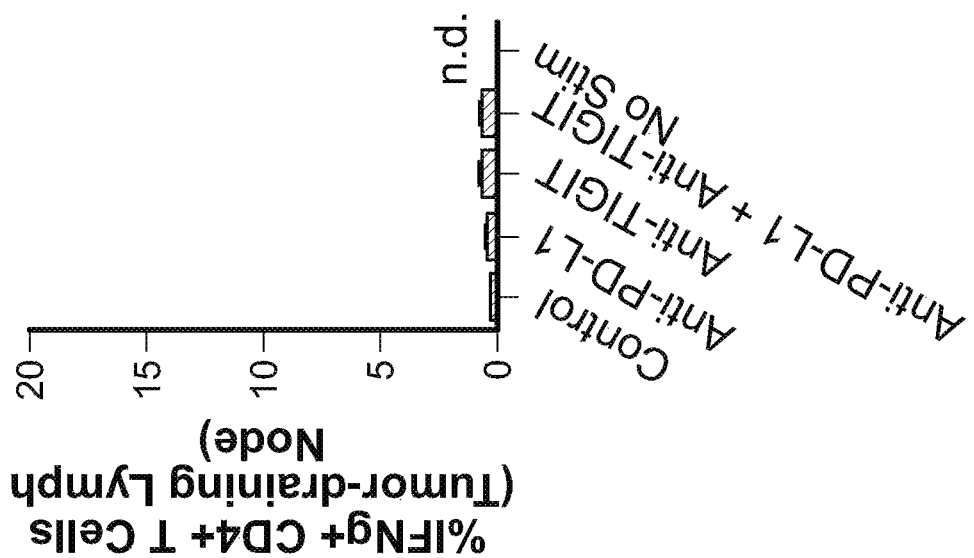
Figure 11A:
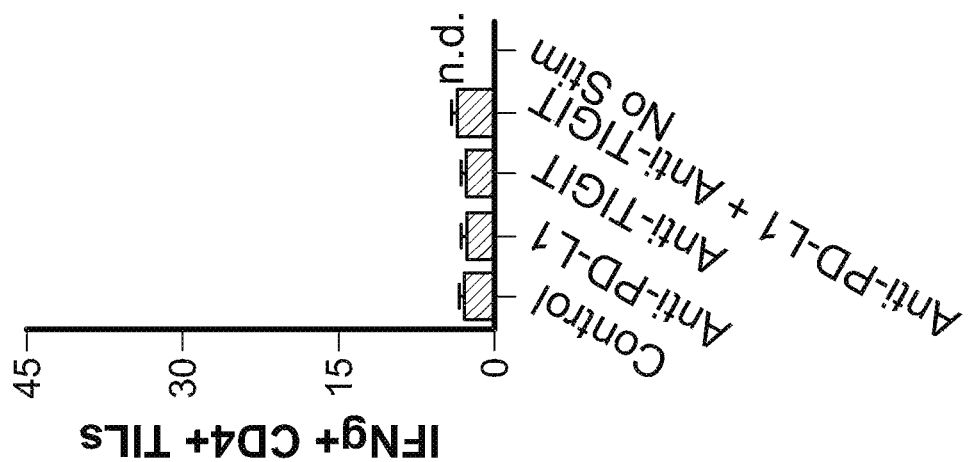
Figure 11F:
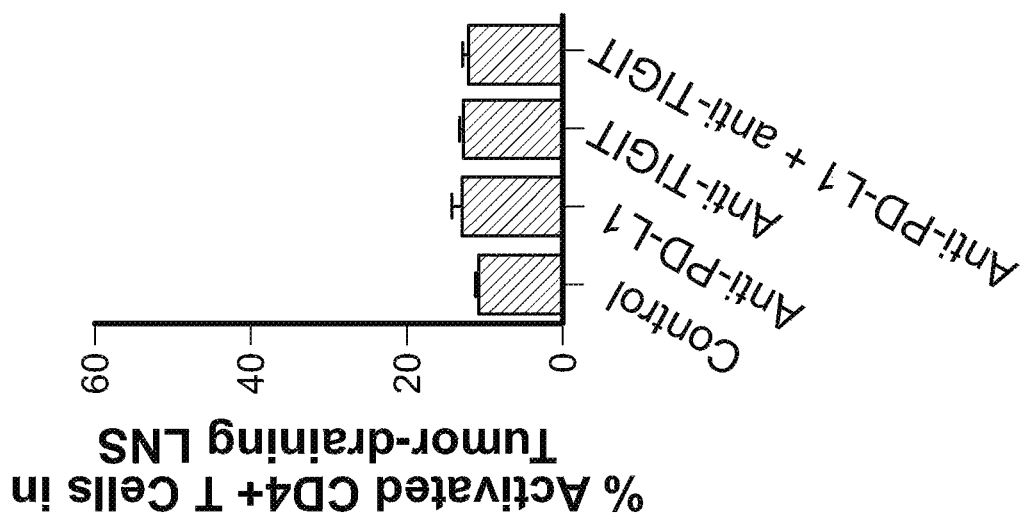
Figure 11E:
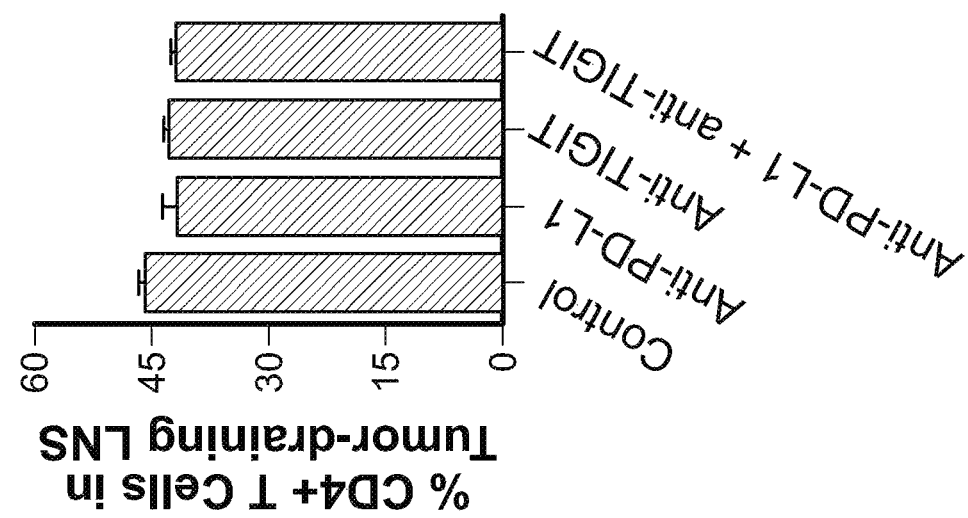
Figure 11D:
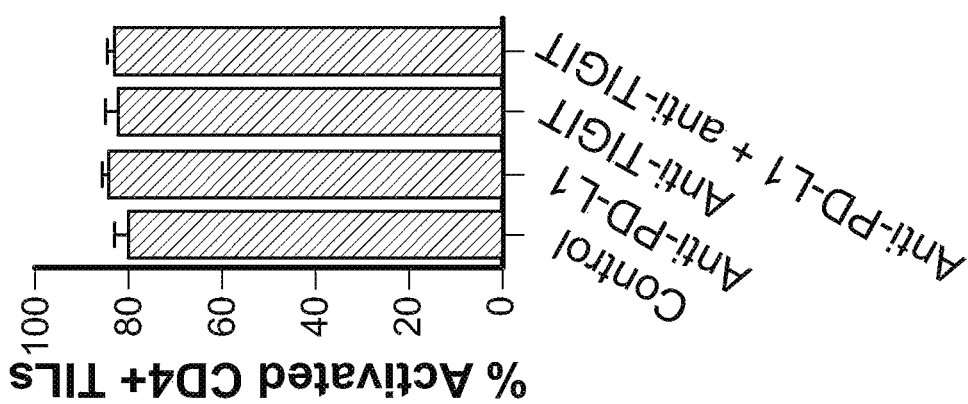

CT26 tumor growth was only slightly slowed by treatment with anti-TIGIT or anti-PD-L1 alone, both of which resulted in a modest 3 day increase in median survival (FIGS. 7C-7D). However, combination therapy with both anti-PD-L1 and anti-TIGIT dramatically reduced tumor growth (75% decrease in median tumor volume by day 16, $P<0.0001$, FIG. 7C and FIG. 10). Moreover, 70% of the mice receiving both anti-TIGIT and anti-PD-L1 experienced complete and durable tumor remission and survived for the duration of the study, even in the absence of further antibody treatment (FIGS. 7C-7D). These effects were also observed in tumor-bearing mice treated with a combination of blocking antibodies against TIGIT and PD-1.

To test the immunity of these surviving mice to CT26 tumor cells, approximately 60 days after initial inoculation, mice in complete remission (CR) that had received anti-TIGIT+anti-PD-L1, as well as nave BALB/c mice, were re-inoculated with CT26 cells in their left (not previously inoculated) unilateral thoracic flanks. These mice were also inoculated with $1\times10^5$ EMT6 breast carcinoma cells in matrigel into the fourth mammary fat pad. Tumors were measured 2 times per week. Animals whose tumors became ulcerated/necrotic or whose total tumor burden exceeded 2000 $m^3$ were euthanized.

Figure 7E:
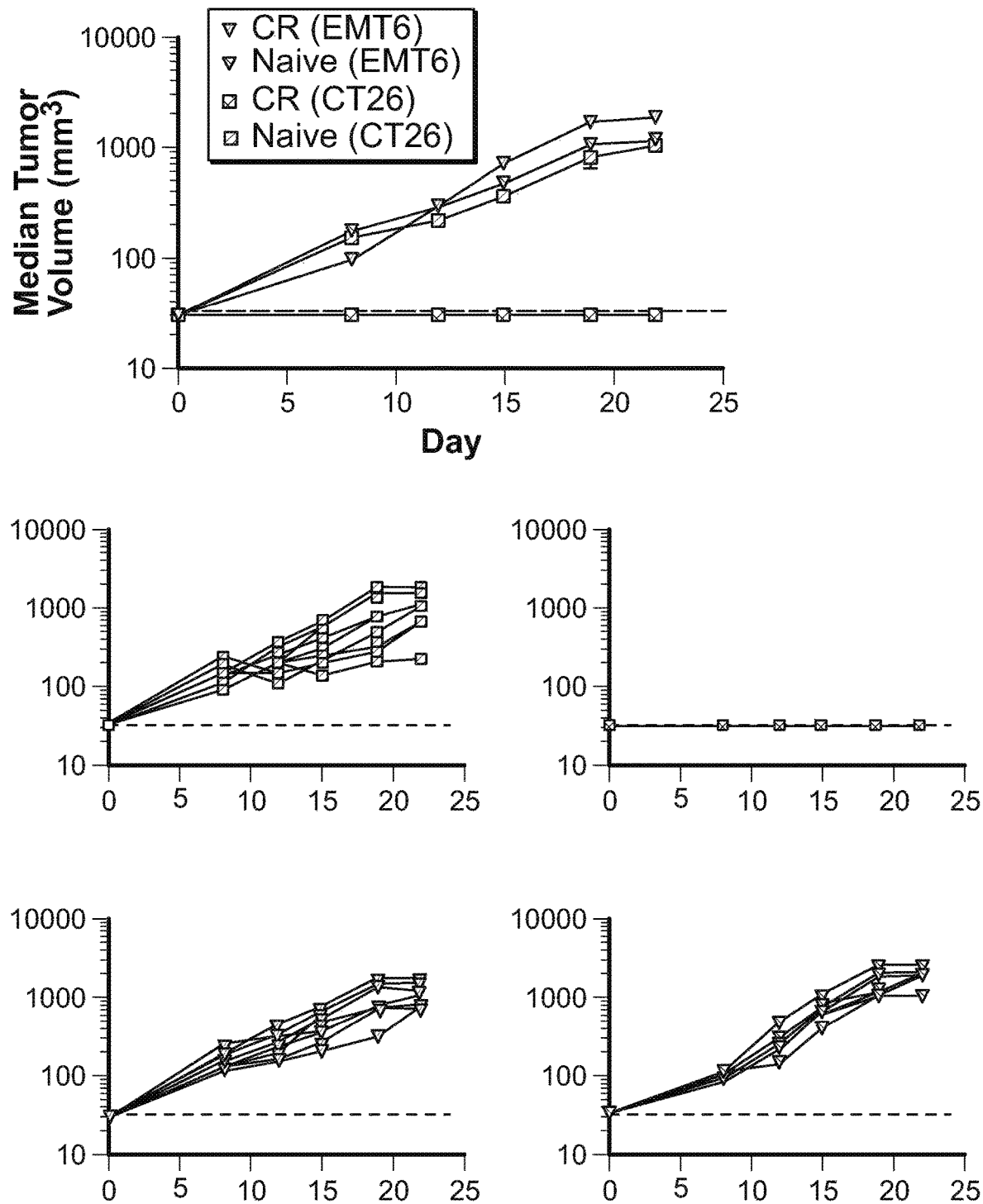
Figure 7F:
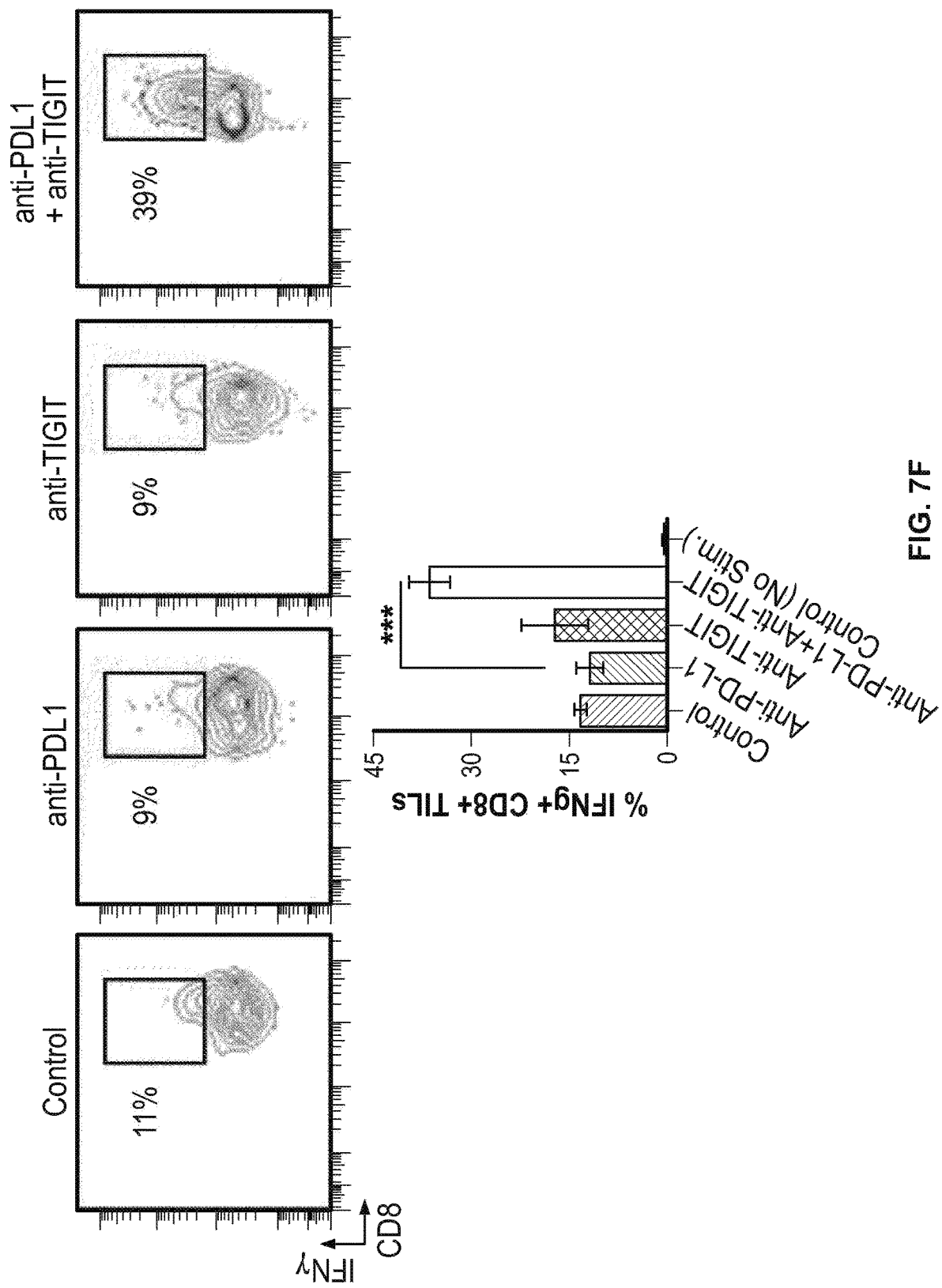

As shown in FIG. 7E, both tumors grew readily in nave control mice, but only EMT6 tumors grew in mice that had previously cleared a CT26 tumor. These results indicated that co-blockade of TIGIT and PD-1 during tumorigenesis established a state of specific immunity to CT26 tumor cells.

Figure 32A:
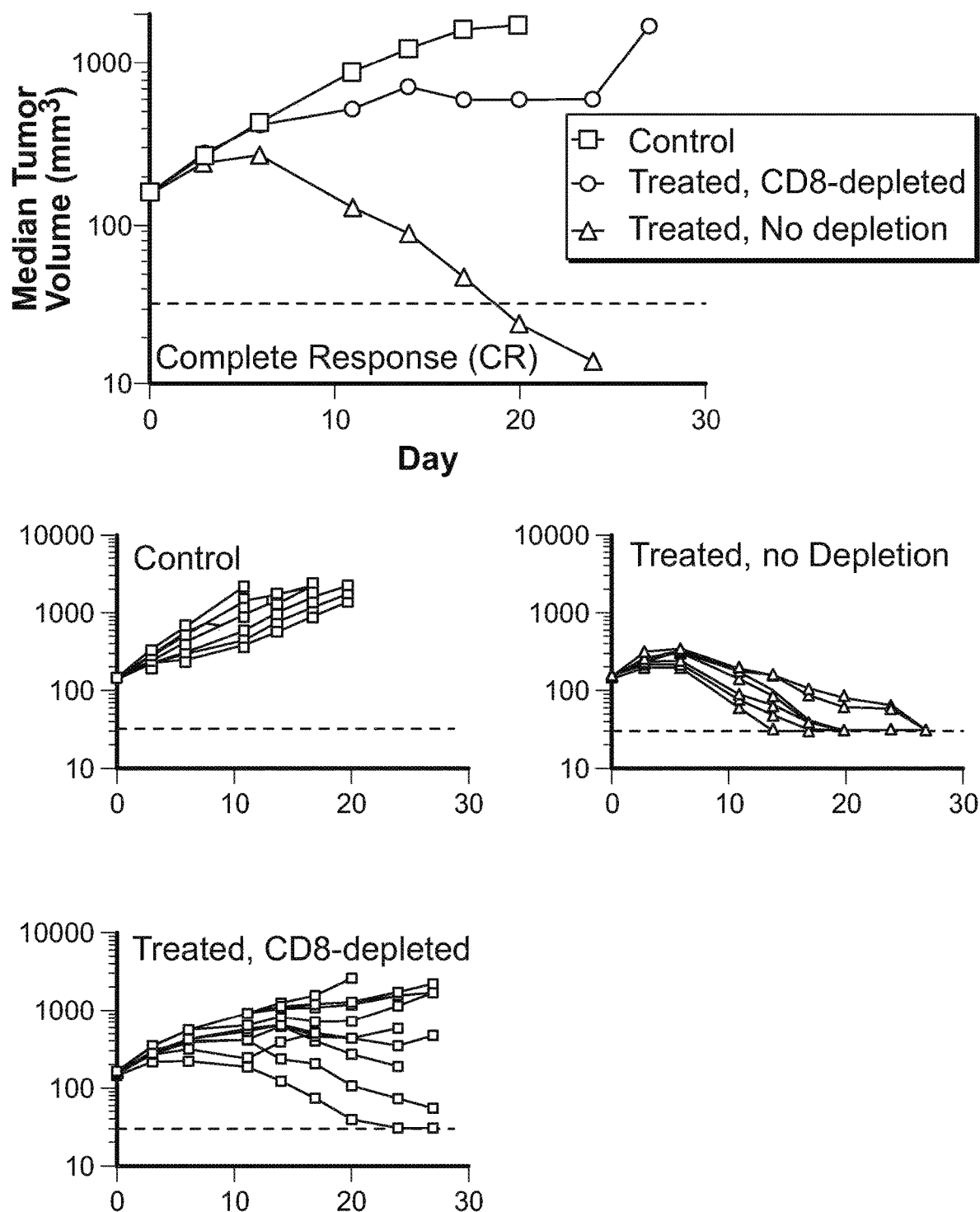

To determine if the efficacy of TIGIT/PD-L1 co-blockade was mediated by $CD8^+$ T cells, CT26-tumor bearing mice were subjected to $CD8^+$ T cell ablation using depleting antibodies at the initiation of treatment with anti-TIGIT and anti-PDLL Mice treated with anti-TIGIT and anti-PD-L1 antibodies were unable to reject CT26 tumors when depleted of $CD8^+$ T cells at the start of treatment (1532% increase in mean tumor volume after 17 days of treatment, $P=0.0004$, FIGS. 32A-32B). Additionally, $CD8^+$ T cell depletion impaired the ability of previously treated CR mice to control re-inoculated CT26 tumors (FIG. 32C). Taken together, these results demonstrated that anti-TIGIT and anti-PD-L1 acted through $CD8^+$ T cells to elicit effective primary and secondary anti-tumor immune responses.

Figure 33:
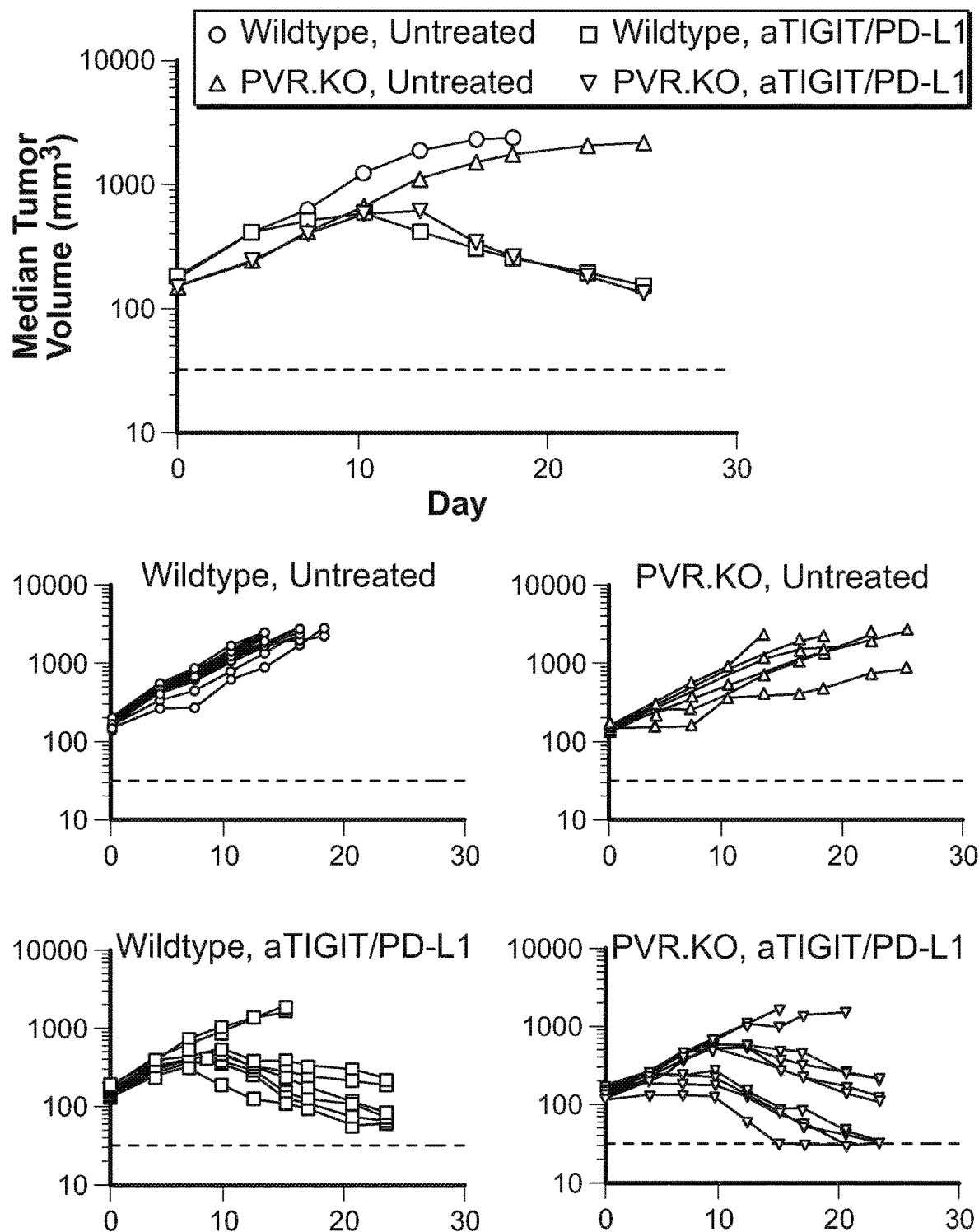
FIG. 33 shows that PVR expression on tumor cells is dispensable for TIGIT/PD-L1 co-blockade efficacy. Wildtype BALB/c mice were inoculated with wildtype or PVR-deficient (PVR.KO) tumors as described. When tumors reached 150-200 mm$^3$ in size, mice were treated with anti-TIGIT+anti-PD-L1 or isotype-matched control antibodies. Data are representative of one experiment; n=10/group.

To determine if PVR expression of tumor cells is dispensable for TIGIT/PD-L1 co-blockade efficacy, wildtype BALB/c mice were inoculated with wildtype CT26 tumors (which express PVR) or PVR-deficient CT26 tumors. Briefly, wildtype CT26 tumor cells were transiently transfected with a nucleic acid that reduced expression of PVR. Approximately two weeks after transfection, CT26 cells were subcloned on the basis of loss of PVR expression by flow cytometry and qPCR. When tumors reached 150-200 $mm^3$ in size, mice were treated with anti-TIGIT and anti-PD-L1 antibodies, or isotype-matched control antibodies. Mice treated with anti-TIGIT and anti-PD-L1 antibodies were able to reject both wildtype and PVR-deficient tumors, as compared to tumor-inoculated mice treated with control antibodies (FIG. 33). These results demonstrated that anti-TIGIT and anti-PD-L1 act independently of tumor-expressed PVR.

Figure 25A:
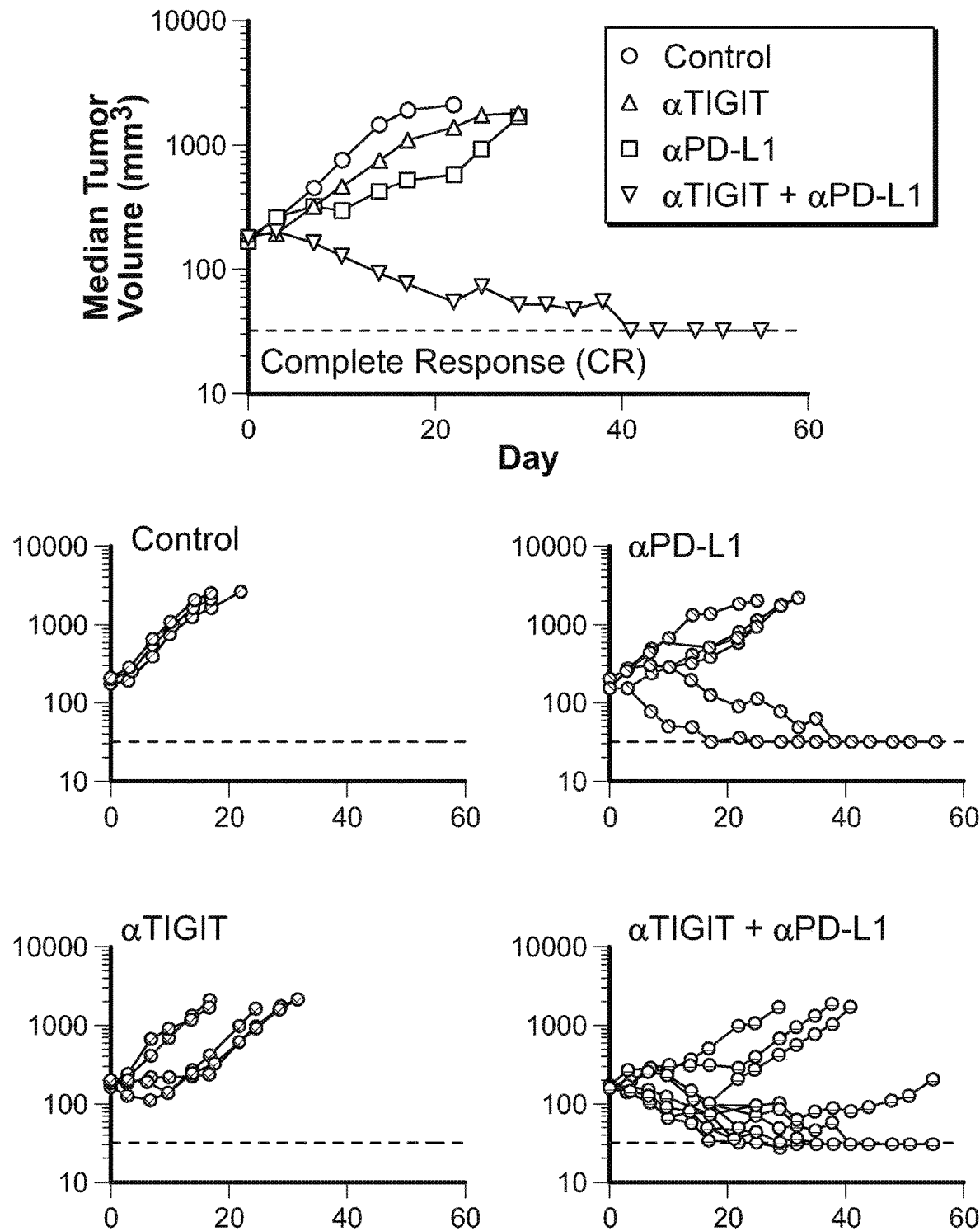
FIGS. 25A-25C show the efficacy of TIGIT/PD-L1 antibody co-blockade in mice bearing MC38 tumors.
Figure 25B:
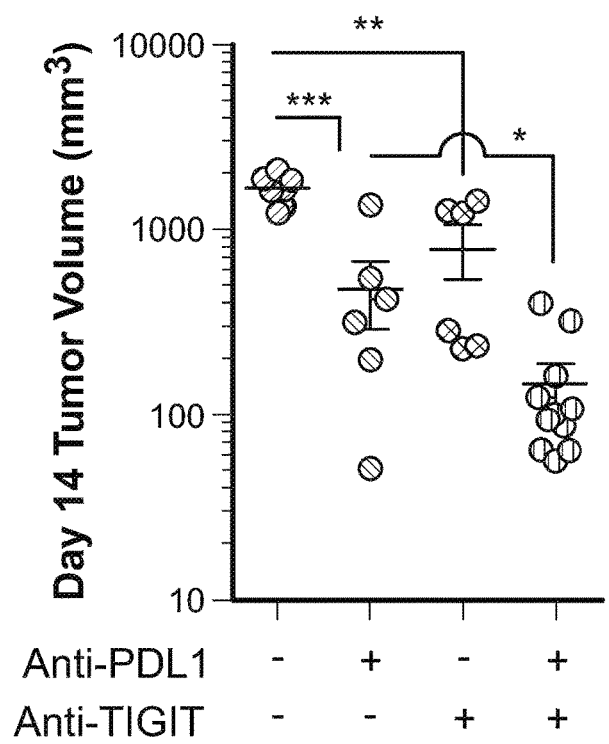
Figure 25C:
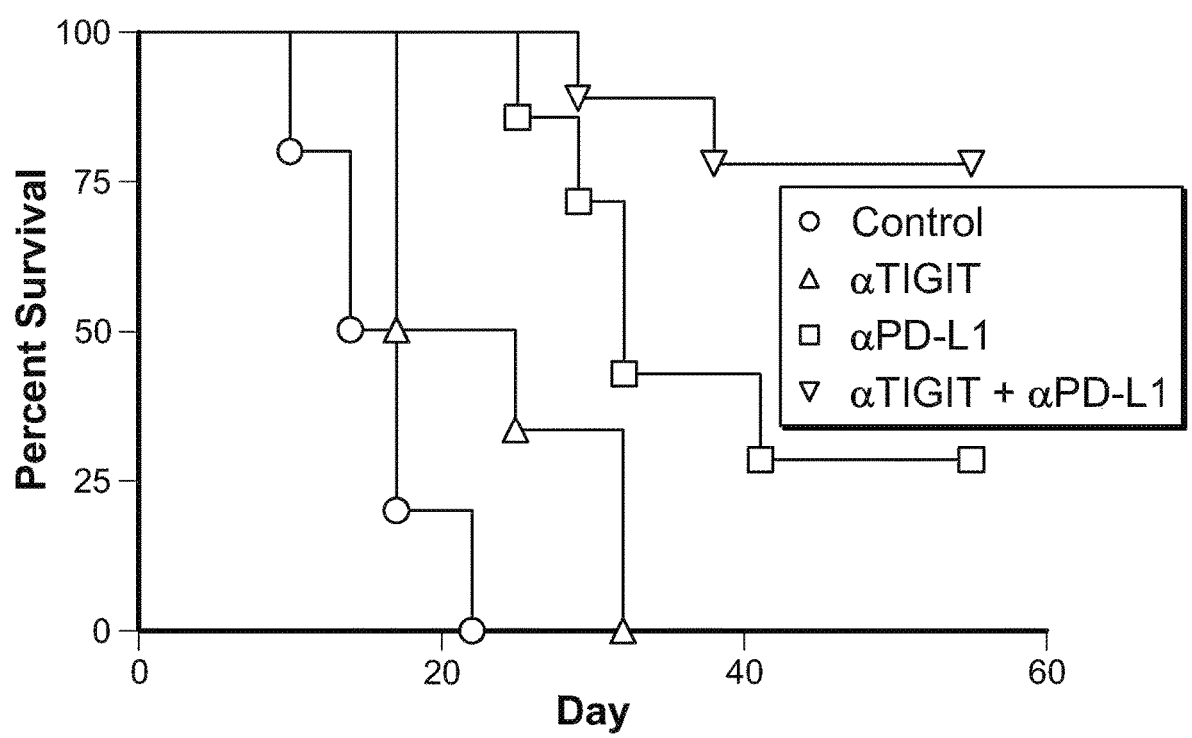
Figure 26E:
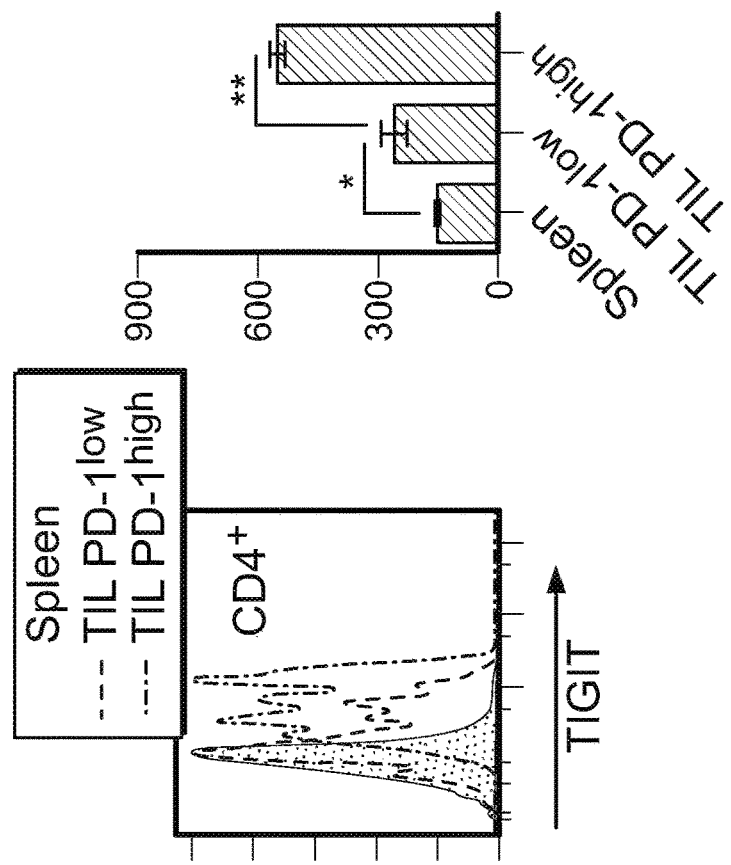
Figure 26D:
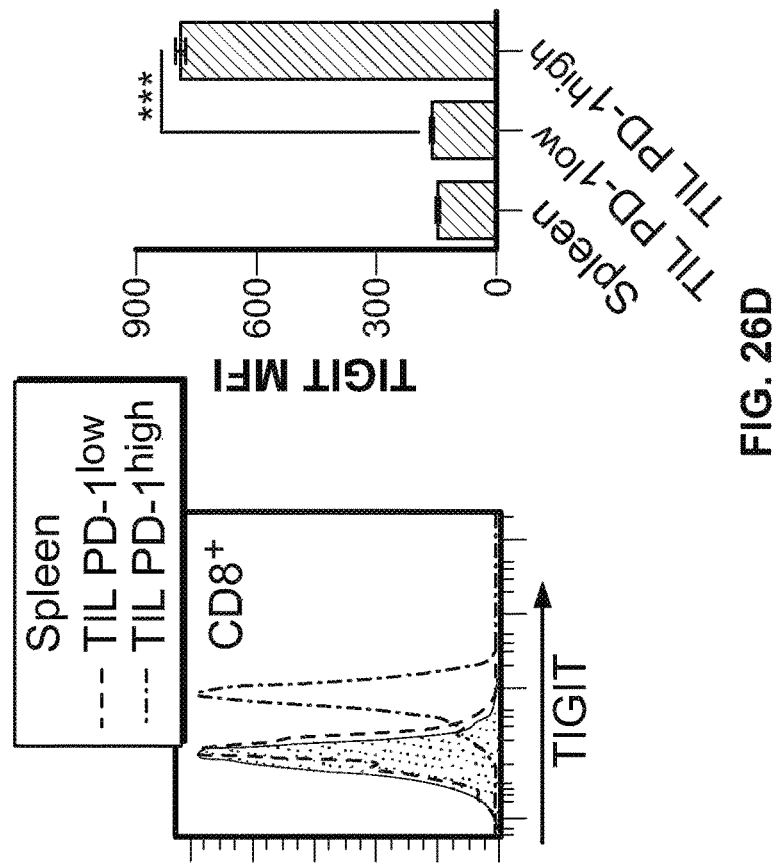
Figure 34:
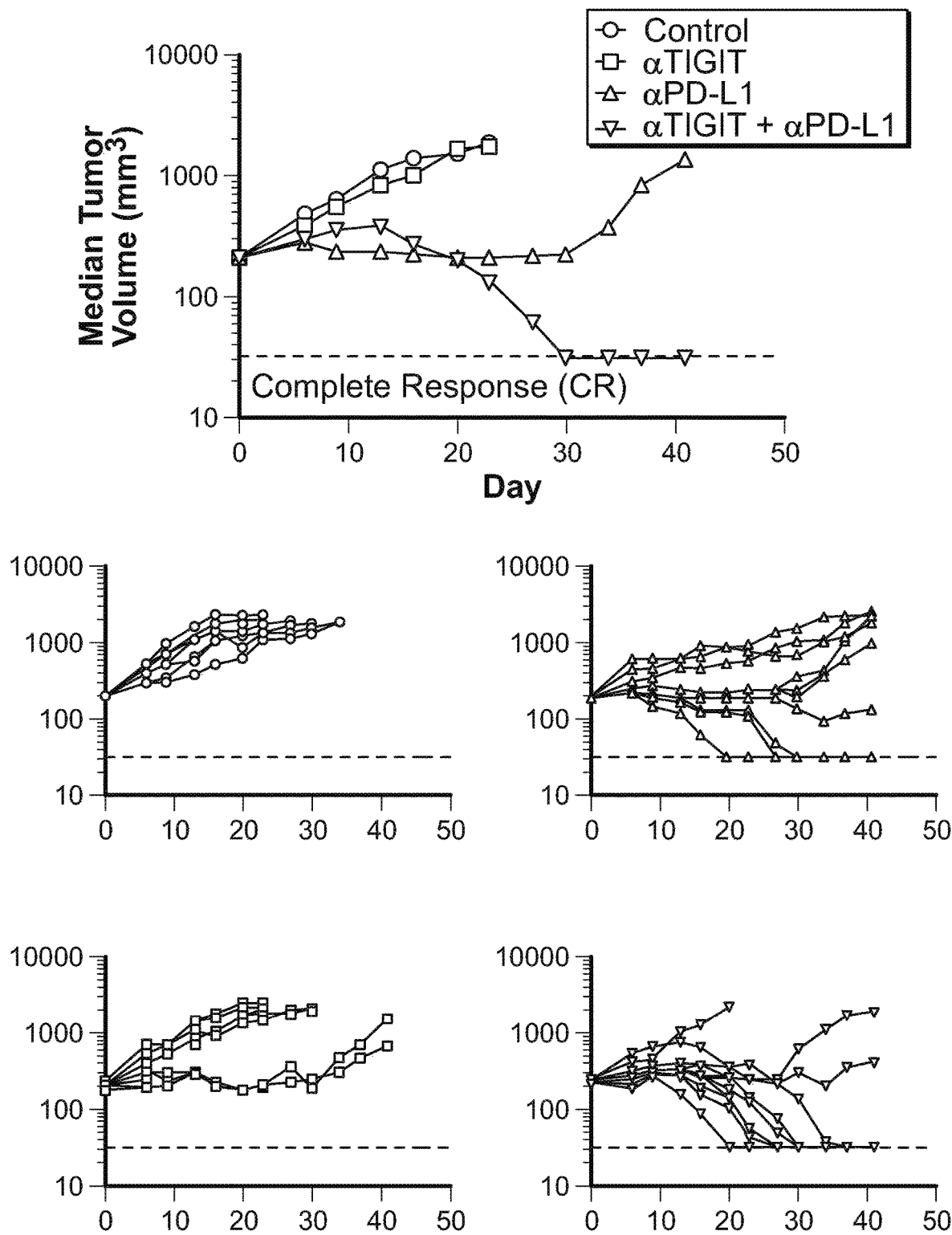
FIG. 34 shows the efficacy of TIGIT/PD-L1 antibody co-blockade in mice bearing EMT6 tumors. EMT6 tumor-bearing mice were generated as above and treated with blocking antibodies against PD-L1 (red), TIGIT (blue), TIGIT and PD-L1 (purple) or isotype-matched control antibodies (black) for three weeks. N=10 (control, anti-PD-L1 alone, anti-TIGIT alone) or 20 (anti-TIGIT+anti-PD-L1).

The efficacy of TIGIT/PD-L1 co-blockade in the MC38 tumor model was also tested and confirmed. Wildtype C57BL6/J mice were subcutaneously inoculated with syngeneic MC38 colorectal carcinoma cells and treated established tumors with a combination of TIGIT and PD-L1 blocking antibodies, as before. Unlike the CT26 model, treatment with anti-PD-L1 alone was sufficient to induce a complete response in some mice (FIGS. 25A-25C). However, as in the CT26 model, treatment of MC38 tumor-bearing mice with both anti-TIGIT and anti-PD-L1 synergistically reversed tumor growth and induced tumor clearance in most mice (FIGS. 26A-26E). These effects were also observed in mice inoculated with syngeneic EMT6 breast carcinoma cells (FIG. 34).

These results demonstrated that co-blockade of TIGIT and PD-1 could elicit a sustained and antigen-specific anti-tumor immune response. These results also suggested that adaptive anti-tumor responses were fully functionally and reactivated in therapeutically treated mice.

To assess the functional effects of TIGIT and PD-1 blockades on the tumor-infiltrating lymphocytes themselves, mice were inoculated with CT26 tumor cells and treated with anti-TIGIT and/or anti-PD-L1 as before. Seven days after the start of treatment, tumors and tumor-draining lymph nodes were collected for analysis by flow cytometry.

Figure 12C:
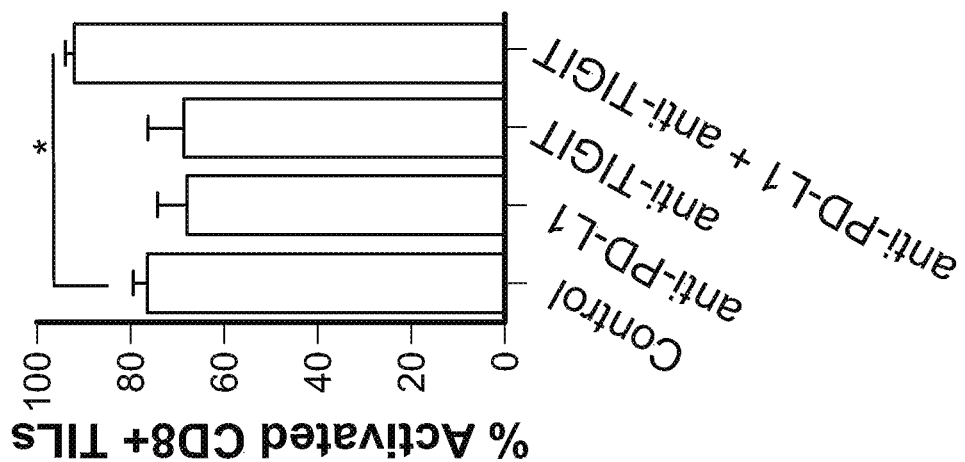
FIGS. 12A-12C show further flow cytometric analysis of CD8+ TILs. BALB/C mice were inoculated with CT26 colorectal carcinoma cells and treated with isotype control, anti-PD-L1, anti-TIGIT, or anti-PD-L1+anti-TIGIT antibodies as described in FIGS. 4A-4H. Tumors were harvested after 7 days of treatment and analyzed by flow cytometry. Data are representative of two independent experiments; n=5.
Figure 12B:
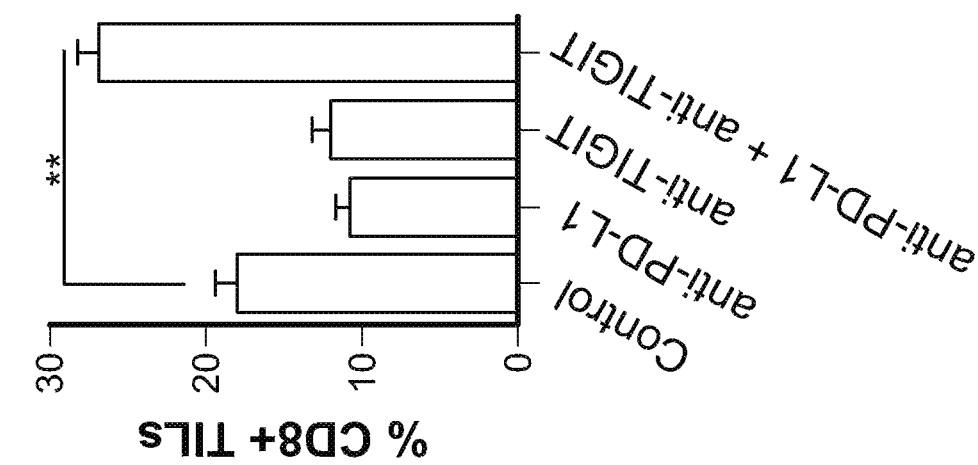
Figure 12A:
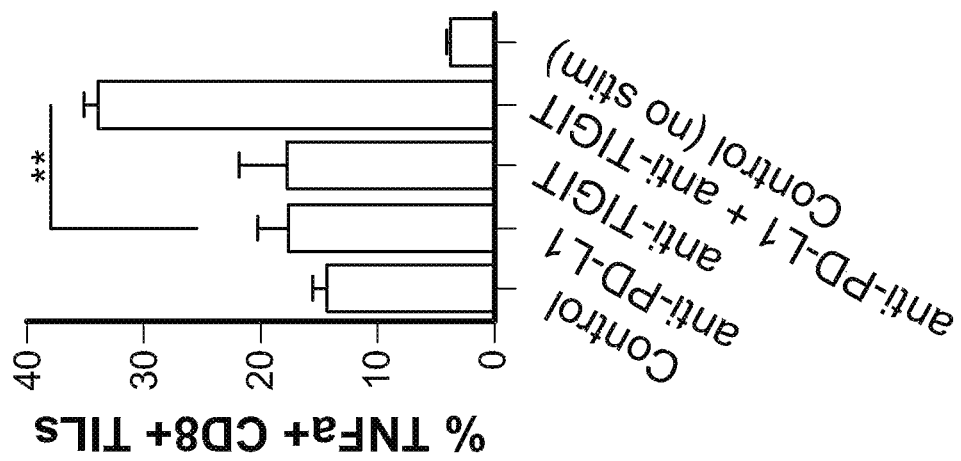
Figure 13A:
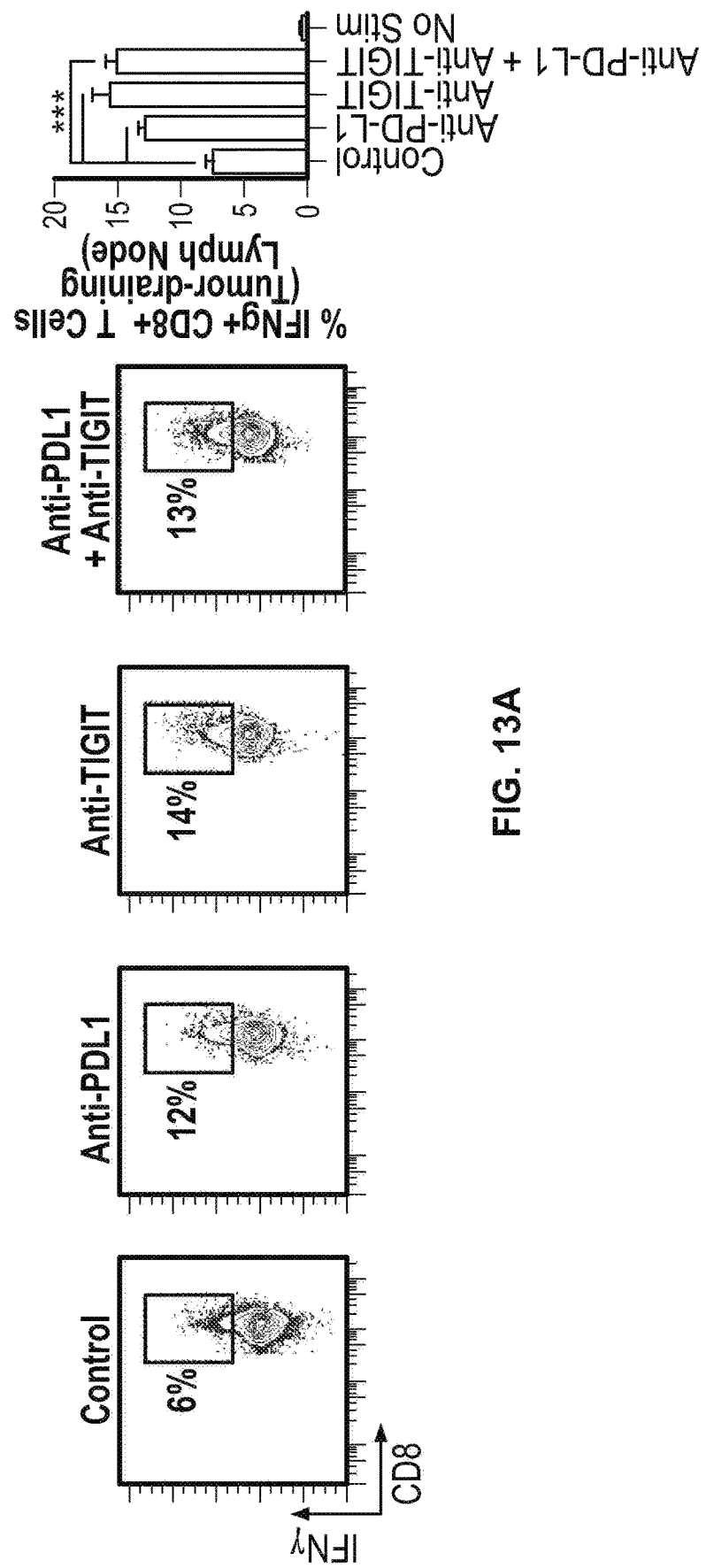

Tumor-infiltrating and tumor-draining lymph node resident $CD4^+$ T cells produced little IFNγ, and did not produce more upon TIGIT/PD-1 blockade (FIGS. 11A-11F). However, tumor-infiltrating CD8+ T cells from mice treated with both anti-TIGIT and anti-PD-L1, but not those from mice treated with anti-TIGIT or anti-PD-L1 alone, were significantly more competent to produce IFNγ upon stimulation in vitro (174% increase relative to control, P=0.0001, FIG. 13D). Similar results were observed for CD8+ TIL production of TNFα (FIGS. 12A-12C).

Figure 35A:
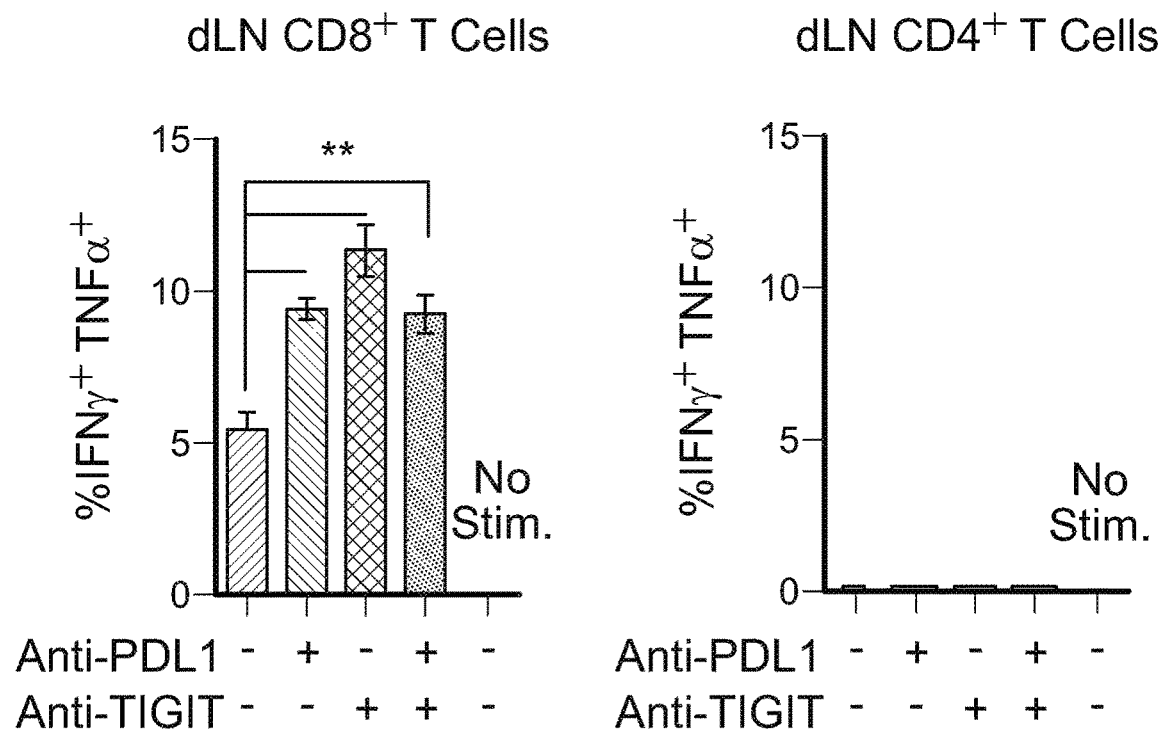
FIGS. 35A-35B show that TIGIT regulates tumor-infiltrating CD8$^+$ T cell effector function. BALB/C mice were subcutaneously inoculated with CT26 colorectal carcinoma cells in their right thoracic flanks and treated with anti-PD-L1, anti-TIGIT, or anti-PD-L1+anti-TIGIT, as described in FIGS. 7A-7F. Tumor-draining lymph node (dLN) resident and tumor-infiltrating T cells were analyzed by flow cytometry 7 days after the start of treatment. Data are representative of two independent experiments; n=5.
Figure 35B:
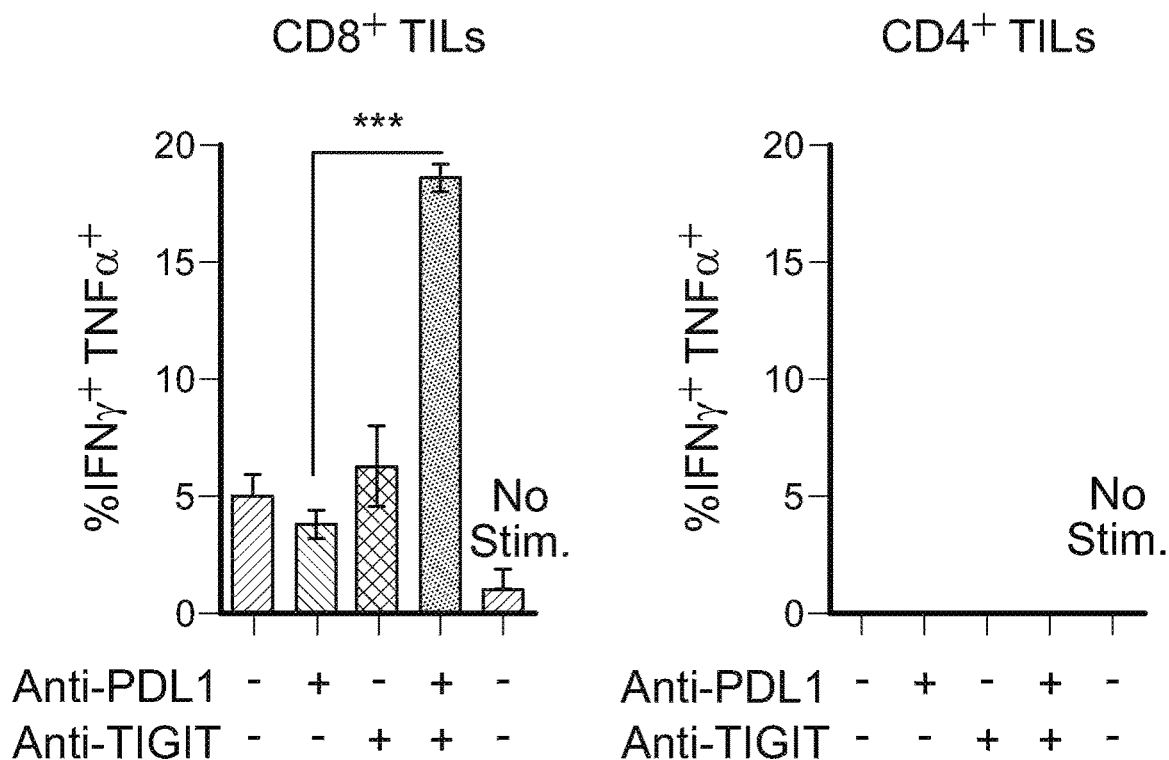

Interestingly, mice treated with either anti-TIGIT or anti-PD-L1 alone, or both, all saw increased cytokine competency of tumor-draining lymph node resident CD8+ T cells (75-113% increase, P<0.001, FIGS. 13A-13D), suggesting that lymph node-resident CD8+ T cells were under lesser degree of suppression than their tumor-infiltrating counterparts. Accumulation and phenotypic activation of tumor-infiltrating and tumor-draining lymph node resident CD8+ T cells and CD4+ T cells were unchanged and weakly enhanced by single antibody treatment and dual antibody and dual antibody treatment, respectively (FIGS. 12A-12C and FIGS. 13A-13D). The frequencies of IFNγ/TNFα dual-producing CD8+ T cells in tumors and tumor-draining lymph nodes followed similar patterns (FIGS. 35A-35B).

Consequently, while blockade of either TIGIT or PD-L1 alone was sufficient to enhance CD8+ T cell effector function in tumor-draining lymph nodes, blockade of both receptors was necessary to restore the function of exhausted CD8+ T cells within the tumor itself, consistent with the notion that tumor microenvironments are highly immunosuppressive.

Example 6

TIGIT Co-Expression with CD226 on Tumor-Infiltrating CD8+ T Cells

TIGIT competes with the co-stimulatory receptor CD226 for binding to Poliovirus Receptor (PVR) (Yu, X., et al. The surface protein TIGIT suppresses T cell activation by promoting the generation of mature immunoregulatory dendritic cells. *Nature immunology* 10, 48-57 (2009). Given that CD226 deficiency can enhance T cell exhaustion during chronic viral infection (Cella, M., et al. Loss of DNAM-1 contributes to CD8+ T-cell exhaustion in chronic HIV-1 infection. *European Journal of Immunology* 40(4), 949-954 (2010); Welch, M., et al. CD8 T cell defect of TNA-a and IL-2 in DNAM-1 deficient mice delays clearance in vivo of a persistent virus infection. *Virology* 429(2) 163-170 (2012)), it is possible that TIGIT may inhibit T cell responses in part by interfering with CD226 activity.

To evaluate whether there is a relationship between CD226 and TIGIT in inhibiting T cell responses, the expression of TIGIT and CD226 was determined on tumor infiltrating CD8+ T cells.

As shown in FIG. 14, C57BL6/J mice were inoculated with MC38 colorectal carcinoma cells. Splenocytes and tumor-infiltrating lymphocytes (TILs) were analyzed by FACs analysis approximately 14 days after inoculation, when tumors had reached approximately 200 mm3 in size. Representative histogram of CD226 expression by splenic B cells (gray), splenic CD8+ T cells (blue), and TIGIT+ tumor-infiltrating CD8+ T cells (red). Data are representative of two independent experiments; n=5. FIG. 14 illustrates that splenic CD8+ T cells highly express CD226 and furthermore, that tumor-infiltrating TIGIT+CD8+ T cells also highly expressed CD226. The data demonstrates that TIGIT and CD226 are coordinately expressed on murine tumor-infiltrating CD8+ T cells, and may regulate each other's function on CD8+ T cells. This observation is similar to that in activated CD4+ T cells and NK cells, which also co-express TIGIT and CD226.

Example 7

Co-Immunoprecipitation of TIGIT and CD226 on Transfected Cells

To determine whether TIGIT interacts with CD226 at the cell surface, cells were co-transfected with human-TIGIT and human-CD226 and subjected to immunoprecipitation. Briefly, COS 7 Cells in 15 cm plates were co-transfected with expression plasmids containing the cDNA for either TIGIT-HA (5 ng) or CD226-Flag (10 ng) tagged proteins, or a control plasmid (pRK). 23 hrs after transfection the cells were washed with PBS and harvested in 4 ml of ice cold PBS and centrifuged at 300×g for 5 min and cell pellets were re-suspended in 2 ml of Lysis buffer at 4° C. The cells were lysed over 50 min with vortexing every 15 min and subsequently centrifuged at 10,00×g for 15 min at 4° C. The resultant supernatant was pre-cleared with 160 μl of CL6B sepharose slurry by rotating for 30 min at 4° C., and centrifuged for 2 min at 3000×g. The supernatant was equally split into two tubes and immuno-precipitated with either an anti-HA or an anti-flag using standard procedures. The immune-precipitated proteins were subjected to SDS-PAGE and western blotted. Western blots were probed with either anti-Flag-HRP or anti-HA-HRP.

As shown in FIG. 15, anti-TIGIT pulled down CD226 and anti-CD226 pulled down TIGIT, demonstrating that TIGIT and CD226 are in physical contact at the cell surface.

Example 8

TIGIT and CD226 Interact in Primary CD8+ T Cells

Figure 16:
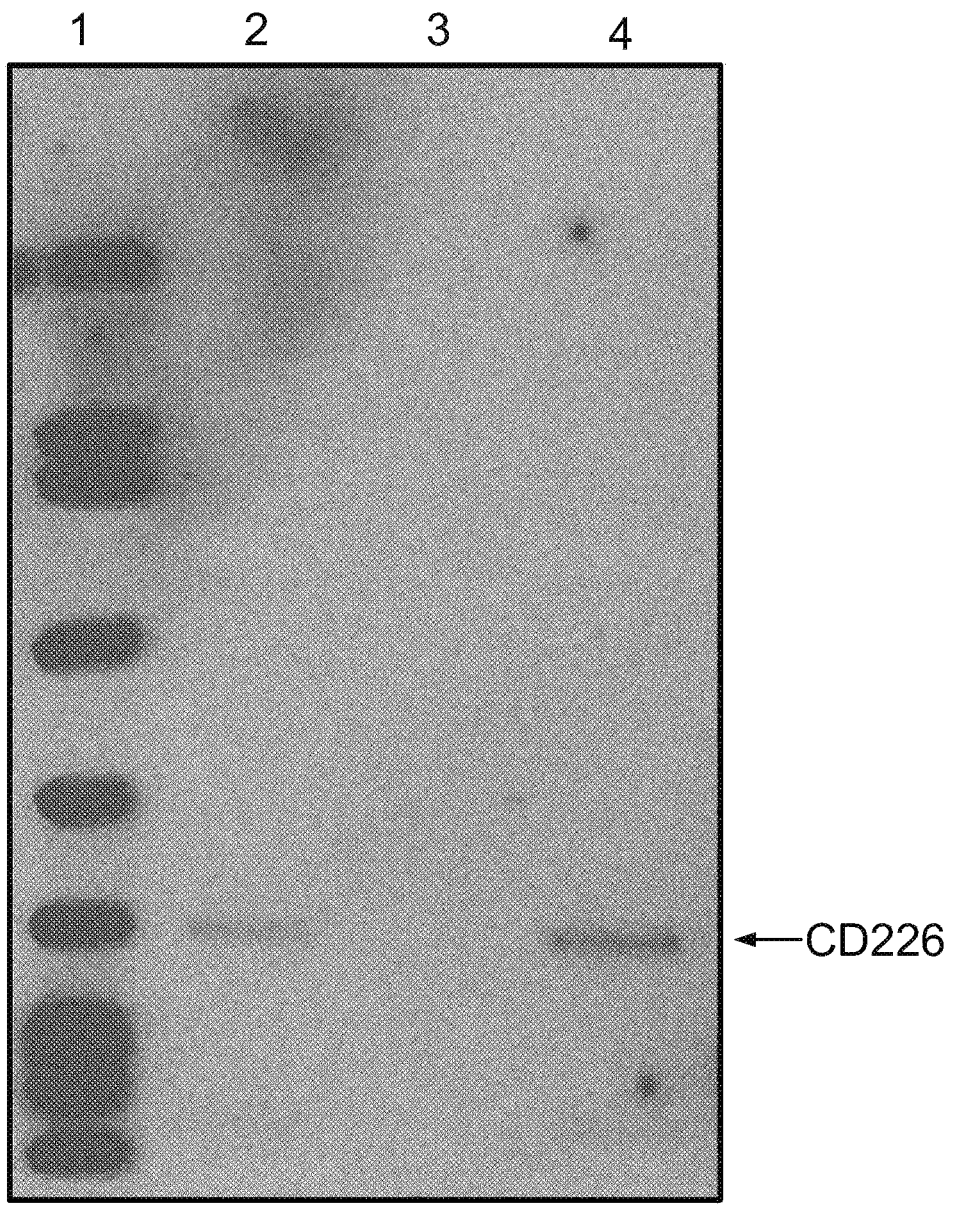
FIG. 16 shows TIGIT and CD226 interact in primary CD8+ T cells. MACS-enriched splenic C57BL6/J CD8+ T cells were stimulated with plate-bound anti-CD3 and anti-CD28 antibodies and recombinant IL-2 for 48 hours and lysed. Cell lysates were immunoprecipitated with anti-TIGIT and probed with anti-CD226. Lanes: molecular weight ladder (1), input (2), co-immunoprecipitation flow-through (3), and co-immunoprecipitate. Arrow denotes the expected molecular weight of CD226.

In addition to demonstrating the ability of CD226 and TIGIT to interact in transfected cells, the interaction of CD226 and TIGIT in primary CD8+ T cells was also evaluated. Briefly, MACS-enriched splenic C57BL6/J CD8+ T cells were stimulated with plate-bound anti-CD3 and anti-CD28 antibodies and recombinant IL-2 for 48 hours and lysed. Cell lysates were immunoprecipitated with anti-TIGIT and probed with anti-CD226. FIG. 16 illustrates that TIGIT and CD226 interact in activated primary CD8+ cells as both were detectable in the co-immunoprecipitate. This data demonstrates that CD226 and TIGIT also interact with each other on primary cells.

Example 9

TIGIT/CD226 Interaction on Transfected Cells Using TR-FRET (Time Resolved-Fluorescence Resonance Energy Transfer)

To assess whether there was any molecular interaction between TIGIT and CD226, TR-FRET methodology was employed. FRET (Fluorescence Resonance Energy Transfer) is based on the transfer of energy between two fluorophores, a donor and an acceptor, when in close proximity. Molecular interactions between biomolecules can be assessed by coupling each partner with a fluorescent label and by detecting the level of energy transfer. When two entities come close enough to each other, excitation of the donor by an energy source triggers an energy transfer towards the acceptor, which in turn emits specific fluorescence at a given wavelength. Because of these spectral properties, a donor-acceptor complex can be detected without the need for physical separation from the unbound partners. The combination of time resolved (TR) measurements of FRET allow the signal to be cleared of background fluorescence. This is typically done by introducing a time delay between the system excitation and fluorescence measurement to allow the signal to be cleared of all non-specific short-lived emissions.

Using TR-FRET, here we demonstrate that TIGIT and CD226 elicited a FRET when expressed in the same cell, indicating molecular interaction of these two molecules. Briefly, COS-7 cells were transfected with SNAP-tagged (ST) CD226 and HA-TIGIT using Lipofectamine 2000 (Life Technologies) and seeded in a white 96-well plate (Costar) at 100,000 cells per well. 24 hours later, cells were labeled with 100 nM of donor-conjugated benzyl-guanine SNAP-Lumi-4Tb (Cisbio) and 1 µM donor-conjugated benzyl-guanine SNAP-A647 (New England Biolabs) diluted in DMEM 10% FCS for 1 h at 37° C., 5% CO2. After three washes in PBS, the FRET signal was recorded at 665 nm for 400 µs after a 60 µs delay following laser excitation at 343 nm using a Safire2 plate reader (Tecan). When the anti-TIGIT antibody was tested, the FRET signal was also recorded after a 15 min incubation. The FRET ratio was then calculated as the FRET intensity divided by the donor emission at 620 nm. The FRET intensity being: (signal at 665 nm from cells labeled with SNAP-donor and acceptor)–(signal at 665 nm from the same batch of transfected cells labeled with SNAP-donor only).

Figure 17B:
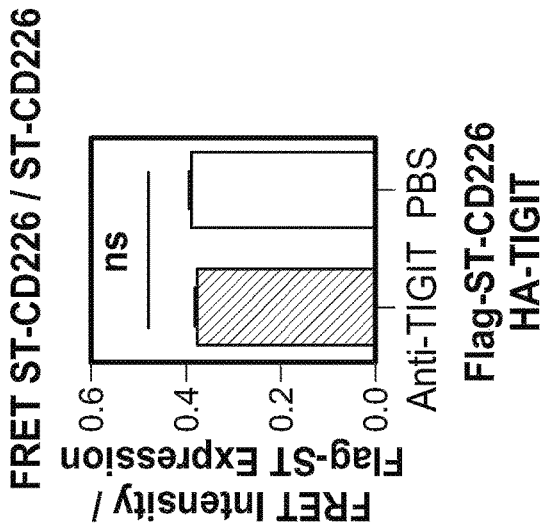
FIGS. 17A-17D show the detection of TIGIT/CD226 interactions by TR-FRET.
Figure 17D:
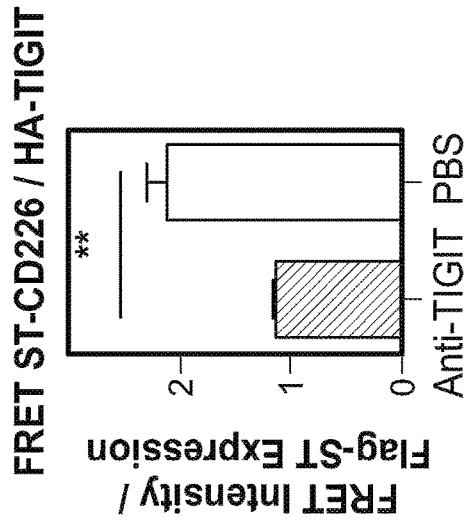
Figure 17A:
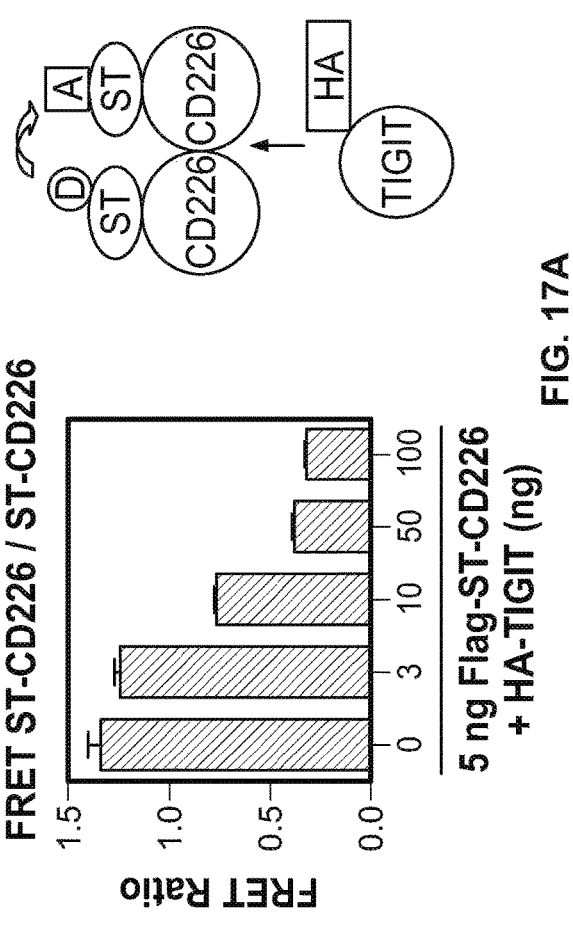

As shown in FIGS. 17A-17D, TIGIT was able to directly disrupt and cause dissociation of CD226 homodimers. As shown in FIG. 17A, the dissociation of Flag-ST-CD226 homodimers was observed with increasing concentrations of HA-TIGIT as illustrated by the decreasing FRET ratio between Flag-ST-CD226 measured on COS-7 cells expressing a constant amount of Flag-ST-CD226 and increasing concentrations of HA-TIGIT. However, as shown in FIG. 17B, when anti-TIGIT antibody was added to the cell culture, this blocked the ability of TIGIT and CD226 to associate. This is illustrated by the lack of a decrease in the FRET intensity of Flag-ST-CD226 homodimers. This demonstrates that CD226 and TIGIT are associated as complexes but that anti-TIGIT antibodies can disrupt these interactions (FIGS. 17A-17B).

Figure 17C:
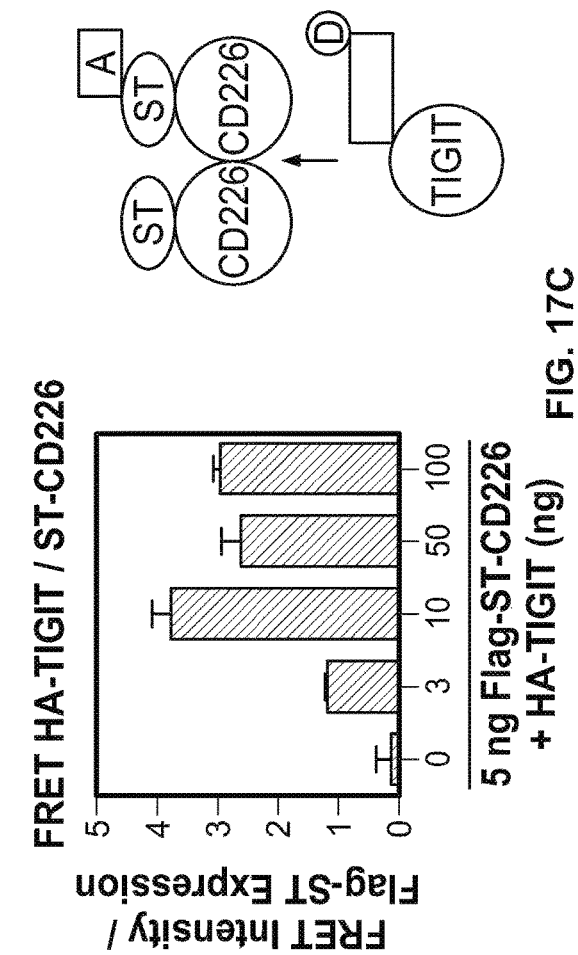

Using TR-FRET, the ability of TIGIT to associate with CD226 was also demonstrated and shown in FIGS. 17C-17D. Briefly, after SNAP-tag labeling using 1 µM of donor-conjugated benzyl-guanine SNAP-A647 (see above), cells were washed three times in PBS and incubated with 2 nM of anti-HA donor-conjugated Lumi-4Tb (Cisbio) diluted in PBS+0.2% BSA for 2 hours at room temperature. The FRET signal was then recorded. In that case, the FRET intensity is: (signal at 665 nm from cells labeled with SNAP-acceptor and anti-HA donor)–(signal at 665 nm from mock transfected cells labeled with SNAP-acceptor and anti-HA donor).

As shown in FIG. 17C, association of Flag-ST-CD226 with HA-TIGIT was observed as illustrated by the increasing FRET intensity between Flag-ST-CD226 and HA-TIGIT measured on COS-7 cells expressing a constant amount of Flag-ST-CD226 and increasing concentrations of HA-TIGIT. When anti-TIGIT antibody was added, the FRET intensity decreased between Flag-ST-CD226 with HA-TIGIT, as shown in FIG. 17D, suggesting that the interaction of TIGIT with CD226 can be blocked by an anti-TIGIT blocking antibody.

Figure 18:
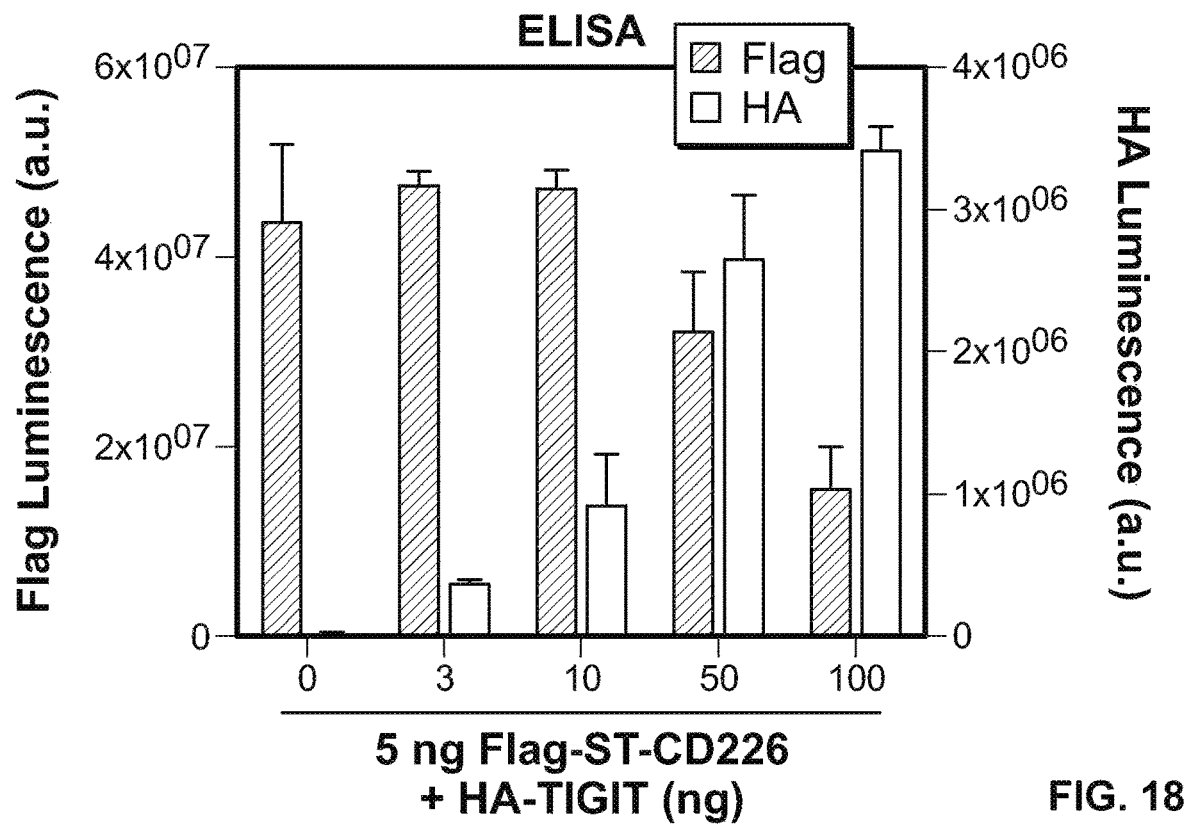
FIG. 18 shows cell surface expression of Flag-ST-CD226 and HA-TIGIT. Anti-Flag and anti-HA ELISA on intact COS-7 cells expressing the indicated tagged-constructs. Data are representative of 3 independent experiments, each performed in triplicate.

To confirm the cell surface expression of Flag-ST-CD226 and HA-TIGIT in the FRET experiments, anti-Flag and anti-HA ELISA on intact COS-7 cells expressing the indicated tagged-constructs was performed. Briefly, COS7 cells were fixed with 4% paraformaldehyde, washed twice, and blocked in phosphate-buffered saline+1% fetal calf serum (FCS). Cells were then incubated with an anti-HA monoclonal antibody (clone 3F10, Roche applied science) or anti-Flag-M2 monoclonal antibody (Sigma), both conjugated with horseradish peroxidase. After washes, cells were incubated with a SuperSignal ELISA substrate (Pierce) and chemoluminescence was detected on a Safire2 plate reader (Tecan). Specific signal was calculated by subtracting the signal recorded on mock transfected cells. As illustrated in FIG. 18, cell surface expression of both CD226 and TIGIT were confirmed in the ELISA assay.

Figure 24:
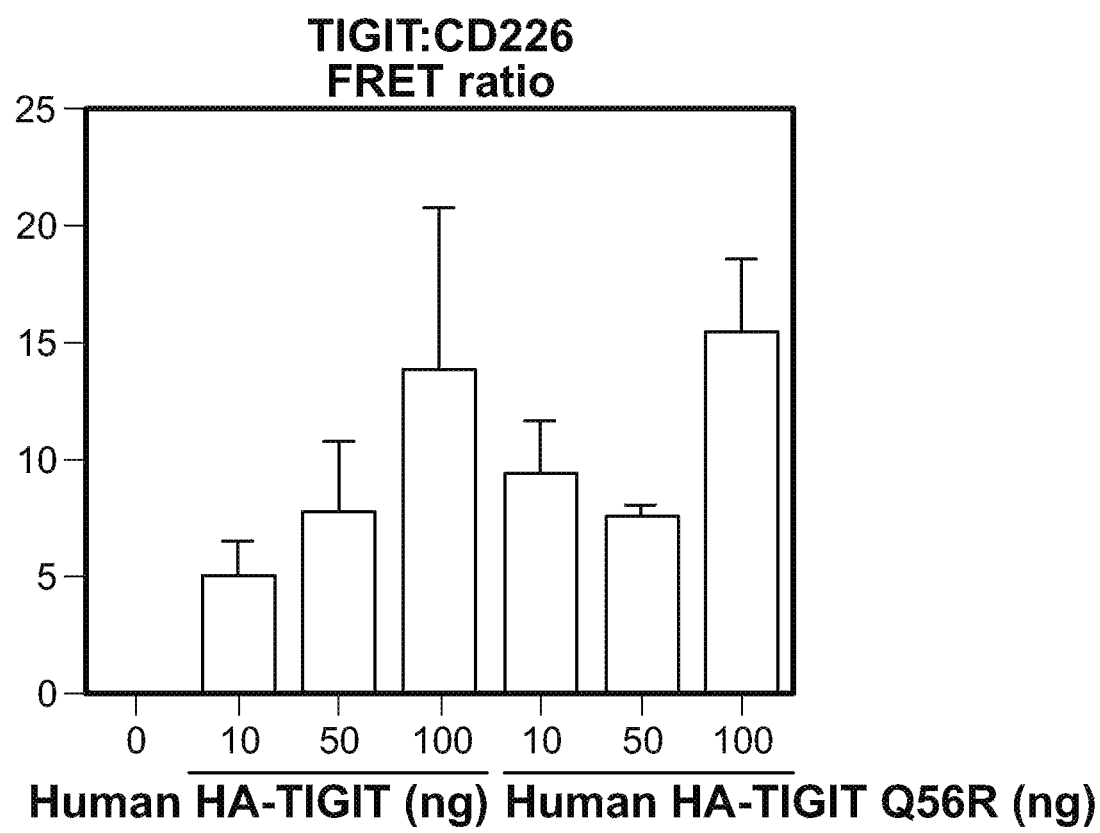
FIG. 24 shows that the TIGIT:CD226 interaction is not driven by PVR TIGIT:CD226 and TIGIT Q56R:CD226 interactions were detected by TR-FRET and the FRET ratio between Flag-ST-CD226 and HA-TIGIT or HA-TIGIT Q56R shows that WT and Q56R TIGIT bind CD226 with the same efficacy. Data are representative of three independent experiments performed in triplicate.

To confirm that the TIGIT:CD226 interaction is not driven by PVR binding, Flag-ST-CD226 and HA-TIGIT (WT) or HA-TIGIT Q56R were generated as described in Stengel et al., (2012) *PNAS* 109(14):5399-5904 and FRET ratios were determined as described. As shown in FIG. 24, WT TIGIT and Q56R TIGIT bind CD226 with the same efficacy.

This data not only demonstrates the CD226 and TIGIT are associated as complexes, but that an anti-TIGIT antibody can disrupt these interactions and that the TIGIT:CD226 interaction is not driven by PVR binding. The data supports a role for TIGIT in limiting CD226-mediated activation of T cells and that interference with CD226 activity may be an important mechanism of action by which TIGIT inhibits T cell responses and activity.

Example 10

CD226 Blockade Reverses the Effectors of TIGIT/PD-L1 Blockade In Vivo

To test the physiological relevance of the CD226 and TIGIT interaction, mice were chronically infected with Clone 13 LCMV and then treated with anti-TIGIT+anti-PD-L1 in the absence or presence of anti-CD226 blocking antibodies. Briefly, C57BL6/J mice were briefly depleted of CD4$^+$ T cells and infected with Clone 13 strain LCMV. For chronic infections, mice were intravenously infected with 2×10$^6$ PFU Clone 13 strain LCMV and treated with 500 ug and 250 ug of depleting anti-CD4 antibodies (clone GK1.5) 3 days before and 4 days after infection, respectively. Where indicated, mice infected with Clone 13 strain LCMV received intraperitoneal injections of 200 ug of isotype control antibodies, 500 ug of anti-CD226 antibodies, 200 ug of anti-PD-L1 antibodies+500 ug of anti-TIGIT antibodies, or 500 ug of anti-CD226 antibodies+200 ug of anti-PD-L1 antibodies+500 ug of anti-TIGIT antibodies 3 times per week from days 28 to 42 post-infection. Treatment was started at 28 days post-infection because the T cell response is largely exhausted at this time-point in this model of chronic viral infection (Wherry et al, Molecular Signature of CD8$^+$ T cell Exhaustion During Chronic Viral Infection, Immunity. 2007 October; 27(4):670-84). Splenocytes and liver viral titers were analyzed 42 days after infection.

Figure 19A:
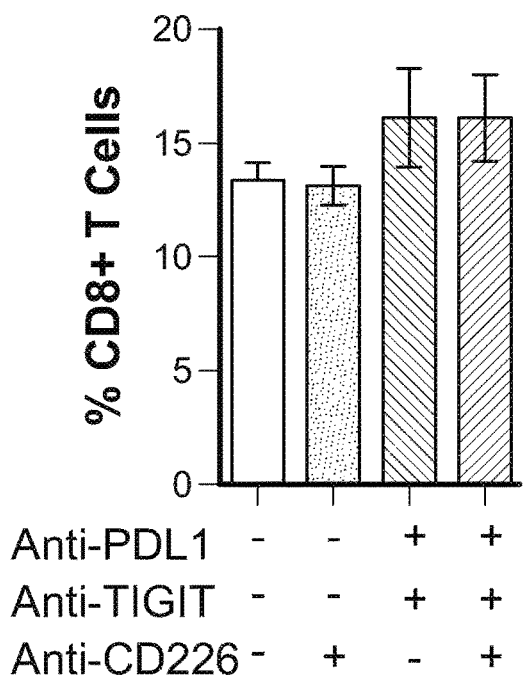
Figure 19B:
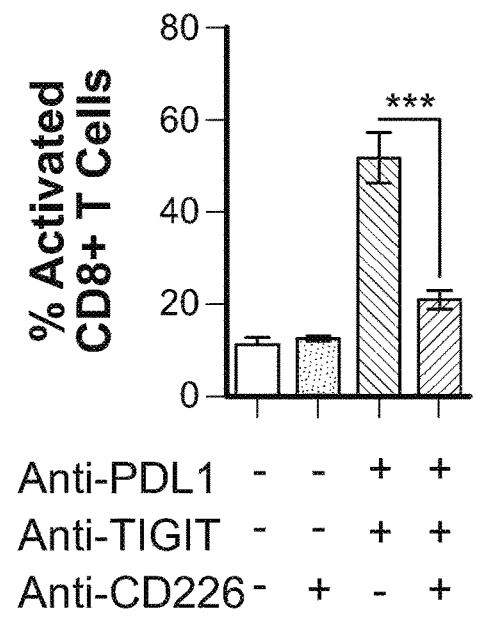

In these mice, anti-CD226 treatment alone had limited effects on CD8$^+$ T cell frequency, activation, or cytokine competency (FIGS. 19A-19C). However, anti-CD226 treatment potently reversed the increases in CD8$^+$ T cell activation and IFNg production seen in mice treated with anti-PD-L1+anti-TIGIT (59% and 58% decreases, respectively, $P<0.001$. FIGS. 19B-19D).

Consistent with these results, LCMV viral loads were significantly higher in mice treated with anti-CD226+anti-PD-L1+anti-TIGIT than in mice treated with anti-PD-L1+anti-TIGIT alone (272% increase, P<0.001, FIG. 19D).

This data suggests that a primary mechanism by which TIGIT limits chronic T cell responses is interference with CD226-mediated co-stimulation. The data identifies a previously unknown role for TIGIT in interacting with and disrupting CD226, resulting in the reduction or loss of a key co-stimulatory signal in CD8$^+$ T cells. The data demonstrates that interference with CD226-mediated T cell costimulation may be a major mechanism by which TIGIT limits chronic T cell responses such as during cancer or chronic viral infection. The data also defines an essential parameter for anti-TIGIT antibodies intended to restore the effector function of chronically stimulated or exhausted CD8$^+$ or CD4$^+$ T cells by interfering with TIGIT's ability to interact with CD226 and/or TIGIT's ability to disrupt CD226 dimerization.

Materials and Methods
Mice.

C57BL/6J and BALB/c mice were purchased from the Jackson Laboratory and Charles River Laboratories. CD4$^{cre}$ mice and TIGIT$^{loxP/loxP}$ mice were generated on a C57BL/6J background with standard techniques and crossed. TIGIT expression was ablated with 96% efficiency from T cells in TIGIT$^{loxP/loxP}$ CD4$^{cre}$ mice.

Flow Cytometry.

Single cell suspensions of spleen, lymph node, and tumor were prepared with gentle mechanical disruption. Surface staining was performed with commercial antibodies against CD4, CD8, CD44, CD62L, PD-1 (eBiosciences) and CD226 (Biolegend). TIGIT antibodies were generated at Genentech as previously described (Yu, X. et al. The surface protein TIGIT suppresses T cell activation by promoting the generation of mature immunoregulatory dendritic cells. *Nature immunology* 10, 48-57 (2009)) and conjugated to Alexa Fluor 647 according to the manufacturer's directions (Molecular Probes).

For intracellular cytokine staining (ICS), cells were stimulated for 4 hours with 20 ng/mL Phorbol 12-myristate 13-acetate (PMA, Sigma) and 1 μM Ionomycin (Sigma) in the presence of 3 μg/mL Brefeldin A (eBiosciences). After stimulation, cells were stained for surface markers as described and fixed and permeabilized with eBioscience's FoxP3 fixation buffer set according to the manufacturer's directions. Fixed cells were stained with antibodies against IFNγ and TNFα (eBiosciences).

Blocking Antibodies.

A blocking anti-TIGIT IgG2a monoclonal antibody (clone 10A7, reactive against both mouse and human TIGIT) was generated as previously described and cloned onto a murine IgG2a backbone. A blocking anti-PD-L1 IgG2a monoclonal antibody (clone 25A1) was generated by immunizing Pdl1$^{-/-}$ mice with a PD-1-Fc fusion protein and cloned onto a murine IgG2a backbone. Clone 25A1 was modified with previously described mutations abolishing binding to Fcγ receptors. A blocking anti-CD226 IgG2a monoclonal antibody (clone 37F6) was generated by immunization of hamsters with recombinant murine CD226 and cloned onto a murine IgG2a backbone. These antibodies were also used in tests described in other Examples described herein.

Viral Infections.

For acute infections, mice were intravenously infected with 2×10$^6$ plaque-forming units (PFU) Armstrong strain LCMV. For chronic infections, mice were intravenously infected with 2×10$^6$ PFU Clone 13 strain LCMV and treated with 500 ug and 250 ug of depleting anti-CD4 antibodies (clone GK1.5) 3 days before and 4 days after infection, respectively. Where indicated, mice infected with Clone 13 strain LCMV received intraperitoneal injections of 200 ug of isotype control antibodies, 200 ug of anti-PD-L1 antibodies, and/or 500 ug of anti-TIGIT antibodies 3 times per week from days 28 to 42 post-infection.

Viral Titer Assay.

Monolayers of MC57 cells were cultured with an overlay of 1% methylcellulose and infected with serially diluted liver homogenates from LCMV-infected mice. 72 hours after infection, the cells were fixed with 4% paraformaldehyde and permeabilized with 0.5% Triton-X. Viral plaques were stained with anti-LCMV NP (clone VL-4) and HRP-conjugated anti-rat IgG and visualized with O-phenylenediamine (OPD, Sigma).

Bioinformatics.

Breast cancer gene expression data microarray data was obtained from the Cancer Gene Atlas Network (Network, T.C.G.A. Comprehensive genomic characterization of squamous cell lung cancers. *Nature* 489, 519-525 (2012)). Processing and normalization of microarray data were performed using the R programming language (http://r-projec-t.org) and Bioconductor's limma package (http://bioconductor.org). Microarray intensity values from each channel were preprocessed using the normal+exponential background correction method, as previously described[22]. Corrected intensity values were then normalized using quantiles normalization, as previously described[23]. Normalized log-ratio data was calculated by subtracting the reference channel from the test channel for each array. Data were further filtered using a non-specific filter, as previously described[24], removing probes that do not map to known genes, and reducing the dataset to one probe per gene. For differential expression analysis, moderated t-statistics were calculated with the limma package, as previously described (Smyth, G. K. Linear models and empirical bayes methods for assessing differential expression in microarray experiments. *Statistical applications in genetics and molecular biology* 3, Article 3 (2004)). To evaluate correlation, Pearson's correlation coefficients were used.

CT26 Colon Carcinoma.

BALB/c were subcutaneously inoculated with 1×10$^5$ CT26 colon carcinoma cells suspended in matrigel (BD Biosciences) into the right unilateral thoracic flank. After two weeks, mice bearing tumors of approximately 200 mm$^3$ were randomly recruited into treatment groups receiving 35 mg/kg of isotype control antibodies, anti-PD-L1 antibodies, and/or anti-TIGIT antibodies by intraperitoneal injection 3 times per week for 3 weeks. Tumors were measured 2 times per week by caliper. Animals whose tumors became ulcerated/necrotic or grew larger than 2000 mm$^3$ were euthanized.

EMT6 Breast Carcinoma.

BALB/c mice were subcutaneously inoculated in the fourth mammary fat pad with 1×10$^5$ syngeneic EMT6 breast carcinoma cells in matrigel (BD Biosciences). After two weeks, mice bearing tumors of 150-200 mm$^3$ were randomly recruited into treatment groups receiving 35 mg/kg of isotype control antibodies, anti-PD-L1 antibodies, and/or anti-TIGIT antibodies by intraperitoneal injection 3 times per week for 3 weeks. Tumors were measured 2 times per week by caliper, and tumor volumes were calculated using the modified ellipsoid formula, ½×(length×width$^2$). Animals whose tumors shrank to 32 mm$^3$ or smaller were considered to be in complete response (CR). Animals whose tumors grew to larger than 2000 mm³ were considered to have progressed and were euthanized. Animals whose tumors became ulcerated prior to progression or complete response were euthanized and removed from the study.

CT26 Re-Challenge.

Where indicated, BALB/c mice previously inoculated with CT26 colon carcinoma cells as described above were re-inoculated with CT26 cells into the left (not previously inoculated) unilateral thoracic flank. These mice were also inoculated with 1×10⁵ EMT6 breast carcinoma cells in matrigel into the fourth mammary fat pad. Tumors were measured 2 times per week. Animals whose tumors became ulcerated/necrotic or whose total tumor burden exceeded 2000 mm³ were euthanized.

Statistics.

Statistical tests were conducted using unpaired (paired where specified) 2-tailed Student's t-tests. Error bars depict the standard error of the mean.

Animal Study Oversight.

All animal studies were approved by Genentech's Institutional Animal Care and Use Committee.

Example 11

TIGIT Expression is Elevated in Human Cancer and Correlated with Expression of CD8 and PD-1 and CD8+ T Cell Infiltration Materials and Methods Bioinformatics. Processing and analysis of RNA-sequencing data was performed using the R programming language (http://www.r-project.org) along with several packages from the Bioconductor project (http://www.bioconductor.org). RNA-sequencing data for cancer and matched normal samples were obtained from the TCGA for five different indications: breast cancer (Network, C.G.A. Comprehensive molecular portraits of human breast tumours. Nature 490, 61-70 (2012)), colon adenocarcinoma (Network, T.C.G.A. Comprehensive molecular characterization of human colon and rectal cancer. Nature 487, 330-337 (2012)), renal clear cell carcinoma (Network, C.G.A. Comprehensive molecular characterization of clear cell renal cell carcinoma. Nature 499, 43-49 (2013)), lung squamous cell carcinoma (Network, T.C.G.A. Comprehensive genomic characterization of squamous cell lung cancers. Nature 489, 519-525 (2012)), and endometrial carcinoma (Network, T.C.G.A. Integrated genomic characterization of endometrial carcinoma. Nature 497, 67-73 (2012)).

Raw RNA-seq reads were processed using the HTSeqGenie Bioconductor package. Briefly, reads were aligned to the human genome (NCBI build 37) using the GSNAP algorithm (Wu, T. D. & Nacu, S. Fast and SNP-tolerant detection of complex variants and splicing in short reads. Bioinformatics (Oxford, England) 26, 873-881 (2010)). Uniquely aligned read pairs that fell within exons were counted to give an estimate of gene expression level for individual genes. We used the library size estimation from the edgeR package (Robinson, M. D., McCarthy, D. J. & Smyth, G. K. edgeR: a Bioconductor package for differential expression analysis of digital gene expression data. Bioinformatics (Oxford, England) 26, 139-140 (2010)) to normalize across different samples for their respective sequencing depths.

To derive a T cell specific gene signature, we manually curated the T cell genes identified by the IRIS project, removing genes associated with cell cycle processes, genes highly expressed in other tissues, and known co-activating and co-inhibitory receptors. This yields a 15-gene signature that is specific to T cells. To calculate the T cell gene expression signature score in the lung squamous cell carcinoma data, we first performed a variance stabilizing transform on the raw count data using the voom function from the limma Bioconductor package. We then calculated the first eigenvector of the centered and scaled variance-stabilized data from the 15-gene T cell signature. This approach yields a robust per-sample estimate of relative T cell abundance. A linear model including the T cell signature score was then fit for each gene, again using the limma package. We then ranked the genes by their correlation with the T cell signature in our linear model, choosing only genes positively correlated with the T cell signature. For visualizing T cell-associated genes as a heatmap, we centered and scaled the variance-stabilized data to unit variance, allowing for comparison of genes with different average expression levels.

To determine the correlation between expression of TIGIT and other genes, we normalized RNA-sequencing count data to account for differences in library size, using the method from the edgeR Bioconductor package (Robinson, M. D., McCarthy, D. J. & Smyth, G. K. edgeR: a Bioconductor package for differential expression analysis of digital gene expression data. Bioinformatics (Oxford, England) 26, 139-140 (2010)). We then calculated Spearman's rank correlation coefficient on the normalized counts. We consider rho>0.75 to be indicative of strong correlation, rho≤0.75 but >0.5 to be indicative of moderate correlation, and rho≤0.5 but >0.25 to be indicative of weak correlation.

For calculation of TIGIT/CD3ε ratios across each indication, we first calculated the variance-stabilized data for each RNA-sequencing data set. We then calculated the log 2 ratio of the variance-stabilized data for TIGIT and CD3ε. To calculate the difference between tumor and normal samples, we performed standard linear model analysis using standard R functions. We accepted a p-value of <0.01 as evidence of a significant difference between tumor and normal.

Figure 21:
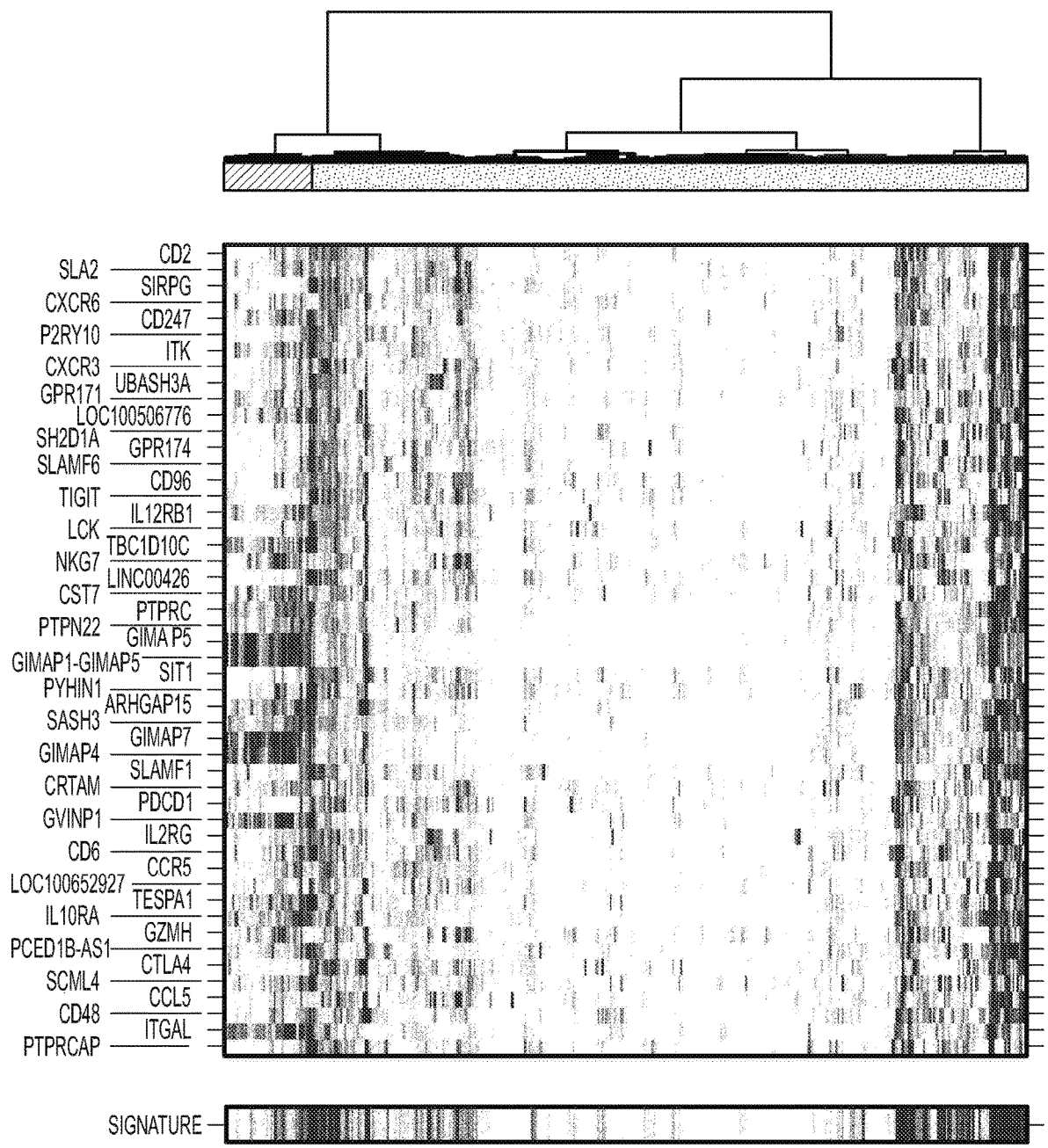
FIG. 21 shows the analysis of T cell-associated gene expression in Lung Squamous Cell Carcinoma (LUSC). Gene expression in LUSC and normal tissue samples was analyzed as described in Example 11 and a heat map of the genes best correlated with the gene signature in LUSC samples was generated. Genes and samples were both clustered using hierarchical clustering using Ward linkage on the Euclidean distance matrix for the centered and scaled expression data.

To identify genes associated with tumor-infiltrating T cells, we used a gene signature-based approach to interrogate gene expression data from the Cancer Genome Atlas (TCGA) lung squamous cell carcinoma (LUSC) collection (Network, T.C.G.A. Comprehensive genomic characterization of squamous cell lung cancers. Nature 489, 519-525 (2012)). Using immune cell-specific gene sets defined by the Immune Response In Silico project (Abbas, A. R. et al. Immune response in silico (IRIS): immune-specific genes identified from a compendium of microarray expression data. Genes and immunity 6, 319-331(2005)), and the methods described above, we developed a highly specific 15 gene signature. Examining the genes most highly associated with the T cell signature, we identified several co-inhibitory receptors previously associated with T cell dysfunction in tumors, particularly PD-1 (FIG. 21). In LUSC, expression of TIGIT and CD3ε were highly correlated, with a Spearman's rank correlation coefficient (ρ of 0.82 (FIG. 20A). Indeed, TIGIT and CD3ε expression were also highly correlated in many additional TCGA tumor gene expression datasets, including colon adenocarcinoma (COAD), uterine corpus endometroid carcinoma (UCEC), breast carcinoma (BRCA), and kidney renal clear cell carcinoma (KIRC), with ρ ranging from 0.83 to 0.94 (FIGS. 20B-20E). Furthermore, expression of TIGIT was elevated relative to expression of CD3ε in many tumor samples, with increased TIGIT/CD3ε ratios in LUSC, COAC, UCEC, and BRCA tumor samples compared to matched normal tissue (116%-

419% increase, FIGS. 20A-20D). The ratio of TIGIT to CD3ε expression in KIRC samples was unchanged, though expression of both TIGIT and CDR was much higher in KIRC samples than in normal tissue samples (FIG. 20E). These data indicated that TIGIT expression was up-regulated by tumor-infiltrating lymphocytes (TILs) in a broad range of solid tumors.

TIGIT has been previously described as an inhibitor of CD4+ T cell priming, with no known function in CD8+ T cells. However, TIGIT expression in LUSC samples was highly correlated with CD8A and only weakly correlated with CD4 ($\rho$=0.77 and 0.48 respectively, FIG. 20F). Expression of TIGIT was also correlated with expression of its complementary co-stimulatory receptor, CD226, as well as with expression of PD-1, a key mediator of T cell suppression in tumors and during other chronic immune responses ($\rho$=0.64 and 0.82 respectively, FIGS. 20G-20H). Although some non-lymphocyte cell sources of these genes exist in tumors, these data strongly suggested that tumor-infiltrating T cells, particularly "exhausted" CD8+ T cells, expressed high levels of TIGIT.

Example 12

TIGIT and PD-1 are Coordinately Expressed by Human and Murine Tumor-Infiltrating Lymphocytes Materials and Methods
Human Tumor and PBMC Samples.

Matched whole blood and fresh surgically resected tumor tissues were obtained from Conversant Biosciences or Foundation Bio. All specimens were obtained with written informed consent and collected using a protocol approved by the Hartford Hospital Institutional Review Board (IRB) (NSCLC patient 1, depicted in FIGS. 22A-22G) or the Western IRB (NSCLC patient 2 and CRC patient 1, depicted in FIGS. 23A-23D and FIGS. 37A-37B). Normal adult whole blood was obtained from a healthy volunteer. PBMCs were purified from whole blood by Ficoll gradient centrifugation. Tumor tissues were cut into small pieces, and incubated with collagenase and DNAse (Roche), and disassociated using a gentleMACS Disassociator (Miltenyi).

Flow Cytometry.

Single cell suspensions of mouse spleen, lymph node, and tumor were prepared with gentle mechanical disruption. Surface staining was performed with commercial antibodies against CD4, CD8, CD44, CD62L, PD-1 (eBiosciences) and CD226 (Biolegend). TIGIT antibodies were generated at Genentech and conjugated to Alexa Fluor 647 according to the manufacturer's directions (Molecular Probes).

For intracellular cytokine staining (ICS), cells were stimulated for 4 hours with 20 ng/mL Phorbol 12-myristate 13-acetate (PMA, Sigma) and 1 µM Ionomycin (Sigma) in the presence of 3 µg/mL Brefeldin A (eBiosciences). After stimulation, cells were stained for surface markers as described and fixed and permeabilized with eBioscience FoxP3 fixation buffer set according to the manufacturer's directions. Fixed cells were stained with antibodies against IFNγ and TNFα (eBiosciences).

Human tumor and PBMC samples were prepared as described above. Surface staining was performed with a viability dye (Molecular Probes), commercial antibodies against CD45 (eBiosciences), CD3, CD4, CD8, PD-1 (BD Biosciences), and with anti-TIGIT antibodies prepared as described above.

All samples were acquired on LSR-II or LSR-Fortessa instruments (BD Biosciences) and analyzed using FlowJo software (Treestar).

Figure 22A:
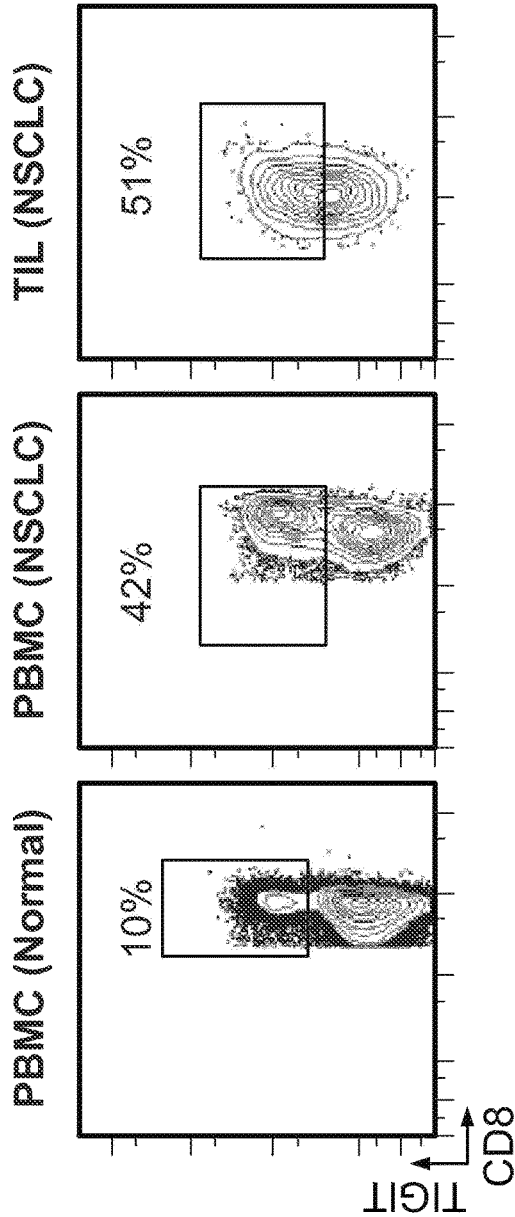
FIGS. 22A-22G show that TIGIT and PD-1 are coordinately expressed by human and murine tumor-infiltrating lymphocytes.
Figure 22B:
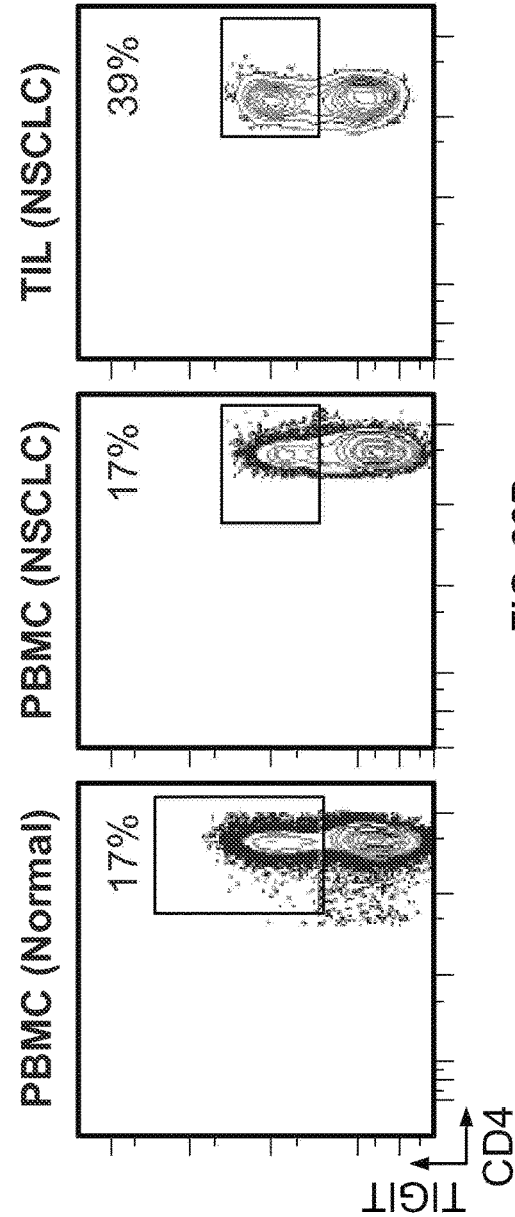
Figure 22C:
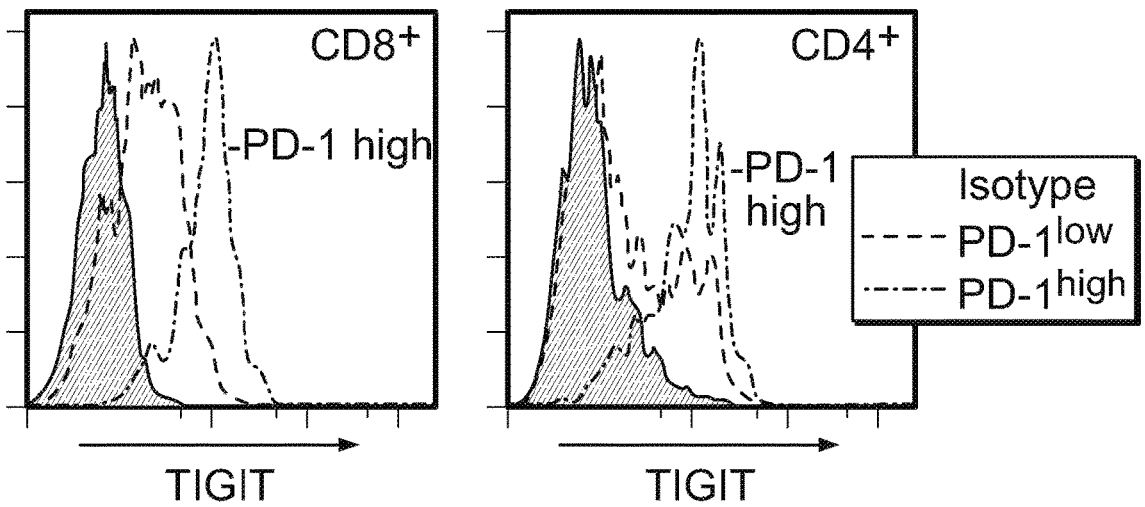
Figure 22D:
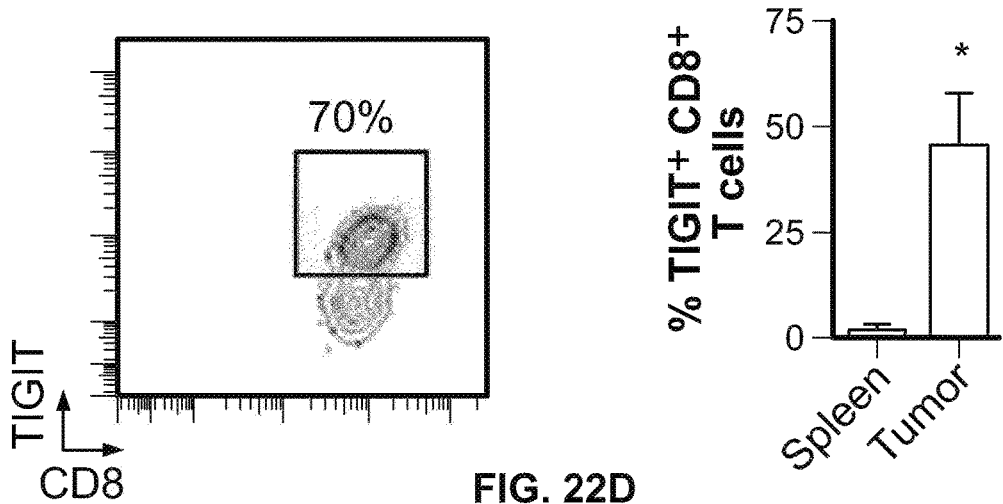
Figure 22E:
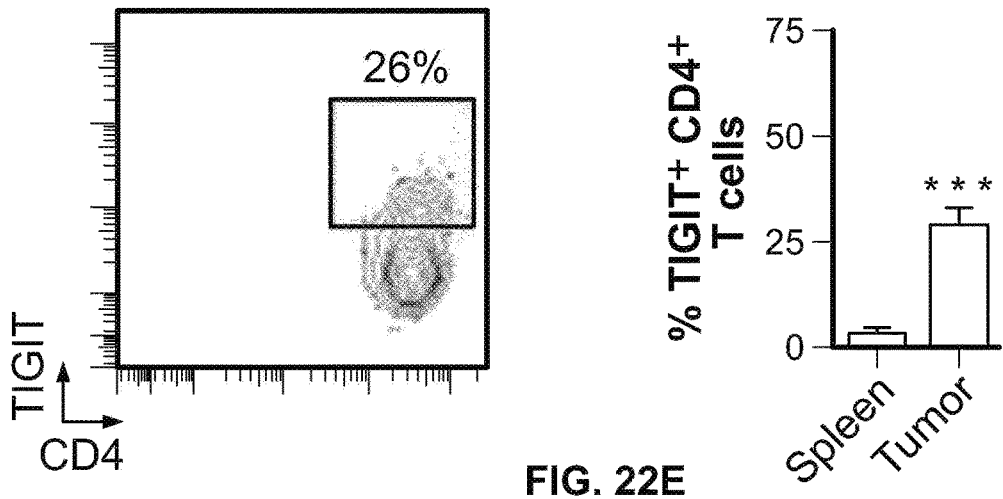

To confirm up-regulation of TIGIT by tumor-infiltrating T cells, we assessed TIGIT protein expression on human non-small-cell lung carcinoma tumor-infiltrating T cells, matched peripheral T cells, and normal donor peripheral T cells. Cell surface TIGIT was expressed by subsets of NSCLC-infiltrating CD8+ and CD4+ T cells (51% and 39% respectively, FIGS. 22A-22B. FIGS. 36A-36B further demonstrates that cell surface TIGIT was expressed by a large percentage of NSCLC-infiltrating CD8+ and CD4+ T cells (58% and 28% TIGIT+ respectively, FIGS. 36A-36B). Interestingly, peripheral CD8+ and CD4+ T cells from the NSCLC tumor donor also expressed higher levels of TIGIT than did cells from healthy donors (FIGS. 22A-22B and FIGS. 36A-36B). Similar results were obtained with a second set of matched NSCLC and PBMC samples and in a set of matched colorectal carcinoma (CRC) and PBMC samples (FIGS. 23A-23D and FIGS. 37A-37B). Nearly all tumor-infiltrating T cells expressing high levels of TIGIT co-expressed PD-1, consistent with the correlation between TIGIT and PD-1 expression described in FIGS. 1A-1D (FIG. 22C).

Figure 22F:
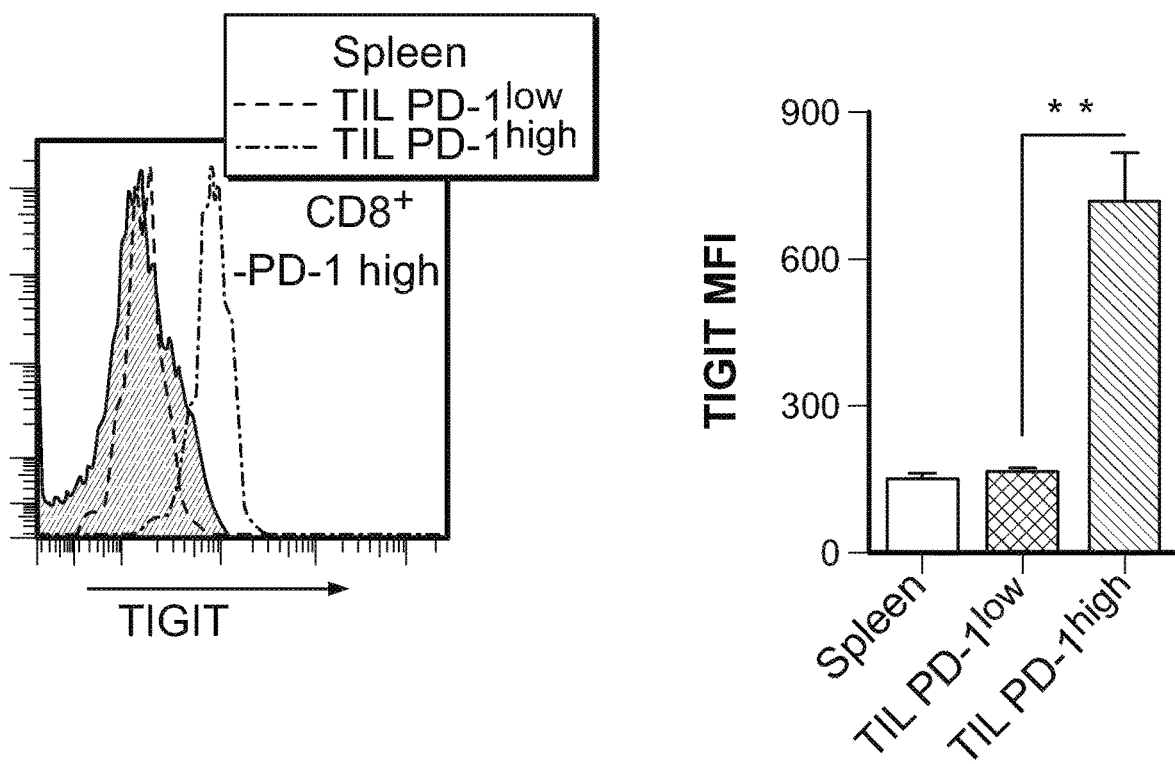
Figure 22G:
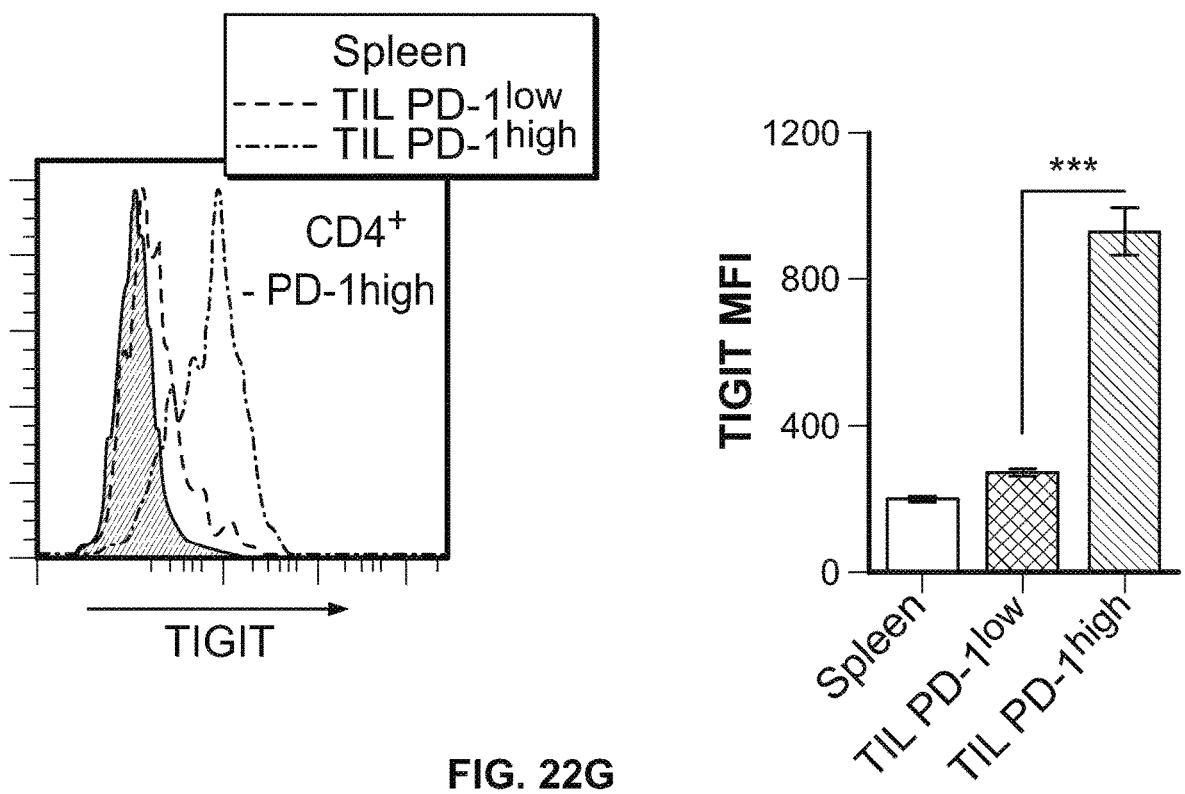
Figure 23D:
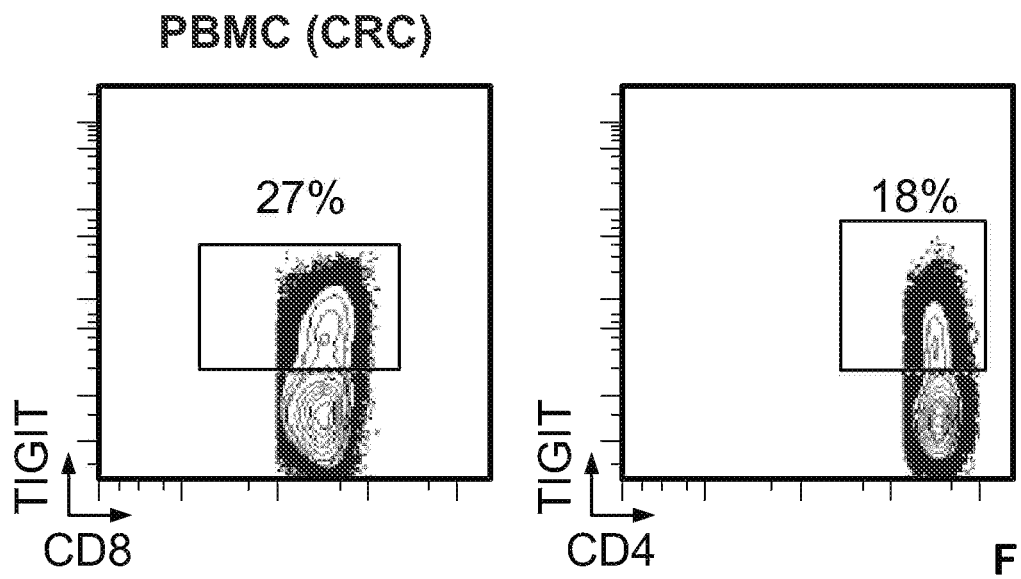

To extend our human findings into pre-clinical cancer models, we characterized TIGIT expression by T cells infiltrating subcutaneous CT26 and MC38 colorectal tumors in wildtype BALB/c mice and C57BL6/J mice, respectively. Two weeks post-inoculation, when CT26 and MC38 tumors had become established and grown to 150-200 mm$^3$ in size, TIGIT was expressed by approximately 50% of tumor-infiltrating CD8+ T cells and 25% of tumor-infiltrating CD4+ T cells, at levels similar to those of primary CD8+ T cells stimulated in vitro (FIGS. 22D-22E and FIGS. 26A-26E). In both CD8+ and CD4+ murine TILs, CD226 was constitutively expressed, and TIGIT and PD-1 expression were again tightly correlated (FIGS. 22F-22G).

These results confirmed that TIGIT was highly expressed by tumor-infiltrating T cells, and that expression of TIGIT occurred in parallel with expression other co-inhibitory receptors, most notably PD-1.

Example 13

TIGIT Suppression of CD8+ T Cells Responses is Dependent on CD226

Figure 27A:
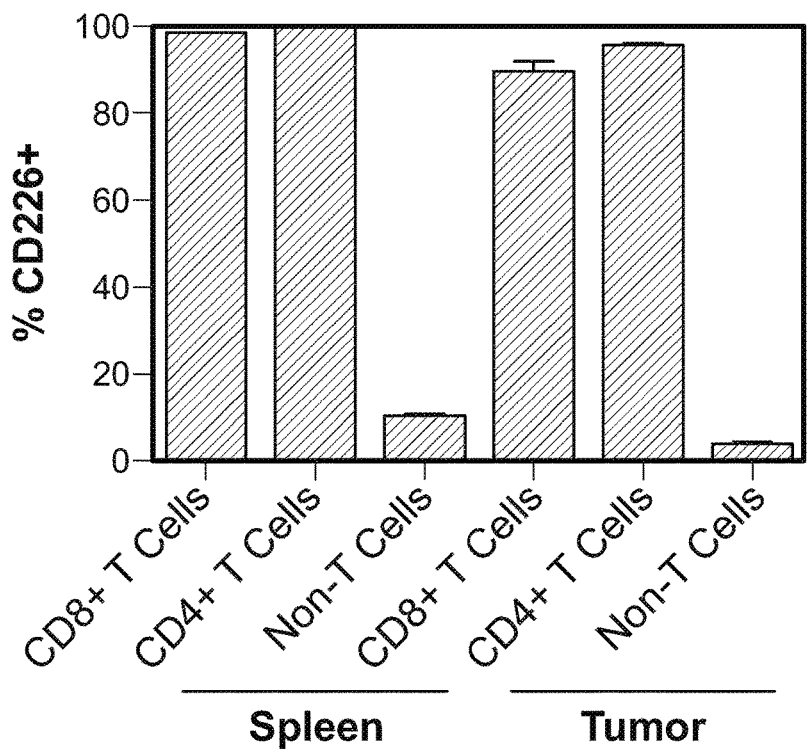
FIGS. 27A-27B show that tumor-infiltrating CD8$^+$ and CD4$^+$ T cells maintain a high level of CD226 expression. Wildtype BALB/c mice were inoculated with CT26 tumor cells as described herein. After tumors have grown to approximately 150-200 mm$^3$ in size, tumors and spleens were analyzed by flow cytometry.
Figure 27B:
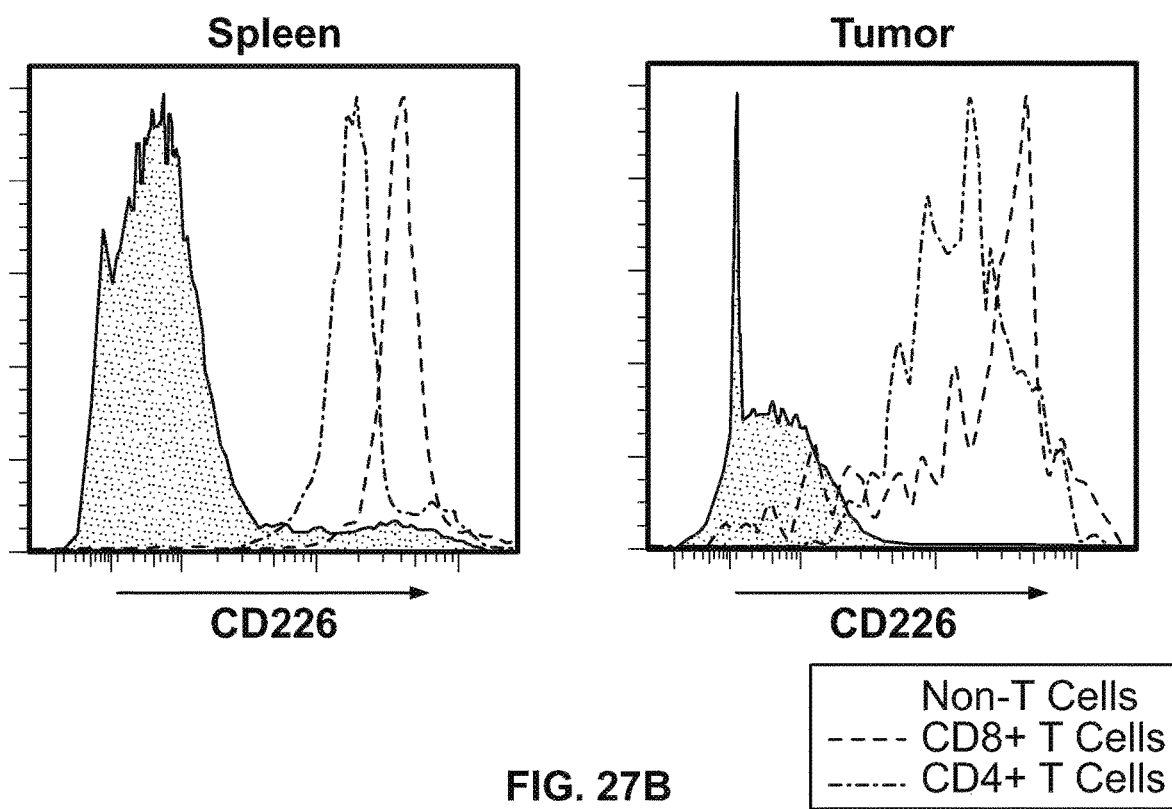

Unlike PD-1 or CTLA-4, there is no direct biochemical evidence of a T cell inhibitory signaling cascade initiated by TIGIT in cis. However, co-inhibitory receptors can also function by limiting the activity of a complementary co-stimulatory receptor, such as with the suppression of CD28 signaling by CTLA-4. Having established TIGIT as a negative regulator of tumor-infiltrating and anti-viral CD8+ T cells, we asked whether TIGIT induced T cell exhaustion indirectly via suppression of its complementary co-stimulatory receptor, CD226, which is highly expressed by peripheral and tumor-infiltrating CD8+ T cells (FIGS. 27A-27B).

Figure 28A:
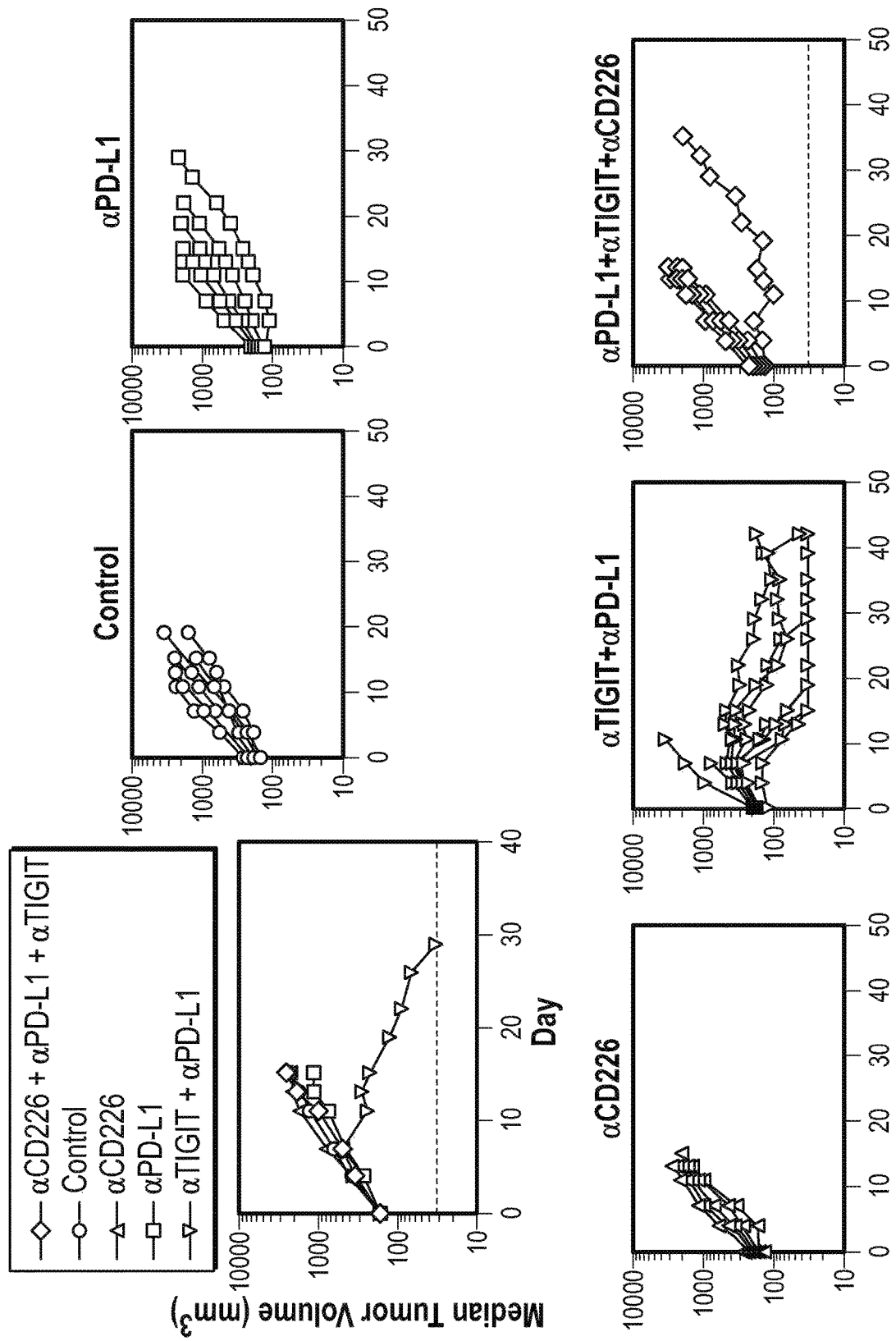

Wildtype BALB/c mice bearing 150-200 mm$^3$ CT26 tumors were treated with a combination of anti-PD-L1 and anti-TIGIT antibodies in the presence or absence of blocking anti-CD226 antibody, or with anti-CD226 alone. Treatment with anti-CD226 alone slightly accelerated tumor growth, relative to control mice, resulting in a decreased median survival of 2 days (anti-CD226 alone vs. control, P=0.0118, FIGS. 28A-28B). Strikingly, the addition of anti-CD226 blocking antibodies to mice treated with anti-TIGIT and anti-PD-L1 co-blockade greatly enhanced tumor growth and fully reversed the efficacy of TIGIT/PD-L1 co-blockade on tumor regression and survival (FIGS. 28A-28B). A similar effect was observed on LCMV titers in chronically infected mice treated with anti-TIGIT, anti-PD-L1, and/or anti-CD226 (FIG. 19D). These data indicated that CD226 contributed to anti-tumor and other chronic T cell responses, and that TIGIT suppressed these responses at least in part by suppression of CD226.

To more fully understand how TIGIT and CD226 activity affected anti-tumor T cell responses, we tested how CD226 alone and in concert with TIGIT influenced T cell activation, tumor infiltration, and effector function. We analyzed tumors and tumor-draining lymph nodes from CT26 tumor-bearing mice treated as above for seven days. As before, co-blockade of PD-L1 and TIGIT enhanced IFNγ production of both tumor-infiltrating and tumor-draining lymph node-resident $CD8^+$ T cells (130% and 99% increase, respectively, $P<0.001$, FIGS. 28C-28D). Blockade of CD226 alone had no effect on IFNγ production by tumor-infiltrating and tumor-draining lymph node-resident $CD8^+$ T cells, suggesting that the effects of CD226 co-stimulation were already limited in exhausted T cells (FIGS. 28C-28E). However, CD226 blockade did impair both the frequency and effector function of tumor-infiltrating $CD8^+$ T cells in mice treated with combination anti-TIGIT and anti-PD-L1 (57% decrease, $P=0.0015$, FIG. 28D). Treatment with anti-CD226 had no such effect on $CD8^+$ T cells residing in the tumor-draining lymph nodes, whereas anti-PD-L1 alone enhanced $CD8^+$ T cell effector function, suggesting that PD-L1 blockade was sufficient to enhance $CD8^+$ T cell effector function even in the absence of CD226. CD226 blockade also resulted in a reduced frequency of tumor-infiltrating $CD8^+$ T cells (53% reduction, $P=0.0044$, FIGS. 28E-28F). Taken together, these data suggested that CD226 functions to support both the accumulation and effector function of tumor-infiltrating $CD8^+$ T cells, and that TIGIT counteracts the latter.

Example 14

TIGIT Impairs CD226 Function by Directly Disrupting CD226 Homodimerization

To test if TIGIT may antagonize CD226 activity in cis, TIGIT's effect on CD226 co-stimulation in vitro was tested. TIGIT-deficient $CD8^+$ T cells stimulated with sub-optimal levels of anti-CD3 responded more robustly to PVR co-stimulation than did wildtype littermate $CD8^+$ T cells, and this enhanced response was dependent on CD226 (46% increase in proliferation, $P=0.0061$, FIG. 29A). Consistent with these data, wildtype $CD8^+$ T cells, stimulated with sub-optimal anti-CD3 and PVR, proliferated more robustly in the presence of anti-TIGIT antibodies than they did in the presence of isotype-matched control antibodies, and this effect was also dependent on CD226 (105% increase in proliferation, $P=0.0010$, FIG. 29B).

To test the relevance of TIGIT to primary human $CD8^+$ T cells, we purified $CD8^+$ T cells from healthy donor blood and stimulated them with sub-optimal levels of plate-bound anti-CD3 and recombinant human PVR-Fc fusion protein. In the presence of isotype-matched control antibodies, PVR co-stimulation moderately enhanced T cell stimulation and proliferation. Furthermore, addition blocking anti-TIGIT antibodies significantly enhanced the effects of PVR co-stimulation, consistent with TIGIT's effects on primary murine $CD8^+$ T cells (69% increase in proliferation, $P=0.0071$, FIG. 29C). These data demonstrated a cell-intrinsic role for TIGIT inhibition of CD226 function on primary murine and human $CD8^+$ T cells.

Figure 29E:
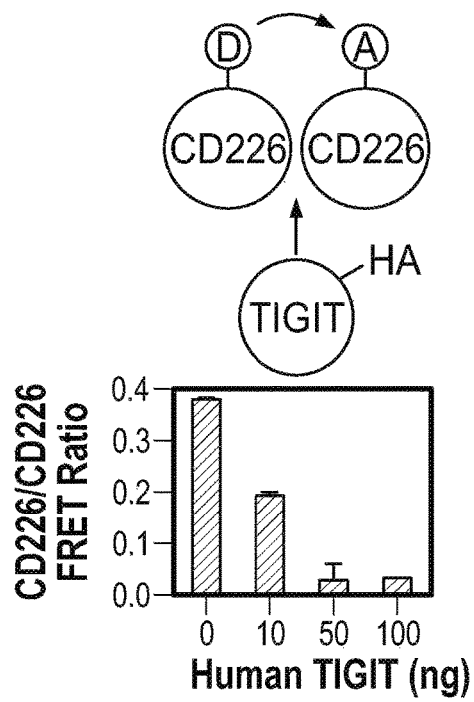
Figure 29F:
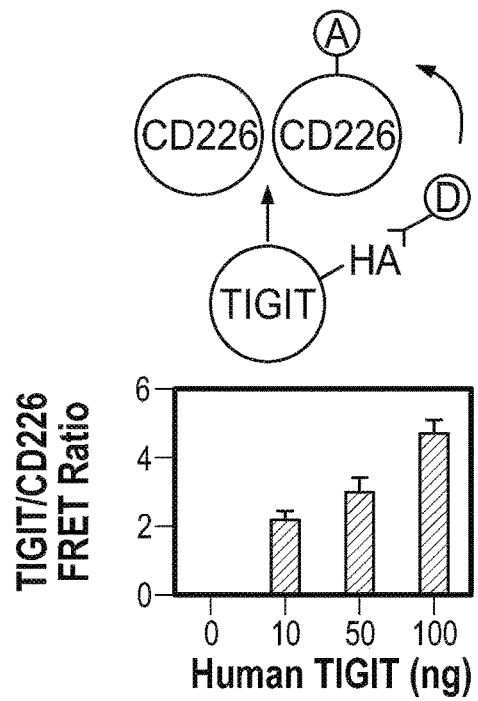
Figure 29G:
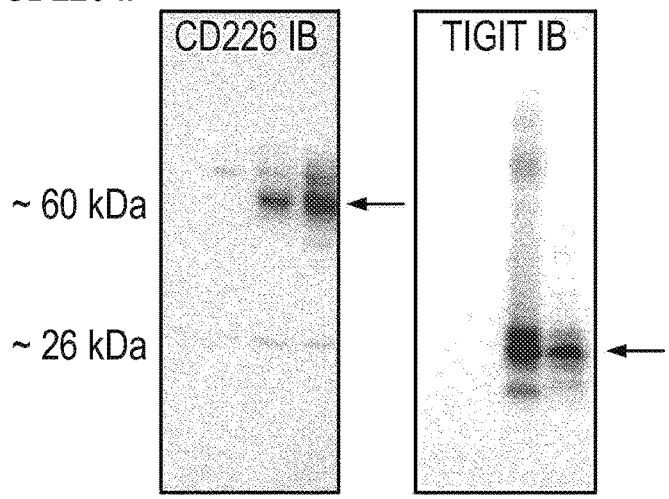

TR-FRET (Time-resolved Fluorescence Resonance Energy Transfer) was used to determine the molecular mechanism by which TIGIT impaired CD226 activity. First, we expressed and labeled human ST-CD226 with non-permeant donor and acceptor fluorophores. These cells yielded a strong FRET signal, confirming the ability of CD226 to homodimerize (FIG. 29D). To monitor CD226 and TIGIT interactions on the cell surface, we expressed ST-CD226 in absence or in presence of human HA-TIGIT that we labeled with the SNAP-tag substrate and an anti-HA antibody, respectively. Strikingly, co-expression of increasing amounts of TIGIT (monitored by ELISA) attenuated the CD226/CD226 FRET signal, indicating that TIGIT could disrupt CD226 homodimerization (FIG. 29E). Indeed, acceptor CD226 and donor TIGIT also resulted in a significant FRET signal, indicating a direct interaction between these two proteins (FIG. 29F). This interaction was further confirmed by co-immunoprecipitation (FIG. 29G). These data demonstrated that TIGIT and CD226 directly interact at the cell surface, and that this interaction can impair CD226 homodimerization.

Figure 29H:
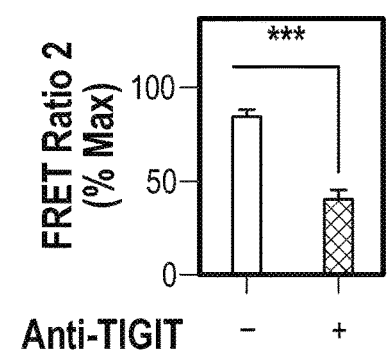

To test the effects of TIGIT antibody blockade on TIGIT-CD226 interaction, we again co-expressed human ST-CD226 and HA-TIGIT, this time in the presence or absence of blocking antibodies against human TIGIT. The addition of anti-TIGIT to the cell cultures significantly reduced the ability of TIGIT and CD226 to associate (FIG. 29H). These data suggested that anti-TIGIT treatment can limit TIGIT's interaction with CD226, and are consistent with the notion that suppression of CD226 activity is a key mechanism of action by which TIGIT enforces $CD8^+$ T cell exhaustion. This is also consistent with the ability of anti-TIGIT antibodies to enhance CD226 co-stimulation.

Next, we confirmed the capacity of endogenous TIGIT and CD226 to interact (FIG. 30). Primary human T cells were stimulated in vitro with anti-CD3 and anti-CD28 antibodies, sorted on the basis of TIGIT expression, rested, re-stimulated, and labeled with antibodies against endogenous TIGIT and CD226 that were conjugated to fluorophores compatible with TR-FRET. TIGIT-expressing T cells labeled with donor-conjugated anti-TIGIT and acceptor-conjugated anti-CD226 antibodies yielded a strong FRET signal (FIG. 30). In contrast, only a negligible FRET signal was detected on T cells that did not express TIGIT or that were labeled with donor-conjugated anti-TIGIT and acceptor-conjugated anti-HVEM antibodies (FIG. 30), confirming the specificity of the detected interaction between endogenous TIGIT and CD226.

These results demonstrate that endogenous TIGIT and CD226 can directly interact at the cell surface, and that this interaction impairs CD226 homodimerization. Given the role of CD226 as a co-stimulator of T cell responses in vivo, and without wishing to be bound by theory, it is believed that suppression of CD226 may be a key mechanism of action by which TIGIT enforces $CD8^+$ T cell exhaustion during chronic viral infection and cancer.

Materials and Methods

Time-Resolved Fluorescence Resonance Energy Transfer with Transfected Cell Lines.

CHO cells were transfected with N-terminus SNAP-tagged (ST) CD226 and N-terminus HA-TIGIT using Lipofectamine 2000 (Life Technologies) and seeded in a white 96-well plate (Costar) at 100,000 cells per well. 24 hours later, cells were labeled to measure TR-FRET either between SNAP-donor/SNAP-acceptor or between SNAP-acceptor/anti-HA donor. 1) SNAP-donor/SNAP-acceptor labeling: Cells were incubated with 100 nM of donor-conjugated benzyl-guanine SNAP-Lumi-4Tb (Cisbio) and 1 μM acceptor-conjugated benzyl-guanine SNAP-A647 (New England Biolabs) diluted in DMEM 10% FCS for 1 h at 37° C., 5% CO2. Cells were then washed three times in PBS before reading of the FRET signal. 2) SNAP-acceptor/anti-HA donor: Cells were incubated with 1 μM acceptor-conjugated benzyl-guanine SNAP-A647 diluted in DMEM 10% FCS for 1 h at 37° C., 5% CO2. After three washes in PBS, cells were incubated for 2 hours with 2 nM anti-HA Lumi-4Tb (Cisbio) in PBS+0.2% BSA at room temperature. The FRET signal was then recorded at 665 nm for 400 μs after a 60 μs delay following laser excitation at 343 nm using a Safire2 plate reader (Tecan). When anti-TIGIT was tested at 10 μg/ml final, the FRET signal was also recorded after a 15 min incubation. For the Flag-ST-CD226/Flag-ST-CD226 interaction, the FRET ratio was calculated as the FRET intensity divided by the donor emission at 620 nm, which is proportional to the CD226 expression. The FRET intensity being: (signal at 665 nm from cells labeled with SNAP-donor and acceptor)−(signal at 665 nm from the same batch of transfected cells labeled with SNAP-donor only). For the Flag-ST-CD226/HA-TIGIT interaction, the FRET ratio represents the FRET intensity divided by the Flag-ST-CD226 expression as measured by an anti-Flag ELISA. In that case, the FRET intensity=(signal at 665 nm from cells labeled with SNAP-acceptor and anti-HA donor)−(signal at 665 nm from mock transfected cells labeled with SNAP-acceptor and anti-HA donor).

Time-Resolved Fluorescence Resonance Energy Transfer with Human T Cells.

Human anti-TIGIT (Genentech clone 1F4), anti-CD226 (Santa Cruz Biotechnology), and anti-HVEM (eBioscience) antibodies were conjugated fluorophores compatible with TR-FRET (Cisbio). Primary human T cells were MACS-enriched from blood, stimulated in vitro with plate bound anti-CD3 and anti-CD28 for 72 hours. TIGIT-expressing and non-expressing T cells (all expressing CD226) were then sorted, rested without stimulation for 72 hours, and re-stimulated for 48 hours. Each population was then washed once with Tris-KREBS buffer (20 mM Tris pH 7.4, 118 mM NaCl, 5.6 mM glucose, 1.2 mM KH2PO4, 1.2 mM MgSO4, 4.7 mM KCl, 1.8 mM CaCl2) and cultured under the following conditions, in triplicate: 1) Anti-TIGIT Ab-Lumi4-Tb (5 μg/ml), 2) Anti-TIGIT Ab-Lumi4-Tb (5 μg/ml)+anti-HVEM-d2 (10 μg/ml), 3) Anti-TIGIT Ab-Lumi4-Tb (5 μg/ml)+anti-CD226 (10 μg/ml), 4) Anti-TIGIT Ab-Lumi4-Tb (5 μg/ml)+anti-CD226 (10 μg/ml)+cold anti-TIGIT Ab (clone 1F4) (50 μg/ml). The indicated concentrations were optimized to ensure the highest FRET signal. Cells were incubated for 2 hours at room temperature on a rotator and then washed 3 times in Tris-KREBS buffer. T cells were then seeded at 400,000 cells/well in a white 96-well plate (Costar) and TR-FRET was recorded at 665 nm for 400 μs after a 60 μs delay following laser excitation at 343 nm using a PHERAstar plate reader (BMG Labtech). FRET intensity was expressed as the signal at 665 nm from cells labeled with Ab-Lumi4-Tb+Ab-d2 minus the signal at 665 nm from the same batch of cells labeled with Ab-Lumi4-Tb alone. The non-specific FRET signal was given by the T cells incubated with Lumi4Tb+d2+an excess of cold Ab.

Co-Immunoprecipitation.

Briefly, COS 7 Cells in 15 cm plates were co-transfected with expression plasmids containing the cDNA for either TIGIT-HA (5 ng) or CD226-Flag (10 ng) tagged proteins, or a control plasmid (pRK). 23 hrs after transfection the cells were washed with PBS and harvested in 4 ml of ice cold PBS and centrifuged at 300×g for 5 min and cell pellets were re-suspended in 2 ml of Lysis buffer at 4° C. The cells were lysed over 50 min with vortexing every 15 min and subsequently centrifuged at 10,00×g for 15 min at 4° C. The resultant supernatant was pre-cleared with 160 μl of CL6B sepahrose slurry by rotating for 30 min at 4° C., and centrifuged for 2 min at 3000×g. The supernatant was equally split into two tubes and immuno-precipitated with either an anti-HA or an anti-flag using standard procedures. The immune-precipitated proteins were subjected to SDS-PAGE and western blotted. Western blots were probed with either anti-Flag-HRP or anti-HA-HRP.

All patents, patent applications, documents, and articles cited herein are herein incorporated by reference in their entireties.

What is claimed is:

1. A method of treating or delaying progression of a cancer in an individual, the method comprising administering to the individual an effective amount of (i) a PD-L1 binding antagonist that inhibits the binding of PD-L1 to PD-1 and/or B7-1, a PD-1 binding antagonist that inhibits the binding of PD-1 to PD-L1 and/or PD-L2, or a PD-L2 binding antagonist that inhibits the binding of PD-L2 to PD-1 and (ii) an agent that inhibits and/or blocks the interaction of CD226 with TIGIT, wherein the agent is an inhibitory anti-TIGIT antibody or antigen-binding fragment thereof.

2. A method for treating or delaying progression of a viral infection in an individual, the method comprising administering to the individual an effective amount of (i) a PD-L1 binding antagonist that inhibits the binding of PD-L1 to PD-1 and/or B7-1, a PD-1 binding antagonist that inhibits the binding of PD-1 to PD-L1 and/or PD-L2, or a PD-L2 binding antagonist that inhibits the binding of PD-L2 to PD-1 and (ii) an agent that inhibits and/or blocks the interaction of CD226 with TIGIT, wherein the agent is an inhibitory anti-TIGIT antibody or antigen-binding fragment thereof.

3. A method of increasing, enhancing, or stimulating an immune response or function in an individual, the method comprising administering to the individual an effective amount of (i) a PD-L1 binding antagonist that inhibits the binding of PD-L1 to PD-1 and/or B7-1, a PD-1 axis binding antagonist that inhibits the binding of PD-1 to PD-L1 and/or PD-L2, or a PD-L2 binding antagonist that inhibits the binding of PD-L2 to PD-1 and (ii) an agent that inhibits and/or blocks the interaction of CD226 with TIGIT, wherein the agent is an inhibitory anti-TIGIT antibody or antigen-binding fragment thereof.

4. The method of any one of claims 1, 2, and 3, further comprising administering at least one chemotherapeutic agent.

5. The method of claim 3, wherein the individual has a cancer.

6. The method of claim 1 or 5, wherein the cancer has elevated levels of T cell infiltration.

7. The method of any one of claims 1, 2, and 3, wherein the inhibitory anti-TIGIT antibody or antigen-binding fragment thereof is a humanized antibody, a chimeric antibody, a bispecific antibody, a heteroconjugate antibody, or an immunotoxin.

8. The method of any one of claims 1, 2, and 3, wherein the PD-L1 binding antagonist is an anti-PD-L1 antibody.

9. The method of claim 8, wherein the anti-PD-L1 antibody comprises a heavy chain comprising HVR-H1 sequence of GFTFSDSWIH (SEQ ID NO:17), HVR-H2 sequence of AWISPYGGSTYYADSVKG (SEQ ID NO:18), and HVR-H3 sequence of RHWPGGFDY (SEQ ID NO:19); and a light chain comprising HVR-L1 sequence of RASQD-VSTAVA (SEQ ID NO:20), HVR-L2 sequence of SASFLYS (SEQ ID NO:21), and HVR-L3 sequence of QQYLYHPAT (SEQ ID NO:22).

10. The method of claim 1 or 5, wherein the cancer is selected from the group consisting of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphomas, a myelomas, a mycosis fungoides, a Merkel cell cancer, and a hematologic malignancy.

11. The method of any one of claims 1, 2, and 3, wherein the inhibitory anti-TIGIT antibody or antigen-binding fragment thereof inhibits and/or blocks the ability of TIGIT to disrupt CD226 homodimerization.

12. The method of any one of claims 1, 2, and 3, wherein the inhibitory anti-TIGIT antibody or antigen-binding fragment thereof inhibits and/or blocks the interaction of TIGIT with CD226, without impacting PVR-CD226 interaction.

* * * * *

Disclaimer

10,611,836 B2 - Jane Grogan; Robert J. Johnston; Bryan Irving, all of San Francisco, CA (US); Jason Hackney, San Carlos, CA (US); Xin Yu, South San Francisco, CA (US); Dan Eaton, San Rafael, CA (US); Kristin Bowles, South San Francisco, CA (US); Laetitia Comps-Agrar, Foster City, CA (US). METHODS OF TREATING CANCER USING PD-1 AXIS BINDING ANTAGONISTS AND TIGIT INHIBITORS. Patent dated April 21, 2020. Disclaimer filed June 16, 2023, by the assignee, Genentech, Inc.

I hereby disclaim the following complete claims 1-12, of said patent.

*(Official Gazette, August 22, 2023)*